US011999963B2

(12) United States Patent
Rojas et al.

(10) Patent No.: US 11,999,963 B2
(45) **Date of Patent: *Jun. 4, 2024**

(54) PSEUDOMONAS PROTEGENS AND PRODUCTS THEREOF TO CONTROL BACTERIAL PANICLE BLIGHT OF RICE

(71) Applicant: THE BOARD OF TRUSTEES OF THE UNIVERSITY OF ARKANSAS, Little Rock, AR (US)

(72) Inventors: Clemencia M. Rojas, Fayetteville, AR (US); J. Alejandro Rojas, Springdale, AR (US); Jackson O. Lay, Jr., Fayetteville, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/341,498

(22) Filed: Jun. 8, 2021

(65) Prior Publication Data

US 2021/0388374 A1 Dec. 16, 2021

Related U.S. Application Data

(60) Provisional application No. 63/036,202, filed on Jun. 8, 2020.

(51) Int. Cl.
*C12N 15/82* (2006.01)

(52) U.S. Cl.
CPC ................................ *C12N 15/8281* (2013.01)

(58) Field of Classification Search
None
See application file for complete search history.

(56) References Cited

U.S. PATENT DOCUMENTS

| | | | |
|---|---|---|---|
| 6,689,357 | B2 | 2/2004 | Casida, Jr. et al. |
| 2017/0233712 | A1 | 8/2017 | Shepherd |
| 2020/0068900 | A1 | 3/2020 | Rojas |

FOREIGN PATENT DOCUMENTS

| | | |
|---|---|---|
| WO | 2013/130680 | 9/2013 |

OTHER PUBLICATIONS

Ma et al. Frontiers in Microbiology (2016), vol. 7, article 382.*
Mishra et al. Applied Soil Ecology (2018) 125:35-45.*
Raajimakers et al. Annu Rev. Phytopathol (2012) 50:403-424.*
Akter, S., et al. (2016). In vitro evaluation of Pseudomonas bacterial isolates from rice phylloplane for biocontrol of Rhizoctonia solani and plant growth promoting traits. J. Environ Biol. 37(4)567-602.
Arseneault, T., et al. (2016). Biocontrol of potato common scab is associated with High Pseudomonas fluorescens LBUM223 populations and phenazine-1-carboxylic acid biosynthetic transcript accumulation in the potato geocaulosphere. Phytopathology. 106(6):554-561.
Chandrasekaran, M., et al. (2016). Metaanalysis reveals that the genus Pseudomonas can be a better choice of biological control agent against bacterial wilt disease cause by Ralstonia solanacearum. Plant Pathol J. 32(3): 216-27.
Chin-A-Woeng, T.F., et al., 2000. Root colonization by phenazine-1-carboxamide-producing bacterium Pseudomonas chlororaphis PCL1391 is essential for biocontrol of tomato foot and root rot. Mol Plant Microbe Interact 13, 1340-5.
Compant, S. et al. "Diversity and occurrence of *Burkholderia* spp. in the natural environment" Microbiol Rev (2008) 32:607-626.
Cui, Z., et al. (2014). Susceptibility of the opportunistic Burkholderia glumae to copper surfaces following wet or dry surface contact. Molecules. J19(7):9975-85.
D'Aes, J. et al., 2011. Biological control of Rhizoctonia root rot on bean by phenazine- and cyclic lipopeptide-producing Pseudomonas CMR12a. Phytopathology 101, 996-1004.
Degrassi, G. et al., 2008. Identification, characterization and regulation of two secreted polygalacturonases of the emerging rice pathogen Burkholderia glumae. FEMS Microbiol Ecol 65, 251-62.
Devescovi, G. et al., 2007. Involvement of a Quorum-Sensing-Regulated Lipase Secreted by a Clinical Isolate of Burkholderia glumae in Severe Disease Symptoms in Rice. Appl Environ Microbiol 73, 4950-8.
Dubouzet, J.G. et al., 2011. Screening for resistance against Pseudomonas syringae in rice-FOX *Arabidopsis* lines Identified a putative receptor-like cytoplasmic kinase gene that confers resistance to major bacterial and fungal pathogens in *Arabidopsis* and rice. Plant Biotechnol J 9, 466-85.
Fory, P.A., et al., 2014. Comparative analysis of two emerging rice seed bacterial pathogens. Phytopathology 104, 436-44.
Fuller, A. T., et al. (1971). Psudomonic acid: an antibiotic produced by Pseudomonas fluorescens. Nature. 234:416-417.
Glare, T. et al., 2012. Have biopesticides come of age? Trends Biotechnol 30, 250-8.
Gomez-Lama Cabanas, C. et al. (2018). Indigenous *Pseudomonas* spp. Strains from the olive (*Olea europea* L) hizosphere as effective biocontrol agents against Verticillium dahlia: from host roots to the bacterial genomes. Front. Microbiol. 2018. 9:277.
Gross, H., et al. 2007. The genomisotopic approach: a systematic method to isolate products of orphan biosynthetic gene clusters. Chem Biol 14:53-63.

(Continued)

*Primary Examiner* — Medina A Ibrahim
(74) *Attorney, Agent, or Firm* — Quarles & Brady, LLP

(57) ABSTRACT

The present invention provides biosynthetic products that may be useful for controlling bacterial panicle blight of rice. These products are encoded by four biosynthetic operons found within the genome of a *Pseudomonas protegens* strain designated as PBL3 and deposited as ATCC #, which has been shown to inhibit the growth of *Burkholderia glumae* on rice plants. Also provided are vectors encoding these biosynthetic products, and methods of using the biosynthetic products to inhibit the growth of microorganisms.

5 Claims, 10 Drawing Sheets

Specification includes a Sequence Listing.

(56) References Cited

OTHER PUBLICATIONS

Gutierrez-Barranquero, J.A., et al., 2013. Recruitment and rearrangement of three different genetic determinants into a conjugative plasmid increase copper resistance in Pseudomonas syringae. Appl Environ Microbiol 79, 1028-33.
Haas, D. et al., 2005. Biological control of soil-borne pathogens by fluorescent pseudomonads. Nat Rev Microbiol 3, 307-19.
Ham, J.H. et al., 2011. Burkholderia glumae: next major pathogen of rice? Molecular Plant Pathology 12, 329-39.
Hikichi, Y. 1993. Antibacterial activity of oxolinic acid on Pseudomonas glumae. Japanese Journal Phytopath 59, 369-74.
Howell, C.R. and Stipanovic, R.D. 1979. Control of Rhizoctonia solani on cotton seedlings with Pseudomonas fluorescens and with an antibiotic produced by the bacterium. Phytopathology 69, 480-2.
Howell, C.R. and Stipanovic, R.D. 1980. Suppression of Pythium ultimum-induced damping-off of cotton seedlings by Pseudomonas fluorescens and its antibiotic, pyoluteorin. Phytopathology 70, 712-15.
Iyama, K. et al., 1995. A role of phytotoxin in virulence of Pseudomonas glumae Kurita et Tabeti. Japanese Journal Phytopath 61, 470-6.
Jamali, F. et al., 2009. Influence of host plant genotype, presence of a pathogen, and coinoculation with Pseudomonas fluorescens strains on the rhizosphere expression of hydrogen cyanide- and 2,4-diacetylphloroglucinol biosynthetic genes in P. fluorescens biocontrol strain CHA0. Microb Ecol 57, 267-75.
James, D. W., et al. (1986). Multiple antibiotics produced by Pseudomonas fluorescens HV37a and their differential regulation by glucose. Appl. Environ. Microbiol> 52 (5):1183-1189.
Jousset, A. et al., 2014. Full-Genome Sequence of the Plant Growth-Promoting Bacterium Pseudomonas brotegens CHA0. Genome Announc 2.
Karki, H.S. et al., 2012. Diversities in Virulence, Antifungal Activity, Pigmentation and DNA Fingerprint among Strains of Burkholderia glumae. PLoS One 7.
Kaur, R., et al. (2016). Evaluation of Pseudomonas fluorescens for the management of tomato early blight disease and fruit borer. J. Environ Biol. 37(5): 869-872.
Kawaradani, M. et al., 2000. New selective medium for isolation of Burkholderia glumae from rice seeds. J. Gen. Plant Pathol 66, 234-7.
Keel, C. et al., 1992. Suppression of root diseases by Pseudomonas fluorescens CHAO: importance of the bacterial secondary metabolite 2,4-diaceylphloroglucinol. Molecular Plant-Microbe Interactions 5, 4-13.
Kim, J. et al., 2004. Quorum sensing and the LysR-type transcriptional activator ToxR regulate toxoflavin biosynthesis and transport in Burkholderia glumae. Mol Microbiol 54, 921-34.
Kloepper, J.W. et al., 1980. Pseudomonas siderophores: a mechanism explaining disease-suppressive soils. Current microbiology 4, 317-20.
Knapp, A. et al., 2016. Mutations improving production and secretion of extracellular lipase by Burkholderia glumae PG1. Appl Microbiol Biotechnol 100, 1265-73.
Kohl, J. et al., 2019. Mode of Action of Microbial Biological Control Agents Against Plant Diseases: Relevance Beyond Efficacy. Front Plant Sci 10, 845.
Lee, Y.H. et al. 2015. BGRcast: A Disease Forecast Model to Support Decision-making for Chemical Sprays to Control Bacterial Grain Rot of Rice. Plant Pathol J 31, 350-62.
Lemanceau, P. et al., 1992. Effect of pseudobactin 358 production by Pseudomonas putida WCS358 on suppression of fusarium wilt of carnations by nonpathogenic Fusarium oxysporum Fo47. Appl Environ Microbiol 58, 2978-82.
Lim, J. et al., 2009. Complete Genome Sequence of Burkholderia glumae BGR1. Journal of Bacteriology 191, 3758-9.
Maeda, S. et al., 2016. Overexpression of BSR1 confers broad-spectrum resistance against two bacterial diseases and two major fungal diseases in rice. Breed Sci 66, 396-406.
Maeda, Y. et al., 2004. Implications of amino acid substitutions in GyrA at position 83 in terms of oxolinic acid resistance in field isolates of Burkholderia glumae, a causal agent of bacterial seedling rot and grain rot of rice. Appl Environ Microbiol 70, 5613-20.
Mannulis, S. et al., 2003. Changes in the Sensitivity of Erwinia amylovora Populations to Streptomycin and Oxolinic Acid in Israel. Plant Dis 87, 650-4.
Maurhofer, M., et al., 1994. Pyoluteorin production by Pseudomonas fluorescens strain CHA0 is involved in the suppression of Phythium damping-off of cress but not of cucumber. Eur J Med Chem Eur J Plant Pathol, 221-32.
Mazurier, S., et al., 2009. Phenazine antibiotics produced by fluorescent pseudomonads contribute to natural soil suppressiveness to Fusarium wilt. ISME J 3, 977-91.
Milus, E.A., et al., 1997. Efficacy of Bacterial Seed Treatments for Controlling Pythium Root Rot of Winter Wheat. Plant Dis 81, 180-4.
Mizobuchi, R. et al. 2018. Evaluation of major Japanese rice cultivars for resistance to bacterial grain rot caused by Burkholderia glumae and identification of standard cultivars for resistance. Breed Sci 68, 413-9.
Mizobuchi, R et al., 2016. QTLs for Resistance to Major Rice Diseases Exacerbated by Global Warming: Brown Spot, Bacterial Seedling Rot, and Bacterial Grain Rot. Rice (N Y) 9, 23.
Mizobuchi, R. et al., 2013. Mapping a quantitative trait locus for resistance to bacterial grain rot in rice. Rice (N Y) 6, 13.
Mondal, K.K, et al. 2015. Emergence of Bacterial Paniclbe Blight caused by Burkholderia glumae in North India. Plant Disease 99, 1268-.
Morrison, C.K., et al. (2017). Phenazine-1-carboxylic acid production by Pseudomonas fluorescens LBUM636 alters Phytophthora infestans growth and late blight development. Phytopathology. 107(3):273-279.
Mulaw, T. et al., 2018. Characterization and plant detection of bacteria that cause Bacterial Panicle Blight of rice. American Journal of Plant Sciences 9, 667-84.
Nandakumar, R., et al. 2007. Association of Burkholderia glumae and B. gladioili with Panicle Blight Symptoms on Rice in Panama. Plant Dis 91, 767.
Nandakumar, R. et al., 2009. Burkholderia glumae and B. gladioli cause bacterial panicle blight in rice in the Southern United States. Plant Dis 93, 896-905.
Nicot, P.C. et al. 2012. Review of factors influencing the successs or failure of biocontrol: technical, industrial and socio-economic perspectives. In. IOBC-WPRS Bulletin. 78, 95-98.
Olorunleke, F.E., et al. 2015. Interplay between orfamides, sessilins and phenazines in the control of Rhizoctonia diseases by *Pseudomonas* sp. CMR12a. Environ Microbiol Rep 7:774-781.
Pieterse, C.M. et al., 2014. Induced systemic resistance by beneficial microbes. Annu Rev Phytopathol 52, 347-75.
Raaijmakers, J.M. and Mazzola, M. "Diversity and Natural Functions of Antibiotics Produced by Beneficial and Plant Pathogenic Bacteria" Annual Review of Phytopathology (2012) 50:403-424.
Rodriguez, C. et al., 2006. Lettuce for human consumption collected in Costa Rica contains complex communities of culturable oxytetracycline- and gentamicin-resistant bacteria. Appl Environ Microbiol 72, 5870-6.
Shew, A.M. et al., 2019. Warming increases Bacterial Panicle Blight (*Burkholderia glumae*) occurrences and impacts on USA rice production. PLoS One 14, e0219199.
Shrestha, BK., et al. (2016). Biological Control Activities of Rice-Associated *Bacillus* sp. Strains against Sheath Blight and Bacterial Panicle Blight of Rice. PLoS One. Jan. 14;11(1):e0146764.
Smirnov, V.V., et al. (1997). Fluviols, bicyclic nitrogen-rich antibiotics produced by Pseudomonas fluorescens. FEMS Microbiology letters. 153:357-361.
Suarez-Moreno, Z.R. et al., 2019. Plant-Growth Promotion and Biocontrol Properties of Three *Streptomyces* spp. Isolates to Control Bacterial Rice Pathogens. Front Microbiol 10, 290.

(56) References Cited

OTHER PUBLICATIONS

Sundin, G.W. and Wang, N. 2018. Antibiotic Resistance in Plant-Pathogenic Bacteria. Annu Rev Phytopathol 56, 161-80.
Sundin GW, et al., 2016. Bacterial disease management: challenges, experience, innovation and future prospects: Challenges in Bacterial Molecular Plant Pathology. Mol Plant Pathol 17, 1506-18.
Sundin, G.W. and Bender, C.L. 1993. Ecological and genetic analysis of copper and streptomycin resistance in Pseudomonas syringae pv. syringae. Appl Environ Microbiol 59, 1018-24.
Thomashow, L.S., et al., 1988. Role of a phenazine antibiotic from Pseudomonas fluorescens in biological control of *Gaeumannomyces graminis* var. *tritici*. J Bacteriol 170, 3499-508.
Trippe, K., et al. (2013). Pseudomonas fluorescens SBW25 produces furanomycin, a non-proteinogenic amino acid with selective antimicrobial properties. BMC Microbioloy. 13:111.
Upadhyay, A., et al. (2008). Characterization of a new isolate of Pseudomonas fluorescens strain Psd as a potential biocontrol agent. Lett. Appl. Microbiol. 47(2):98-105.
Voisard,C. et al., 1989. Cyanide production by Pseudomonas fluorescens helps suppress black root rot of tobacco under gnotobiotic conditions. EMBO J 8, 351-8.
Wamishe, Y. et al. 2015. Bacterial Panicle Blight of Rice in Arkansas. University of Arkansas Division of Agriculture Research and Extension: Agriculture and Natural Resources.
Weller, D.M. 2007. Pseudomonas biocontrol agents of soilborne pathogens: looking back over 30 years. Phytopathology 97, 250-6.
Wilkinson, K.A. et al. Prospecting for Biological Control Agents against Burkholderia glumae, the causal agent of bacterial panicle blight of rice. Poster presented at American Phytopathological Society—95th Southern Division Meeting. Feb. 16-18, 2018.
Yasmin, S. et al., 2016. Plant Growth Promotion and Suppression of Bacterial Leaf Blight in Rice by Inoculated Bacteria. PLoS One 11, e0160688.
Yendyo, S., et al. (2017). Evaluation of *Tricoderma* spp., Pseudomonas fluorescens and Bacillus subtilis for biological control of Ralstonia wilt of tomato. F100Res.6:2020.
Zhou, X.G. 2014. First Report of Bacterial Panicle Blight of Rice Caused by Burkholderia glumae frica. Plant Dis 98, 566.
Office Action for U.S. Appl. No. 16/561,697 dated Nov. 5, 2020 (17 pages).
Office Action for U.S. Appl. No. 16/561,697 dated Jan. 4, 2022 (144 pages).
Thomashow, L.S., et al., 1997. Antibiotic production by soil and rhizosphere microbes in situ . . . In: Hurst CJ, Knudsen GR, Mcinerney MJ, Stetzenbach LD, Walter MV, eds. Manual of Environmental Microbiology, ed. Washington, DC: ASM Press, 493-99.

* cited by examiner

A
P. protegens PBL3
P. fluorescens 5-40
P. fluorescens 1-30
B. cepacia
Pseudomonas sp.
P. fluorescens 2-79
Burkholderia sp.
B
Zone of growth inhibition (cm2)
2.5
2
1.5
1
0.5
0
A
C
DE
AB
E
B
CD
P. protegens PBL3
P. fluorescens 5-40
P. fluorescens 1-30
B. cepacia
Pseudomonas sp.
P. fluorescens 2-79
Burkholderia sp.

A

B

A.
B. glumae/
LB
B. glumae/
P. protegens PBL3
secreted fraction
B.
Bacterial growth
Log CFU/in
8
7
6
5
4
3
2
1
0
*
B. glumae/
LB
B. glumae/
P. protegens PBL3
secreted fraction
C.
B. glumae/
LB
B. glumae/
P. protegens PBL3
secreted fraction
D.
Bacterial growth
Log CFU/in
6
5
4
3
2
1
0
B. glumae/
LB
B. glumae/
P. protegens PBL3
secreted fraction A
B. glumae/ LB
B. glumae / P. protegens PBL3 secreted fraction (0.1 g/ml)
B. glumae / P. protegens PBL3 secreted fraction (0.5 g/ml)
Water
B
Average shoot length (cm)
7
6
5
4
3
2
1
0
B
A
A
A
B. glumae/ LB
B. glumae / P. protegens PBL3 secreted fraction (0.1 g/ml)
B. glumae / P. protegens PBL3 Secreted fraction (0.5 g/ml)
Water

SEQUENCE LISTING

```
<160> NUMBER OF SEQ ID NOS: 5

<210> SEQ ID NO 1
<211> LENGTH: 93358
<212> TYPE: DNA
<213> ORGANISM: Pseudomonas protegens PBL3
<220> FEATURE:
<221> NAME/KEY: misc_feature
<222> LOCATION: (1)..(93358)
<223> OTHER INFORMATION: Orfamide biosynthesis gene cluster
<220> FEATURE:
<221> NAME/KEY: misc_feature
<222> LOCATION: (569)..(570)
<223> OTHER INFORMATION: N is an A, T, C, or G
<220> FEATURE:
<221> NAME/KEY: misc_feature
<222> LOCATION: (592)..(942)
<223> OTHER INFORMATION: N is an A, T, C, or G
<220> FEATURE:
<221> NAME/KEY: misc_feature
<222> LOCATION: (972)..(978)
<223> OTHER INFORMATION: N is an A, T, C, or G
<220> FEATURE:
<221> NAME/KEY: misc_feature
<222> LOCATION: (3270)..(3270)
<223> OTHER INFORMATION: N is an A, T, C, or G
<220> FEATURE:
<221> NAME/KEY: misc_feature
<222> LOCATION: (58671)..(62739)
<223> OTHER INFORMATION: N is an A, T, C, or G
<220> FEATURE:
<221> NAME/KEY: misc_feature
<222> LOCATION: (62746)..(62746)
<223> OTHER INFORMATION: N is an A, T, C, or G
<220> FEATURE:
<221> NAME/KEY: misc_feature
<222> LOCATION: (62752)..(62755)
```

<223> OTHER INFORMATION: N is an A, T, C, or G
<220> FEATURE:
<221> NAME/KEY: misc_feature
<222> LOCATION: (62757)..(62757)
<223> OTHER INFORMATION: N is an A, T, C, or G
<220> FEATURE:
<221> NAME/KEY: misc_feature
<222> LOCATION: (62761)..(62761)
<223> OTHER INFORMATION: N is an A, T, C, or G

<400> SEQUENCE: 1

```
atgctggaac caagtcataa cgacgagctc ccggtcattc cgggcaagcg ctacttcacc     60

attggtgagg tcagtgagct ctgtgcggtc aagccgcatg tgctgcgtta ttgggagcag    120

gagtttcctc aactcaaccc cgtcaagcgc cgcggaaatc gccggtatta tcagcgccag    180

gatgtgctga tgatccggca gatccgcgcg ttgctttatg accaggggtt caccatcggc    240

ggggcgcgtc tgcgtctttc cggtgatgag gccaaagacg atacgaccca gtacaagcaa    300

ctgatccgtc agatgatctc tgagctggaa gatgtgcttg tggtgctaaa aaagtaattc    360

tctgttttaa atacttccac ttttcaaaag cttgcggtat attcctcaac gtttcctgag    420

aagtgaaaca gatttcacgc ctagtcgggg cgtagcgcag tccggtagcg cactagcatg    480

gggtgctagg ggtcgagtgt tcgaatcact ccgtcccgac catatttttc aatgacttag    540

ccgctttcga gcggctttgt tgtttctgnn ctgccatagt gacttttcga gnnnnnnnnn    600

nnnnnnnnnn nnnnnnnnnn nnnnnnnnnn nnnnnnnnnn nnnnnnnnnn nnnnnnnnnn    660

nnnnnnnnnn nnnnnnnnnn nnnnnnnnnn nnnnnnnnnn nnnnnnnnnn nnnnnnnnnn    720

nnnnnnnnnn nnnnnnnnnn nnnnnnnnnn nnnnnnnnnn nnnnnnnnnn nnnnnnnnnn    780

nnnnnnnnnn nnnnnnnnnn nnnnnnnnnn nnnnnnnnnn nnnnnnnnnn nnnnnnnnnn    840

nnnnnnnnnn nnnnnnnnnn nnnnnnnnnn nnnnnnnnnn nnnnnnnnnn nnnnnnnnnn    900

nnnnnnnnnn nnnnnnnnnn nnnnnnnnnn nnnnnnnnnn nnactttctt gcgcaactgc    960

gaagcttctg cnnnnnnncg aagcttctcc ggctttttca cgctcgcggg ttcggcctgg   1020

cttgctaggt tatcggctcg atggggggga gggcgcacgg gtggcaacta ctcctgccac   1080

gtccatgact tggtgcttgt tgcggctggc tcactctgcc tagtggaggg tggcaatgcg   1140

ccggttttcg ccaatcctga ttcggtccag cgctcggttg agtgcgtcca gggcattgag   1200

caaggcttgt gcctcggttt cccgaccctg accccagagg cgctcggcca tcttgttcaa   1260

ggcctggatg gagcgctcga tatcggcggc agtgactgcc ttggcatcct ccggctcttt   1320

tctaggcatg ggctgaggcc tcgattgtgg tttgctggcg aactggatga tgggtttgcc   1380

agtgttcgat ggagggctgt ttccggttcg gtctggcgag attcatggaa ggcctgtcac   1440

tgacgacatt tcaaggccgc ggcttgtatg tcggaggcgc taccgacgtt gacgacgctc   1500

atgctgtcgg cgccaagttc ggctgcttta ttgaaggcca tattcagcgc gtccccattg   1560

gaggagccct tcacggtaaa tgccgtcaga accttgcagg cctgtgccga ggaggccgtc   1620

accagatcga cctgccttcc tgcttccgtc agttgtgtgg tgcaagccga gaccgaagcc   1680

gcagcgacga caagcaagac aaggccacgc agattacgca tcactgaaca ctcctgtcga   1740

cgaggttgcc ggcctatccc ggccagccag ccccgggcaa tcatcgcgag tacatcgccc   1800

accagaacac atggcccagg atcgagatct gctgttcctg gatttcggcg aagctatagt   1860

cttcgtccgg atgttcatcc cgattgaagc tgcgcaggcg cagcccgacc ggcaaacggt   1920

aaacctgctt cacgcgcaac tggccattgt ggttgagtgc atacatctcc ccgtcgacta   1980

catccttcag ggcattcctg ccgacgttca cgccaacggt tgcgccgtcg cgcagcaccg   2040
```

```
ggaccatgct gttgccgctg accgacacgc acttggcgtt gttgaactgc accccgttct   2100
gacgcagatc tttcttgaag aagcgcagcc gggcggtatc gctttcttcg atgacaaacc   2160
ggcccgagcc tgcagccagc tccacctcgt gaagaaaggg gacgtagacc tcgttgtcat   2220
cgagcggggt cgcatcgtcc caggtctcga tatcgtccaa atgcacgctt ggctgggtgc   2280
gtgccgatgc ggtatccgcg gccttgagca tttctccaac gccttcagcg agccacatgg   2340
aggaaacgcc gcataccgag gcaatctggg cgacaaaggc cgtggccttc gatttgccac   2400
gttccaggtc ggagattgag gtttgggtca ggccggcacg ttcagcgagc tctgtttgat   2460
tgagctgggc gtggcgacga gctgttttga gtcgatcttt aaattccatc cgcccagtat   2520
tacgggggtt cccataagct tgcaaatggg tattcctata ttgtactata tgggtgttcc   2580
cgtaagggtg tcaggcagat aatcaaatgg atttgcagat gttaaaagaa tgcagatgtg   2640
gaagttgcaa tcgacttctc gctcgagtgg gcgagtttac tgagctccag atcaaatgtt   2700
cccgctgtgg aaccttgaat catgtaaagg ccgcgagtct cgagctatcg ccaggagcgg   2760
ccaggtgtga aagcggcgtc ggtcattgag cctgtgatgc aaaggcacgt ccgggccaga   2820
ggcccgaact cctgttgcat gacggttcca ggccacgcgt agcgctgtcg cagtcattat   2880
tggaatgggt ggagctctca cgccgtggcg gtctgaagct atcgccccct tcgtgaaagc   2940
caagagcttc gatttcctcg cctttgagcg acatgcaggc ggaatcctcc gcatccatca   3000
ttcgactcaa taggtaacaa catggcttgg attcgatacg actttaccga caacggttct   3060
tctgtactgc cagcgcgcta ctacatggcg cccaaccagt accttcagtc ccctaacaag   3120
cgcttcaagc tgctctttca ggcagatggc aacctggcac tgtatgacgg cgcccagttg   3180
gcatgggtgg ctgaccagaa cacgccgttc accaacgtga gcaagggcaa caagaaagat   3240
ccgatgatgg tcttcatgaa ctacggcttn gtcctggatg acccgctgcg tggccgtatc   3300
tggtcgacca ctccgagtga ccccaccatg ggttcgcgcg aagatgcctc gctgcgtgcg   3360
ttcacccagc ttcaggacga cgggaacatc gtcactgtcg acaccatccc gcactggtat   3420
gcgcccaatg gtcgtgtatt caccccggcg gtgggtacgg caatgatcat cagcggtccg   3480
gccgagctgg taccgggcca gctctacagc gctggcgatc acgctctggt cttccagggc   3540
gatggcaacc tggtggtgta cgggccgaac tggagcgtgg tctgggcgac ctatacccag   3600
aacaaaggtg gtgtgcgatg cgtcatgcag gcagacggca acctggtgat ctacgccgcg   3660
aacaatgcgg tcgtctggca gagcggcacg gctggtcacc ccggcgcaac catccgcctg   3720
caggccaacg gcagtttcac gatagtgacc gagcggccga tctgggcccg cttcggctat   3780
accccgacca tcaagccgcc gcgtgtgttc taccccgatc acaagtggaa aaccggtagc   3840
tacacctggg acaacgtgtt ctaacggcct gcaagaggcc ccgcgacgat gcggggcttc   3900
tacaggcttc actcaagggc ccggcaggct tgttctgccg ggctctgccc attggtggcg   3960
cagattgaac ggggtcacga acgggcaagc gacagctggc cttcaaaggc cctgctctca   4020
accttgaaaa acagattctc ctgagtaccg ccattcacct gcttcaggac ggtgtgcgac   4080
aactgcgcgc cgattttctc catggctcgc tgtgagcgga tattcgaacc cgcaacatgg   4140
aaccagacgg tgtcgaccca ctgaaaggcg tgcccgagca tcaggtactt gagttccttg   4200
ttggcactgc ccccccattt ttcgcgcgcc agaaaggtgt agccgatggc aacttcacgc   4260
tggtcctcgt tgaactcgta gtagcgggag ctgcctgcag ccttgccgct gtcgcggtcg   4320
atcacgatca gggtgctctt ggccgccagt gcgtcgtcgt accattggcg aaataccggc   4380
```

-continued

```
tcctgatagc gggtcgagct ttggtgctga gcccagatca agggatcgca ggcgacgcca   4440
tacagcgccg cgaagtccac ggcctcaagt gggcgcagtt caagtgattc accaacgagc   4500
aggggcgaga ggggcagcga ttgcatcagt gatctccaaa ggacgaatgc atctgtttcg   4560
ttgcgcgagg cttgctggat gagcaatatg ctccggttgc atcacggcta cgcgggagcc   4620
ggaaccttaa caaggctctg gcaggcctga atagcgcggc acggctgctg ttggccgcga   4680
gtatccctga tcggcctgtg gcgcatcacc tggccaaccc cgcgcaatac tcaacaagcg   4740
cgcaatcgct ctgagcacat caatggatgg caacgcaacg atgaaatacc ccattagcct   4800
gttggcatgc acgctcttac tggcctcgcc cgcgtgggcg cagggcaagc gggtgattcc   4860
gggtagcgag caggtcgagg cgggttatct ctcgtcgcaa ttgttgctga agccctgtac   4920
ggacgtgacg acgctgggct tcagcgcgga cgacagcgcc ctgcacgatg ccgccgccgc   4980
gcgccaggcc ttgcctgcgg gaacctgcaa cgacgcagcg ctggtggaga aactgttcaa   5040
ggcgcgcttt gtgcagtacg gctcgatcac gcaggtgttc accccgtggc aattggcacg   5100
acaggtcgat aggcagaacc gtgccatcag ccgttgcccg gatacccaat gcctgggccg   5160
cgagctggat gcagtgattg ccgcgctggc gccggtgtat ctcggcgccc gccgggtctg   5220
gcccagggc aaggggctgt gcgccagcga gccggtggac agcccggcga accaggccct   5280
ggcggttctg gggccgaca cccgtcagca gatcaatgcg caatgcgcac aggaggggt   5340
gattgccaca acctgccacg gcccccatgg ccaattgctg ttcttgagct gtggcatgag   5400
cggcaatcag gtcaactcaa gccaatggct ttatcgtgcc ggcaaggcac acgccgagcc   5460
gctgttcgcc gtcgaggatg gtcccctggg cgtactggcg acttcctgca acggcatgcc   5520
cgacctgatg accagtgcac gggtcagtgc cggggagcac aacgacacct tctaccggta   5580
cgacggcaag gcctatcggc aggtgtattc ctacatcagc acctttgtcg gtatcgatgc   5640
caacggcaat gacctggcca tcgcccaggc cggtgcactg gccaaggtcg cgtgccgcta   5700
ggggcgcgca ttgctcacag cgcgcggcaa agatcaagat tgacctccct ggccgacgcc   5760
cagaagatgc ggcccttcgt atccagtctc gggagagggc atgcaggcgc atgacgctta   5820
cttcactatc gacgccgagg cgctgcagga ccgctccctg gccgagctgg ccgccgggca   5880
gccgctgccg ctgcgctgga tctgagcggc caggacctgt cccgcatcag cctgcccggg   5940
gcctggttcg aacgctgcct gctgaccggc gccgatctca ccgcggccaa cctgatcaat   6000
acccgctgga ccagctgccg cggcgcccag gccaacctgc gttctgcagt gcttaccgat   6060
gcccgtttcg aacgctgtga cctgaacaac acgcaatggc agcgcagcaa ggtggcccat   6120
gcaagcttcg atggctgcaa gctcaccggc gcccacttcg gcgacgtgtc ggccctgggc   6180
ctgagctttt ccgactgcct gctcaacagc gccatgctct cgggtatctc gttctacaag   6240
tcgcagttgc acaacattga tttcagcgaa gccgacctga cctactgcga ctttcgcaag   6300
gcggtgtttg tcgacggcgg cagcctgtcc atggcccggg tcaacaatgc ccgcttcgat   6360
gacgccgacc tgcgcgaagc cagcctgcat gggctgcgcc tggtggatgc caagctgttc   6420
aagggggcga tcatttcccg cagccaggcc ggcatgctcc tggccgggct gggcctggcc   6480
gtgctctgac tagagcccgg ccgctgcggg ttgggcctgc agcaattcgt cgagcacccc   6540
catgaaggct tccaccaact ggctgcggcc ctgcttgcgg gtcagtacca gcaactgggc   6600
ggtggcgctg gggtcggcga gggggcggta agtcacgcct tttttcgcca gggtctgggt   6660
gcagcggggc accagggcaa tgccctggcc ggcggcgacc agggcgatga tcgaggtgat   6720
ctgccggccg ctggggcccg ggcgcaatgg caggccgttg cgtcggtaga gttgttcgat   6780
```

```
ggcttcgttg agccccgagc cgtagtcggc gggaaacagg atcagcggat gctcgctaag   6840
ctcggccaga gtcacttgcg cctgcgcggc cagggggctg tcgctggaga tcgccgccac   6900
cagcggttcg tcccccaggg acagggactg gatatcgctc tgctcgctcg gcggttgcat   6960
gcggctcatg ccgatgtcga tgcgcccgtc gacaatctgc gaccactggc tgaccgaagc   7020
accttccacc agggtcaatt gcacgtccgg gaagcgctgg gcgaaggcct ggatcgcctg   7080
gctgaacagg tccgagaggg cgatggaact ggcgtagccc agggccagtt gcccggcgca   7140
acctgcagcc agcttgccgg ccatgacctg ggccaggtcc acctgttcca gcacggcccg   7200
ggcgtacggc aggaaatgcc ggccctgggc agtgagggtc acggtgcggc tggtgcggtc   7260
gaacaggcga aaccccagtt cggtttccag ggccgaaatc tgccgggtca gcggcggttg   7320
cgccaggtgc aggcgcaggg cggcgcgacc aaaatgcagc tcttcggcga ccgtcagaaa   7380
ataacgcaac ttgcgtagat cgagcatcct gttccctggg tattgatcgg tcggaattcg   7440
gtattggtct tggcttggcg acgtatttta taaaggcctt tggtcataaa acgagaggtt   7500
tcatgaattc gcgtcagcat tgtgcgcgca tcgccctgtt tctgtgtggt tgtgcggcat   7560
ttctcaacct gtatgcgacc cagggcattc tccaggaatt tgcccagagc tttcaggtga   7620
gcatccggga agccggctgg agcatcaccg tcaccaccct ggcggttgcc ctcactgcgc   7680
cctttgtcag ccgctttacc gggcgtttcg atcagcgccg ggtgattgtg gtggccgcgc   7740
tgttgctggc ggtgccggcg gggctggcgg cctatgccgg cagctttacc caactgctgg   7800
tctggcgcct ggtggagggc atgctgatcc cggtggtgtt cgccaccagc gtggcctata   7860
tcggcgaccg ctggagcggc ggcaccgtga ccgaagtcac cagtctgtat gtcgccggca   7920
ccgtgctggg cggctttgcc gggcgttttg tcaccggttt catgaccgaa tacgtgggct   7980
ggcgcgaagc ctttgccttg ctcgcgggcc tgagcctgct gatcggggtg gccattcatt   8040
tgctgctgcc ggccaacccg cccctgaccg cgcccccgggc atccggcggc ctcagtgccc   8100
tgcgcgagct gtgccggcgg cccttgctgg cagcctacgg cgtgggcttc tgcgtgctgt   8160
tctcgcaagt ggccaccttt acctacgccg ggctctatct gagccaggcg ccgttcgacc   8220
tgggggctgc tgccctgggc gcgatctaca gcgtgttcct gctggccctg gtggtgatcc   8280
ccatcgccgg gcgcctgagc aagtcgcggc cccaggccga gctgctggtg gccgcggcgt   8340
tgctcggggt ctgcggttcg gccctgaccc tgctgccgtc gctgtggctg atcgtgctgg   8400
gcctggccct gagttccacc ggagtgttcc tggcccaggc cgccgccaac tcctttacca   8460
ccgccaccgc ccgccacaac aaggccggcg ccgtgggcct gtacctgacc tgctactacc   8520
tgggcggcag ttttggcgcc gtggtcccgg ccctgctctg gagccactgg ggctggcagg   8580
gctgcgtggc gctgatcgtg ctgttccaac tgctgtcgct gctgattgcc tggggcggct   8640
ggaagcccct cgaaccccaa accccggtcg cggctcgcga accgtccaac ccgatagatt   8700
catcatccaa caaggaatac gtgaggtgac catgaataac gtactgaccc ggcagagcca   8760
gttgctgaag attgtcgaac ctgtgttgaa cgacatgccg gccagtgtct tgaagcatgc   8820
gctgttcgag gcgttctgga gcgaagaggg cgccctggtg gacatcgagc atgccttcga   8880
gaagctcacc tcccgtcgcc acgagccggc ggtgctgcgc aagttcttcg ccagctggtc   8940
gaagaccaac aactccgcca ccagtgtgtc cgggctggcc aaccgcatca ccttgctggc   9000
ccgctccggg cagggctcgg aagccgccga cggcctgtac cgggcctgcg gcagcctgca   9060
gcggatcacc gatgaagacc tgggcgccct gggcaatacc ctgcattcgg acctgttcta   9120
```

-continued

```
caacatggcc acgccgatct gcggcgatga ccagtggctg ctcaaggaaa actgcctgcc    9180
ctcggcccag ggcttcaagg actggacgga ttttcgccgc ctgcgtgacc gcgacctgct    9240
gcagggcctg ctgaccaccc tgatccacga ggtctacacc cacggcgaag tggagtttat    9300
ccacccgctg tacaagcagt ggttcgtccg cgacatgggg gtgccggcag agaaggcgcg    9360
caccaccgtg gcctgggtca cggtgcacac cggcggcacc gagagcaatc acttcgccca    9420
tgcggtggcg gcggtcaacg agttcgtcga tgccatgcag gtgcgggtcg acccgcaggc    9480
cgcgcgggaa atcttcgccg aatacctgca gcgcaaggct cgggtaatgc gcgactgtgc    9540
ccagctgttg cgttgatggc tccggcccgg ccccggcaac ggggcttgtg gctgacccag    9600
gctcgcctat cctgttgctg attgaccctt ccttttcatt ttgcagcctg cctcgacaat    9660
gaatgacctg aaacatcacg cctcccccgga ggcattgccg gcgtccgatg tgtcggtgcg    9720
ccgccgttcc ctggtggccg gttgcggcgc ccacgcggtg catgacggcc tgactgacgt    9780
gatctatgta ctgctgccga tctggcaggc gcagttcgcc atgagctacg cccagatcgg    9840
cctgctgcgc ggcgcctatt ccgggatgat ggccggcttc cagttgctgg ccagccgtgg    9900
agccaagcgc tggggacgcg agcgcctgct ggtgggtggc actgccctgg ccgggctggc    9960
ctacctgctg gcggggcagg ccgggggggct gggggtgttg ctcctggcgc tgctgctggg   10020
cggcctgggg gccagtaccc agcacccgct ggcgtcctcg atcatcaccg acacccacga   10080
ggctggcggc ggggtcaagg aagcgctgtc ccagtacaac ttcgccgggg acatcggcaa   10140
gaccctgatt cccgggttgg tggggctgct gctgaccgtg atcagctggc gtgccagcgt   10200
gaccctgatc ggcctcctgg ggctggccgc tgcgctggcg ctgtggtggc tgatcccgtc   10260
ccgggcggcg accctggcca tgcaggaaaa ggcgccgaag acggtcaagg gccagggctc   10320
ggtcggcggc ctgcgggcac tgatcctcac cggcaccctg gacagtgcgg tacgcatggg   10380
tttcctgacc ttcctgccgt tcctgctcaa ggccaagggc gccggcaccg ccggtatcgg   10440
cctggccctg accctgctgt tcgtcggtgg cgctttcggc aagctgctgt gcggttacct   10500
cggggcgcgt atcggcatga tgaagaccgt gtggatcacc gagttcacca ccgccagcct   10560
gatcgtgctg gcggtgttcc tgccctatgt ggggttgatg gtgatgctgc cgctgctggg   10620
gctggcgctg aacggcacct cgtcggtgct ctatggcgcg gtgccggacc tggcgggggc   10680
gggcaagcgc gagcaggcgt tctcgctgtt ctacaccggc accatcggcg gcggggcact   10740
ggcgccggtg ctgttcggca gcctcggcga cgtcaccggg attcccctgg cggtgatggc   10800
cctggccgcg accctgctgc tgaccctgcc gctgtcctgg tacgtgcagc gtggcctgga   10860
cgccgacgcc cggtccttgc ccagccccgg ctgaggtccc gccaatgcat tgaaagcgca   10920
ggcccggagc gggattgtcc gggcctgctg cttgctggtg gagcgctagc cgcgcaggcg   10980
ccattcgggc cccgcggcag gggccggcag cggcgctgcc agggtcctgg ccagttcgac   11040
gaagcgctcc aggcagcgcg accccagggg cgtgcgccaa ctgaccgtct gttccagcac   11100
atagggctcg gccagcggca catagaccac cccgggacgc tgcagggtcg cggtgtagtc   11160
gggcaccacg gccaccccgc gctccgccgc caccagggac accagggtgg tcatctgtga   11220
cgccgtgggc cccaggcgcg ggatgatccc gctgtgggcg cagaggtcct ccagggcggt   11280
gttcagggcc gatccgtagg cgctcggaaa ggtcacgaag gattccccccg ccagttcgca   11340
aaaccccagg ctgctcctgc cggcgaaagc gctgcgcgac ggtaccgcca ccaccaggga   11400
atcgcgcgaa ctcaccagcg actgcaaacc gtgggccggc aagttgggcg ccccccagcc   11460
aaagccgata tccaggctgc catcgatcaa ctgctggcgc tggctggcgg tggacacctc   11520
```

```
gcgaaacgcc agctccacct ccggcaggct gcggctggtg ttgcggatca tctcggagaa  11580
agcgttggac aggggaatcg agctggcata gccgatgacg atacggccga tggcgccatg  11640
ggcgatcttg cgcgcggtgg cctcggcctc gccgacggca ctgatcaccc cccgggcctg  11700
ctgcaggaac agttcgccct ccggggtcag gcacacggtg cgggtcgagc gttcgaacag  11760
gcggatgccc aggcgcgcct ccagggcggc gatatgccgg gttagcggcg gttgggcgat  11820
ccgcaggcgc agggcggcgc ggccgaagtg caattcatcg gcaacggtga cgaaataacg  11880
cagacgacgg agctctagca tttcttgttt ttccagtatc aatcacgacg caaacagtat  11940
tggccgctat ttgcgactgt catcagaatg taagacgacc agcctagacc agctttccag  12000
gttgccggag gcgcatgggt acaggctcgg ttcactctgt tttccgattg ttttcgcagg  12060
tacaaaaatg acaagcagcg aagccacggc cgtccgtttt tccttgtccc agcgtgcgct  12120
gggcctcagt gccccaggca cctcgagcat gcgcagcaaa gccaacgccc tgaaggaaag  12180
cgggatcaag gtgatcaatt tcgccgccgg cgaattgtcc ttcgatgcct gcgaggacat  12240
gcgtgccggg gccatcgaag ccatcgctaa tgcgcgcaac cgctacaccc cgcccatcgg  12300
cctgccggcc ctgcgcgaga agctcgcgca acgggtcagc cagcgcaccg gggtggagtt  12360
cgccgccaat gaagtggcgg tcaccgccgg ggccaagcag gcgctctaca acgcctgcat  12420
ggtgctgctc aaccccgggg acgaggtgat agtgccgacc ccgtactggg aaacctttcc  12480
cacccagatc cgcctggccg gcgccacccc ggtgtgcgtc cagacccgcg ccgaccacta  12540
ccggctgacg gtggacgcgg tgtgtggcgc gctcaccgag cgcacccgga tgatcgtcat  12600
caacaccccc aacaacccca ccggcaccgt ctatgaacgc gagcaactgc tggccatcgc  12660
ccagttggcc caggagcggc aactgtgggt gatgttcgac gagtgctatc gcggcctggt  12720
gcgcgaaggc cacgagcacc acaacatcct ggcgctgtgc ccggcattga aagggcagac  12780
ggtgctgatc gattccttct ccaagagcca ggcggtgacc ggctggcggg tcggctacgc  12840
ctgcgccccg gcgccggtga tcgcggccat gcacaacctg caggggcaca ccacctcaaa  12900
ccccagcagc ctgtcccagt acgccgcgct caataccctg aacgccgatt cgtcgcactt  12960
tgccgacctg gtcaacccgt tcctgcaacg ccagctgcac gccgcacgca cctacctcga  13020
ccgcctggaa ggggtgagct atgcgccgcc ggaaggcgcc ttctacctgt atatcgatgt  13080
ctcttcccgg ctcggcggct actaccaggg cgaagcggtg cgcgatgtgg atcacctggc  13140
cgacctgctg ctgaccgagg cgcacatcgc ggtggtgccc ggttccggtt gtggcgatcc  13200
ccactgcatc cgcatttcct acgccgtgga atatgaggaa ctgatcgaag gcctgggccg  13260
tttcgcccag ttcatctcgg cgatcgtcat cgactgaagc ggctcccggc agcccagccc  13320
ccagggggat caagcccgtt cccgagcccg ccgtggcccg ggccggcgtc gttcatcttg  13380
ttgtccgtga agtgaagaac aattacagga gaaaaacatg gagagttccc gcaaggcgtt  13440
catcggctac gtgcaccagg ccctggtgga tgtcgaggac cgcaacctgg tggaggccct  13500
gctgacgggc tttgaaaacc accccgacaa gctggacggc tactgcctga cctaccagcg  13560
catgacctcg cgcaagtggt ccgaggactc gctgtgcacc tttttctgcg gctggcgcag  13620
cccggatggc gcggctcatg cggtgtccag catcatcgtg cggctgctgc aggagtccga  13680
ggacctgccc ggtgatgaca acaagctcaa gctgctggag gcggcccggc actgcggcga  13740
gatcatcgtc gaggacgtcg gcctgggcga gatgcacggc catccccacc attccaagct  13800
ctaccaccgc atggcctcgg ccatctgcgg ctcggacaac tggcgcctgc aggacaagta  13860
```

-continued

```
cctgaacccc atcaccaagg agttctccac ctgggtcggc gagaagcgcc cgctggcccc  13920
gaacctggtg gaagccctgg agatgatggc cctgaccgag ctgttcaaca ccggcgagta  13980
caacctgatg acaccgctgt ggaagaactg gctgcgcgaa tcctgcggtt accccgccgg  14040
ggaagccaac cgcatcgccg gcttcctcag cgttcactgc ggcgccgtcg aggcccggca  14100
tttccgccac gccaccgacg ccctgaagct ctacacccag gccaccggcc agcaggtcaa  14160
ctaccggcgc atcgctgcgc tgtccgatga gtacgtgctg cgcgcctgcc agcacctgga  14220
gaagatggcc tccgtactca aggaataagc gcctgccaac caggccgggc agggcgcctg  14280
cccggcaccg caggccggac cctcattcat ttattggaga actacccaca tgcgtcttga  14340
atccgactcg atgggttcca tttcggtacc gtccaacaag tactggggag cccagaccga  14400
acgctccatc cacaacttcc ccattggccg tgcacgcttc cagtgggggg cgccaatgat  14460
ccgcagcatg ggcatcctga agaaggccgc ggccctggcc aacctcaagc tcggcgagct  14520
gccggaagcc attgcgctgc ccatcgtcaa ggcggcggat gaggtgatca gcgggcaact  14580
ggacgagcat ttcccgctgg tggtgttcca gaccggttcc ggcacccagt ccaacatgaa  14640
cgccaacgaa gtgatcgcca accgggccat cgagatgctc ggcggcgagc tgggcagcaa  14700
gaagccgatc caccccaacg accacgtcaa ccgtggccag tcgtccaacg acaccttccc  14760
cacggcgatg tacatggtgg tggtgacgga gatcttcgaa accctgctgc cgggcgtctc  14820
ggtgctgcgc gacacgctgt tcgagaaggc cgagcagtac cgcgatgtgg tcaaggtcgg  14880
acgcacccac ttgcaggacg ccaccccccat caccctgggc caggagatcg gtggctgggt  14940
cgagcagatc gactatgccc tggcggccat ccagcacaac ctcaccggcc tctacgacct  15000
ggccatcggc ggcacggcgg tgggcaccgg gctcaactcc cacccgcagt tcggcgacga  15060
gtgcgcacga atcatcgccg agctcaccgg ctacccgttc aagtcctgcg ccaacaagtt  15120
cttcgccctg tcggcccatg acgcgctgat caacacctcg gcggcgatcc gcaccctggc  15180
catggccctg atgaagatcg ccaacgacgt gcgctggctg gccagcgggc cgcgctgcgg  15240
catcggcgag atcgacattc cagagaacga gccgggctcc tcgatcatgc cgggcaaggt  15300
caacccgacc cagtgcgagg cgctgaccat ggtctgtacc caggtcttcg gcaacgacgc  15360
caccgtggcc ttcgccggca gccagggcaa tttccagctc aacgtctaca agccggtgat  15420
ggtgcacaac gtgctggaaa gcatcacctt gctggccgag tcctgccggg ccttcaacga  15480
ccactgcgcg gtgggcatcg agccgaaccg ggcgcgcatc gaggccaata tcgagaagaa  15540
cctgatgctg gtgaccgccc tcaaccgcca catcggctat gacaaggccg cgatcatcgc  15600
caagaccgcc caccacgagg gcaagtcgct gcgggaagtg gcccagcagc tgggctatgt  15660
ctcggcggcg gatttcgacc gctacgtggt ggccctggac atgacccatc cctgagcgaa  15720
cccggtgttc cccaaccaca agaggcgtgt gaatcccatg caggaagctg atattcgccg  15780
aaccaacctg agccagttgc tgcgccgcaa gcgctgcctt cgcgtgctcg aagcccacag  15840
cccgatctcc gccctgctgg cggagcaatc caggctggag cggggcagcg gaccgagcct  15900
ggtctacgac gccatctggt ccagctccct taccgactcg acccacaagg gcctgccgga  15960
catcgagatc ctctcgccga gcaaccgctt gcacggcatc cgcgagatct tcgatgtgtg  16020
ttcgttgccg atgattttcg acggcgatac cggaggcaag gccgagcact tcgccatcca  16080
cgtgaagatg ctggaccggg ccggggtctc ggcggtggtg atcgaggaca agtgcgggct  16140
gaagaagaac tcgctgttcg gcaacgcggt gagccagctc caggactcca tcgaggagtt  16200
ctgcgaaaag atccgcgtgg gctgcgccaa ccgcagccac gaggatctgc tgatcatcgc  16260
```

```
ccgttgtgaa agcctgatcc tcgacaaggg catggacgat gccatcgagc gctgcctggc  16320
ctatgtcgcg gccggcgccg acgggatcat gatccacagc cgcaagaagg acggcctgga  16380
gatcctcgag ttcgcccggt tgttccgccg ccactgcccg cgggtgccgc tgatctgtgt  16440
gcccaccagc tacgctcact tgagtttcga cgagctggag gggccggct tcaacgcggt  16500
gatctacgcc aaccacatgc tgcgcagtgc ctacatggcc atgcgtgatg tggcggtggg  16560
gattctcgag catggccgga ccctggaggt ggagccgcgg tgcctgggca tcgacgagat  16620
cctcgacctg gtgccgggca cccgttaggc actcgcggcc aacccccttc gcagggccgt  16680
ggaacgggcg tgctttatcc gattccactc cgagattcgg aacgttctga attcagaatt  16740
ttcctacaga cgctgtgggg ggcgctgtct agactcgctc cccgttcgcc cggccagcta  16800
ccacaggcaa cacgctgaat ggcggtggtt ggtcagggcg ggctgcaaca cggctgtacc  16860
tgcctgcccg gtccatgttt cgcctactgc ccaggctgac cgggttggtt ctacagcgtg  16920
gggcactcat ggccccggtc cccgcatccc cccaacctct catcgcccca gcccccctgat  16980
acccggccat cgccagtggc tcagggcaag gtctgggcgc gggccaggct cggtgcctgc  17040
gcgccatcct cccaggcacc acccagggcc cggaacagat ttacctcggc cagcaactgc  17100
gccaggcggt cgttgatcag cccttgctgg gcgctgaaca gcgagcgctg ggcgtcgagg  17160
aacaccaggt tgctgtcgac gccgatgcgg tagcggtgct cggccaggtt gtagtagtcc  17220
tggctggcct gcaccaggct gtgctgggca ctcagttgct gctggaaggt ctggcgcgcg  17280
gccaggccgt cggcgacttc ctggaaggcg gtctggatgg ccttttcata ctgggcgacg  17340
ctgatgtcct tctgcagccg ggcgtaatcc aggctggccc gcaggctgcc ggcattgaag  17400
atcggcaggt tgatctgcgg ctggaaggtc caggccccgg caccaccctt gaacagcccg  17460
gacagctcct tgctggcgct gccggcgttg gcggtcaggc tgacgctggg gaagaacgct  17520
gcacgggccg cgcctatatt ggcgttggcg gcctgcaact ggtactcggc ctggagaatg  17580
tccgggcgcc gctgcagcag gtccgagggc aggcccgcgg gcacctgggc cagcatgccc  17640
tcggccagcc cgcgccgggg cagggcgtcg ggcagcggcg cccccaccag cagcgtcagg  17700
ttgttcaggt cctgggccac ctggcgctgg tagcgggcca ggctggcgcg ggcactgtcg  17760
acgctggtgc gggcctgggc cacatccagg gccgagatct tgccggcgct gccattgcgg  17820
gcggtcaggc gcaggctctg ttcgtccgcg gccagggtct tgcgggtcag ctccagcaac  17880
tcctggtcgg cacaccagct caggtaggcc gtggcgacat tggccaccag gctcaactgc  17940
gcgctgcgcc gtgcctcttc gctggacagg taggtcatca gcgcctgctg gctgaggctg  18000
cggatgcgcc cgaagaagtc cagctcatag gcactgatgc ccaggttggc ggagtagctg  18060
gagctgatca gtgccttgct gccggtcatc tgttccggca ggcgctggcg cttgcccgag  18120
acgccggcgc tcaccgccgg gaacaggtcg gcacgctgga tgcggtactg ggcctggtag  18180
gccgcgacat tcagcgccgc cactcgcagg tcgcggttgt tctgcagggc gctgtgaatc  18240
aattgctgca gcaacgggtc ctggaacagt ccctgccagt cggcccccgg gttgccggca  18300
gcgggggcga aggctgcgcc ctgtgggtac tggggcgcca cgggagcggt cgggcgctgg  18360
tagtccgggg ccagggagca gccgccgagg gccagggcca gggccgccag ggtcagtggg  18420
gagttacgca ttgatcagcc tcgtgacaag gacatcctga tggcggacag ccaggggcgt  18480
gcgggcggtt tcaggcgccg accatccact tggccagccc gtgacggccg ctgaccccga  18540
gcttggcggc ggcgcgcttg aggtaggttt ccaccgagct gttcttgacg ctcaggcgct  18600
```

```
gggccatttc cggcacggtg ccgccggtca gcaaccccag gcagacttcc ttttcccgcg  18660
ccgagagggt gatgtcaccc agggacaggc gctcatcgaa ctcccgttgc agcggtgtct  18720
gctgcaaggc atcggcgggc ttggcactcc agctgcgcag gttcttcagg gcctgttgcc  18780
ggtgcagctg ggcgtggcgt tccagcaacg gcagcagggt ctgcgacagg ctcttgagaa  18840
acgacagttc ggacagggaa aagccgccct ggtcgggagc ccggtagagg gcgatgacac  18900
agcggcgatt ggctttgcgc gagaccaggt ggcattggtg cgcggtggtg cgggaagggc  18960
cgctgcgggc ctgggcattc atttgaatca gcagcgagtc gtccatttcc agcatttgct  19020
gcagcagcgg gtcatggcgt cgcggcggct ccggcagtgg caggtccttg tgcagcccgg  19080
cgcgccccag cagggtaatg gccagggggc tggcctgacg ttcgtccagg gtccattcgc  19140
tgagcaccag ttgggtcagt ggcaccagct tgtccaccag ttgcagcatt tcgctggcga  19200
actgcgggtg gccggagctg gaaatcaact gccccagttc gaagtagaag tgcggggttt  19260
ccaggttcgc aatactgctg gtcagactca tatccttatc atccttgatc gagacaaatc  19320
gctgatcgat gcgcgcttgc cgcggcatgc cgtggcagat tcccgatgaa cctgatccag  19380
ttcccgggcg ttgatttaag cctatggctt tgcctggcgt ctgtaggggg aaaccgggac  19440
atcatggccc tgccagggcc tcgccaaggc tctgggtcaa gcccttgcga cggccccgtc  19500
gcgcccgccg gcggggtgtt tcccggcgtc aaggttgccc gaggggcaag cctgcggtgg  19560
aacgcaaaag ccctccgcag gccatgagcg tcgttcacgc gtagccaatt tcctacagcc  19620
gattcagctg atcagcagag ctgctgcaac agcccggcgc ggtgctgccc gaggtggccg  19680
accggggccg gaactgtccg ggtttcgggt gacatacagg ccctggggcc gatgcttaaa  19740
tccgcggacg ccggtgcccg ggcccatcac atgagaagga tcttatgacg catttttccg  19800
ccgcagccgt gggcgctttc gtcgcgccag tcaccccagc cagccactgc ccgccatggg  19860
ccgggcaccc cgcccggggg cgcgcatgaa cgccggtccg gtacaggccc ggggcctgcc  19920
gctgaccgcc gggcagcgcg atatctggct cgaccaactg agccggggcg actcgccgct  19980
gtacaacatc ggcggctatg ccgtgctcaa ggggccgttc cggcccgagc tgatgcagcg  20040
caccgtggag ctgctggtgg acaagcacga cgtgctgcgc acggtgctgt ctctggaggg  20100
cagcgtcgac ggcctgccct tgcagcactt cgaccggcag tggccggtgg agctggtgtt  20160
ccatgacctg tccgcggcgg ccgatccgct ggcggcggcc caggcgcaga tccgccggca  20220
gatgcagcag gcgttcaagc tcgacggcga acggttgtgc cgcttctcgc tgttccgggt  20280
gggccccgag catcacctga tggaagtcga ggcccatcac ctgatcctcg acggctgggg  20340
gttcgcccag ctgtcccagt ccctgggcgg gctctacagc gccctggcca gcggcgagga  20400
gccccaggcc acggcgccgt cctttgtcga cttcatcgag gacgacgccc gctaccacca  20460
gtccagccgc tatgcccggg accgcgacta ctggctggac aagtaccaga gcctgccgga  20520
gccggtgctg cgcccgcgct accggcccgc cgccgacgcc gcgaccccgg gggcgaccct  20580
ggtccaggcg ttccccgcgg ccttgcacga acgcatgaag gccctgggca agagcaccgg  20640
ggcctcggcc tttcatgtgc tgctggcggc gctgcatgtg tacttcaccc gcaccctgca  20700
acgggacgaa tgggtcctgg gcatgccagt gctgaaccgc cccaatgcgg ccttcaaggt  20760
gaccctgggt tccttcaccc aagtcagcgc ggtgcgcatg gacttcggcc gcgaactgag  20820
cttcgaggcc ctggtggggg cggtgcgcga tgtactgaaa caggacttcc gccaccagcg  20880
ctttcccctg agcgaactca accgcgccct cggcctgctg cgcgaagacc gcgcgcagct  20940
gttcgagctg tcgctgtcct acgaattgga agacctggac taccgctacg gcgaggcggc  21000
```

```
ggcctcgtcg gtgaaagtct ccaaccgcca cgagcccacg cccctggcca tccacctgcg  21060
cagcaacagc ttcgatgaca gcgcctggat gcactacgtc tacgactcgg cgtatttcca  21120
gcccgaggaa atcgaggccc tggccgcgcg cctgctgcat gtgctggagc aggggctgga  21180
caatgtgcaa ctgccggtgg cccgcttctc cctgctgcct gccgccgagc tgcgccgctt  21240
gcaggcctgg aacgccaacg aacagccagc cgccgccgaa cagcggattc acgcccgggt  21300
cgcggcctgg gcccggcgca cgccccaggc cattgccctg gtcgcccagg gccaggccct  21360
cagctatgaa cagctcgacc gccgggccaa cgccctggcc ctgcacctgc gcgagctggg  21420
agtggggccg gatgcgcggg tggccattgt cgcccggcgc agcccggaaa ccctggtggg  21480
gctgctggcg attctcaagg ccggcgcggg ctatgtgccc ctggacccgg cccatccggc  21540
tgagcgcctg gccttcctgc tgcacgacag cgcaccgcgg gcggtgttga cccagggcgc  21600
cctgcgccag tgcctgccga cgctgaacgt gccgctgatc gacctcgaca acggccagtg  21660
gctggacggc ccgggcgaga ttgccgaggc cgccgggctg accgcggagc acctggccta  21720
cgtgatctac acctccggct ccaccggcca gcccaagggc gtgatggtgg agcaccagag  21780
cctgtcgaac ctggtggact ggcatggccg ggctttcgac ctccaggctg gcagccacac  21840
ctcatgcctt gccggtttcg gcttcgatgc catggcctgg gaagtctggc cggccctgtg  21900
cgccggggcg accctgcacc tggcgccggt cagcgacggc cccgaggagc tggaccgcct  21960
gctggcctgg tggcgcgccc agccgctgga ggtgagcttt ctgccgaccc cggtggccga  22020
gtacgccctc agccagcaac tgggccaccc gaccctgcgc accttgctga tcggcggcga  22080
ccgcctgcgc cagttgcctg ctgaccccgg gtttgccgtg atcaacaatt acggccccac  22140
cgaggccacg gtggtcgcca cttccggtgc catcgaggcc gggcaggccc tgcatatcgg  22200
ccggcccatc gccaataccc ggatctacct gctggatgaa cagcagcaac tgctgcccat  22260
cggcgtgccc ggcgagctct atgtgggcgg tggcggggtg gcccggggtt acctcaaccg  22320
cgatgggatg aatgccggac gcttccttgc ggaccccttc agcgaccgtc ccggcgcgcg  22380
catgtaccgc agcggcgacc tggctcgctg gcgggaggac ggcagcctgg aatacctggg  22440
gcgcaacgac gatcaggtga agatccgcgg cctgcgcatc gagctggggg aaatcgagac  22500
ccgcctgggg gatcacccgg cagtgcgcga ggcgctggtc caggcccggg acggccagtt  22560
gctggcctgg ttcattccgc gccaggcggt cacggccctg caactgcggg aatttctgcg  22620
ccagcagttg ccggagtaca tgttgcccat ggcctacgta ccgctcgacg cctggccgct  22680
gaccggcaac ggcaagctgg accgccgggc gctgccggcg ccggggcccg gggacctgat  22740
cagccgcgcc tacgaggcgc cccagggccc gctggaaatc accctggccg ggctctggag  22800
cgagctgctg caggtggagc aggtgggccg ccacgatcac ttcttcgaac tgggcgggca  22860
ttcgctgctg gccctgcaac tgatccagcg catggcccag gccggcctgc aggccgatgt  22920
gcgggtgctg ttcggccagc cgaccctggc cagtctcgct gcggcggtga gcaccgggca  22980
ggtcgtcgag gtcccggcca accgcgtccc gcccgactgc cagcgcatca ccccggcgat  23040
gctgcccttg gtggagctgg accaggacag catcgaccgg gtggtggcct gcatccccgg  23100
cggcgctgcc aatgtgcagg acatctaccc cctggcgccg ttgcaggagg gcctgctcta  23160
tcaccacatg accgccgccc gcgatcccta ccagcagcac gcgctgttcg ccttcgccgg  23220
gcgcgaggac ctggacgcct tcgccctggc gctgcaggca gtgatcgagc gccacgacat  23280
cctgcgcacc agcctggtct gggacgtgct ggagcagccg ctgcaggtgg tctggcgcca  23340
```

```
ggcccggctg acggtgcaag agtggcaggc cgggcccggc ggccatgtag cggagcgcct  23400
gcgcgagcac ttcgacccgc agcacaaccc gctggatatc cgccaggcgc cgatgctggc  23460
cctggcctgg gccgaggacc gggccaatgg gcgctggatc ggcctgctgc gcttccatca  23520
cctggtcaac gacgccacca gcaccgcggt gctgctggcg gaaatcgccg cccatgtgca  23580
aggccggcaa gccagcctgg cgcctgccta tgcctaccgt gactacgtgg cccgcacgcg  23640
cctggggcag gccgcccaca aggcgttctt cgaggccggc ctgggcacgg tggacgagcc  23700
gaccctggcc ttcgaactgc aggaacggcc cggggaacaa ctggacctgc agcacgccag  23760
cggcctgctg gaagccgagc ttggccagcg cctgcggacc caggtgcgcc agctcggggt  23820
cagcgccgcc agcctgtttc acctggcctg ggccctggta ctggggcgta ccagcggccg  23880
tgaggacgtg ctcttcggca gtgtattgct gggccgcctg caagccggag cgggggccga  23940
ccgggccctg ggcatgttca tcaacacctt gccactgcgc ctggagctgg cggggctgac  24000
ggtggccgag ggctgggcc aggcccagca gcgcctcagt gccttgctcg cccacgagca  24060
ggcgccgctg tccctggccc agcgctgcag cgcggtggcg gcgccgaccc cgctgttcaa  24120
tgccttgctc aactatcgcc acaacctcgg cggcgacctg ttgcagggtt tgcctggggt  24180
cgagttgctg agcagcgaag aggtgctcag ctacccgctg atgctggcgg tggacgacct  24240
ggaaccgggg ttccgcctgg gctgccgggc cccgcggcgg atcggcgcgc aacgcctgct  24300
gggctacctg agcaccgctc tcgaagcgct ggtgctggcc ctggaacagg cgccgcagac  24360
gccgttgcac agcctgtcga tcctgccgcc ggtggagtcg cgctacctgc tgcaaacgct  24420
caatgccacc cgttcgcaat acccgcggga gctgaccctg catgccctgt tcgaagccca  24480
ggtgcggcgc acgcccgagg ccattgcact gcaggccggc gcgcggcaac tgagctaccg  24540
gcagctcaac cagcgcgcca accagctggc ccattacctg cgcgagcagg gtgtggggcc  24600
ggatgtgcga gtcgggctct gcgtgcagcg cagcccggaa ctgctgatcg gcctgttggg  24660
catcctcaag gccggcggtg cctatgtgcc cctggacccg gactacccgc tggagcgcct  24720
gcgctacctg gtgcaggaca gccagccact ggcggtgctg gtgcaccagc cgacccgcga  24780
gctgctgggc ccgctgcccc tgtcgctgat cgacttcgac cgcagtacct gggagcaggc  24840
gccgcagcat gatcccgtgg tggcagggct gacggtttcg cacctggcct acgtgatcta  24900
cacctcgggt tccaccggta cccccaaggg ggtgatggtg gagcaccgcg gcctgggcaa  24960
cctgatgcac tggagttcgc agctgtgtgg cgagcgggcc cggggcaccc tgctgcaaaa  25020
ggcgccgttc agtttcgacg gctcggtctg ggagctgttc tggcccctgg tcacgggcat  25080
gcgcctgttg ctggcgcggc ccgacggcca gcgcgatccg ctgtatctgg cgcaattggt  25140
gcgcgaggag caggtgagca tgatcaagtt cgtgccggcc atgctcctgc aatttctgca  25200
gctggaagag gccggccagt gccacagcct gaccgatgtg ttctgcggtg gcggcgagct  25260
gaccgaggcg attgcccggc tgttccgcca gcgcctgccc ggagcccgtt tgcataatgt  25320
ctacggcccc accgaggcca ccgtggacag cagcgcctgg accctggagc ccggggcagc  25380
ggtgccgccg gtacaactgc cgatcggcaa ggccatcacc aacacccggc tgtatgtgct  25440
ggatgcccat gaccagccgg tgccccaggg cgtcagcggc cagctgcaca ttggcggggt  25500
cggggttgcc cggggttacc tgggcttgcc gcagttgcag gccgagcgct ttatcgacag  25560
cccctttgtc gccggcgacc ggctgtaccg cagcggtgac cgggtgcgct acaacgctga  25620
cggcgacctg gagttcctcg ggcgcaacga cttccaggtc aagctgcggg ggttgcgcct  25680
ggagctgggg gaaatcgagg cgcggctggc cagccacccg gccctgcgcg aggtggcggt  25740
```

```
gctgatgcgt ggcgagcgcc tggtggccta tttcagcctg caccccgggg tggcggcgcc  25800
ggggatcgag gcgctgcggg cccatgtcct ggagcgtctg ccggagtaca tggtgccggc  25860
agcctatgtg caactggcgg cgctgcccct gagcgccaac ggcaagctgg cgcgcgatgc  25920
actgccggag ccgggcctgg aagcggtgct gagccgcgat ttcgagccgc cccaggggcc  25980
gcttgaaacc accctggcgc ggctctgggc cgaggtactg caagtggagc gggtagggcg  26040
ccacgaccac ttcttcgaac tgggcgggca ttccctgctg gcggtcagcc tggtggcgcg  26100
gatgcgccag gaaggcctgc acgccgatgc ccgcctgttg ttcagccagc cgaccctggc  26160
ggcgctggcg gcccataccc tgggccagtt gcagcgcctg gaaatccccg ccaccaccat  26220
cccccagctc aagcgccagc ggcgtctctg aggccgctgc aagtgctttt ccccgcgccg  26280
gccccagggc cggcgcgggc cgtggtgcct cagcgggaca ggccccgcgc catgtcccgg  26340
cttcccatgt cagccccgct gcggcggatg ttttagcgtc tgcgagctac cagcaagcct  26400
ggcgggctca ctgtccctgg tgctttttgc gcaacggcgc gacagccccg cgcggtgcct  26460
ggcagcggcg cttgtcgccc gtccgggcag tggggcgccg gtgaaaggtt gcatctgaaa  26520
caaggacgtt ctcttcaacc gtttccgaat tctcaggcag gttacaagat gcagttcagc  26580
gaattgatgg cagtgctttc gaccctggcg atccgtcttc aacgggaaca ggaggacctg  26640
ctcgtccagg gcgatgacga ggcgctggac gacgggctct gggacagcct ggtgcagcac  26700
aaggcccggc tcctggaact gctcgacggc cagggcggca gctggctgag cccggccttc  26760
aggatcaccc cggacatgct gcccctggtg cagctggacc cgcccgccat cgagcgtatc  26820
gtcgccgcag tgcccggtgg cgccgccaac gtgcaggaca tctacccccct ggcgccgctg  26880
caggagggca tgctctatca ccatttgtcc gccgcccagg gcgacccccta tgtgctgcag  26940
gcgcgcttcg cctttgccag tgccgagcga cggcaagcct tcgccgaagc cttgcaatgg  27000
gtcatcgacc gccacgacat cctgcgtacc gccatcgcct gggaaagcct ggatgagccg  27060
ttgcaggtgg tctggcgcca ggcgccgctg gtgatcgagg ccgtggcgct ggacccggcc  27120
gacggcgatg tgctcggcca gttgcaggcc cgctacgact cccggcactt tcgcctggac  27180
ctgcgtcagg cgccgctgct gcgcctggtg cacgccgagg acccggccaa ccagcgccag  27240
gtggcgctgc tgctgttcca tcacctggcc ctggatcact ccgcgctgga cctggtacgc  27300
caggaaatcc acgcccgcct gcaagggcac agcgagcgcc tgccggcccc ggtaccgttt  27360
cgcaaccatc tggcccaggc cctggcaagc cgcagcgagg cggcccacga acgcttcttt  27420
cgcgagatgc tcggcgatat cgacgagccg accctgccgt gcggcctggg ggatgtgcag  27480
ggcgccgggc gggtgatcga agaggcccgg ctgaccctgg accgcgagct cagccagcgc  27540
ctgcgggccc aggcccggca gctgggggtg agcagcgcca gcctgatgca cctggccctg  27600
gcccggatgc tgggccagtt gtcggggcgc gaagcggtgg tgttcggcac cgtgctgctg  27660
ggccgcatgg aggccggcga aggcggcgag cgggccctgg gcatgttcat caacaccttg  27720
ccgctgcggg tggatgtcgg cgcccagggc gtgcgcgccg gggtcctggc cacccatcag  27780
cggctcagtg ccttgctcgc ccatgagcat gcgtccctgg ccctggccca gcgctgcagc  27840
ggggtcagtg cgccgacgcc gctgttcagc gccatgctca actaccgcca cagccacgcc  27900
gccgatggcg cccaggtgca ggaggtggcc ccgggcatcc aggtgctggg cgccgaagaa  27960
cgcaccaact acccgctgac catcaacatc gatgacctgg gagaggattt ttgcatcacc  28020
gccctggtgg atcggcaact gggcgcagag cgcatcgccg gctacctgct gaccgccctg  28080
```

```
gagagcctgg ccctggcctt gcagagcact ccgcaggcac cgctgtacag cctggagatg  28140
ctcccggcca gcgagcgccg ctacctgttg cagggcctga acacgccgct ggggcactac  28200
ccggacagcc cgctgatcca ccagcaggtg gaagcccagg cccgggtcca gcccgaggcc  28260
ccggcgctgc tgttcggcga gctgcggctg agctacggcg agctcaaccg gcgcgccaac  28320
caggtggccc accgtttgct ggcgctgggc gtacgcccgg accagcgggt ggcgatctgt  28380
gtcgagcgcg gcgtggaaat gatcgtcggc ctgctgggca tcctcaaggc cggcggcgcc  28440
tacgtgccca tcgacccggc ctacccccgc gagcgcatcg cctacaccct gcaggacagc  28500
gacccggtgg cgctgctggt gcaggccggc acccagtccc tggtggccga cctgcgggtg  28560
ccgctgatcg acctcgacag ccgcaccctg gcccatgaag cccaggacga ccccgaagtg  28620
ccggggctga ccccggccca cctggcctat gtgatctaca cctcgggctc caccggcctg  28680
cccaaggggg tgatggtgga gcaccgcaac gtggcccggc tgttcagcgc cacccgcgac  28740
tggttcgact tcaactggcg ggacgtgtgg gcgctgttcc attccttcgc cttcgatttc  28800
tcggtgtggg agatctgggg ggcgctggtg catggcggcc agttgctggt ggtgccccag  28860
gccgtcagcc gttcgccgga tgactgctac cggctgctct gcgaagcccg ggtgagcatc  28920
ctcaaccaga cccccagcgc cttccgttcg ctgatcgcgg cccaggacca gagccccctc  28980
aagcactccc tgcgccaggt gatcttcggc ggcgaggccc tggaaccggg gatgctcaag  29040
ccctggtatg cccacctgga aaacgtcggc acccagctgg tgaacatgta cggcatcacc  29100
gaaaccacgg tgcacgtgac ctatcgcccg ttgcaggcgg cggatgccca gctggtgggc  29160
agcagcccca tcggccggcg cattcccgac ctgcaactgt atgtgctcga tgcccaccgc  29220
gagccgctgc ccagcggcgt ggtgggtgag ttgtatgtgg gcggcgccgg ggttgcccgg  29280
ggctacctca accgcgatca gctgaccgcc gagcgcttta tcgccgaccc cttcagccac  29340
gagccggggg cgcggctgta caagaccggc gacctggcgc gctggcgcag cgacggcagc  29400
ctggagtacc tggggcgcaa cgatgaccag gtgaagatcc gcggctttcg catcgagctg  29460
ggggagatcg aggcccgcct ggcggcctgc gacggcgtgc gcgaagcggt agtgatcgcc  29520
cgggaagaca ccccggggga caagcgcctg gtggcctatg tgatcccccg gccgggggcc  29580
gctgccagcg ctgcgcaact gcgcgagcaa ctgcaacaga gcctggccga gcacatgctg  29640
cccagcgcct ttgtgacgtt gcaggcctgg cccctgaccc ccaatggcaa gctcgaccgc  29700
aaggccctgc cggcgccgga cagccaggcc ctggcccggc gtgaatatgc agcgccccag  29760
ggcgaggtgg aacaggccat cgcgacgatc tggcaagagc tgctgggctt gccgcaggtc  29820
gggcgccagg acaacttctt cgagctgggc gggcactcgc tgctggcggt caagctgatg  29880
gagcgcatgc gccaggtgga cctgtgcgcc gatgtgcggg tgctgttcgg ccagccgacc  29940
ctggccgcgc tggcggcgac cgtgggcggg cagcgcgagg tgcaggtgcc agccaaccgc  30000
atcgccgccg attgccgcca catcaccccg gacctgctgc ccctggcgga cctcgatcag  30060
gccgccatcg accggctgct ggcgcgggtg cccggcggcg ccgccaacgt ccaggacatc  30120
tatgctctgg cgcccttgca ggcggggatc ctctatcacc acctgagcag cgccgagggc  30180
gatccctatg tgctccaggt gcagttcgaa tttgccggcg aagacgccct gcaaaccttc  30240
accctggcct tgcagcaggt catcgcgcgc cacgacatcc tgcgcagcag catggcctgg  30300
gaaggcctgg aacagccggt gcaggtggtc tggcgccagg cgcccctgga cattcaggtg  30360
gtcgagacgg acccggccca gggcccggtg ctggagcagc tgcaggcgcg tttcgacccc  30420
cgtcgctacc gcctggacct gagccgggcg ccgctgctgc aactggcctg cgccgcggac  30480
```

ccggggcagc agcgctggct gggcctgctg ttgttccacc acctggccct ggaccacagc 30540
tccctggagg tgttggtgga ggagatcagc gcggtgctgc agggcgccgc cgcgcagttg 30600
ccggcgccgg caccgtaccg caactatgtg gcccaggcgc gcctgggcca tggcgaggag 30660
cagcaccagg cgttcttccg cgagatgctg gcggacatcg acgagccgac cctagccttc 30720
ggcctgcagg acgtgcagcg cgacggcagc ggcatccggg agcgtcaact gcgcctcgac 30780
ccggcgctgt gccggcgcct gcgagagcag gcgcggcacc tgggagtgag cctggccagc 30840
ctgctgcacc tggcctgggg ccgggtgctg ggcaactgg cgggccgcga tgacgtggtg 30900
ttcggcaccg tgctgctggg aaggatgcag ggcggcgccg gtgccgaccg ggccctgggc 30960
atgttcatca acaccttgcc gttgcgggtc agtgtcgggg agcagggtgt ggccgaggcc 31020
ttgcgcgcca cccacgcccg gctggcccga ttgctgggcc acgagcacgc ctccctggcc 31080
ctggcccagc gctgcagcgg cgtgccggca tcgctgcccc tgttcaactg cctgctcaac 31140
taccgccaca gcgctgccga caccgcgcag caggggccgg cgagctggga ggggatccgc 31200
gtgctcgact cccgggagcg cagcaattac cccctggcgc tgaatatcga cgatgacgcc 31260
cagggcctgc gcctgaccgt gcaggccgtg gcgcaggtgg acggcgatcg ggtctgtggc 31320
tacctgcagt gcgtgctgga acacctcgcc caggccttgg agcagacccc ggccctggcc 31380
ctggagaaca tcccggtact gccggcggcc gagcgccgcc aggtattgct ggagttcaat 31440
gccagcaccc gcgactaccc gcgccagcac accgtgcacc ggctgttcga ggcccaggcc 31500
caggcccacc cgcagcgggt ggcggcggtc gaaggccagg cgcagctcag ctacggcgag 31560
ctcaataccc gggccaacca gttggcccgg cacctgctgg agctcgggct gcagcccggc 31620
gaccgggtgg cgatcctgct gccccggtcc ctggacctgc tggtgagcca actggccgtc 31680
tgcaaatgcg ccgcggccta tgtgcccctg gatatcaacg ccccggccca gcgccaggcc 31740
ttcatggtgg aagacagcgc cagcgtgctg ctgctcagcc gcagcgacca ggtgcttgcg 31800
tgcccggcca gaagggtcga cctggaccgc ctgcaactgg cgccattgcc cgggcacaac 31860
ccggacctgg cgcagtcgtc cgagaccgtg gcctacatca tgtacacctc cggctccacc 31920
ggcgtgccca agggcgtgca ggtgccgcac cgggccatca gccgcctggt gctcaacaac 31980
ggctatgccg atttcaaccc cgaggaccgg gtggcgttcg cctccaaccc ggccttcgac 32040
gccagcacca tggatgtctg gggcgccttg ctcaatggcg gccgggtgct ggtgatcgat 32100
cactacaccc tgctggaacc tgcgcgtttc ggccgggccc tgagcacggc cggggccacg 32160
gtgctgtttg tcaccacggc gctgttcaac cagtacgtgc aactgattcc cgaggccctc 32220
aagggcctgc ggattctcct ctgcggcggc gagcgtgccg acccggcggc ctttcgccgc 32280
ctgctggcgc tggcgccgcg gctgcgcctg gtgcactgct acggccccac cgaaaccacc 32340
acctacgcca ccacccatga agtcaccgcc ctggccgatg acgccgagca cgtgcccatc 32400
ggccggccga tcggcaacac ccgggtgtat gtcctggacg cccagcagcg gccgctgccc 32460
atcggtgccc cgggggagat cgtgatcggc ggcgacggcg tggccctggg ttatctcaac 32520
cgccccgaac tcaacgccga gaaatttatc cgcgaccctt tcagcgaaca gcccggggcc 32580
ttgctgtacc gcaccgggga cattggccgc tggctgggca acggcctgct cgaatgcctg 32640
gggcgcaacg acgatcaggt gaagatccgt ggcctgcgca tcgagctggg ggaaatcgag 32700
gcgcgcctca ctgcctgcgc cggggtcaag gaggccgtgg tcctggcccg ggaagacgag 32760
cccggggaca agcgcctggt ggcctactac accctgcagg cggacgccgc gccgctgccg 32820

```
gccgaagccc tgcgcgcggc cctgcagcag caactgccgg actacatggt gcccctggcc  32880
tacgtgcagt tgcaggcctt gcccctgacc aacaacggca agctggaccg caaggcgctg  32940
ccggcgccgg ccccgtcggc cctgctcagc cgtgaattcg tcgccccccg gggcgaggtg  33000
gaaatcgccc tggcgcggat ctggagcgag ctgctcaagg tggagcaggt ggggcgccac  33060
gaccacttct tcgaactggg cgggcactcg ctgctggcgg tgagcctgat cgagcgcatg  33120
cgccagatcg gcctgagcgc cgatgtgcgg gtgctgttca gccagccgac cctggccgcc  33180
ctggccgatg ccgtgggcag cggccgggaa gtgcaggtgc cggccaacct catcagcgct  33240
gattgcccgc gcatcacccc ggacctgctg cccctggtgg aactggacca ggaggccatc  33300
gatcgggtgc tggccagcgt gccgggcggc gtggccaatg tgcaggacat ctaccccctg  33360
gcgccgttgc aggagggcat tctctatcac cacctgagcg ccgggcaggg cgacccctac  33420
ctgctgcaat cgcgcctggc cttcgacagc ctggagcgcc tgcagcgttt cgccggggcc  33480
ctgcagcagg tcatcacgcg ccatgacatc ctgcgcaccg cggtgctctg ggaaggcctg  33540
ccgcaaccgc tgcaagtggt ctggcgccat gccgagctcc gggtcgagga acagcacctg  33600
gacccggccg agggcgacct gctggcgcag ttgcagcagc gcttcgacgc ccgtcactgg  33660
cgcctggacc tggcccaggc gccgctgatc cgcctggtct atgcgcgaga gcccgggcag  33720
cagcgggtgc cggcgatcct gctgttccac cacctggccc tggatcacac cgccatggag  33780
gtgatcggcg aggaaatgcg cgacctgctg ttcgaccgcg cgcagcacct gggcacaccg  33840
gtgccgtacc gcaactatgt ggcccaggca cgcctgggtg ccgggcaggc ggaacacgag  33900
gcgttctttc gcgacatgct cggggacatc gacgagccga ccctggcctt cggcgtagag  33960
gatgtacagg gtgacggcct gggtatcgaa gaggccgagc tggtgctgcc cgaggccctg  34020
agccggcgcc tgcggcaaca ggcgcggcac ctgggggtga gcgccgcggc cctgatgcac  34080
ctggcctggg gcctggtgct ggggcagttg gccaaccgtc gccaggtggt gttcggcacc  34140
gtgctgatgg gccgcatgca gggcggcgcg ggcgccgacc gcgccctggg ggtgttcatc  34200
aataccctgc cgctgcgggt cgatgtgcag ggcagcgtgc gtgccgcggt caaggccacc  34260
cacgcccggc tcagcgcctt gctcggccat gagcacgcct ccctggccct ggcccagcgc  34320
tgcagcgcgg tggcggccgg cgcgccgctg ttcaacacct tgctcaacta ccgccacagc  34380
gtgccgaaca cggcggcgcc ggacggcctg gatatctggc agggcgtcga actgctgggg  34440
ggcgaggagc gcagcaacta cccgctgagc ctcagcgtcg atgacctggg cgaaggcttc  34500
agcctggcgc tgctggccca ggccggaatc ggtgcgcagc gtgtcggcgc ttatatgcaa  34560
agtgccctgg agcaactggc ccaggccctg gaacacaacc cgcaggcggc cctcgaacag  34620
tgctcggtgc tgccgccaca agagcgcgag caactgctgg agggctgcaa tgccagcacc  34680
gccgactacc cccgcgggca gaccctgcac gggctgttcg aggcgcgagc ggcacaggct  34740
cccgacgccg tggcgctggt gcaggggccg ttgcgcctga gctaccgcca gctcaaccag  34800
caggccaatc agctggcccg gcaactgctg gagttgggcg tgcacccaga cgatcgcgtg  34860
gccctgtgcc tgcaacgcgg gccgcacttg ttgcggggca tgctggcggt cctcaaggcc  34920
ggggcggcct atgtgcccat cgacccgagc ctgccggccg aacgcatcgc ctacctgctg  34980
caggacagcg cgccgctggc ggtgctggta caaagcgcca cccgcgagct gccgggcagc  35040
cttgcggtgg tgtcgatcga tctcgatggg gttgcctggc aggaggccga gctgggcaac  35100
ccgcttctgc cgcacctgac cccggcgcac ctggcctatg tgatctacac ctccggttcc  35160
actggcctgc ccaagggcgt gatggtggag caccagagcc tggaaaacct ggtgcactgg  35220
```

```
cactgcgcga gtttcgacct gggcccgggg cggcacagct ccagcgtcgc cggcctgggc  35280
ttcgacgcca tggcctggga ggtctggccg accctgtgca gcggcgcgac cctgcacctg  35340
ccgcccgccg atgtgggcag ccaggatatc gaagcgctgc tgcactggtg gcgcgcccag  35400
cccctggatg tcagcttcct gccgaccccg gtggccgaat acgccttcag ccaggggctc  35460
ggccacccca cactggacac cttgctgatc ggtggcgacc gcctgcgcca gttcgccgcc  35520
gacccgggtt ttgcagtgat caacaactac ggccccaccg aagccacggt ggtggccagc  35580
tccgggcgga tcgaggccgg tagcgccctg catatcggcc ggcccgtggc caatgcgcgg  35640
ctctacctgc tggacgaact gcagcgcccg gtgccccagg gggtcagtgg cgagctgtat  35700
gtggccggcg ccggggtggc ccggggttac ctcaaccgcc cgcaaatgac cgctgaacgc  35760
tttctcaacg accccttcag cgccgagccc gaggcacgca tgtaccgcac cggtgacctg  35820
gcccgctggc gcgccgacgg caacctcgac tacctggggc gcaacgacga ccaggtgaag  35880
gtgcgcggca tgcgcatcga acctggggaa atcgaggcgg cgctgctcac ccatccggcc  35940
ctcaaggaag ccctggtgct ggtccgcgag gggcgcctgc tggcctattt cacttcccgt  36000
accgagggtg tgcaagccgc cgccgaagac ctgcgcgacc acctgcaagg ccggctgccg  36060
gactacatgc tgccggtggc ctatgtgcgc ctgccggcca tgcccctgac cgccaacggc  36120
aagctcgacc gcaaggccct gccaccgccg ggggaagagg cctggctgaa ccgggaattc  36180
gtggcccccg aaggcgaggt ggaacaggcc ctggcgcgga tctggagcga ggtgctgcag  36240
gtggaggcgg tggggcgcca tgatcacttc ttcgaactgg gcgggcattc gctgctggcg  36300
gtgagcctga tcgaacgcat gcgccagatc ggcctggacg ccgacgtgcg ggtgctgttc  36360
ggccagccga ccctggctgc gctggcggct gcggtgggca gtggccgcga ggtcgcggtc  36420
ccggccaacc ggatcaccgc ggattgcccg cgcatcaccc cggacctgct gccgctggtg  36480
gaactggagc aggaagccat cgaccgagtg gtggccagcg tgcccggcgg cgtggccaac  36540
gtgcaggaca tctacccccct ggcgccgttg caggagggca tcctctatca ccacctgagt  36600
gcccggcagg gcgaccccta cctgctgcaa tcgcagctgg ccttcgccag ccggcaacgc  36660
ctggatgatt tcgccgcagc cctgcagcgg gtggtcgagc gccacgacat cctgcgcacc  36720
gcggtgctct gggaaggcct gaagcagccg ctgcaagtgg tctggcgcca ggcaggtgtg  36780
caggtgcaag aggtgcaagc gaaccccgcc cagggcgagg tcctggagca actgcaggcg  36840
cgcttcgatg cccggcacct gcgcctggac ctgacccggg cgccgctgat gcgcctggtg  36900
tatgcccagg acccggcccg ccagcgcatc gtcgccatcc tgctgttcca tcacatggcc  36960
ctggaccaca ccgccctgga ggtggtacgc gaggaaatcc aggcctgcct gctggggcag  37020
tcgcccgcgg gcacggcgat tccctatcgc aactacgtgg cccaggcgcg cctgggtgtg  37080
agccgtgaag agcacgaggc attctttcgc gagatgctcg gcgatatcga tgagccgacc  37140
ctgccgttcg gcctgcagga cgtgcagggc gatggcgatg ccatcgaaga gcgccagcag  37200
gccctggagc cgtcactgag tgcgcgcctg cggacccagg cccggttgct gggggtgagt  37260
gcggcgagcc tgttccacct ggcctgggcc cgggtcctga gcgtcacctc gggccaggac  37320
cgggtggtgt tcggcaccgt gctgctgggg cgcctgagcg ccgggcaggg cgccgaccgg  37380
gccctgggca tgttcatcaa caccttgccg ctgcgggtcg acctggatgc gcgtggcagc  37440
cgtgccgcgg tcaaggacac ccacgcccgg ctcagtgcct tgctgggtca tgaacacgcc  37500
tccctggccc tggcccagcg ttgcagcggg gtggccgcgc cgctgccgct gttcagtgcc  37560
```

```
atgctcaact accgccacgg cagcgacggg gtgccgagcc aggccgtgca acaggcctgg  37620
cagggcatcg agaccctgca cagcgaggag cgcaccaact accccctgag cctcaacgtc  37680
gacgacctgg gccaggggtt ccgtctcacc gccatgaccc tggcgcggat cggtgccgag  37740
cgtatctgcg gctacatgca gcaggccctg ctggccctgg tggagaacct ggagacggcg  37800
ccgcagcggc ccctgcgcga ggtgccgatc ctgccgccgc aggagcgtca gcacctgctg  37860
caagggttca acgccacggc cgtggattac cccctggagc agaccctgca cgggctgttc  37920
gaggcccagg tacggcgcag ccccgaggcc actgcggtac aggccggcga gcagcagctg  37980
agctacggcg aactcaaccg gcgcgccaac cagctggccg ggcacctgct gcaactgggc  38040
gtcggccccg acagccgggt ggcgatctgt gtcgagcgcg ggctggaaat ggtggtcggc  38100
ctgctggcga tcctcaaggc cggcggcgcc tatgtgccca tcgacccggg ctaccccgcc  38160
gaacgcatcg cctacatgct cgacgacagc gcgcccctgg cggtgctggc ccagggcgcg  38220
acccgggcat tgctcggcga actggcgcgg cccctggtgg acctcgacca gctggcctgg  38280
agcgggccgg cgccgggcaa cccgcaagta gaggggctga ccccggggca cctggcctat  38340
gtgatctaca cctccggttc caccggccag cccaagggcg cgatgaacga gcaccgggcc  38400
gtggtcaacc gcctgttgtg gatgcaggcg cagtaccgcc ttggcaccga ggacgcggtg  38460
ttgcagaaga ccccgttcag tttcgacgtc tcggtctggg agttcttctg gccgctgttc  38520
accggcgcgc gcctggtgat ggcgcgcccc gacgggcaca aggacccggc ctacctgcgc  38580
caggttatcc gcgagcaggg catcagcacc ttgcacttcg tgccctcgat gctcgatgtg  38640
ttcctggccc agggcgaggg cgccgaggac ctgggcctgc gccaggtgat gtgcagcggc  38700
gaggcattgc cgggcagcct ggtgcggcgc ttcaagcagc aactgccaca ggtggcattg  38760
cacaacctct acggccccac ggaggccgcg gtggacgtca ctgcctggga ttgcagcggc  38820
ccgctggccg ataccccgga ccacacgccc atcggcaagc ccatcgccaa tacctgcatc  38880
tacctgctgg acgcgcagat gcagccggtg cccctggggg tggtgggcga gctgtacatc  38940
ggcggggtgc aggtggcccg gggttacctg aaccgcgagc agttgagcgc cgaacgtttc  39000
ctcaaggacc cgttcagcca ggaaccgggg gcgcgcctgt accgcaccgg cgacctcggg  39060
cgctatcagg ccgacggcac tatcgagtac ctggggcgca acgacgacca ggtgaagatc  39120
cgcggcctgc gcatcgaact gggggagatc caggcgcgcc tgacccagct ggaggaggtc  39180
aaggaggcgg tggtactggc ccgcgaggat gtgcccggcg accagcgcct ggtggcctac  39240
tacaccaccc acgatagcgc ccggcgcctg cccgtcgagc acctgcgcac gcaactgctg  39300
cagcacctgc cggagttcat ggtgccggcg ctgttcgtgc acctggcggc gctgcccctg  39360
agcgccaacg gcaagctggc gcgcaaggaa ctgccggccc cggggctgga ggcggcccag  39420
gtgcgcgagt acgaggcccc ggtgggcgac accgaaatcg ccctggcgcg gctgtgggcc  39480
gaactgctca atgtcgagcg ggtggggcgt cacgatcatt tctttgaact gggtgggcac  39540
tcactgctgg cggtcagcct gatcagccgc atgcgtgagc taggcatgga agccgatgtc  39600
cgggcgttgt tcgaacagcc gaccctggcg gcctacgcgg ccatgaccga acgaatggag  39660
atcgtcctgt gagcgtgatc gaactgttgg cgacactgaa ggaaaaggat gtgcaactgg  39720
tgctcaagga cgaccagctg gtggtccagg gcaacaagca ggccctgagc gaaccgcagc  39780
tgctggcccg cttgcgcgag cacaagccgg agctgatcga gctgatccgc gccggccagt  39840
attcgccgag caaggccggg caggtgcagg tgccggccaa tggcatcacc ccgggcatca  39900
gccgcatcac cccggcgatg ctgcccctgg ccaacctcga ccaggaggcc atcgagcgca  39960
```

```
ttgtcgccag cgtcccgggc ggggtcgcca acgtgcagga catctacccc ctggcgcccc  40020
tgcaggaggg cattctctac caccacgtca gtgcgcagca gggcgacccc tatgtgatgc  40080
aggcgcagtt cgccttcgcc agcgaggaac gcctggaagc ctttgccgag gccctgcgcg  40140
gggtcattgc gcggcacgac atcctgcgca ccgcggtgct ctgggatggc ctggagcagc  40200
cgatgcaggt ggtctggcgc gaggccgggc tggagctgca agaggtcgag accgaccctg  40260
cggccggtga ggttctggcc cagttgcatg cgcgtttcga cgcccgccac tatcgcctgg  40320
acgtcagcca ggcgccgctg ctgcgcctgg tgcatgcccg ggatgaagcc gggcagcgca  40380
tcgtcgccat gctgctgttc caccacatgg ccctggacca cagcgccctg gatgtggtgc  40440
gccacgagat gcaggccttc ctcaccgggc aggccgagcg cctggggccg gccatgccgt  40500
ttcgcaacta cgtggcccag gcgcggctgg gcatcagcga acaggagcac gaagcgttct  40560
tccgccagat gctcggcgat atcgacgagc cgaccctgcc ttacggcctg caggatgtgc  40620
agggcgatgg ccgggccatc gaggaatgca cccaggccct gccaaccgag ttgagccagc  40680
gcctgcggac ccgggcccgg ctggccgggg tcagcgcggc cagcctgttc cacctggcct  40740
ggggccgggt gctgggcacc ctggcgggca agcacaaggt ggtgttcggc actgtgctga  40800
tgggccgcct gcaaggcgcc gaagccaccg agcgggccct ggggatcttc atcaacacct  40860
tgccgtttcg cctggatgtg gacagccagg gcctgggcga ggccctcaag gccacccacg  40920
cccggctcac caccttgctg cgccacgaac acgcggccct ggccctggcc cagcgttgca  40980
gcggcgtgag cgcaccgacc ccgctgttca gcgccttgct caactaccgg cacagtgctg  41040
ccggggccag tgccgcggcc caggccgcct gggccgggat cagcaccctg agctccgagg  41100
agcgcaccaa ctacccccctg accctgagcg tcgacgacct cgggcaggat ttcagcctga  41160
ccctgctggc cagcacccag gtcgacccgc ggcgcatcct cggctacctg ctgtgcaccc  41220
tggagaacct ggcccaggcc ctggagcaga cgccgcaact ggccctggag cagttgccga  41280
tcctgccggt ggcggaacgc gagcaggtgc tggaaggctt caaccgcagc gcggtggact  41340
acccccccggg gcaggctatc catggccgca tcgaggccca ggcgcagcgc accccagacg  41400
ccctggcggc ctgctaccag ggccgctcgc tgagctatgc cgagctcaac caacaggcca  41460
atgtcctggc ccggcaactg cgcgggctgg gggtgcagcc cgatgaccgg gtggccatcg  41520
ttgcccggcg cagcctggaa acggtggtgg gcctattggc gattctcaag gccggggcct  41580
gctatgtgcc catcgacccg gcccacccgg ccgagcgtct gaactacctg ctccaggact  41640
gcggcccgcg ggcggtgctg acccaggccg agctgctggg acgcctgccg gccctggcgg  41700
tgccggtgat cgaactcaac cagcggttgt ggctcgatca gacggcggac aatacccagg  41760
taccggggct gagcgcggcc aacctggcct atgtgatcta cacctccggc tccaccggcc  41820
tgcccaaggg ggtgatggtg gagcaccgga ccctgggcaa cctggtggac tggcactgcc  41880
aggccttcga cctgcgtccc ggcagccagg cctcgtgcct ggccggcttc ggtttcgatg  41940
ccatggcctg ggaggtctgg ccggcgctgt gtgtgggcgc gaccctgcac ctggcaccgg  42000
cccaggacgg cagcgaggac ctggatgcct tgctcgcctg gtggcgtgcc cagcccctgg  42060
acgtgagctt cctgccgacc ccggtggccg agtacgcctt cagccaggag cagggccacc  42120
cgagcctgcg caccctgctg atcggcggcg accgcctgcg ccagttcagc cacgaccagg  42180
gctttgccct gatcaacaac tacggcccca ccgaagccac ggtggtggcc agttccgggc  42240
cgatccacgc cggtggcgag ctggacatcg gccggccggt ggccaacgcg cgcatttacc  42300
```

```
tgctggattc ccagcagcgc ccggtgccca tcggcgtcgc cggtgagctg tatgtgggcg  42360
gcgccggggt ggcccggggg tacctcaacc gcccgcaatt gaccgccgaa cgctttctcg  42420
acgatccctt cagcgaccag cctgaggcgc gcatgtaccg cagcggcgac ctggcgcgct  42480
ggctggcgga cggacgcatc gactacctgg ggcgcaacga cgatcaggtg aagatccgcg  42540
gcgtgcgcat cgagctgggg gaaatcgaga cccgcctctg ccagttcccc ggtatccagg  42600
aagccgtgct gctggcccgc gaggatcagc cgggcaaccc gcggctggtg gcctatttca  42660
cccagcagca ggacgtcgcc ctggacgtgg cgcagttgcg cgcccacctg ctggcgcagt  42720
tgcctgacta catggtgccg gtggcttatg tacggctcga cgccttgccc ctgaccgcca  42780
acggcaagct cgaccgcaag gccctgccgg cgccggatca ggcggcgctg tttggccgtg  42840
aataccaggc cccgcaaggc gccaccgaaa ccaccctggc cgcgatttgg caggaggtgc  42900
tgcacctgcc gcgggtcggg cgccaggatc actttttcga gctgggcggc cattcgctgc  42960
tggccatgcg catggtgtcc caggtacgcc agcgcctggg ggtggaactg gccctgggcg  43020
agctgttcgc caatgccgag ctgagcgcgg tggccgcggt gctggagcgt gccgggcgca  43080
gccatctgcc ggagatcttc ccggcggtgc aggatcacga cctgccgctg tccttcgccc  43140
agcagcgcct gtggttcctg gcgcagatgg acggtgccgc cagcgcctac aacattccca  43200
tcggcctggg cctgcgcggg cagctcgatc gctcggcgct gcgccaggcg ctgcaggcca  43260
tcgtcagccg ccacgccacc ttgcgcagcc gtttcgtgcg cgtcgaggac cagccccagg  43320
tgctgatcgg gcccctggac agcgctctgg acctgcacga ggaagacctg cgccaggcgc  43380
cgctgaccct ggccgggcgg gtgcgtgccg aagccgccca ggccttcgac ctggagcagg  43440
ggccggtgat ccgcgcgcgc ctgctggccc tggcggacga tcaccatgtg ctgctcctga  43500
ccctgcacca catcgttgcc gatggttggt ccatgggcgt gctgacccgg gagctggtgg  43560
ccctgtacca ggccttcagc cagggccggc ccgatccctt ggctccgctg gcggtgcagt  43620
acagcgactt tgccctgtgg caacggcgct ggctcagcgg cgaggtgctg cagcagcaga  43680
gcgactactg gcgccaggcc ctggccggcg cgcccagcct gctgatgctg cccaccgacc  43740
ggccgcggcc gcagcagcag gatttcagcg gtggcagcat cgagctgctg ctggaccggg  43800
ccctgagcga ccagctcaag gccctgagcc agcgccatgg ctgcaccctc tacatgaccc  43860
tgctggccgg ctgggggctg ctgctgagcc gcctttcggg gcaggacgat ctgctgatcg  43920
gcagcccggt ggccaaccgc atgcgcgccg aggtggaagg gctgatcggg ctcttcgtca  43980
acaccctggc cctgcgcctg gacctggacc cggggcagag cgtgagcggg ctgctggccc  44040
aggtccgcgc ccgcagcctg gaggcccagg ggcaccagga cctgccgttc gagcaggtgg  44100
tggaaatcgt ccggccccag cgcagcctgt cccatagccc gctgttccag gtggtgctga  44160
cctgggtcga caacttcgcc caggacctgc aactggggga cctgaaactc gaaggtgtgg  44220
ccggggccag cgcggtggcc aagttcgacc tgaccctgag cctgggagaa agccaggggc  44280
agatccgcgg aaccctggac tacgccaccg cgctgttcga tgaggccacg gtgcagcgct  44340
atgccgccta cctggtgcag gtgctgcggg ccatggtggc cgacgatcag caatgcctgg  44400
cccaggtgca gtggctggat gagaccgagc gccggcaact gctggaggat ttcaacgcca  44460
gcgccgtgga ctacccacgg ggccggaccc tggcccagcg cttcgaggcc tttgccgctc  44520
ggcagcccga ggccacggcc ctgcaggtgg gcgcgcagcg cctgagctat ggccagttga  44580
atgcccgggc caaccaactg gcctggcact tgcgggagct gggggtgggc ccggatcagc  44640
gggtggcgat ctgcgtcgag cgcgggccgg ggatggtgat cggcctgctg gggattctca  44700
```

```
aggccggtgg cgcctatgtg cccatcgacc cgggtcaccc cgcggaacgc atcgcctacc  44760
tgctgcagga cagcgcgccg ctggcgctgc tggtgcaggg cagcacccgg gccctggtgg  44820
gccaaccggc catggcccgg gtggacctcg accagcccga gtggcaggcc cgccccgagg  44880
gcaacctgca ggtgccgggc atgagctgcg cgcacctggc ctatgtgatc tacacctccg  44940
gttccaccgg cctgcccaag ggcgtgatgg tggagcatgc cagcctggaa aacctgctgg  45000
actggcattg ccaggccttc gacctggggc cggggcgaca tgcctccagc gtcgccggtt  45060
tcggcttcga cgccatggcc tgggaactct ggccgacgct ctgcggcggc gccaccctgc  45120
acctgccgcc ggccggtatc ggccaccagg acctcgacca actgctgcac tggtggcagg  45180
cccagcccct ggacctgagc tttctgccga ccccggtggc cgaatacgcc ttcagccagg  45240
gcctgggcca cccgaccttg cgcaccctgc tgatcggcgg cgaccgcctg cgccagttca  45300
gccaggagcc gagctttgcc gtggtcaaca actacggccc caccgaaacc acggtggtgg  45360
ccagctccgg gcggctgctg gccggcgggc ccctggacat cggccggccc atcgccaatg  45420
cacggatcta cctgctggac ccgcagcagc ggccggtgcc catcggcgtc gccggtgagc  45480
tgtatgtggg cggcgccggg gtggcccggg gttacctcaa ccgcccggag ctgacggccg  45540
aacgcttcct tgaagacccc ttcagcaccg tgccgggcgc acgcatgtac cgcagcggcg  45600
acctggcgcg ctggcgggcg gacgggcgca tcgactacct ggggcgcaac gacgaccagg  45660
tgaaggtgcg tggcgtgcgc atcgagctgg gggagatcga gacctgcctc aaccgccttc  45720
cgggcatccg cgaggcggtg ctgctggccc gggaagacca gccggggcag acccggctgg  45780
tggcctattt cagtgcaacc cccggcgccg agccgagccc ggccgagctg cgcaggcgcc  45840
tgctggagca actgccggag tacatggtgc cggcggccta tgtgcacctc gctgccttgc  45900
ccctgaccgc caacggcaag ctcgaccgcc gggcgttgcc gcaaccgccg ctggaggcgc  45960
tgctgagccg ggactatgtg gcccccgagg gcgacagcga gatcgccctg gcgcagatct  46020
ggagcgagct gctgcaggtc gagcgggtag ggcgccacga tcacttcttc gaactgggcg  46080
gccattcgct gctggccatg cgcatgctgt cccaggtgcg gcagcgcctg gggtggagc   46140
tggccctggg cgagctgttc gccaatgccg aactgtgcgc cgtggccgcg gccctggccc  46200
gggccgagcg cagcagcctg ccggacctgc tgccggcgcc gcgcaaccag ccgctggcgc  46260
tgtccttcgc ccagcagcgc ctgtggttcc tggcgcagat ggaaggggcc aacaccgcct  46320
acaacattcc catcggcctg cgcctgcgcg ggccactgga cggcgcggcc ctgcagcagg  46380
ccctggagcg catcgtcgcg cgccatgaaa ccctgcgcag ccgctttgcc cagtacggtg  46440
acgaagccca ggtgctgatc gccccggccg aatccgggct ggagctgctg ctggaaaacc  46500
tgcggggcca cccccaggcc agcgacgcct tgcaggccct ggtgcagggc gaggcctcgg  46560
cgccgttcga cctgcaacgc gggccgctga tccgcgggcg cctggtcagc ctggcggacg  46620
accaccatgt gctgttgctg accctgcacc atatcgtcag cgacggctgg tccatgggcg  46680
tgctgacccg ggaactggtg gcgctgtacc aggccttcag tcgtggcctg cccgaccccc  46740
tggcgccgct ggcggtgcag tacagcgact ttgcccactg gcagcggcac tggctcagtg  46800
gcgcggtgct ggagcagcag gcgcagtact ggcgccaggc cctggagggg gcgccgccgt  46860
tgctcatgct gcccaccgac cggccacggc cggcccagca ggactacgcc ggcagcagcg  46920
tcgaggtgcg cctggatgcg caattgaccg ccggcctgcg ggccctgagc cagcgccatg  46980
gcaccacctt gtacatgacc ctgatgggcg cctgggcgct gctgctgggg cggctctcgg  47040
```

```
ggcagtccga ggtggtgatc ggcaccccgg tggccaaccg catgcgcgcc gaggtggaag  47100
ggttgatcgg gctgttcgtc aacaccctgg ccctgcgcct ggacctggag gcggcgcccc  47160
gggtccaggc gctgctggcc caggtccgcg cccgcaccct ggaggcccag gctcaccagc  47220
acctgccgtt cgagcaggtg gtggagatcc tgcggccgtt gcgcagcctg tcccacagcc  47280
cgctgttcca gaccctgttc acctggcaga acggcgacgg cccgcagctg gagctggggg  47340
acctgcaact ggagggcatc cacgaggcca gccacttcgc caagttcgac ctgtccctga  47400
gcctggggga ggtgcaggac cgcatcgaag gcagcctgga atacgccacg gcgctgttcg  47460
atgaaaccac catgctgcgg tatgccggct acctgcagcg ggtgctgcag gccatggtgg  47520
ccgatgaaca gatgctgctg gcacaggtgc cgctgctgga tgccgccgag cgcgaacagc  47580
tgctgcacgg cttcaatgcc accgcccgcg actacccccct ggaacagacc ctgcacgggc  47640
tgttcgagac ccaggtgctg cgcagccccg aggccatcgc cgtgcaggcc ggcgagcagc  47700
agctgagcta ccgcgagctc aaccagcagg ccaaccagct ggccgggcac ctgctgcacc  47760
tgggcgtcgg ccccgacagc cgggtggcga tctgcgtcga gcgcgggctg cccatggtgg  47820
tgggcctgct gggcatcctc aaggccggcg gcgcctacgt gcccatcgac ccgggctacc  47880
ccgccgaacg cattgcctac atgctcgacg acagcgcgcc ccaggcgctg ctggccgata  47940
gcgcgacccg gccgctgctg ggcaacctgg cgctgcccct ggtggatctc gaccagccgc  48000
aatggcaccg ccagccccgg gtcaacccgc ggctcaacgg cctgaccccg agccacctgg  48060
cctatgtgat ctacacctcc ggttccaccg gccggcccaa gggcgcgatg aacgagcacc  48120
gggccgtggt caaccgcctg ctgtggatgc aggagcagta ccgtctcact gccgaggacg  48180
cggtattgca gaagaccccg ttcagtttcg acgtctcggt ctgggagttc ttctggccgt  48240
tgttcaccgg cgcacggctg gtgatggcgc gccccgatgg gcacaaggac ccggcctacc  48300
tgcgccaggt gatccgtgat gaacgcatca gcaccttgca cttcgtgccc tcgatgctcg  48360
atgtattcct ggcctatggc gacacccgcg aatgcgccgg cctgcgccag gtgatgtgca  48420
gcggcgaggc gctgccgggc agcctggtgc ggcgcttcaa gcagcagttg ccgcaggtgg  48480
cgctgcacaa cctctacggc cccacggaag cggcggtgga cgtcaccgcc tgggattgcg  48540
ccggcccgct ggcacagacc ccggacaaca cccccatcgg caagcccatc gccaataccc  48600
gcatctacct gctggacgcg cagatgcagc cggtgccccg gggcgtggtg ggcgagctgt  48660
acatcggtgg ggtgcaggtg gcccggggtt acctgaaccg cgaacaactg agcgccgaac  48720
gcttcctcaa ggacccgttc agccaggaac cgggcgcgcg cctgtaccgc accggcgacc  48780
tggcccgcta cctggccgac ggcactatcg agtacctggg gcgcaacgac gaccaggtga  48840
agatccgtgg cctgcgcatc gagctggggg aaatccaggc gcgcctgacc cagctcgaag  48900
gggtcaagga agcggtggtg ctggcccggg aagatgtgcc gggcgaccag cgcctggtgg  48960
cctactacac caccgttgcc gggcagccgg ccctggcggt ggaacaactg cgccgggcgc  49020
tgctggaaca cttgccggag ttcatggtgc cggcgctgtt catgcacctg gcggcgctgc  49080
ccctgagccc caatggcaag ctggaacgca aggccctgcc ggccccgggg ctggaggcgg  49140
cccaggtgcg cgaatacgag gccccggtgg gcgacaccga gatcctcctg gcgcaactct  49200
gggccgaact gctcaaggtc gagcgggtgg ggcgccacga ccacttcttc gagctgggcg  49260
gccattcgct gctggcggtg agcctgatcg gccgcatgcg ccgggccggg ctctcggcgg  49320
atgtgcgggt gctgttcggc cagccgaccc tggcggccct ggccgctgcc gtgggccgcg  49380
gtcgcgaggt gcaggtaccg gccaacctga tctaccgcga ctgcccgcgc atcaccccgg  49440
```

```
acctgctgcc gctgctggca ctggaccagg ccgccatcga ccgggtggtg gccacggtgc  49500
cgggcggtac cgccaatgtg caggacatct acccactggc gccgttgcag gccggcatcc  49560
tgttccacca tctggcggct ggagcgggtg accccctacgt gttgcaggcg cagttcgcct  49620
ttgccagcac cgagcgcctg caggccttcg cccaggcctt gcaggggggtg atcgaacgca  49680
atgacatcct gcgcagcgcg gtgctctggg aaggcctgga gcagccgctg caagtggtct  49740
ggcgccaggc gccgctgtgc tgcgaagaga tcgccctgga gcctggcgac ggcgaggtgc  49800
tgggccagtt gcaggcgcgc ttcgacagcc gtcgctaccg cctggacatc gcccaggcgc  49860
cgctgctgcg cctggtgcat gccgccgacc cggtgaacca gcgagtggtg gccctgctgc  49920
tgttccatca cctggtgatg gaccacgtgg ccctggaggt gctgcagcac gaactgcaag  49980
ccttcctcct gggccagcag cagcgcctgg gggaagcggt gccgtaccgc aactacgtgg  50040
cccaggcgcg cctgggcatc ggcgaggccg agcatgaggc gttcttccgc cagatgctcg  50100
gcgatatcga ccagccgacc ctgccgctgg gcctgcagga agtaccggga ggcagcgccg  50160
aactcagcga agcgcgccag cccctggacc gcctgctgag ccggcgcctg cgcttgcagg  50220
cgcggcaact gggggtcagt gccgcaagcc tgatgcacct ggcctggggc cgggtgctgg  50280
gcagcctggc ggggcagcag caggtggtgt tcggcaccgt gctgctgggg cggatgcagg  50340
gcggcgaggg cgccgaacgg gccctgggag tgttcatcaa caccttgccg ctgcgggtcg  50400
atctgggcga gttgccggtg cgcgaggccc tgctggccac ccatgagcgg ctggcgcagc  50460
tgcttggcca cgaacaggcg cctctggccc tggtccagcg ttgcagtggg gtggagccgg  50520
gtacaccgtt gttcagcagc ctgctcaact accgccacag tgccccggcg gcaaaccagg  50580
cggggcaggc cgacagtgcc tgggagggca tgcagttgct caatgcccag gagcgcagca  50640
actacccgct gaccctgagc atcgacgacc tgggggacgg cttcatgctc accgccgtgg  50700
ccgccgggat cgatgcccgg cgcatttgcg actacctgca cggcaccctg gaacagctgc  50760
tgctggccct ggagcagcaa ccggaacagg ccatcggcca ggtgccggtg ctgccgcagg  50820
ccgagcgccg gcaggtactg gagggcttca acgacacggt gcgcgactac ccgcgcgagc  50880
aggtcctgca ccagtgtttc gaggagcagg tgctggcccg gccgcagcag gtggcagcgg  50940
tgcagggcgc cgaacagctc agctatatcc agctcaacac ccgggccaac caactggccc  51000
agcatctgct gcaactgggg gtgcagcccg gggatcatgt ggcgctgctg ctgccgcgct  51060
ccctggacct gctggtgagc caactggcgg tgagcaagtg cggcgccgcc tatgtaccgc  51120
tggacgtcaa tgccccggcc gagcgcctgg ggttcatgct ggccgacagc ggggcgccgg  51180
tgctgctcag ccacagcgag cgggtgctgg aagctgcggt gcaacgggtc gacctggacc  51240
gtctgcgctt cgaccggctg gccgggcaca acccgaacct ggcgttgtcg tccgaggcgg  51300
tggcctacgt catgtacacc tccggttcca ctggagcgcc caagggcgtg cgggtgccgc  51360
accgggccat cacccggctg gtgatcaaca acggctatgc cgatttcaac cccgaggacc  51420
gggtggcctt cgcctccaac ccggccttcg acgccagcac cctggaggtc tgggggccgc  51480
tgctcaacgg tggccgggtc gtggtggtgg accacgcgac attgctggac ccgcacgcct  51540
tcggctcgct gctggaacgc accggggtca gcctgctgtt cctcaccacc agcctgttca  51600
accagtacgt gcaactggtt ccccaggcct tcaaggggct gcgcatgctg ctctgtggcg  51660
gcgaacgggc ggatgccacg gccttccggc ggatccaggc cgagctgccg cacttgcgcc  51720
tggtcaacgg ctacgggccc accgagacca ccacctttgc cgtgacccat gagcccggtg  51780
```

```
agctggcggc ggatgccgac agcgtgccca ttggccggcc gctgtccaac acccgggtgt  51840
acgtgctcga tgccctgggc cagccgctgc cggtgggggt ggtgggggag ctgtacatcg  51900
ggggtgatgg cgtggccctg ggctacctca accgtccgga cctgtcggcg cagaagttcc  51960
tcatcgaccc gtttcaccag caaacccagg gcaccgctgc gccggccctg atgtaccgca  52020
ccggcgacct gggccgctgg ctggaaaatg gtcttctgga atgcatcggg cgcaatgacg  52080
agcaagtgaa gatccgcggc ctgcgcatcg aacccgggga aatccaggcg cagttggccc  52140
gcttccccgg cctgcgggac ggcgcggtcg tggtgcgtga agacagcccc ggggacaagc  52200
gcctagtggc ctactacacc ctgcacgagc acaccccggc gccggatgcc gagcaactgc  52260
gcagccacct gcaacagcag ttgccggact acatggtgcc cctggcctat gtgcacttgc  52320
aggccttgcc cctgacccgc aacggcaagc tggaccgccg tgcgctgccg gcgcccggca  52380
gcgcggccca gctcgaccag gcctatgccg cgccccaggg cgcgctggag caggccctgg  52440
ccgggcattg ggcggcggtg ctgaagctcg agcaagtagg gcgccacgac cacttcttcg  52500
aacagggcgg gcattcgctc tcggccatcc agttgctcaa ccgcctgcaa caggcggcgt  52560
tcgacgtgac cctggcggag ctgttccagc acgccacggt ggcggccatg gcgcgcctgt  52620
tgagcgagcg cacggccgcg ccgcgctcca ccgagctgat cccggtgcgc accggcggca  52680
gtggcccggc gctgttcctg gtccatgagt tcaccgggct ggacgtgtat ttcccggccc  52740
tgggccagca cctggaaggc gatttcccga tctacggcct gcccggcgtg gcggtcggcg  52800
agccgcagtt gcgcaccctg gaatgcctgg ccacacgctt gcttgacgtg atgcgcaagg  52860
cccagccgca ggggccgtat cgcctggccg gctggtcctt cggtggggtc ctggcctatg  52920
agatcgccca gcagttgctg ggcctggacc aggaggtgga gttcctcggc ctgatcgaca  52980
gctacgtgcc gcgcctgacc gaccagggca aggctcgctg gtctggcgag cacgcgcaca  53040
agcgccacct gctgttgcag tgccgcgcct actggagcgc ccagggcgcg gccggggtgc  53100
agcccctggc gcacctggaa caactggagg cgctgctgga gccactggac tttgccgacc  53160
tgctgcaacg ctgccgcgac caggggctgc tgttcgagca actggccacg gcgccgccgc  53220
aagcgctcgg ccattacctg gaccgcgagg tcgcccacgg ccatgccctg gcccattacc  53280
gggtccatcc cctgggcatg ccggtgcatc tgttctgcgc cgccgaacgg cccaccgagc  53340
tgtcccggcg cagcccgacc ctgggctggg gcgagatcct gccggcgggc gaactgcact  53400
gcatcagcgt gcccggggac cacctgagca tgatgaaggc gccgcatatc caggccctgg  53460
gtcacgccct gggccaggcc ctggcggcgg ccagggccaa gggcgcggtg agcgctgtgc  53520
cgcaccagcc cttgctgcgg atccagagcg ggcgccccgg gcacacgccg atcttctgcg  53580
tgcccggggc cggtgacagc atcaccggct ttatcggcct gagcgaggcc ctgggggccg  53640
aatggccgat cctcggcctg caggcccggg gcctggacgg ctgcggggtg ccccatggcc  53700
aggtcgaagt ggcggcccgg cattacctgg aggccatcac cgccgagtac cccgacgggc  53760
cgctgcacct gatcggccat tccttcggcg gctgggtggc attcgagatg gccggggccc  53820
tgcaggccgc cggtcgcgaa gtggtgtcgc tgaccctgat cgacagtgag gctcccggag  53880
gcaatggcgc gctagggcgg ccctataccg ccaccgcggc gctgtggcgc ttgatcgaat  53940
ccatgcaact ggctgcaggc caggacatgg gcatcgaccc cgagcgcttc gccgccgagg  54000
acgacggcat gcagatgcac ctgctgcatg ccggcatggt gcgggtcggg ctgttgtccc  54060
cgcgcgccga cccgcgggcc atgcacggcc cggcgcgaac cttcgccagc gccctgcgta  54120
cccgctacca gcctcggcgc ccgtaccagg gcaaggtgcg cctggtgctg gcggatgacc  54180
```

```
cgagcctgga cgccgccggc aaccgccggg agcagcaggg gatggtccag ggctggcgcc  54240
ggcaggctgc gcacctgcag gtgtggtacg gcccgggcaa ccacttcagc ctgctcaagg  54300
cgcccaacgt ctaccacctg gcggcctggt ggcatgacgg cctggcgctg ccccaggggg  54360
aggtcatgtc atagggcgcg gggcaacaca ggcgctggcc ctgccggcgc ctggacaccc  54420
ggtttcattc atctggaaca ccgctcacta cggcagcacg gtgttctgta agggggctcg  54480
ccgctggccg gtgcagcccg ccctcaacgg acttgtggtc atctatggaa aagtcgaagt  54540
ttcgcaaaat cggtatgggg ctgttgctgg tggttgtggc cgggttgatt ttctatacgg  54600
tgcaggcgcc ggcggagccg ccgcagtacc tgaccgccaa ggtcgaacgg ggggatatcg  54660
agaacgcggt cctggcctcg ggcctgctcg aaggcatcaa gcaggtggat gtcggggccc  54720
aggtctccgg gcagttgaag tcgctcaagg tcaaggtcgg ggacaaggtg aaaaagggcc  54780
agtggctggc ggaaatcgac ccgctggtgc tgcagaacac cctgcgccag gcccaggtgg  54840
acgaggagaa cctgcaggcc aagcgccgcg ccaccgcggc ccagctcaag gaaaccaagg  54900
ccatctacga gcgctaccgt gacttgcagt ccgacgcctc gatttcccag caggattacg  54960
agaccgccga atccaactac gaggtgcagc gggccaacct gctgtccctg gacgcgcaga  55020
tcaagagcgc gcacatccag atcgacaccg ccaaggtcaa cctggcctac acccgcatcg  55080
tcgcgccgat cgatggcgat gtggtggggg tggtgaccca ggaaggccag acggtgatcg  55140
ccaaccagct ggcgccggtg ctgctcaaac tggcggacct ggacaccatg accgtcaagg  55200
cccaggtttc ggaggccgat gtgatccata tcgcccccgg ccaacaggtg tacttcacca  55260
tcctcggcga ggcggaaaaa cgctactacg ccaaactgcg gggcactgag ccggcgccgc  55320
agaactttct cgaaacccag accgccggca cccccaagca gaacaccgcg gtgttctaca  55380
acgcgctgtt cgacgtgccc aacccggacc atcggctgcg catttccatg actgcccagg  55440
tgcgcatcgt gctggatacc gccaaggacg tgctgatggt accggtggcg gccctgggcc  55500
cgcgcaatgc cgacggcagc ttcgcggtgc gggtgctgga cgccaagggc catgcccagg  55560
cgcgcaacgt cagcaccggg atcaacaaca acgtcaaggt gcagatcaag gacggcctgg  55620
cggagggtga ccgggtggtg attggtgatc cgctgcccgg cacggcaggg gcctgagcat  55680
gagcgagccc ctgctgcacc tcaccggcat cagccgcagc ttcaccgccg gggatcggga  55740
gttcctggcc ctcaagcaca tcgacctgag catccaggcc ggggaaatgg tggcgatcac  55800
cggggcctcg gggtcgggca agtcgaccct gatgaacatc ctcggctgcc tggactacgc  55860
caccgccggc agctacaagg tcaacggccg ggaaacccgc gacctcgacg accaggccct  55920
ggcggaactg cgccgcgact acttcggctt catcttccag cgctaccact tgctgccgca  55980
cctgagcgcc atgcacaacg tcgagatgcc ggcgatctac gccggtaccc cgcaagtcag  56040
gcgccatggc cgggcccggg aactgctggc gcgcctgggt ttgtccgggc acctgggcca  56100
ccggcccagc cagctctccg gcggccagca gcagcgagtg agcatcgccc gggcgctgat  56160
gaacggcggc gaagtgatac tcgccgacga acccaccggt gccctggaca ccgccagcgg  56220
caaggaggtg atgaacatcc tccaggaact gcacggcctg ggcacacggg tgatcatcgt  56280
cacccacgac cccaaggtgg cggccaacgc ccagcgcatc atcgaagtgc gcgacggcga  56340
gatcgtcagc gaccgggcca acccgcgccc ggcggacgag gcgccgagcg agccaccggt  56400
cagcgtgcgg cccgccggtg cgcggcgcct ggtggccagc ctggggctgt tcaaggaggc  56460
cttcgtgatg gcctgggtgg cgctggtctc gcaccgtatg cgcaccctgc tgaccatgct  56520
```

```
cgggatcgtc atcggcatca cctcggtggt gtccatcgtg gccatcggcg agggcgccaa  56580
gcgctacgtg ctcaaggaca tccaggccat tggcagcaac accatcgaca tcttccccgg  56640
ggccagtttc ggcgacagcc gggcggcggc gatccagacc ctgatgcccg ccgacgtgac  56700
ggccctgaac cagctgtact acgtcgacag tgccacgccc atggtcggcc gcagcctgtt  56760
gctgcgctac ggcaacatcg acctcaacgc cacggtcaac ggcgtcagcc acctgtattt  56820
ccaggttcgc gacatcaagc tggccagcgg catttccttc agcgagaacg acgcgcggcg  56880
ccaggcccag gtggtggtga tcgaccacaa cacccgcaac cgcctgttcg ggccggatgt  56940
cgacccgctg gggcaggtga tcctggtggg caacctgccg tgcacggtga tcggcgtgac  57000
ccgggagaac aagaacatgt tcgccgccag caacctgctg aacgtctggc tgccctacga  57060
gaccgccgcc gggcgggtgc tcggccagcg ccacctggac agcatcagcg tgcggatcaa  57120
ggacggccag ccgagcaaag tggtggagga gcatgtgaag aagctgatgg agcagcgcca  57180
cggcaccaag gatttcttca ccaacaacct cgacagcatc atgcagacgg tgcagcgcac  57240
cagccgctcc ctggccctgc tgctgtcgct gatcgcggtg atttccctgg tggtgggggg  57300
aatcggggtg atgaacatca tgctggtgtc ggtcaccgag aggacccggg agatcggcat  57360
ccgcatggcg gtgggggccc ggcagtcgga tatccgccag cagttcctgg tggaggcggt  57420
gatggtctgc ctgatcggcg gggccatcgg catcagcctg tcgttcgcca tcggctacct  57480
gttcaccctg ttcatcaagg agtgggagat ggtgttttcc atggggtcga tcattaccgc  57540
gttcgcctgt tcgaccctga tcggcatcgt cttcggcttc gttccagcgc gcaacgccgc  57600
gcgcctggat cccatcgagg ccctggcccg ggattgacag gccgtagacc gaaccgccgg  57660
cgctggggcc ggcgggggtt acagggccaa ggccggatca ggccgtcggg gtttcgctgc  57720
tgtgcggcgc ttgttcctcg ggcgagtaca tccagcgcag cagcgagtgc cggccactga  57780
tgccgagctt gatggcggcg cgcttcaagt agctttcgac ggtattgacc ttgagcttga  57840
gctgctcggc cagctgcggc gcggtgcgcc cggccagcag cccgacacag acctccagct  57900
cgcggttgga caggcgcagc ccggactgtt ccaagcgcgc ggcaaagcgc aggcgcaggt  57960
ttgccaggcc ctcgatggcg gcactgtcct gctcggcggc atcgccccgg ggctgcaggg  58020
cgctgatgtg tttttccacc atgggcagca gcaacggcga gatgtcctcc agcagcaggc  58080
gttcctgggg ggaaaagctc tggtcctggc tgctgcggta caccgagagc acgtagtggt  58140
aggagtcctt gcgcccggtc aggtgcagtt gtgccgggtc cgcgtggccg cgctggcgtt  58200
gcagcgacgg gcccggggcc ggttcgccgg gttgttcggg aaagccggtg agcagcagcg  58260
ggtcattgct ggcatgggca tcgctgtaca gcgggtggcg ggtctgcatc agggtgttgc  58320
cggttctgcc gatggcctgt tccgggtcgg cccgcagttg ggtgatatgg gtggcgtcca  58380
cagccagctg ggtgagtatc aggtcgtgca gcatgcgcgg aaagttgcgg ctgccggtgc  58440
tggcgatgac cttaccaatg tgtggaaaca gtatttgtga gttcatcatt tcatccatga  58500
atgtgaaggt gtggaggggg gctgccttat agcaacgagt ttgggtcagg gttgatttac  58560
ctcctgtttg ctctgggcga caaagggtcg cctcgtatcc tagtacaggg ttgcggtggc  58620
tgtttgatga agtgcgcaaa atctttcccg gcgggcgcag cggtgcggtg nnnnnnnnnn  58680
nnnnnnnnnn nnnnnnnnnn nnnnnnnnnn nnnnnnnnnn nnnnnnnnnn nnnnnnnnnn  58740
nnnnnnnnnn nnnnnnnnnn nnnnnnnnnn nnnnnnnnnn nnnnnnnnnn nnnnnnnnnn  58800
nnnnnnnnnn nnnnnnnnnn nnnnnnnnnn nnnnnnnnnn nnnnnnnnnn nnnnnnnnnn  58860
nnnnnnnnnn nnnnnnnnnn nnnnnnnnnn nnnnnnnnnn nnnnnnnnnn nnnnnnnnnn  58920
```

nnnnnnnnnn nnnnnnnnnn nnnnnnnnnn nnnnnnnnnn nnnnnnnnnn nnnnnnnnnn 58980
nnnnnnnnnn nnnnnnnnnn nnnnnnnnnn nnnnnnnnnn nnnnnnnnnn nnnnnnnnnn 59040
nnnnnnnnnn nnnnnnnnnn nnnnnnnnnn nnnnnnnnnn nnnnnnnnnn nnnnnnnnnn 59100
nnnnnnnnnn nnnnnnnnnn nnnnnnnnnn nnnnnnnnnn nnnnnnnnnn nnnnnnnnnn 59160
nnnnnnnnnn nnnnnnnnnn nnnnnnnnnn nnnnnnnnnn nnnnnnnnnn nnnnnnnnnn 59220
nnnnnnnnnn nnnnnnnnnn nnnnnnnnnn nnnnnnnnnn nnnnnnnnnn nnnnnnnnnn 59280
nnnnnnnnnn nnnnnnnnnn nnnnnnnnnn nnnnnnnnnn nnnnnnnnnn nnnnnnnnnn 59340
nnnnnnnnnn nnnnnnnnnn nnnnnnnnnn nnnnnnnnnn nnnnnnnnnn nnnnnnnnnn 59400
nnnnnnnnnn nnnnnnnnnn nnnnnnnnnn nnnnnnnnnn nnnnnnnnnn nnnnnnnnnn 59460
nnnnnnnnnn nnnnnnnnnn nnnnnnnnnn nnnnnnnnnn nnnnnnnnnn nnnnnnnnnn 59520
nnnnnnnnnn nnnnnnnnnn nnnnnnnnnn nnnnnnnnnn nnnnnnnnnn nnnnnnnnnn 59580
nnnnnnnnnn nnnnnnnnnn nnnnnnnnnn nnnnnnnnnn nnnnnnnnnn nnnnnnnnnn 59640
nnnnnnnnnn nnnnnnnnnn nnnnnnnnnn nnnnnnnnnn nnnnnnnnnn nnnnnnnnnn 59700
nnnnnnnnnn nnnnnnnnnn nnnnnnnnnn nnnnnnnnnn nnnnnnnnnn nnnnnnnnnn 59760
nnnnnnnnnn nnnnnnnnnn nnnnnnnnnn nnnnnnnnnn nnnnnnnnnn nnnnnnnnnn 59820
nnnnnnnnnn nnnnnnnnnn nnnnnnnnnn nnnnnnnnnn nnnnnnnnnn nnnnnnnnnn 59880
nnnnnnnnnn nnnnnnnnnn nnnnnnnnnn nnnnnnnnnn nnnnnnnnnn nnnnnnnnnn 59940
nnnnnnnnnn nnnnnnnnnn nnnnnnnnnn nnnnnnnnnn nnnnnnnnnn nnnnnnnnnn 60000
nnnnnnnnnn nnnnnnnnnn nnnnnnnnnn nnnnnnnnnn nnnnnnnnnn nnnnnnnnnn 60060
nnnnnnnnnn nnnnnnnnnn nnnnnnnnnn nnnnnnnnnn nnnnnnnnnn nnnnnnnnnn 60120
nnnnnnnnnn nnnnnnnnnn nnnnnnnnnn nnnnnnnnnn nnnnnnnnnn nnnnnnnnnn 60180
nnnnnnnnnn nnnnnnnnnn nnnnnnnnnn nnnnnnnnnn nnnnnnnnnn nnnnnnnnnn 60240
nnnnnnnnnn nnnnnnnnnn nnnnnnnnnn nnnnnnnnnn nnnnnnnnnn nnnnnnnnnn 60300
nnnnnnnnnn nnnnnnnnnn nnnnnnnnnn nnnnnnnnnn nnnnnnnnnn nnnnnnnnnn 60360
nnnnnnnnnn nnnnnnnnnn nnnnnnnnnn nnnnnnnnnn nnnnnnnnnn nnnnnnnnnn 60420
nnnnnnnnnn nnnnnnnnnn nnnnnnnnnn nnnnnnnnnn nnnnnnnnnn nnnnnnnnnn 60480
nnnnnnnnnn nnnnnnnnnn nnnnnnnnnn nnnnnnnnnn nnnnnnnnnn nnnnnnnnnn 60540
nnnnnnnnnn nnnnnnnnnn nnnnnnnnnn nnnnnnnnnn nnnnnnnnnn nnnnnnnnnn 60600
nnnnnnnnnn nnnnnnnnnn nnnnnnnnnn nnnnnnnnnn nnnnnnnnnn nnnnnnnnnn 60660
nnnnnnnnnn nnnnnnnnnn nnnnnnnnnn nnnnnnnnnn nnnnnnnnnn nnnnnnnnnn 60720
nnnnnnnnnn nnnnnnnnnn nnnnnnnnnn nnnnnnnnnn nnnnnnnnnn nnnnnnnnnn 60780
nnnnnnnnnn nnnnnnnnnn nnnnnnnnnn nnnnnnnnnn nnnnnnnnnn nnnnnnnnnn 60840
nnnnnnnnnn nnnnnnnnnn nnnnnnnnnn nnnnnnnnnn nnnnnnnnnn nnnnnnnnnn 60900
nnnnnnnnnn nnnnnnnnnn nnnnnnnnnn nnnnnnnnnn nnnnnnnnnn nnnnnnnnnn 60960
nnnnnnnnnn nnnnnnnnnn nnnnnnnnnn nnnnnnnnnn nnnnnnnnnn nnnnnnnnnn 61020
nnnnnnnnnn nnnnnnnnnn nnnnnnnnnn nnnnnnnnnn nnnnnnnnnn nnnnnnnnnn 61080
nnnnnnnnnn nnnnnnnnnn nnnnnnnnnn nnnnnnnnnn nnnnnnnnnn nnnnnnnnnn 61140
nnnnnnnnnn nnnnnnnnnn nnnnnnnnnn nnnnnnnnnn nnnnnnnnnn nnnnnnnnnn 61200
nnnnnnnnnn nnnnnnnnnn nnnnnnnnnn nnnnnnnnnn nnnnnnnnnn nnnnnnnnnn 61260

```
nnnnnnnnnn nnnnnnnnnn nnnnnnnnnn nnnnnnnnnn nnnnnnnnnn nnnnnnnnnn  61320
nnnnnnnnnn nnnnnnnnnn nnnnnnnnnn nnnnnnnnnn nnnnnnnnnn nnnnnnnnnn  61380
nnnnnnnnnn nnnnnnnnnn nnnnnnnnnn nnnnnnnnnn nnnnnnnnnn nnnnnnnnnn  61440
nnnnnnnnnn nnnnnnnnnn nnnnnnnnnn nnnnnnnnnn nnnnnnnnnn nnnnnnnnnn  61500
nnnnnnnnnn nnnnnnnnnn nnnnnnnnnn nnnnnnnnnn nnnnnnnnnn nnnnnnnnnn  61560
nnnnnnnnnn nnnnnnnnnn nnnnnnnnnn nnnnnnnnnn nnnnnnnnnn nnnnnnnnnn  61620
nnnnnnnnnn nnnnnnnnnn nnnnnnnnnn nnnnnnnnnn nnnnnnnnnn nnnnnnnnnn  61680
nnnnnnnnnn nnnnnnnnnn nnnnnnnnnn nnnnnnnnnn nnnnnnnnnn nnnnnnnnnn  61740
nnnnnnnnnn nnnnnnnnnn nnnnnnnnnn nnnnnnnnnn nnnnnnnnnn nnnnnnnnnn  61800
nnnnnnnnnn nnnnnnnnnn nnnnnnnnnn nnnnnnnnnn nnnnnnnnnn nnnnnnnnnn  61860
nnnnnnnnnn nnnnnnnnnn nnnnnnnnnn nnnnnnnnnn nnnnnnnnnn nnnnnnnnnn  61920
nnnnnnnnnn nnnnnnnnnn nnnnnnnnnn nnnnnnnnnn nnnnnnnnnn nnnnnnnnnn  61980
nnnnnnnnnn nnnnnnnnnn nnnnnnnnnn nnnnnnnnnn nnnnnnnnnn nnnnnnnnnn  62040
nnnnnnnnnn nnnnnnnnnn nnnnnnnnnn nnnnnnnnnn nnnnnnnnnn nnnnnnnnnn  62100
nnnnnnnnnn nnnnnnnnnn nnnnnnnnnn nnnnnnnnnn nnnnnnnnnn nnnnnnnnnn  62160
nnnnnnnnnn nnnnnnnnnn nnnnnnnnnn nnnnnnnnnn nnnnnnnnnn nnnnnnnnnn  62220
nnnnnnnnnn nnnnnnnnnn nnnnnnnnnn nnnnnnnnnn nnnnnnnnnn nnnnnnnnnn  62280
nnnnnnnnnn nnnnnnnnnn nnnnnnnnnn nnnnnnnnnn nnnnnnnnnn nnnnnnnnnn  62340
nnnnnnnnnn nnnnnnnnnn nnnnnnnnnn nnnnnnnnnn nnnnnnnnnn nnnnnnnnnn  62400
nnnnnnnnnn nnnnnnnnnn nnnnnnnnnn nnnnnnnnnn nnnnnnnnnn nnnnnnnnnn  62460
nnnnnnnnnn nnnnnnnnnn nnnnnnnnnn nnnnnnnnnn nnnnnnnnnn nnnnnnnnnn  62520
nnnnnnnnnn nnnnnnnnnn nnnnnnnnnn nnnnnnnnnn nnnnnnnnnn nnnnnnnnnn  62580
nnnnnnnnnn nnnnnnnnnn nnnnnnnnnn nnnnnnnnnn nnnnnnnnnn nnnnnnnnnn  62640
nnnnnnnnnn nnnnnnnnnn nnnnnnnnnn nnnnnnnnnn nnnnnnnnnn nnnnnnnnnn  62700
nnnnnnnnnn nnnnnnnnnn nnnnnnnnnn nnnnnnnnnc cccggngttg cnnnncntgc  62760
ngcgttggct tgcaggtggg ccgggttacg ggcgcttctc gcaattgacc atccatggca  62820
caccaaagcg gtccaccagc atgccgaagc gctcggccca gaaggtggct tccaggggca  62880
tctgcacgtt gccctgttcg gccagggcgg cgaatacccg ttcggcttcg gcggcgttgt  62940
cgatgttcag cgagatcgaa cagccgtgga tgcccaggta gggcagctca ggggtggtgt  63000
ccgagcccat cagcacctgg tcgccgacgc tcaggcgggt gtgcatgatg cgttcgtgac  63060
agtcggcaga gatgtgatca cgggccgggc tttcaccgaa ggtcatcatc atttccaggg  63120
tgccgttcag gcattgggca tagaaggtga aggcggcctt gcaggtgccg ttgaacacca  63180
ggtaggggtt gattttcatg ctgtgctccg gtcgcaggta acgggcaggc acgcgggcct  63240
gtggacgaac ttccatagca aagccgctat cggccctgcg cggaggtttt tttatagatg  63300
gtttttccat gctcgcccgt ggcgatataa ccgtcgccgc gccattgggg gcgcggcggc  63360
ggtgcgggcg gggttacag gcgcggctgc tcctggggcg tgccgagcaa ctggtgcagg  63420
gtgttgatca gcgcctgctg gcgcagccgg tcttcctggt gccgggcttc ggcggcggca  63480
acatcggcgt tgcagtgcgg gcaggtgctt tcatgggcgt ggatgtactc caggcaactg  63540
cgacacaggg ccaggcgcgg cgggatgcgg ccttcctcgg gcgacgcctg gccctggttg  63600
acccaggcca gcttgatcac ctggccgctg tcgttgacgc tcgataccgc ctcgccggtg  63660
```

```
tcgatgcgtt cggtgatcag gtcgaaacgg cccaccgaga acgacgccgg gccggcgtct  63720
tcgagcttga cgatgcgttc gcgcaggccc tttttcgcca ggtccagggt ccggtagtgg  63780
cagtagggat tgttccccgg cttgcccagc agagagtgcg aggtccaggt gcagccgccg  63840
cggcagacat cgttgtagta acaggtgcgg cagtagcccc acaggtcgtc caccgagcgc  63900
aggcggccga agtggatgcc ttcgctgtag tgccagatgt cgtgcaggct catgctgcgc  63960
acgttgccac cggagaaacc cacggtggcc agggacgggc agcccttgac cgtgccgtcg  64020
gcctccaggg ccaggaccgt ctgcccggcg gcgcagccgc tccagtgcac gcggtcgtcg  64080
ccgaagccgc gccacatgtg ctcgtagggg ccgtagtagc cgatgttgtt gcccacattc  64140
atcagcagcc cgcgctcggc gccttcgcgg tacaggcgcg ccagcagcgg catcacctcc  64200
agcaactggt agggctgcag cagcagctcg gggtgatcca ccgcattgcc catggccacg  64260
gtcagctgga tctgccagtg gctggcgccg gcatcgatga tcagttccat cagggccggc  64320
aggtcgggca gggtggcggc gccgatctgc gtgttgacgc tgaccttgag cccggcctgc  64380
ttggcccggc gcagggtatc cagggccttg tcgaaggagc cggggacatt gcgcaccgcg  64440
tcatgcagcg gcgccaggcc atccagagag acgccgacgc cattgagccc ggcatccacc  64500
gcggcctgca tcttggccgg ggtcaggttg cgcccgccgg tctggatcgc cacgtacatg  64560
ccgtggtcgt ggatggcctg gatcagccgc gtccagtcct tgcgcagata ggcttcgcca  64620
ccgatcaggg tgacttcccg ggtgcccagg gcggcgatcg aatcgattac cgacaggcat  64680
tcctgggtat tgagttcgcc cgggcgccga tgcccggcgc gggagccgca atgcaggcac  64740
ttgaggtcgc aggcgagggt gatttcccag accacatgca ccgggacaaa gcgcttgagg  64800
tcggtttcgc tgaggtagcg ggcggggaga cggtctgaca tgagagttcc ttgcgcaccc  64860
ggcggtgcgc ggcaccaacc catcgaaata ggcgcgcctt ccttgtgtcg caatggcgcg  64920
gtcgttttgt ggcagccccc ggggccgcgg cgggcggccc cgggtgctgg tggtcagcgc  64980
tgttccaggc ggctgatttc tgcctgcaac tgctgcaccg cctgggtcag gttgtcagcg  65040
ttggccagtt gctgctcgcc ctgggccacc agtgccttga gccgcgccag gtcgccgctg  65100
gcctgggcct gctgcagcgc cacggcatac agcgggtggc gcacttcggc ggccgggccg  65160
gcctggctgg cgtagtccgc tgcctgcgcc tgctccaccg gggccgggct cacggcggcg  65220
tgttgcacca cgtgccagtg cccctggaac tggtacttgt agctggcgaa gccgctggcc  65280
cagtccaggc cgaggatgcc ctgcaggtgg aaggtctcgg cgatctggct ggtggggccg  65340
ctggggttgc cggccaggct gaggatgatg tgcccctcgc tggaggggtc gagcttgacc  65400
tgcgagtagt cgccccacac gtcggcatgg aactgcaccg gtggcgaggt gctctgggtc  65460
acgcgggcaa cgccgctgac gcgtttcttc ggggtatcga ccagcaggtc gagggtcagc  65520
accggcccac cgatcacggg gttggcgacg atgaggcggg tatggaacag tccgattgtc  65580
atgctgcaac tccttatctt cttgaagaca tcaggttcga tggacggccg ggctcagcgc  65640
cgctcctgct ggctgatctc ggccttggcg gccaccagtg cggtgcggat cagcggcagc  65700
tgttccagtt gctgggtggc gaccttgtgc aggctcttca tctgcgccag gtcaccgctg  65760
gcgatggcac catggatcgg cgccccgtac agcgccgaga tcggcggcag cggatggttg  65820
ggctggccgc ggtgcagagg ggccgacagg gtgctggact gcacggtttc ctgcaggtgg  65880
gcgggcacct ggttgaccgt cacccagctg tggccgttgt agtactgata gttggccacg  65940
ccttccttcc agtcgtcgct gaccaccagg tgcagcttga agttgatcac cgagttcgac  66000
```

```
cccgggccgc cctggttgcc ctgggccgtg atgaggatct tgctggtgct gggcggcatg  66060
acggtgaggt aggtgtactg gccccagaca tcgctgtgca ggtccagggg cgggttgacc  66120
gcctgggtga tgctggaagt gccgcgcaca ctgtgttccg gggtataggc cagcaggttg  66180
aggatcaggg tgggtgcgcc gggttgcgag gtgccgatgc ggtagctcag ggggaacagg  66240
ccttcggctt gcgagtagtt gccggacatt tgctttgcct ccattcaatg acaggggaac  66300
cgcgatcagc ggcgttccag gcgggcgact tcctgggcca gctgttcgta ggcgttgtgc  66360
agatccttgg gttcgttcct ggccggatcg cgcttggcca gcagggcttt catctccggc  66420
agcttgcctt cgctgatggc cgactggatg gcgactccgt aggggggat cacatgttgg   66480
gatgcattgc tcatggcgtt tgccttccgt gggtgtggat ggggtgctgc gctactcggc  66540
agcttttgca gttaagcagc gcgggtggaa ttggcagggt aatggcacat tgattttgtg  66600
ggtttccgac cggtggattc acggtcggta aagggttgat tttggagaca ttccaaaggg  66660
cgatatgcag gcgggaggtg attgcggatg gcgataggag gggtgagaa agggggcga    66720
gcgtaggcac cggctgccgg cgaagaggcc cgcgacagcc atgcatcgcc ctggccggcg  66780
ccttcgctgg caagccagcc cctacggggt gtcagtgcgc tcggaccacc cccaactcct  66840
ccagccggcg ccgggtctca gccgccgtca catgatgaat cgcatgccac cccagcgccg  66900
ttgcggcgac gatattgggc gcatggtcgt caatgaacac cagttcctcg gggccaccc   66960
ctggcaaatg cgcacgaatg cgccccaggg tcgtgtgata gatctcggca tccggcttga  67020
tctggcgctc ttgccccgac acgacgatgt cgcgaaagcg ctgcagaaac gggtaattgt  67080
cccaggcata gggaaaggtt tcccgggacc agttggtcag cccgaacagg ggcacctgcg  67140
cctggtgcag ttcttccagc agggctacgc cctgatccag tggcccttg agcatctccg   67200
gccagcgccc gtaataggcc tcgatcaagg gggcatggtc ggggtgctcg gccaccaggc  67260
tgcgggtcgc ctcggccagg ctgcggccgg cgtcctgccg ggtattccag gcctgggtgc  67320
agatggtgtc gaggaaccac tggcggcgct catcgtcggg gatcagctgg cggtacaggt  67380
ggtgcgggct ccagtcgaac agcacgccac caaaatcgaa aaccacggca cgaatcgtca  67440
tgaacacgtc cttttgagcg gttatgggcc aggcgccatc ctgcgacgcc cggcagcaca  67500
atgcaatttg ccgctggccg ctggtccgct cgccggcacc ctggccacga atcgtgatcc  67560
aacccctgta tccggccttt tccaggctgg cacaggagct gcccatgact gccaagaacc  67620
ccacggggcc gcgctcgtcc gagcatgcct cgaatcatca tgacccgggt ttcgaccccg  67680
attcgccaga cctggccgac ccccaggtag acccggtagg cccggccagg gcacccctgg  67740
accgccctga acccgagcac cggcgcaatc gctcgcgggc ctacgatccc ctggccaacc  67800
tgaagaagtg acccggcgcg ccgacatgcg gcagtcgccg ggcggtgtgg cgggtgtaag  67860
gtaaaacgcc caagccccag gctcgccgag gaaaaaggag gtgtccatga gcacgccgct  67920
gctgaacaaa ctgcagatca acggctatca ggtcttgagc gtcaaccacg ggccctggaa  67980
ggtctgcacg ccgggtgacc ggcttgctac cttcggcacc cgggaagagg ccatggcctt  68040
tgccgccgcc ctgccggcgc gcaggcaacg accggccgcc accggtggct agcgcccagg  68100
caggaaaaaa gccccgaccg gttcggggct tttttatgcc tggccggggg catggccgga  68160
cggggcgagg gcgcagcggg gcgcaattac ggctgcatga aactcagcag cgggaggatg  68220
aaggctgctg ccagggccag tgcccacagg gtctgcagaa acagctcatc ggcgttgtcg  68280
gcggcgggcc gcggggcgag gcggcggcgc cagtagaagt acaggccgct gaccacgaac  68340
acacaggtga tgcccatcat gtactccagc tcccacttct gggggctgat ggccaggctg  68400
```

```
ccgtcctggt catccgggta gtcgagccgc caccaggcgc ccagcagcag cggcaccagt  68460
ccggccagga gccaggccag gcgcgcgccg ggcatccggg tcagcagggt cacggccagg  68520
ccgatcaggc acagcaccca gacaaagagg tacagctgaa agcccatggc cccaccgaac  68580
agcgtgctgc tgacatcccg cggctgcatc atctgcacgt cgcacagcag catcagcgac  68640
aagggcgcgg caacgacgat ccagcacaga gggcggtaga gccacaacca cagggtaaac  68700
aggcgagaca tgggcacact catcgaggtt tggtgaagca agaaagaggc ggggttgacg  68760
gtcagtcgac aatgacccgg gtgccagggc ccaggcacag gctcaactgt tcgccggccc  68820
ggttgaaggc gcagtacggc aggggcgcct tgctggcatt gaccaagggg gggatgaaga  68880
agccccccag caacaccgcc catgcaatcc gcaacgacag ctcacggagg gtggcggggg  68940
ctctcggctt gagccgctgc tggtgaatca ggtagatgcc gctgtagacc agggcgaaac  69000
cgaagaccat cacatagtcc agctcccggg cctggatgct gaagatcagg ttgccgtcga  69060
aatcatccgg gtagtggatc cgccaccaca ggcccagcag caactgcacc agcccaccga  69120
tgatccaggc caggcgggcg ccgggcacac gggtcagcac ggccaggccc aggccgatga  69180
cgctgaaggc ccagccgccc aggtacagca tgaaacccat ggagccgccg aacagcgtgc  69240
cgccgacttc ccgggggacg atcaggtgca ggttgcaacg gatcatggtg gccaattgtg  69300
cggccacggc gatccagcac aggaggtagt agagccggga ccagaaggtg tgcaggggcg  69360
acatgcagag actcgaaaaa aacagggccg atgagagtgt gtggtgggct gggttcaaac  69420
caacggcaaa ccgcaggcaa ccgcgaacag cgccagggcg atgctgatgc ccgccagggg  69480
aatgcgaaac cagtaacgga tggccagcac ccacaggctg gcgagaaacc ccaggccgat  69540
cagcagcaag ccacgggcct ccagcagcag ggccgggtgc agccaggcga ggtagccata  69600
gaccaggccg aacagcatgg cgcccaggct gtggctggcg ttgaagccga cccaggcccg  69660
ccacaggctg gtctggcggg tgatcatcgg tgacacctgg cgcatgcgtt cggccagggc  69720
cgggtcccgg ggctggaatt tgtcggtggc gaaggtgtag atcaggtgca gggtgccgag  69780
cagcagcacg atggctgagc tggcgatgat cagggcgggg gccaacacgt ttcttccttg  69840
ggcggtgctc gggtgcgcgg agtatgccgg gccgcccggg gttttgcacc tgcgggcggt  69900
ggtttttgc cagcacgggg cagggcgccg ggcgccctgc ccaggggctc agaagtgctc  69960
ggcgtcgagg ccgaacaagg aggcgctgcc ggcgcggatg ctctgctcca ggctgaggat  70020
gcgcggcagc atgcggctga agtagaagcg cgcggtggcc agcttggcac cgtagaaacc  70080
gtcgtcctcg gaacgcttgt gctcggccac ctgggccatg cgcgcccaca gataggcata  70140
ggccacgtag ccgaacagtt gcaggtattc gacgcaggcg ctgcccaccg cgtgggggtt  70200
ctgcgccgcc tgttcacgca gccagtcgct gaggtcttcc aggcgctgca ccgcatccag  70260
cagctcggcg gcgtaggcgg cgccgggcag gtaggcgtag tcgcggatct cgccggtgaa  70320
caggcgcagg gccacgccgc cgttgcccac caccttgcgc cccaacaggt ccagggcctg  70380
gatgccgttg gtgccctcgt agatctgggc gatgcgcaca tcccgcacca gttgctcctg  70440
gccccattcg cggatgtagc cgtggccgcc gaagatctgc tggcccagca cgcaactgtc  70500
caggccggtg tcggtgaaga acgccttggc caccggggtc agcagcgcca ccagggcctc  70560
ggcgttgtgc cgctcatggg gctggtcggc gaacttggcc aggtccagct gctggccgac  70620
gtagctggcg aaggcgcggc cgccttcggt catggccttc atggtcagca gcatgcgccg  70680
cacatcgggg tggacgatga tcgggtcggc gatcttgtcc ttggccaccg ggccggccgg  70740
```

```
ggagcggctc tggatgcgct cgcgggcgta ggttcgggcg ttctggtagg agttctcggc  70800
gcagccgata ccctggatgc cgatggacag gcgctcgtag ttcatcatgg tgaacatcgc  70860
cgccaggccc ttgttggcct cgccgatcag ccagccgctg gcgccgtcga agttcagcac  70920
gcaggtggcc gaggccttga tgcccatctt gtgctcgatg gaaccgcagc tcaccgcgtt  70980
ggccgcgccg agattgccgt tggcgtccac atggatcttc ggcaccagga acagcgagat  71040
gcccttgggc ccggccgggg cgtccggcaa cttggccagc accaggtgga tgatgttctc  71100
ggtcaggtcc tgctcgccgc cggtgatgaa gatcttgctg ccgctgatgc ggtaactgcc  71160
gttggcctgg ggctcggcgc gggtgcggat gatccccagg tcggtgccgg cgtgggcctc  71220
ggtgaggcac atggagccgg cccagcggcc ttcgtacatc ggcggcaggt acagctgttt  71280
cagcgcttcg ctggcgtggg cgtcgatggc caggcaggcc ccggaactca gggccgagta  71340
cagggcgaaa ctggaattgg cggcgtagag catttcctcg aactgcaccg cgagcatctt  71400
cggcatgccc atgccgccgt aggccgggtt gccgctcagg ccgacccagc cgccctggat  71460
ataggtgctg taggcctcct tgaaaccggc cggggtgcgc acctgcccgg cgtgccagct  71520
ggcgccttcc tcgtcgccgc tgcggttgag cggggcgatc aggttgccgg tgaccttggc  71580
cgcttcttcg agaatggcgt cggcggtgtc gccgtccacg gtatcggcca gggccggcag  71640
gcgcgcccag agcttgggtg cgttgaacac ttcatgcagg acaaagcgca tgtcgcgcag  71700
cggagcgttg aattcgggca ttgcaggaac ctcgggcaaa agtggaggtt gagcggcctc  71760
ggccgcatga atcgacaacg aaaaccccgc caccttgtag gagccggctt gccggcgaag  71820
aggcccgcaa gccatgcatc gccctggccg acgccttcgc tggcaagcga agcgccgccc  71880
ggccagctcc tacaagggct gggtaggtgt attcaggcta gaggtttttc gccatgtcgc  71940
gcaggacgaa cttctggatc ttgccggtgg aggtcttggg caacgggctg aagaccacgg  72000
tacgcggcac cttgaagcct gccaggtgtt cgcgacagaa ggcgatgatc tcggcttcgc  72060
gcacgtcctg atgatcggcc ttgagggtga tgaaggcaca gggcgtctca ccccattttt  72120
catcgggccg ggccaccacc gccgcttcca gcaccgccgg gtggcgatag agcacgcctt  72180
ccagttcgat ggtggaaatg ttctcgccgc cggaaatgat gatgtccttg agccggtcgc  72240
ggatctccac gtagccgtcc gggtgggtta cccccaggtc gccggtgtgg aaccagccgc  72300
cctcgaaggc ttcggcggtg gccgtggggt tcttcaggta gcccttcatc acggtgttgc  72360
cgcgcatgaa gatctcgccg atggtctggc cgtcccgggg cgtgggttcg agggttttcg  72420
ggtcggccac catcacccct tccagggtcg ggtagcgcac gccctggcgc gacttgatct  72480
gcgcccgctg ttccaggggc agttcatccc aggcggcgtg ccaggcgcac agggtcaccg  72540
ggccatagac ctcggtcagg ccgtagacgt gggtcacctt gatgcccatt tcctccactg  72600
cgccgatcac cttggccggc ggcgcggccc cggccaccat ggcgttgacc gggtggtcga  72660
tggccgcctt ggcggtgtcg ggcatgttca ccagggcatt gagcacgatg ggcgcgccgc  72720
acaggtgcgt gacctgatgc tcgcggatca ggtcgaggat cttctgcggg tcgacccggc  72780
gcaaaaacac atgcactccg gccagggcgg tgacggtcca ggggtagcac cagccgttgc  72840
agtggaacat tggcagggtc cacaggtaca ccgggtggtt gcccatggcc caggtcatct  72900
ggttgcccag ggcattgagg taggcgccgc ggtggtgata gaccacgccc ttggggttgc  72960
cggtggtgcc cgaggtgtag ttcagggcga tggcctgcca ctcgtcatcc ggccactgcc  73020
aggcaaactc gggatcgccc tcggcgagaa aggcctcgta atccagatcg ctgaccggct  73080
ggccttcgcc gtattccggg tcgtcgaggt cgatcaccag gggcgggtga tcgagcatgg  73140
```

```
ccacggcggc gtggatcacc tcatggaact cgcggtcggc gatcagcacc ttggcttcgc  73200
cgtgggccag catgaaggcg atggcctcgg cgtccaggcg cacattgagg gcattgagca  73260
cggcgccgat catcggcacg ccgaagtgtg cttcgagcat tgccgggatg ttgggcagca  73320
tcaccgccac cgtgtcgttc ttgccgatgc cgcgcccggc cagggccgag gccaggcgcc  73380
ggcagcggct gtaggtctgg gcccaggtgc gacggatcga accgtggatc accgccgggt  73440
aatcggggta aaccgcagcg gtacgctcga tgaagctcaa gggggagagg gcgatatggt  73500
tgacggcagt cggcgccagg ccttgctcgt agatggacat ggttcgggta cccggtggct  73560
gattattagc tctattggcc gaggcttggg tggcgtgtgc tgtgtacctg ggggcactga  73620
ctgtaggagc cggcttgccg gcgaaagcga tcccacgggc ctcttcgctg gcaagccagc  73680
tcctacgttc ggcgttgctt acaggtacgc agcacaccca gcgaaagctc ggtgacttat  73740
ccggggtctt ttatatactg tttgtcgatt gatatggaag tactacctga gttgtatagt  73800
ggttgtacta taaaaagaat ctacccttcc ggccgcgaga ctgatcgacc atgcccgact  73860
ctacccacct gcgtcactgg ctgcgcctgc agcgtgaagg ccagttgccg gactcgccct  73920
ggctcggcca cgacccgcaa cccagcctgc tgctggacgc ccaggcgcag ccgctggacc  73980
tcaacccggc actgcgccag tggctggacg atgctgccac tggcgatctc gcggccctgc  74040
tgccggtcaa ccacccggcc ctggtacggg cctgcctgga gcagcagcgg gccatcgagc  74100
aggtggaagc ccagtggggg gagcgcatcc tgctctggag ctttatcccc gatcctcatc  74160
gccagcgggt actggcgcgc tgccaggaag ccacggacca ggtccgggcc gagcgcgagt  74220
cggccaaggc ccggcgcctg taccgcctga tcaccgaaaa caccactgac ctgatttccc  74280
ggcacacccc ggacggcagc ttcctcgacg cctcaccggc ctcctggacc ctgctcggct  74340
actggcccga gcaactgcgc gggcgcctgg cccgcagcct gttccacagc caggacctgg  74400
ccgggctgat gcagcgcacc cgcgatgccc tggagcagga cggctaccac accatgacct  74460
atcgcatccg ccatcgcgac ggccactacc tgtggttcga aaccgcctgc cgcggcattc  74520
gcgacaccta caccggcacc gtggtggaag tggtggcggt gtcccgggac atcaccgccc  74580
gggtccaggc cgaagagaac aagcggcgcc tggcggaagt ggtagaggcc aaccccgacc  74640
cggtgctgtt catccagccc ggcggcgcgg tcacctacct caacccggcg gcgcggcgca  74700
ccctggggct cggcgacggg caggcaatgc cgccactggc ggccattctc agcgctgcgg  74760
tactcgacag cctgcaacgc gaaggctggg accgcgctga acacagcggc cgctggaaca  74820
tcgaggcgcg cctgcaaccg ccggccggcg gcgcctcggt gccggtctcg ctgatgctcc  74880
tggcccaccg cgcggccagt ggcgagcgtt tctattccct ggtggcccac gaccagagcg  74940
agcgcgaact gcgcgaagcc cagcagcgcc atcaccagga cgaactggcc cacaccgcgc  75000
gcctggtgac cctgggcgaa ctggcctcgg gtatcgccca cgagatcaac cagccgctgg  75060
ccgcagtggt caactacgcc aatgccagcc agcgctactt gcaggccctg ggcacccagc  75120
ccgaggccgc ccgcaaggtg gcccagggcc tggaacggat tgccgagcag gcgacccacg  75180
ccgccgaagt gatcaagcgc ctgcgggcct ttttgcgcaa gggcgggcgc cgggtgcagg  75240
ccttggacat cgccgaagtg gcccgggaaa ccgtgcgcct gtgtgcctgg gaagcccagg  75300
ccagccaggt gacgatcgac ttgcagctgg cggataatct gccgccggtg tacgccgacc  75360
gggtgctgtt ggagcaggtg ctgctgaacc tgctgcgcaa cgccatcgag gccaaccgcg  75420
aagtgcatgg gcagcagggc tcgcacattg tgctggccgc cgaggcgacg gccgaaggcg  75480
```

```
gggtgcagat cagcgtcagc gaccagggcc ccggtgtctg cgccgagcaa ctgccgcagc  75540
tgttcacccc gttctacacc agcaaggcca atggcctggg gctcgggctg tccatgagcc  75600
gcagcatcgt cgagggcttt ggcggcgact tgcaggccca gccccaggcc gtcggcctgc  75660
gcatgtgctg ccggctgccg gccagtgccc cggccgaccc ctcggcaacg tcccaggcaa  75720
cttcccccgc aacgacagga gcaaggcaat gacgagtgtg gcgcagcaac tggtgtatgt  75780
ggtcgacgac gacccgggca tgctcgactc caccgtctgg ctcttggagt cggtggggct  75840
caaggcgctg cccttcacca gtggccgcga gtttctcgaa cactgcgacc cgagcctcaa  75900
tgcctgcgtg ctgctggatg tgcgcatgcc cggcatgggc gggctgaacg tccaggaaga  75960
gctgcgccag cgcgatatcc gcctcccgct gatctttgtc agcggccacg ccgacgtgcc  76020
catcgtggtc cgcgcgttca aggccggggc ggtggatttc attgaaaagc cctacaacga  76080
acagctgctg ctggacagcg tgcagcaggc cctgagccgc gccgacaacc atcagaacca  76140
gagtgccggg caggcccggg tgcaggcgct gctggaaagc ctgacgccac gggagaaaga  76200
cgtgttgctg ccgctggtgc agggctacac caaccgggaa attgccgagc aactgggggt  76260
cagcatcaag accatcgacc tgtatcgctc acgggtgatg aaacgcatgc aggccgaaca  76320
cctgccggaa ttggtgggca tggctattgc cgccgggctg gtagacccgc tgcacctgcg  76380
ctgaggctca ggccaccgcg ctgcgcacgg gcacgccgcc cagcagccgc tcgatggcgc  76440
cgctcagcag gttttccaac agggcttcgc gttcacgctc ggccaggggt tgttcgctga  76500
accagctggg ggcgctgttg agcaggttgg ccaaagcatg ggccgcggcg cgctgcgcct  76560
gtgggccaag gccggtcggg gtgcccagca actgcaccag ctgttgttcg tagcgctcgc  76620
gcaattgccc gacccgcagt tgctggtcgg gattgaggca gccgctgtcg cgctccacca  76680
ggcggaaatg ccgcggcaat tcccggtgca gcttcaggtg ggcgcggatc agcgccggca  76740
ggcagtcgcc ctgcaacttg cgccgttgca ggcgcttgag ggtgctgtgc agctcatcga  76800
agaactcctc gatcaggtcc agcaacaggt gctgcttgct cgggtaatgg tggtacagcg  76860
agcccggggt cagccccaga tggctcgcca gctcacgcat gccgacctgg ccgaagccct  76920
tgctggcgaa cagctccagg gccttgtcgc ggctttcggc aaagcgtgag caacgctcag  76980
ccatagtgat ggaaaccccg accggtcttg cgccccaggt agccggcggc aaccatttcc  77040
ttgagcagcg gcgcggggcg gtacttgctg tcgttgaagc cgtcgtagaa ggcttcaagg  77100
atcgccagca gggtgtccag gccgatcagg tcggccaggg ccagcgggcc gatcggctgg  77160
ttgcagccca ggcgcatgcc ggcgtcgatg tcctcggcgc tggccaggcc ttcctggaac  77220
accaggatcg cctcgttgat catcggcacc aggatgcggt tgaccacaaa acccgggcgg  77280
ttgccggcgg tgatcgcggt cttgcccagg cgctgggcca tgtccatggc cagggcgtgg  77340
gtcgcgtcgc tggtctgcag gccgcggatc acttcgatca ggcccatcac cggcaccggg  77400
ttgaagaagt gcaggccgat gaaccgctcg ggcgcgctga cgctggcggc cagttgggtg  77460
atcgacagcg acgaggtgtt ggaggcgatc acgcactcgg cgctgacctg ggcggcgatc  77520
tgctgcagca ccttgagctt gaggtcgagg ttctcggtgg cggcttcgat caccagttgc  77580
gcatccttga gcacgccgta gtcggtgctg atgcggatcc ggcccagggc ggcgagcttg  77640
tcgtcttcgc cgagggtgcc cttgctcacc tggcggtcga ggttcttgcc gatggtggcc  77700
agggcctttt ccagggcgcc ctgggcgatg tccagcaggg tcacgtcaaa gcccgcctgg  77760
gcgcagacct gggcgatgcc gttgcccatg gtgccggcgc cgatcacccc gatattcgca  77820
agattcatct tcagctcttc ctttgttcat tgccttcgcg gagcatggcg cggttgcctt  77880
```

```
gcacagcgcg ttatccagcg cgagtctaga gcccggcgcg gtggccggcc tatgccgaaa  77940
gcggtcaagc gtgctggcgt tttttgccat aggtccagct acgggagcac agcctctaca  78000
tgcgtgaatc ggattcggtc gcggtctact ttgtccgggt gatgacccac gccctgcgcc  78060
agcagccggc gcggctggcg gccgtgctgc gcgaggccgg catcgacccg gcgttgctcg  78120
accagccccg ggcgcgggtg cccggcagcg cctttgccgc cctgtggctg atccagatcc  78180
gcgagttgca ggacgaattc ttccagctcg actcccgggg catgccgccg gggcctttg  78240
ccctgatctg ccgcgggctg atccaggagc ccaacctgga aaaggccctg cgccagtgcc  78300
tgaacaactt cggcctgttc ctgcgggacg tcggcgccag cctcagcctg cggggcaagc  78360
gtgcggtgat cagcctcgtc agccgctgcg ccgacccgct gcgcagccac tacgccgagg  78420
aaaccctgct ggtgctgatc atcagcctgt tgtgctggct cggcgggcga cggattccca  78480
tcgaccgcgc cgattttcgt cattcacgcc tgagcctcag cgatgacccg ctgctgtggg  78540
gcagcaacct gacctggaac gccgggcgca ccgagatcga attcgccagc cgcttcctgc  78600
gcctgccggt ggtccaggac ctggcctcgc tcaaggtgtt cctgcgcagc gccccgcaat  78660
ggctggtgat ccgctttcgc aaccagcacg ggctgaccac ccaggtgcac cagcgcctgc  78720
ggggcagcca ctacagccag tggccgaccc tggaagcctt cgcccgcgaa gtgcagatga  78780
gcgccagcac cctgcgccgg cgcctggagc gcgaaggcgg ctcctatcaa gagatcaagg  78840
acgaagtacg ccgcggcgtc gccgtcgaac tgctacgccg caccagcgtc agcatcagcg  78900
agattgccga actcaccggc tttcaggagc ccagcgcctt ccatcgcgcg ttcaagaaat  78960
ggaccggcga aagccccggg cgctaccgcg cgcgtttcca gccagccccc gcctgattcc  79020
acgacatccc ggctcctacg gatttcgcca catcacacag cccccccgt aggagctggc  79080
ttgccagcga aggcgcccgc acccccgtag gagctggctt gccagcgaag gcgcccgcaa  79140
gatcaccgcc tgatccgagg gcctgctcgc cggcaagccg gcgcctacgg ttggtgtgga  79200
ttaggccggg ctgcggccgg gcatctggat gccgtgctgc tgcacgcggc ggtacagggt  79260
ggcgcgggaa atgcccaggg ctttggctgc cgccacgggt ttccagcggt ggcgcaccag  79320
ggcatccaac agggcctggc gctcggggct ggtggcggtt tccagggcgg gcagggcgcc  79380
ttcggcctcg gcgccgcgca gttgttcggg caagtcatgc agttggatca gcggtccttc  79440
gcacaccgcg caggcgtagc gcagcacatg gcgcaattgc cgcacgttgc ccggccagcg  79500
gtagcccagc aggcattcca gcgccgcatt gcccagttgc accggcgcac cgcagcgctt  79560
ggattcctct tcgacaatcc gggtgatcag cgccagccgg tcgctgcgct cgcgcagcgg  79620
cggcagctga aaacgcgcgc cccccaggcg gaaatacagg tcctcgcgaa agctgccttc  79680
ggccaccagc gcttccaggt cgcggtgggt agcgcagatc acctggatat ccaccgcctt  79740
gcgttgcgcg gcccccaggg gcgccacttc accctcggcc agcacccgca gcaggcgggt  79800
ctgcaaggcc aggggcatgt cgccgatctc atcgaggaac agggtgccgc catcggcctg  79860
ttgcagcagg ccctgcatgc ccttgttcga agcgccggta aaggccccgg cgacgtagcc  79920
gaacagttcg ctttcgatca ggttctcggg aatcgccgcg cagttcaccg cgacaaaggg  79980
ccggtcccga cgctggctgg cctggtgcag ctggcgggcg aagacttcct tgccggaacc  80040
ggtctcgccc tggatcagca ccggcaggtg gcggtccttg acccgcaccg ccaggcgcag  80100
gctctgttcc acccgcgggt ccagcggttc gccggtcagg ctcaggcgcg ggcgctgtgc  80160
cgggcgcctt ggcgcttgca ggcggccgtg caggttgtcg gaaagggggc acagggcttc  80220
```

gtctcgggcg cgctgcaaca gctgcgggtc gaacacctgg gtgatgtgct gcggcaagcg 80280
gccatagcgc cgcagcaggt aatggcgcgc cgccgggttg agcgcgcgca ggcagccgtc 80340
gtcgtcccag gccagcaggt aatccggctg gctgtcgaca taacccgggc tggcatgggc 80400
ccgcagcacc cagtaaccct gggcgctgtt catgaagaat gcctgttcga tctcccgcgc 80460
gctctgcacc accatctgcc ggatcaggtg ctgggagcga cggtcatccg gggagcgcac 80520
cgccgacacg tccagcaccc ccagcaactc gccctggggg tcgaacaccg gggcggcgga 80580
acaggtcagg ccgatgaacg cggcgcgaaa gtggtcgcgc ttgtgcacgg tgatcggcgt 80640
gcgcgcggtg agcaccgccg ccacgccgca ggtgccttct tcaccctccg accagcaggt 80700
gcccaggtac agcccggcct tgcggcagtc gttgcgcagg gtggactcca cccggtagtc 80760
gatggtctgg ccttgggcgt cggtgagcag cacgcagtag tcggcgtcgc gcacccggcc 80820
atgcaggcgg gccacttctt cgctggcgat gcgcaggaac agctcggaac gctcgcggca 80880
ttccttgagc acgttttcgg acaggatgcg cggcccctgc agcgagccgg ggtccagttg 80940
gtgctgctcc atggagcggc gccaggaatc gaggatcagg ctcggcaccg gcgcctgggg 81000
caggtgatcg gcgtttttca ggacccggct gacgcagtcc acatgggctt ttgaatgtgc 81060
ggaaagcatg aaggcctccg gttgcagctt cttatcgttg tgggcgcatt aagcgccgat 81120
ccgcggctcc cgacaagcac cgggcggcgc cgtgggggcg ctgagacgca acgtctcagg 81180
gtctcgccaa ggccccgtgc agcctgacat gcaacgtctc aggcgcaggg cttcccgaca 81240
cctgcaggcg agtgcaacag ccgctctgcc acgggccttt gcagcggttt ttccataact 81300
ggcaccggcc ttgctctggc tcttggcaac cagttctcgg caacccgcgt cgactggccc 81360
atcgaagaat aagaacgagg tgcccgatgt tttctcctgc ctgtgctccg cccgcggtga 81420
gcccatgaac cgccgccccc tcaccgtcgg catcatcgcc aacccggctt cgggccgtga 81480
tgtgcgccgc ctcaccgcca acgccggcct gttctccagc accgacaagg tctcggtgat 81540
ccagcgcctg ctggcggcct tcggcgccac cggcatcgag caggtgctga tgcccaccga 81600
catgaccggc atcgccgccg cggtgcagaa gaacagccgc agccgccagg cccgggagca 81660
gcactggccg gccctggaat tcctcgacct gaccctgcgc cagagcgtcg aggacacccg 81720
ccaggcagcg cgctggatgg ccgagcgcgg ggtgtcgctg atcgccgtgc tcggtggcga 81780
tggcacccac aaggcggtgg ctgccgaggt tggcgacatt ccgctgctga ccctgtccac 81840
cggcaccaac aacgcctttc cggagctgcg cgaagccacc agcgccgggc tggccggtgg 81900
gctctacgcc aacagccggg tgcccgccga gatcgccctg cggcgcaaca agcgcctgct 81960
ggtgcgcgaa ccgacccgag gcctgtgcga ggtggccctg gtggatgtgg cggtgtcgcc 82020
cctggccttt gtcggtgccc gggccatcag ccgcgccagt gatctggccg aggtattcgt 82080
gaccttcgcc gaaccgcagt ccatcggcat ttccgcgctc tgcgggctgt ggctgccggt 82140
gactcgccag gaaccccacg gcgcctggat gcgcctggac ccgcaatccc ccgaggcgct 82200
gctggtgccc ctggcccccg gcctgctgca gggctgcggg gtgctggacg ccggctacct 82260
gcaacccgat gtgccccagc ccctgtgcct gaacgccggc accctggccc tggatggcga 82320
gcgcgagatc gaattcaacc cccacgaccg gcccacggtc accctggatg ccggcggccc 82380
gctgagcatc gacgtcaacg cggtcctgga acacgcggcg cgccagcgcc tgctggccat 82440
cgaccgcgat caccggcaac accccgtgaa ccttcagtcc gaagacaccc tggagaataa 82500
aaatgtcgac acccctgacc actgaccagt tgctccacgc ctaccgggtg atgcgcacca 82560
tccgcgcatt cgaagaacgc ctgcacgtgg aattcgctac cggcgagatc cccggtttcg 82620

```
tccacctcta tgccggggaa gaagcctcgg ccgccggggt catggcccac ctgcgcgacg  82680
acgactgcat cgcctccaac caccgtggcc acggccattg catcgccaag ggcgtggacg  82740
tctacgggat gatggcggag atctacggca agaagaccgg ggtctgccag ggcaagggcg  82800
gctccatgca catcgccgat ttcgagaagg gcatgctcgg cgccaacggc atcgtcggtg  82860
ccggcgcgcc gctggtggtg ggcgcggccc tggccgcccg gctgcaaggc accgacggcg  82920
tgtcggtggt gttcttcggc gacggcggct ccaacgaagg cgcggtgttc gaggccatga  82980
acatggcctc ggtgtggaac ctgccgtgcc tgttcatcgc cgagaacaac ggctacgccg  83040
aagccacggc ctccaactgg tcggtggcgt gcgaccacat cgccgaccgc gccgccggtt  83100
tcggcatgcc cggagtgacg gtggacggtt ttgatttctt cgccgtgcac gaagctgccg  83160
gcgccgccgt ggagcgggcc cgggccgggg aggggccgtc gctgatcgag gtcaagctga  83220
cccgctacta cggccacttc gagggcgacg cccagaccta ccgcgccccc gacgaggtca  83280
agcattaccg cgagcacaac gactgcctga tgcagttccg cgagcgcacc acccgttcgg  83340
gcctggtgca ggccagccag ctggaccaga tcgatgccga cgtggaagcg ctgatcgaag  83400
acgcggtgcg caaggccaag tccgacccca agccgagccc cgccgacctg ctcagcgacg  83460
tgtacgtcgc ttatccataa cgccccacag aacaacaaga gaccaccatc atggcgagaa  83520
aaatcagtta ccagcaggcc atcaacgaag ccctggccca ggaaatgcgg cgcgacccca  83580
gcgtgttcat catgggtgaa gacgtggcgg gcggcgccgg cgcccccggc gacaacgacg  83640
cctggggcgg cgtgctcggg gtgaccaagg gcctctacca tcaattcccc gggcgggtgc  83700
tggacacccc gctgtcggag atcggctacg tcggcgccgc ggtcggcgcc gccacccgtg  83760
gcgtgcgccc ggtgtgcgag ctgatgttcg tcgacttcgc cggctgctgc ctggaccaga  83820
tcctcaatca ggcggcgaag tttcgctaca tgttcggcgg caaggcccag accccgctgg  83880
tgatccgcac catggtcggc gccggcctgc gcgccgcggc ccagcactcg caaatgctga  83940
cctcgctgtg gacccacatc cccgggctga aagtggtctg cccctcgtcg ccctacgacg  84000
ccaagggcct gctgatccag gccatccgcg ataacgaccc ggtgatcttc tgcgagcaca  84060
agctgctcta cagcctgcag ggcgaagtgc cggaggagtc ctacgcgatt cccttcggcg  84120
aggccaactt cctgcgcgac ggcaaggacg tgaccctggt gtcctacggg cgcacggtga  84180
ataccgccct ggacgcggcc cgcagcttgg ccgggcgcgg tatcgactgc gaggtgatcg  84240
acctgcgcac caccagcccg ctggatgaag acagcatcct ggaaagcgtg gagaagaccg  84300
ggcgcctggt ggtgatcgac gaagccaacc cgcgctgctc catggccacc gacatctcgg  84360
ccctggtggc gcaaaaagcc ttcgcttccc tcaaggcgcc gatcgaaatg gtcaccgcgc  84420
cccacacccc agtgccgttc tccgacgccc tggaagacct gtacatcccc gacgcggcga  84480
agatcgagaa agccgtgctc actgtgatcg agtggagccg ctgatgagcc agatccatac  84540
cctgaccatg cccaagtggg gcctgtcgat gaccgagggc cgggtcgatg cctggctcaa  84600
ggaagaaggc cagagcatca gcaagggcga tgaagtgctg gacgtggaga ccgacaagat  84660
ctccagcagc gtcgaggcgc cgttctccgg catcctgcgt cggcagatcg cccgccagga  84720
cgagaccctg gcggtgggcg cgctgctggg catcgtggtc gatggcgagg ccagtgacgc  84780
cgagatcgac gcggtgatcg agcagttcca ggccagcttc gtgcccggcg acagcgccga  84840
tgaagatagc ggcccggcgc cgcagaaggt cgaactgggc ggccgcctga tccgctattt  84900
cgagcgcggt gaaggcggta cgccgctgct gctggtgcac ggctttggcg gcgacctcaa  84960
```

```
caactggctg ttcaaccacg aagccctggc cgccgggcgc cgggtgatcg ccctcgacct  85020
gccgggccat ggtgagtcgg ccaaggccct gcaacggggc gacctggacg agttgagcca  85080
ggtgctgctg gcgctgctgg atcacctgga gattcccgtg gcccatctgg tgggccactc  85140
catgggcggc gcggtgtccc tcaacaccgc gcggctggcg ccggaccgcg tgcgcaccct  85200
gaccctgatc ggcagcgccg ggctgggccg cgagatcaac ggcgactacc tgcaaggttt  85260
tgtcgaggcc agcaaccgca atgcgctcaa gccgcagctg gtgcagctgt tctccaacgc  85320
cgagctggtg aaccggcaga tgctcgacga catgctcaag tacaagcgcc tggaaggggt  85380
gcaggcggcc ctcgggcagt tggccggcaa cctgtttgcc gacggccgcc agcacgccga  85440
cctgcgcccg gtggtgcagg acggcccgca gccggtgctg gtgatctggg gcagcgacga  85500
ccggatcatt ccggtgagcc acagcgccga tctcaaggcg cagatcgagg tgctgccggg  85560
gcaggggcac atgctgcaga tggaagcggc ggagcaggtc aaccgcctga tcctcgactt  85620
tatccagcag cactgaggtg ttctgcggcg gccagggggc cgtcgcagct ctacaagaat  85680
aaggagaagc caagatgagt gtttccctca agcctgtttc cagcatgcgt gccgcggtct  85740
ggcacggccg ccacgatatc cgcgtcgaag acgtaccgct gcccgacgcg ccgcctgccg  85800
gctgggtgca gatccgcgtt gactggtgcg gcatctgcgg ctccgacctg cacgaatacg  85860
tggccgggcc ggtgttcatt ccggtggacg caccgcaccc gctgaccggg atcaagggcc  85920
agtgcatcct cggccacgag ttctgcggcg aaatcgtcgc cctgggcgaa ggggtccagg  85980
gtttcagcgt tggccagccg gtggccgccg acgcctgcca gcactgcggc acctgctact  86040
actgcaccca cggcctgtac aacatctgcg aaaacctggc ctttaccggg ctgatgaaca  86100
acggcgcctt cgccgaattg gtcaacgtgc cggccaacct gctgtacgcc ttgccggcca  86160
actttcccgc cgaggccgga gcgctgatcg agccgctggc ggtgggcatg cacgcggtga  86220
aaaaagccgg cagtttgttg gggcagaacg tggtggtggt cggcgccggc accatcggcc  86280
tgtgcaccat catgtgcgcc aaggccgccg gcgcggccca ggtgatcgcc ctggaaatgt  86340
ccggcgcgcg caaggccaag gccctggagg tgggcgcgac ccacgtgctc gaccccaagg  86400
agtgcgatgc cctggccgag gtcaagcgcc tgaccggcgg gctgggggcc gatgtcagct  86460
ttgagtgcat aggcaacaag cacaccgcca agctggccat cgacctgatc cgcaaggccg  86520
gcaagtgcgt gctggtgggg atattcgaag agcccagcga gttcaacttc ttcgagctgg  86580
tggccaccga gaaaacggtg ctgggggccc tggcctacaa cggtgagttc gccgatgtga  86640
tcgcctttat cgccgatggc cggctggata tttcgcccct ggtgaccggg cgcatccagc  86700
tggaagagat tgtcggccag ggcttcgagg aactggtcaa caacaaggag cacaacgtca  86760
agatcatcgt gtcccccggt cagttgcgac gctcgtaaac gagcgatttg gcgatggccg  86820
gccgcggcca tcgcactttt ttacagtttt gcgttctatc acctggcctg gccgcgccga  86880
tccccgccgc agcccgtgaa ttccgacccg gtgccgatgg cctacgctcc ctcttcttgc  86940
atgatgcaaa cccgctttca gcgcctgttc ctggtggcgc tgctgatgct tggcgccacg  87000
gcctgtaccc aacagcaagg gcgcgatttt gccaaacagt ttcgtgaagg caagcctgac  87060
gaattcttcc agaccagcgt cgatcgcatg gccaccatcg gcatgcgcga caacctgcag  87120
agcctgtacc tgctgatggg caagctctac ctgcgcaacc ccagccagtg gcgcaagtcg  87180
ggtttccccg atggcaccac ggcccagcgc gagatccgca atgccatcga aaagcgccag  87240
ccgctgccgg ccctggggga tcgtcgcgac ctggcggccc tgagctattc cctgagcccg  87300
gagttccagg gcgatcgggt gggggcgttc atctatgcca ttggcagcat gctggtgacc  87360
```

```
gcccatggcg ggcgcaccga gttctacatg accgatacca tcgacccgca gttcatcagc  87420
aacgccgcgc gcaatatcga gaaggccacc tggctgctga gccagcgcca ggatgccaat  87480
ggggtgctgt tgctgttctc caacgagatt tccgaggagg gcagcaacct gagttttgcc  87540
gtggagttcg gcaagatcgt cgcgcgcctg gatttgctca cgcagattct cgatgagcgc  87600
taccggcggg tggggttcaa ttacgcgcag agcctgctgc tgatgaattt cttgccggtg  87660
cagtaggagc tggcttgcca gcgaaggcgc ccgtccaggc gctgcaaggc ccaaggacct  87720
gttcgccggc agccggctcc tacacggcgt ttggcttggc cctctctcag gtcattccga  87780
gtttttacg cgccatcaac agggctacga cgctcaacgc tgccgccagc atcaggtaga  87840
aactcggtgc cagctgtgag ccggtcaggg caatcaatcc ggtagcgatc accggggcaa  87900
aaccgccgaa gatcgtgacc cccaggttgt agctcaggga catgccggtg acccgggtgc  87960
gcaccgggaa gatgtccgcc atcagcgacg gcagcggggc gaagtacacc gccttgatca  88020
gggccatcag cgccaccacc agcagcagcg aactggcact ggggcggctg ttgagccaga  88080
agaacgccgg caggatcgcc acggcataga ccaccgccgc tgccagcatg attttcaggc  88140
gccctatatg gccggacagg tagccgacga tgggcgtgat gatggtcagg atcaggccgc  88200
cggtaagggt cgccaaaaag cccgaggact gggcgatgtt caggctggtg gcggcgtagg  88260
agggcatgta ctggatcatg tagttcgagg cggtcgacac caccagggtg cccatggcga  88320
tcagcagcag ggtcttctgg gtcaccagca cttcgcgcaa agggcgttcc cccggttcgc  88380
tggccttgaa gtccggcgac tcgtccaccg tacggcggat gtacaggccc accgggccca  88440
gcagcaggcc gaagaagaac ggcacgcgcc agccccagtc gagcatctgc tgtgcatcga  88500
ggtgcttggt caggaagtag ccgaaggtcg aggcgatgac cacgccaaag ccctggctgg  88560
cgaattgcag gctggcgaca aagtgccggg tgcgcggcgg cgcgtgttcc agcatgaagg  88620
cggtggaggt gccgaactcg ccaccggcag agaagccttg cagcagccgg gccaggagga  88680
tgccgatcgg cgcggcgagg cccagggtgg cgtagctggg catgatggcg atcagcaggg  88740
tgcccgtcag catgatcagg atcgacaggg tcagggcctt cttgcggccc ttgcggtcgg  88800
cgtaggagcc cagtaccgcc gcgcccaggg ggcggatcag gaacgagatg ccgaaggtgg  88860
cgaaggccag cagcagggag aaggtcgggt ccgcggtggg aaagaacacc tggctgatgg  88920
tcagggcgaa gtaggcgtag atcgacaggt cgaaccactc cagggtgttg ccgatcaggg  88980
cggcgcctat gggtttccac agggccttgg gttcgacccg gggcgcggtc gaggtggtgg  89040
ctaacgctgt catacaggac gctcctgctt attgttggat tttgagcgac aggtgcccgg  89100
ccagggccgg gcggggtaag cgatggcctc aggtccgggg caggtccccc aggtcccaga  89160
acagggccgt catgatctcc aggccttcac gaatcaccgg cagcagcagg tgttcgtccg  89220
gggcgtgctg cgagcagccg gggtaggagt ggggaatcca cagggtcggc agccccagca  89280
cttcggcgaa gatgtcgttg ggcagggtgc ccgccaggtt cggcaacagc gccaggcgct  89340
gcgcactgct acctgcaatc gaggtcttgg cgaacctgac ccaggggttg tccgggtcca  89400
ggcgggtggc cggggagcag cgctccatga cgatctccac ctggctgaaa ccttcacggt  89460
ccaggtgcgc ccgcagcagg ctttccagct gctgccaggg cgtgccgagg acaaagcgca  89520
attggcagaa ggccacggcc cggggcggaa tcgcgttcac cggcttttgc gggttgccgg  89580
cgctgaaggc gaggatttcc agggtgttcc aggcgaacag gcgctcgccc agggtcagcc  89640
ccggttcgcc ccagtgttcg tccagagggc ggcccaggga ctcgcgctgg atctccaggt  89700
```

```
cgacgatggc ggcgcgcacg ttgtcgggaa tgttcgccgg cagcagttcg cggcagcgga  89760
tgcggccgtt ctggtccacc aggctggcca gggcgttggc cagtaccacg ccggggttgc  89820
tcatcacccc gccccagttg cccgagtgca ggcccttgtc ccgggtgttg acctccaggc  89880
ggaactgcgc cgagccgcgg gagccgagga acagcgtcgg ccgggcctga ttcagccgtg  89940
ggccgtcgga ggcgatgaac acatcggccc gcaacagttc gcgctgctcc tggcacagct  90000
ggcgcagccc cggggaaccg gcttcctcac ccatctcgaa cagcagcttg aggttgaagc  90060
ccaggcgccc gtcgcgggcc tttagcactt gctccagggc ggtcaggttg atgctgtgct  90120
ggcccttgtt gtcggcggtg ccacggccgt accagcgttc accctccagg gtcagctgcc  90180
agggattcag gcccgtgcgc cactgttcgg cgtaacccgg caccacgtcg ccgtggccgt  90240
agctgagcac tgtgtgcagg gctgggtctt ccaggcgcgt ggcaatcagg aacggcccac  90300
cggcctccgg gttggccagc agctgacagt cgaagcccag gcgctgcagt agcggctgga  90360
tttcctccag caggtagcgc ggcaactcgc tggcgtgggc cgggtcctgg ctgtcactgc  90420
gaaacgccac ccggcgtcgc aggtcctgtt caaagtggcc gtcgtccagg tactggcgaa  90480
cgccggcgag ggcagcttgc ttggtcattg caactccggt cgggcaaggg gaacggaccc  90540
atggtggagt tggcaaaggc atctgtatat tgctgttttt tgaaggcatg attctaaaaa  90600
ttggatgcct ggcaagggga cgcacatgga ctatcggtat tttctggcgg tgatcgatgc  90660
gggctccctg gccgcggcgg gggagcgttt gcacatcgcc cccagcgcgg tgagccggca  90720
gatcgccctg ctggaagaga gcgttggcgt ggcgctgttc gagcggcgcc cgcggggcat  90780
gcaactcacc gccgctggcg aagccctggc cgaacacgcc cggcgcacct ggctggaaca  90840
ggagaacatc ctcgccgaac tgcggggcga gggttacccg gggggccaagg tgatccgctt  90900
ggtatccacc gagggcctgt cgcggtattt cctgccccgg gtgctgctgg agcattaccg  90960
cctgcggccc ggagccgagt accgcctgga cgtgatctcg ccccacgagt gcgtgcagcg  91020
cattcgccgg ggcgaggcgg acgtggggct gaccttcagc accgagcccg tggagggggt  91080
caacgtgtgc tactcgatcc gctcgccgat tcgcgccctg atgcgcgccg ggcatccgct  91140
ggccagcgcc ggggtgctgt cactggagca ggtgcaggcg tttcccgtgg ccttgacgcc  91200
caagggcacc acccagcggc aactgctgga cctggtgtgc cagatggacg gcctgagctt  91260
cgatcaggtg atgacctgca acttctccgg ggccctgcat gagtttgtgc gccagtccga  91320
cacggtggcc tttgccagtg ccatcagcgg cgaagggcag gggatggatg ggctggtatc  91380
ggtgcccctg tccaacccgc gcttgggcga tcgggacatt caggtgctga ccatgcccaa  91440
gcgggtgttg ccggaaagcc tggcgttctt tatcgacacc ttgattgcgc ggttgcagaa  91500
agagggctga gggaggctgc tgaccgttct cgccgagccg gacacgctca gggcgctggg  91560
cgagttcctg atcaaggctt cagccgacat ggcggccaat ggcctggagc atgtgcacct  91620
gcaagacgtg atcgagcact tctcgcacca gcagcatgtg gatgtgattg ccctcgaccg  91680
ggcgctgatc aagcctgcct gaggcagcgc cgtgcccggc ccggcttaca tgttgcgaat  91740
cctctcgtcg accctgagct cgaactcgaa gccaatgccc acgtcattca gggtttcggt  91800
gacccgggcc atgaagtact cggcctgcgc gggcaattca tacaagccaa tgacccggat  91860
gatcgggtac ttgccatagg cgccggggat ctcggtgtag atctcgccac tttcgatgaa  91920
ggcgatgtag ctgttgattt tctcttgcag cacgagcaag tgctcgcctt gttccgcctt  91980
gtcgccccat tccaggtggt cggtcatcac cagtagcagg tcgttgggag cctccttgga  92040
gatcccccag aaatcgatga ctttgggatt ggtgacggac atggctgatc cttcaggcgg  92100
```

```
cgggggcggg gattgtatta cgtgccccgg ggttcgtggc ggtgctgttg cgcgtgcggc  92160

atggatgggc atgcagcgca cgatgcagga actgttctag tgaccgggcc gggccctgaa  92220

ggcgagaacc gccccggcga ttttccaaca accgttgcgt aatggatagt tggccatagg  92280

atgtgcgcgt tcccgatgat gatcgggccc ccatcgtcgt gatcctttac tcagtttcaa  92340

ggttgctgca tgaatccgga tgacttcaag aaattcaata tcggctccat tgttcgggcc  92400

actcaaagct ctgctgcgct caaacaccag ctcggattcc tgatcagggt tctggaggaa  92460

ctggatatcc agttctccga ctgcgagcag gatcctctgc gcctggcgaa agcctatgtt  92520

gccggggaaa ttcctgctga acgctgcaag gcgcaggctg cactctggtg ggcaaaaatc  92580

gatgagcaag gggcaatacg agggttcaag gatcgggagg tattgaaggc acgactggcc  92640

atttgtctgc tgtcgaatga tgaggacgat atttccgtgt tgggagataa cctctcgtgg  92700

tttcttgagg tgttgggttt cttgaaagtg gaaccgatga agccaattga aatgatgaga  92760

gagtatttcg agttcaaata gaagttcatt cgcgcccggc tcgctctcgg tgccctggcc  92820

ggcagcctga cgacaggcaa gaccccatgc gttttgctgg ctccccccgt cacgctggtg  92880

gggtgctcga cgcgttttcc atgagccgca tgtggatttc attgcgcttg atcgggcgct  92940

gatcctgcct gcacaaggtg ttcctgcgcg cggctcaatc ggcgagcgcg caggggggcga  93000

gctacaggct gggagcctct tcgttcactt tcagctcgaa atcgaagccg atgctccgtt  93060

catggaggat ctcggtaatg cgtttgaaaa accaatcgac ttgctcgggc agttcgtgca  93120

aacccagtac ccggataatc aggtgcttgc cgcaggcatc gggaatttcg ctgtagatct  93180

cttcactttc gatgaaggtg atgtaggtgt tgatcttctc ttgcagcagg agcaggtgtt  93240

cgctgtgtgc cgcttcgtca ccccattcga gggggtcgac catgatcaac agcaggctgt  93300

cgggcgcgga tttggggatg gcccagatat cgatgacttt tggattggtg atggacat    93358
```

```
<210> SEQ ID NO 2
<211> LENGTH: 52750
<212> TYPE: DNA
<213> ORGANISM: Pseudomonas protegens PBL3
<220> FEATURE:
<221> NAME/KEY: misc_feature
<222> LOCATION: (1)..(52750)
<223> OTHER INFORMATION: Pyoluteorin biosynthesis gene cluster
<220> FEATURE:
<221> NAME/KEY: misc_feature
<222> LOCATION: (8367)..(8371)
<223> OTHER INFORMATION: N is an A, T, C, or G
<220> FEATURE:
<221> NAME/KEY: misc_feature
<222> LOCATION: (8398)..(8485)
<223> OTHER INFORMATION: N is an A, T, C, or G
<220> FEATURE:
<221> NAME/KEY: misc_feature
<222> LOCATION: (8488)..(8488)
<223> OTHER INFORMATION: N is an A, T, C, or G
<220> FEATURE:
<221> NAME/KEY: misc_feature
<222> LOCATION: (8502)..(8502)
<223> OTHER INFORMATION: N is an A, T, C, or G
<220> FEATURE:
<221> NAME/KEY: misc_feature
<222> LOCATION: (8508)..(8508)
<223> OTHER INFORMATION: N is an A, T, C, or G
<220> FEATURE:
<221> NAME/KEY: misc_feature
<222> LOCATION: (46331)..(46332)
<223> OTHER INFORMATION: N is an A, T, C, or G
<220> FEATURE:
<221> NAME/KEY: misc_feature
<222> LOCATION: (51264)..(51501)
```

<223> OTHER INFORMATION: N is an A, T, C, or G

<400> SEQUENCE: 2

```
agtgttcaac ggcgttcggg tcacccgcct tttgcgcgag aacgggcggg tctgcggggt     60
gcagatcgag gacagcgaag gcgggcagcc gcagcaggtg cgctgcgcgg tcctggcggt    120
cgctaccggc gcctgggccg agcgcctgcg cccggcggac cgcgtgcgcc aactgcggcc    180
cttgcgcggc agccatctgc tgctgccggg ctggcgcttg ccggtggccc aggccttcag    240
cttcatgcat gccgaggatg gccggccggt gtttgtcttc cctgggaggg gcgccaccgt    300
ggtcggcacc accgacctgg atcaccgcga tgacctggac cagagcgcca gcatcagcca    360
ggaagagctt gagtacctgc tggccgcctg cgcccagcag tttccccagg ccctgatcac    420
tgccggcgac gtgctgtcga cctgggccgg ggtgcgcccg gtggtggcca gcagcgacgg    480
ccagcagggc aagccttcca atgaaacccg cgagcatgtg ctgtggcagg aacccggctg    540
cgtgaccctg gccggcggca agctcaccac cttccggccc caggccatcg aagtgctgca    600
ggcctgcggg gcgatgctcg ggcgtgaagt ggtggacgac ggcgccccgg tcttcacgcc    660
tgtggcgccc ctggagatcc ccggtctgag cggcgcccag gtgcggcgcc tggctggccg    720
ccacggccgc catctgccgc ggctggcgca gtgggtggcg accctgggcg gtgattgcgt    780
cggcgccagc gacaccctgt gggccgaact ggcgtttgcc gccgaggcgg aaatggtcct    840
gcacctggac gacctgctgc tacgccgcac ccgcatcggc ttgctgctgg ccgagggcgc    900
cgcccagtac ctgccggcca tccgccgcct gtgccagccg cagctgggct gggacgacga    960
gcgctggcag gccgaggaac agcgctaccg ggccctgtgg caacgccatc acagcctgcc   1020
gccactcgcc taacgatgct caaccaagag agccccatgg ataaccacaa caacaataag   1080
caggactacc tgctggccat cgacaacggc acccagagcg ttcgtgcgct gctgttcgac   1140
ctcaaaggca acctgctggg caagggcaag gtggagcttg aagcctattt ttccagccgg   1200
cccggctggg ccgaacagca cccggactac tactgggcca agctcggcga agcctgccaa   1260
ctgctctggc agcagaccgg catcgaccgt tcgcagatcc gcggcgtgtc cctgaccacc   1320
cagcgcggca ccctgatcaa cgtcgatgcc cagggccgcg cgctgcgccc ggcgatcctc   1380
tggctcgacc agcgccaggc cgaggtcgaa ggcaagatca aggggccctg ggctggctg    1440
ttcaagttga tcggtgccga ggccacggtg gattattttc gcgcccaggc cgaggccaac   1500
tgggtggcac aggagcagcc cgaggtgtgg gccgccaccg acaagttcct gttgctctcg   1560
ggctttctca cccatcgcct gaccggcaat ttcgtcgact cggtgggctg ctgcgtggcc   1620
tacctgccgt tcgactacaa acgcctgcgc tgggccgccc ccagtgactg gaagtggcag   1680
gccctggcgg tgcgccagga gcagttgccg accctgctca agcccgggga aaccctgggc   1740
cggatcaccg ccgaggccag ccgccatacc ggcatacccg aaggcctgcc gctgattgcc   1800
gcgggtgccg acaaggcctg cgaagtgctg ggctcgggcg tccaggactc caccaccgcc   1860
tgcctgtcct acggcaccac ggccaccatc accaccaccc gttcgcgcta cctggaagtg   1920
gtgcctttga taccgccgta cccggcggcg gtgccggacc actacaactg cgaggtgatg   1980
atctttcgcg gctactggat ggtcagctgg ttcaagcagc agttcggcct gcgcgaagtg   2040
cagcaggcgg cggagcaggg gctggagccg gagcagctgt tcgacgccct ggtccaggcg   2100
gtgccgcccg ggtccatggg cctgaccctg caaccctact ggtcgccggg catccgcgag   2160
ccgggcatgg aagccaaggg ggcgatgatc ggctttggcg acgtgcacac ccgggcgcac   2220
atctaccggg ccattctcga aggcctggct tatgccctgc gccagggcat ggagcgcatc   2280
```

```
gaaaagcgct ccaggctgaa gatcagccgc ctgcgggtgg ccggcggcgg ctcccagagc   2340
gacgcggcca tgcaactgac ggcggacatc ttcggcctgc cggtggagcg gccccatgtc   2400
tatgaagcct cggggctggg tgcggtgatc gcctgcgcgg tgggcctggg gctgtacccg   2460
gacttcgcca cggccatcag cgccatgacc cgggttggcg cagtgttcga gccccagccc   2520
caggcgcagc agatgtacca gcggctgtac agcgaggtct acctgcgcat gtaccgccag   2580
ctcaagccgc tgtaccagag cattcgcgag attaccggtt acccggctta gcgaaagcgc   2640
cggccagcgg ccggcagggg gggcgaacct ctgcggggta aaaagttctt ccaggcgcca   2700
gggctgatct atcgtgatca aggggcaggg ccccttcgac cccccaacgc ctgcgagacg   2760
agcatgaacc gccaggaagc gctgaacatc ctgtggaagc gactgttcct catctttgtg   2820
ctgctattgg cggcatccct ggtgtcggtg gccatggccg atggctacac cattccctcg   2880
gtggtgttca ttgccggcaa catcggcggc tatgtcggtt ttcaccgcca gctttccagc   2940
ctcagcgagg aggaaatcat tggctgtgc agttcctggt tcagcctggt actgccgtca   3000
ttcatcggcg gcatcctcgc ggggctgctg tatatcctgt tcatttccgg ggtggtgcaa   3060
ggggagctgt ttccaaagat cgtcgccgat gaaacctgtc gctacagcga gaacagcttc   3120
tatgtgatct tctgccagca cgccggtggc tatgccgcct acgccaagct attgttctgg   3180
tcctttgtcg cggggttcaa ccagaactac gtggtggacc tgatcgacaa catcaagggc   3240
agccagaaga cggagaatca gccatgagtg aacagagcaa agggccggcg tcgtacttcc   3300
cctccattga aaagcactac ggccagccca tcgggcactg gctggagctg ctggcaacgg   3360
tcgacggcaa aaagcatatg gagctggtgg cctggctcaa gaccgaacac ggcatgggcc   3420
atggccacgc caatgccctg gtggcgcact tcctggcggc cagcaagggc cgctagtccc   3480
cggggcgcca ttcttcgcca gtgaaagcct gactgccgac atccgctttc ctggcgaaaa   3540
aagccaaatt cccctgtgtt ctcttcgttc tttcctacgt cgcaccttgc attgccctct   3600
ttctgcctgt cggagttttc tcgatgtctt cgccaaaatc cttgcccacg gccctgttgg   3660
gcctggccct ggcctgcccg gcatttgccg aaacccgtgc cgtggagctg gctccggcgc   3720
aggtcctggg gcaggaacag ggcggtgagg ggcagccggc gcaggaggcc gcggcgcggc   3780
tggcccaggt gcccggcggc accaatgtgg tggacatgcg ccgcccgctg cagggccggg   3840
tggccagcaa ccaggatgtg ctggcctacc agcccggggt ctatgcccag tcggcgggca   3900
acgaaggggt gaagatctcg atccgcggct cgggcatcaa ccgcgcgccg ggtgcccatg   3960
cctcggggct gtatacgatg ctcgacggct tgcccctgac cggcccccggt ggcacgccct  4020
atgaattgct ggagcccttg tgggtcgacc acgtggaagt gctgcgcggc gccaacgggt   4080
tcgaccgtgg cgccctggcc ctgggtggcg ccatcgatta cgtcagccac accggctatg   4140
acgcaccgct gttgcaggta cgctacgcca ccggtagcca cggttatcag cagcgtcagg   4200
tcagttccgg gcaagtgctg gggatttcg actattacgt gtcactgacc gactccaatg   4260
ccgacggcta ccaggatcac acccgcagcc agagcaaggg gctgatcggc aacttcggct   4320
accgcttcaa cccgaacctg gaaacccgct tctacctgcg ctaccgcgag accgacaacg   4380
atctggccgg gcgcgtgacc aagcgctcca tcgaacacga cccgcgggcg gccaacccgg   4440
cctacgtcag ccgcgacgac cggcgcaagc agccgggcag taccttttgtc ggcaacaaga  4500
ccacctatta cctggacgac gattcgagta tccaggccgg gctggtgtac cacgactacc   4560
ccatggacct gcgcgaaggc cccaaccgcc tgaaggtggc ctacagcgac gtcagcggca   4620
```

-continued

```
ccctggacta caagcgccgc gacagcctct ggggcctgga aagccgcagc accctgggcc   4680
tgcgggtgac caagcacctg cccaatgacg gtgccagcga gttcgtgcgg attcccaccg   4740
gcaataccgc gaactacgcg ccgggcacgc ggatccgcaa cttcacttac cagggctcgg   4800
acaccgtcct gcacgttggc aatgacctgg agatcgccga cgacctgtgg ctgaccaccg   4860
ggctggcggc catctacacc cgccgcgaaa gcgcggtgac ctaccccgag ggcggcggca   4920
agaccagcct tggcgactgg gactacgcgc cgcgcctggg cctgcgctac cagctgaacc   4980
cggatctgca actgttcgcc aacctcagcc gctcggtgga agcgccacac ccctggtcgc   5040
tgatctacag cgccaatcag cgttttccgg ccggcagcgg cgtcgccacc ggcgcccagc   5100
gcgacccggt caagctgcgc aatcagaccg ctaccaccct ggaactgggc gggcgtggcg   5160
atagcagcct gggccagtgg agcctggcct ggtactacgc ccaggtgcgc cacgaactgc   5220
tttcggtgct gccggatgcc aacgccatca cgccttacga actcaacgcc agccccaccg   5280
tgcaccaggg cgtggaagcc agcctgcaga gcgagctgtg gtcgcgcccg ggcgtcggcc   5340
gcctgagcct gcgccaggcc tataccttca gtgatttcca ctaccgcgac gatcagcgtt   5400
tcgccgacaa ccgcctgccg ggcctgccca tgcactacta ccagggcgag ctgcgctacg   5460
actggcccct gggcttcttc gccgcggtca atacccagct ggtgtccaag gtggcggtgg   5520
attacgccaa cagctactac gccgatccct atgcgctgtt cggcgccacc ctgggctaca   5580
acgcgccgaa gaacgactgg cagacctggg tcgatgtgcg caacctgacc gacaagcgct   5640
acgccgccac cgtgaccccg ggctatgacg acaaggggct ggacgcggcg cgttcaacgc   5700
cgggggaagg gctgggggtg tacctggggg tgtcctggag cctgcgctga aagcagggcc   5760
gcgagcgagc cgacaccccc caatgaaagt gcccgcagca gcgggcacct ggttcatgcc   5820
gggcggtgtc agcccgggcg gcagtgattt accactggcc cgagaacacg caggtcagcg   5880
cttcgatggc gctgaacttc cacagcgagt cgccgcagtc gctggcaaag gcgtgggcgt   5940
tggaggcggt gagggccagg gcgatggccg aggcatagac gattttcttg agcgacatgg   6000
gaaaactcct tgttatgaat ccgcacgttc ttgtaggcgc cgtcctgaag gggggggct   6060
gctgcggact ataggcccgt gctgcccccg gcactattag cccgagtgtg ctaatggccc   6120
atgcgcatca ctgtgccgcc cggcccaggc tcagttgcga aaatacagct cgtccagctg   6180
ccgccggcgt atcaccaggt actcctccca gaccttgggg aaatcctcgt cccgggtcag   6240
ggggaaggtc aggtagtaag tccgaccgct gacactgatg tactcccgca cccgcttgta   6300
cgccggctgt tccagcagcg agatgtattc gtcataggcg tagtggtagt gggaaatcgt   6360
cacccgatgg ggcgcgatca tgcagcggga gaagtcgatc acccagccat ggctcatgtc   6420
gctgcccagg tagccgtaga ccccatcctc ggagaggctg atggcttttc gtgcctgtac   6480
cccatcctca tcgttgacca gcacgatctg gctttcgaag tagcggatgg cctgttgctc   6540
ggggccgcgc aactgcaggt tccagccgac ggcgcccatg cggaactcgc cctgctcggt   6600
atattcggca gtccagccgt tggcaaggct aatgcggtgt gtggtcattg tcgtcctggt   6660
gatggctgtc cctgaaggct ggggattgta cgtcagccgc tgtgcgaagc ggcagggccc   6720
gtggcgcccg gtcagtcatg ccagcatgcg agctgtcctg tgactgtggc cgtgccctgt   6780
ggctagttcg ccagtgcgtg gcgcagatgc gccagggccc gggtttcgac ctggccctgg   6840
tcgctccccg gactgaagac cgcgcagcag gcgctggtgc cggcgacgtt ggcgcgatag   6900
accgccagcg tgctgccggg gccgctgccg gtgtggccgt agagcgtcag gccagactcg   6960
acagtgccca ccatcaggcc catggcatag ccgggagcga cccagggccg gccggccatc   7020
```

```
ggcccgccca gaacctgggc ctgctgcatg ccagccagca gtgccggggg caatagcgcg   7080
ccgctcaaca gccgatccag cagcagcgcc gcctccgcca ggggccccac cagcaggccg   7140
tggtagaccc agccggggtg gtagtcgccc aactggccca ggtccacatc ccgcaggtct   7200
tcgcgggtca cagcgaggcg cgtgcgagac aagcccaggg gcgccagtac ccgttgttgc   7260
agggcaaggt gcaggggcag gtccgtcgcc tgctggatca gctgcgccac gaacaggtag   7320
cccacattgg agtagcgcca ctggctgccg gggcgtagc gcaggcggct ggcgtccagg   7380
cgctgcagca tctgtgcacc gggccatgca tcctcgttgc gcaaaaccgc gtcgtggtag   7440
tcgctcagct cgctgtagtc cgccagcccg gcctgatgcc gcagcaactg gcgcagggtg   7500
aaggggccct ggggcagcgg ctcatccagc cccagcaggc cgtcgcgcac cagggtcagg   7560
gccgctgcgc taagcacggt cttggtgaag ctccaccagg gcaccagtgg ctggggttgc   7620
tggggggcca gtggttggcc gttgtggatc agggcatgaa gcacggaggg gatgtccttg   7680
atgggctgtg ttgccgcggg ctgttgggtc aatcaggccg tgagcggccc tacagggtac   7740
ggcataatgc gcggccgttt tggctaaacc taggaattga tcaggaggat caggctggct   7800
atgtacagac ttgggcacat gatagacaac cagtgggtcg agcacagtta tccgccggta   7860
ttcgtggtgg cccccgttgg cgaggggcag cgcgtggtgg cgggcgttcc aggctcggac   7920
ccgcaggtcc tgctcagcct gctgggctgc ctggccgaac cgctggtgct gctgttcgtg   7980
ctgcacacgc cccgggacga atcgcaagcc ggacgctact ggagcccgca gctgtcgcgt   8040
gaggacgttc aggatttcat ctacgacttc aagccactgc tctgtggcga cagccgtttc   8100
gacctgtggg tccactcgcc cgagcaacag gccaccgtgg tctgggaccg gcacaacctg   8160
atctatggct acgggccgct ggaagactac gccacggccc tgcgcgcact gggcttcggc   8220
catggcgagc cgcagttgcc cgtgccccat acccaccact accacccgca gttggacgac   8280
ctgtgccggc agttgctcac ccacttcgat tggcagtact cgccattgcg acctgaggat   8340
gagcagtgat ggtgcaatca agcccannnn nctcatgctc ggtcaatctt ttgaattnnn   8400
nnnnnnnnnn nnnnnnnnnn nnnnnnnnnn nnnnnnnnnn nnnnnnnnnn nnnnnnnnnn   8460
nnnnnnnnnn nnnnnnnnnn nnnnngcnca tgcgggactc gnaggacngg cggcgtttag   8520
gaacggggcc gttgcggccc ccgatccggt ttgtcactgg ccgctgtgca aggccggcgt   8580
gcgcggtgga atcaggcgct tgctgccggt ggcctcgaag gccgaagcca ggcgcagcag   8640
gctcgagtcg tcataggcgc gcccggcgaa ggtcagcccc accggcatgc cgatgtccgc   8700
catcaccccc atgggcacgg taacggtggg cacccccagg tggcggatgg cgaggttgcc   8760
gttggccacc cacacgccat tgctccaggc gatgtctgcc gactcggggt tgatatcggc   8820
atcggccggg ccaacgtcgg ccacggtggg gaacagcacg gcgtccagcc ccaggcggtc   8880
catccagtct tccaggtcga tgcgccgggt ctgctccagg ccgcgcaggc cgtcggccag   8940
ggtgttgatc tggtcccagg tcttgagccc gcgcttggcc atgttcacgt attcgtccat   9000
gccggcggcc aggtcgtctt cgcggttggg cagggtgccg gggtcgtggg ggaagatctg   9060
cggcccgtcg acatccgcca ggcggttgag cttggggtcg tcgttggccc gcaggaagtc   9120
gtcgaaggcc cagcccgaga gctcccacag ctcgtcgtgg aggaactcct tgctgaccag   9180
gccgcggttg tacacggtcg gcgcgccggg gcggtcgccc tcgcagttgg acaccagggg   9240
gaagtccact tccagcactt gcgcgccggc ggcttccagg gcctggcgcg cctgctccca   9300
aaggctgatc accgagggcc gggtatggat gcgctggccg gtggggccgc cgatgcccgg   9360
```

```
tttctcgctg gtgccggcct cagggtcggc attgatgtac atgcgcggca cgccaaggcg   9420
cttgcccttg agcgccgcgg cgccggccgc cagttgcggg taggaggccg ggcgcaccga   9480
agcgacgctg ggatcggca cccagggttg caggcgccac aggtcgccgc gggtgtccgg   9540
gtcttcggcc accaccacgt ccagcacttc caggaggtcg gccatggtcc gggcaaaagg   9600
caccaccacg tccatggtcg gggtcagcgg ccagttgccg cgcaccgaga tcaccccgcg   9660
cgacggggtg taggcgcaca gcccgttgtt ggaggccggg ccacggccgc tggaccaggt   9720
ttcctcggcc aggccgaagg cggcgaagct ggcggcggtg gcggtgccgg cgccattgga   9780
cgagcccgag gcgaagggcg cggtcaggta agcggcgtta taggggcttt cggcgcggcc   9840
atacacgcca cgctgcatgc cgccgttggc catgggcggc atgttggtct tgcccaggca   9900
gatggccccg gcagcccgca ggcgctcgat ggtgaaggcg tcgcggtagg ccaccagctc   9960
ggcgaaggcc gggctgccgg aagcagccgt caggcccttg accaggtagc tgtccttggc  10020
ggtgtaggga atgccgtcca gcgggcccag ggtctggccc ttggcgcggc gctcatcggc  10080
ggcccgcgcc tcgttcagcg cctcggggtt gcgcaccacc acggcgttga gggcggtggc  10140
ggtgttcggg ccgtcatagg cctcgatccg cgccagatag gcctggacca gttccaccga  10200
ggtggtctgc ccggattcca gggcagcgcg caggtgggca atggagactt cggtgacttc  10260
gatcatgctg ctaccgccgt tggctggtgg gtgatgaggt gcagagggcg caacggggcg  10320
cgggttttcg ggtattggct gtgcatggtg attctcgtgg tacggctggc acgacaaggg  10380
tggcatggga acgctggggg cctttttagc atctagtgcg gggcagagga atcggcttga  10440
tggattattg cttcaggcca gctgcgccag ggcctgcggg ctccacgttg aactcgccaa  10500
ggtagtccag ggttgccgtg cttgcgggct ggcgttgatt ggcgccgccg gagatcgatt  10560
tgtggtcacc gtaaatcgac tcgcagccaa cgatgatgaa atggctgtag ccggagtcga  10620
cgcgcgtgcg cagctgcttt ttttcggcgt cgctgcggat cagcgattcc aggtattgcg  10680
ggccgtcttc actgccgatc agctcgacga aatcggagtc catgtagtac cccagctcct  10740
gtttgaggcc ccagctgggg ttgcgtgctt cccaagcgct gaactcggca tcgctggcgt  10800
cggccgcggg ttcgggctcc cactgttcga aggcaaaccg ttcggcctct gcctggtccg  10860
ggaaccgggc agcgaacagg tagaaaggaa agtaggcatc ggcttctgac atggacggct  10920
aggctccttg gttcagatca ggctggcgcg ctgcaaatgg ctgacatgag catggccggc  10980
ggcgctcaag cgcacggcca ggtcttcccg ggcctgggcc ccgccgctgc gcacgtactc  11040
cagctccgcg gcggtgatca gcaccaccgg caccagggtc acgggggaca gcggcatgtc  11100
ttccaggcgt gtcgggaagt ccggggccgg gccgcccacc agtaccccgg cgcagtcgtc  11160
ggcgctgatg aaatgcgctg gcagttgctc actcatggcg cgggactggc tgacgccggg  11220
cagttccagg gacagcaccc cgtagcgctg caggcgtgca gtgaggccac cggcatcggc  11280
cgtggtgttg gctacgcagc gcagcagttc gaaagcccag ctatcggcga acggatagac  11340
atcacccacc gcgccctggg catggggtgg gatgtccggg gtttcgacga acagttccat  11400
ctcgaaacca ttgcccagat catcacctgt gaccccatcg aacggatcgg acaggccctc  11460
ggtggcgaga atgatgccgt tgttgcgacg cacgatgcga taggcctggc gcgtggaggg  11520
ccagtgcgag ccgcccatga aactggggct gatggcgaag cccaggacgt cttgctcaca  11580
gtggccgacc gcttgccagt ggcgatcgag gcaggcggca ccggcctcca tcagggcaat  11640
gccggccagc tctgcttcgg ttggctggta ctgggcgtag ggctcctctg cggcggccgg  11700
ctcgccggcg ggcagggtgg gctcggcctt ttgtggcgcc ggctttttga agacgctgag  11760
```

```
cagtttttcc aggaaattca tcgggcgatc cttgcggggc aagtgcgttg cacaaggcgc  11820
acagcacagg ggtagagaga gggggcacat tgtgacgggt ttgccatgcc catggaaacc  11880
gacggatgca agttgcacga agccttgcct tgccggtgtg gctgcccgag aatccgcccc  11940
ggtccgctat caaggaaagt gatcagcatg tcttacccga agaagctaag tccggagttt  12000
tccggggcac tgagaacctt cagtttctgg gtcgccaacg gcaccttggg ctatccgttg  12060
ctggaaggcg tcgactaccg cagttgcctc ggggacgagc cgagcatgct ggagatggcc  12120
tatgccattt ttgccaatgt gctggagctg gacgagcagg gcgtaccggt gaatgccaag  12180
tacgccgagc accgggcggc gcagtacatc cgccagtatt gcgatccggg ctaccaggca  12240
cggccggcgt tcgaggactg ggagcaggag ctgtacggcc cgcccgaccg ggacgacagc  12300
aagccctggc cagccggcgt ggcctaggtt tttcgacggc tggatacaag cctcgggcac  12360
tatggcttcg aaacgacgaa ccccctcatc aaggattatg aatgtcgctg atttcgcaac  12420
gtgtagaact ggcccgccag ggtgccaacg acaaggtgat ttgccgcatg gcttcgggct  12480
gggcggtgat gggcgatgtg cagtttcttg agggctattg cctgttgttg ccggacccgg  12540
tggtggccag cttgaacgac ctggatgccc aggcccgggc cacctacctg ctggacatgg  12600
cccgcatcgg cgatgcgctg ctcgaggcca ccggagcgct gcgcatcaac tatgaaatcc  12660
tcggcaactc ggagcctgag ttgcattgcc atatctttcc ccgctacgcc tcggagccgg  12720
aaggcaagcg ccggatgccg gtgtggttct acgactggaa gaccgcgccg ccctatgtcg  12780
aggccgagca cggcccattg cgccagcagc ttgcccggat actggctggc caattgtagg  12840
agcgagcttg ctcgcgatgg tctctaacga aaacgccgca ctcactgggg gagcgcggcg  12900
tgcttgagtg cttcgcgagc aagctcgctc ctacaagggg ctgttgatca gcggtttgct  12960
gcgctccact tggctcgcgc tgcgtgcagc ttcttgtagc tgtcgatcag ccgcaggtgg  13020
cggtccaggc cttcgagctg caggttggtc ggggtcaggc cgtagaagcg cacgctgcct  13080
tgcaccgagc cgatcaccgc gtccatccgt tcgttgccga acatgcgccg caagttggcc  13140
tcgtagtcgc ccagctccag ctcgtcgtcc agctccactt ccagcaccgc gttcagggcc  13200
tggtagaaca gcccgcgctc gacggtgttg tcgttgtatt gcaggaacat ctccaccagt  13260
tccttggccg ggtcgaactg ccccagggcc acgtggatca gcagcttcag ctccaggatg  13320
gtcaactggc cccaggcggt gttgtcgtcg aactcgatgc cgatcagggt ggtgatgtcg  13380
gtgtagtcgt ccagttcgct ttcttccagg cgctccacca gcgagcgcag gccgtcttcg  13440
tccaggctgt gcaggttgag gatgtcttca cggaagaaca gcgccttgtt ggtgttgtcc  13500
cagatcaggt cgtccaccgg gtagatttcc gagtagtccg gcaccaggat gcggcaggcc  13560
gtggccccca ggtgttcgta caccgccatg tagacttcct tgcccaggcc ctcgaggatg  13620
ccgaacaggg tcgcggcctc ctcggcgttg gccgccgctc tttcaccgct gctgccctgg  13680
ctggtgaagt cccactcgac gaattcgaaa tccgccttgg cactgaagaa acgccacgac  13740
accacgccgc tggagtcgat gaagtgctcg acgaagttgt tcggctccat cagcgcctgg  13800
ctttcgaagg tcggctgcgg caggtcgttc aaaccttcga aactgcggcc ctggagcagt  13860
tcggtgaggc tgcgctccag cgccacctcg aagcttgggt gggcgccgaa cgaggcgaac  13920
acgccgccgg tgcgcgggtt catcagggtc acgcacatca ccgggaactc accgcccagg  13980
gacgcatcct tgaccagcac cggaaagcct tgttcttcca ggccctggat gccggccaga  14040
atgctcgggt acttggccag cacttcctga ggcacatccg gcagggccat ctcgccttcg  14100
```

```
agaatctggc gcttgaccgc ccgctcgaag atctccgaca ggcactgcac ctgggcttcg  14160
gccagggtgt tgccggcgct catgccgttg ctcaggtaca ggttctcgat caggttggag  14220
gggaaataca ccacctcgcc gtcggactgg cgcacataag gcaggcagca gataccgcgc  14280
tcgatattgc ccgagttggt gtcgtacaga tgcgagccgc gcagctcgcc atccgggttg  14340
tagatggcca ggcagtgctc gtcgaggatc tccttgggca gctcatcctt gcgccccggc  14400
tggaaccagc gctcgtccgg gtaatgcacg aactcggcgt tggcgatctc ttcgccccag  14460
aactgatcgt tgtagaagaa gttgcagttc aggcgctcga tgaactcgcc cagggccgag  14520
gccagggcgc tttccttggt ggcgcccttg ccgttggtga agcacatcgg cgactgcgca  14580
tcgcggatat gcagcgacca gacgttgggc acgatattgc gccacgaagc gatttcgatc  14640
ttcatcccca ggcccgcgag gatcccggac atgttggcga tggtctgctc caggggcagg  14700
tccttgccgg caatgtaggt gccttcgctg gagcctgatt gcggcatcaa cagcgcctgg  14760
gcatcggcgt cgaggttttc cacttcctcg atgatgaatt cggggccggt ctgcaccacc  14820
ttcttcaccg tgcaacggtc gatggaacgc aggatgccct ggcggtcctt gtcgctgatg  14880
tccgccggca gctcgacctg gatcttgaag atctggttgt agcggttttc cggatcgaca  14940
atgttgttct gcgacaggcg gatattgtcg gtggggatat tgcgggtctg gcagtacagc  15000
ttcacgaagt acgccgcgca cagcgccgaa gaagccagga aataatcgaa cggacccggc  15060
gccgaaccat cgcccttgta gcggataggt tggtcggcca ccaccgtgaa gtcgtcgaac  15120
ttggcttcaa gtcgaaggtt gtcgagaaag ttgaccttga tttccatggg ggcaccggca  15180
tcacaaagca aaaaatggcg ggcattatcc gggtttttgc gcgggaagtg ttgtggtttt  15240
cggcggacgg gtggatcgcc agggctggct gccggtcaca gacaccggca cccggccccg  15300
ggcatcactc aggcattcag actttgagga tgaaacgatt ggatatccgt gaatagccca  15360
ggggcaacaa ctcggcttcg tgctccttga tcagctcatg cagcgcgttg gcggtttcgg  15420
ccaccggcct ggcttgctcc ctggcctgtt gcatgacctg gcacgactgc ctgaacaggc  15480
tttcgtaggc gggcgagtcc agggacaggc agccagggaa gcgcaccgcc tcaagcgctg  15540
catcgaactg gcgggcgtcg ccactgtgtt ccaggtcgtg cagcagcttt tgcagaaagg  15600
cactgcccag gttggagccg ctgagccaga cccgatgcca cacgttccac aggtgaaagt  15660
cgctgaaggc ttcataggag caggagacca actggtcatt ggtcgccacc gcgttcaggc  15720
aatggcgctc gacttcgatg aactgttccc gttgccagcg gttgctgcgg gcggcgtcca  15780
gcaccttggg ggccagcctg aggatggact cgaaggtggt gatcaacccc ctggagaaca  15840
gcgggtcgat aaaccctgtg gcttgcggca gcaggcagaa gcgatccccg acattttgca  15900
cgctgcggta gttgatgcgc ggcgcgtaga tccactcccg ggcattgacc gcatccttga  15960
agtgttcgcc gatggccggg tactttttca gcagtttgcg aaactcgatc tccggcgcct  16020
cggtgggacg gtacttggcg ttgttgaact ggaagccgat gctgcacaac tgattggtgc  16080
cctgcgggtg gttgttgaag gggatgaccc acaaccagcc ctcttcgaag atgtggtgca  16140
aggtgctctt gaacagttcg atgggggaac gagtgcggga caacggagcc agggcatctt  16200
cgtagctctt cacattgagc atgtgggtga agaatgagca ggtgtcggtc gccagccctt  16260
cggtggtgcg caagcccagt tggcgggaaa gcggagagcc ctgggcagca gcgtcaatga  16320
tgaacgcggc cttgacgggg gcggcgttgg acaatgccac ctcgaccccg tcgtcgttga  16380
ggctgatcga ctcgatcttg atgttctgtc tggattcggc gccgtgtttc agggcaatca  16440
tcagggcgaa atagtcgatg tcctgccgga aaagatgggc ttccggcacc ttcagcggcg  16500
```

```
gggccacaag gtggtcgggg gacgacggcg cgttctcttg atgccaggca aaactgaagc  16560
ccagcttgat cccgcaggcg ctcgaaccga cgtgctggat gatcttgtcg gggtgcgaga  16620
ggtaggcgat ttcagggatg tcgaagcgct ttgagagcaa acgcagcaga aaaccgcttt  16680
ccggtgtcgc cgcttcgccg acggagaatc gtgggtgctg ggccgagtcg aggatcagaa  16740
cgttcagccc ggacttcgcg aggacggcgc cggtcagcgc gccggcgata ccactaccga  16800
tgataatgac gtcgtactga ttcatgatgt ctggctcttg tcttgcaagg tggtcgctct  16860
ggaaagcgct gaatgcattg cggtatcgaa atgcagggtg gccagggtct gcggtatttc  16920
cttttcaaac ggcaagtccc agtaaggcgt gctgccgatc gagcgtttca actcattgat  16980
gaacaggcgg gtcttggccg ggacaacgct gctgcgtgcc ctcagtgcgt agatcgctcc  17040
ctgttgcgga tcggcctcgc aatattcgtc gagcagcgac accagttggc cgctggcgat  17100
ctgttcatgc accagccagg tgggcgcgtg gatgattcct atgccctgaa gggcgccgtc  17160
caccagcaac tcggaactgt tgaccgatag ccggctgctg ggcatgagct tcttgagcag  17220
gccatcgacc ttgaattgcc aggtcagtga gaagttgctg caggtgctgt ggatcaggca  17280
ggcatgttgg tacaggtctt caagagtttg cggacagccg tgttgccgga tgtattccgg  17340
gcttgcgcag agcacgcgcc gcatatccgc aagtttcgtt ggaatcagat tactgtccgg  17400
caatatgccc agcttgatac agatatcgac gttatcgatg ctggggtcga gagctttgtc  17460
gttaagcgag aattcaattt tcaaaccggg atgatggttc agtattctgc tcaataaagg  17520
cgctacatgg cgccgtccaa aggccacggg tgctgaaacc ttgagaacgc caagggtcga  17580
tgcagtgtgt tcttttactt ctgatctagc atgcccaatg catctcgaga tgttctttgc  17640
atgttcgaga aagagcaggc ctgtttcggt aagtatcaag cattttgtcg atcgattgaa  17700
tagacaggtt tcaagttctt tttcgaggct attgattctg cgcatcaccg aagaaggtgg  17760
gatgccaagt agtcttcctg tttcggagaa actacccgtt ttagttacgg atatataaag  17820
gtctatgtca ttgacaacgc ctagcgcctt cattcctaaa tccttttaga atttttagtg  17880
tcttattttt gtaaaggcaa attacaaata gatcatgaca gcctccttag tacggctagg  17940
ctttttgttt gtcaagcagt gctggggcca tgattagttg gctttgggaa aattgattca  18000
taacatttca ggcgccacag ctctacccgg cgcagagcgg aacaccgtcc aagtgcaagg  18060
cttggtttgc actatctgga tacaaaaata gttctagtgg ctaattgcgc agagcgccaa  18120
aactatgctt gggcgctcga agatgacttt ctgaaggccg tcatataggc ctgtggaaca  18180
tcgttaagtt gtgttggctt cgatgttgtc ggggctgttt tgcctttgcg gatatgcaaa  18240
ggccttttgc aaaaacggct attcacaagt gcattcttat tgaggattgt agacgggttt  18300
tcccaaccca cgattgtcga atgcaggagc gtacgtctat ggacggagag gaagttaaag  18360
aaaagattcg tcgctacatc atggaagatt tgatcgggcc aagtgcaaag gaagatgagc  18420
ttgatgacca gactccacta ctggagtggg gcattctcaa ctcgatgaat atcgtcaagc  18480
tcatggtcta catcagggat gaaatgggtg tctcgattcc aagtacccat atcaccggaa  18540
aatattttaa agacctgaat gcaatatcca ggactgtcga gcaactaaag gccgagtgcg  18600
cctaacaggg agtgggcaat gagcgatcat gattatgatg tagtgattat cggtggcggg  18660
ccggcgggtt cgaccatggc ctcctacctg gcaaaagccg gtgtcaaatg cgcggtgttc  18720
gaaaaagaac tgttcgagcg cgagcatgtt ggcgagtcgc tggtaccggc caccactccg  18780
gtgctgctgg aaatcggggt gatggaaaag atcgagaaag ccaacttccc gaagaagttc  18840
```

```
ggcgctgcct ggacctcggc agattccggc cccgaagaca agatgggctt ccaggggctg  18900
gaccacgatt tccgttcggc ggaaatcctc ttcaacgagc gcaagcagga aggggtcgat  18960
cgcgacttca cgttccacgt cgaccgcggc aagttcgacc gcattcttct ggagcacgca  19020
ggttcgctgg gggccaaggt cttccagggc gtggagatcg ctgacgtcga gtttctcagc  19080
ccgggcaatg tcattgtcaa tgccaagctg ggcaagcgca gcgtggagat caaggccaag  19140
atggtggtgg atgccagcgg tcgcaacgtg ctgctgggcc gccggctggg cttgcgagaa  19200
aaggacccgg tcttcaacca gttcgcgatt cactcctggt tcgacaactt cgaccgcaag  19260
tcggcgacgc aaagcccgga caaggtcgac tacatcttca ttcacttcct gccgatgacc  19320
aatacctggg tctggcagat cccgatcacc gaaaccatta ccagcgtggg cgtggttacg  19380
cagaagcaga actacaccaa ctccgacctc acctatgaag agttcttctg ggaagcggtg  19440
aagacccggg aaaacctgca tgacgcgctg aaggcatcgg agcaggtccg cccgttcaag  19500
aaagaggcgg actacagcta cggcatgaaa gaagtctgtg gcgacagctt cgtgctgatc  19560
ggcgatgccg cacggttcgt cgacccgatc ttctccagcg gcgtcagcgt tgcactcaac  19620
agtgcgcgca tcgccagcgg cgacatcatc gaggcggtga agaacaacga ctttagcaag  19680
tccagtttca ctcactacga aggcatgatc aggaatggca tcaagaactg gtatgagttc  19740
atcacgctct attaccgcct gaacatcctc ttcaccgcgt tcgttcaaga cccacgctac  19800
cgcctggaca tcctgcaatt gctgcaaggg gacgtctaca gcggcaagcg cctggaagtg  19860
ctggacaaga tgcgcgaaat catcgctgcg gttgaaagcg acccggaaca cctctggcac  19920
aagtacctgg gcgacatgca ggttcctacc gccaaacccg cgttctaaac actaaacacc  19980
cagtcgaagg agatgactga atggatgctc gtgcgcccat ggattttgaa cccattgcaa  20040
tcatcgggag tggatgccgc tttgccaaag gtgcatcgac ccccgaggca ttctgggagc  20100
tccttcgtgc tgggaccgat tttgtcggac cggttcccgc agagcgctgg gacacagcgg  20160
cgatctacga tgagagcgct gctgaaaccg gtacgaccta cagcaaggtg ggggcgttcc  20220
tcgagcacat cgatcgcttc gatgcgcatt actttggcat ctcggcctct gaagccaagg  20280
aaatggaccc ccagcagcgc ctgctgctgg aggtcgcctg tgaaagcgtg gcccgtgccg  20340
gcctgacccg cgagcagctc aaaggcagca ggaccgcggt ctatgtcggc atgctgggca  20400
tggattacct ggcactgcac tcccgcgagg ccggcatcga acagatcaac ccctactatg  20460
ccgccggcaa ggaattcagc ttcgccgccg ggcgtattgc ctaccacctg ggtgttcatg  20520
ggccggcaat gaccgtgacc actgcatgct cttcttccct ggtggccatg cacctggcct  20580
gtcgcgcctt gcaggcaggg gaggcggaca tggccctggc cggaggggtg aacctgatgc  20640
tggcgccgga cctgacgatc tacatgagcc agatcagggc gatctcgccc agtggtcgct  20700
gccgggtatt cgatgcggcg gccgacggga tcgtccgggg cgaaggctgc ggggtcacgg  20760
tgctcaagcg cctggcagat gccctacgcg atggcgatcc gatccaggcg gtgatcaggg  20820
gctcggcgat caaccaggat ggcgccagtg ccggccagac cgtgcccaac gccaatgccc  20880
aggctgcagt gatcagccag gccctgaaag tggccggctt gagcgtggac gacatcgact  20940
atgtcgaggc ccacggcacc ggtacgcccc tgggcgatcc gatcgaactc tcttcgctgg  21000
acagtgcctt ccaggggcgt gagcggccgc tgtgggtggg ctcggtcaag gccaacatgg  21060
gccatctgga tgcggccgcc ggaatggcca gcgtgatcaa gaccatgatg gttctcaagc  21120
acgccgaggt gcctgcgcaa ctgcatcttg cacagttgaa cccactggtg gactggaagc  21180
gttcccggct ggcggtgccc acggcgatcg agtcgttgcc cgaccggccg cgcctggctg  21240
```

gaatcagtgg tttcgggctc agtggcacca acgtccacat gattctcgaa gatgccagcg 21300
tctatcggca ggcacagccg cagcaggaac gatcggcaca gggccggccc tgggtcctgc 21360
cggtatcggc caggtccgcg caggccgtgg tggagcaggc cagggcctat gccgttcatc 21420
tgccgcagca ggacgatggg caattgcaag cctttgtcgc cagcgccatt catcgtcgtg 21480
atcactttcc ctaccggtcg gccgtggtgg gtgcgaacgc cgggcaattg aagagccagc 21540
tggagcagct gccggccccg accttggcct gcacgacgga cgaagaggat cggcgcgggc 21600
ccgtgctggt gtttaccggg cagggcgccc agtgggtggg aatgggccgc gacctgcttg 21660
aacgggagcc ggccttcctg gcgatgatcc ggcgttgcga ccaggcgctg gcccagtggg 21720
caagctggtc ggtggaggcc gagctgcgca gcgacgccag tgggtcccgc ctgcacctga 21780
ccgaatttgc ccagccctgc atctttgcca tccaggtggc gatcagtgaa tgcctgcgcc 21840
agtggggtgt gatcccggcg gcggtggtcg gccactccat gggggaagtg gccgcggcct 21900
attgcgccgg agcactggac ctggagtcgg cggtgcgggt catccaccat cgggcccagg 21960
ccatgaagga caccctgggg caggggcgga tgctggtggt gggcttgccc gcgccgacgc 22020
tccagtcgcg tctggcgaac aacccgcaac tggaactgtc ggtggtcaac agtcgaaaca 22080
gctgtgtggt gtccggtagc ccgcaggctg tacaggctct ggatcagcaa ctgcgtgacg 22140
aaggcatctt cacttacctg atgccggcgg aatatgcctt ccactcctgc cagatggatg 22200
agtgcctgac gcagatccgc gcggggctgg aggatttgcc ggtggttgcc gcgcacacgc 22260
cctggatttc caccagcgcg atgcccgagg agccgatcct ggcagatgcc gactactggg 22320
cgaggaatgc ccgtggcatc gtgcgcttcg atcgcgccat cgaacagttg atcgagcagg 22380
ggcaccggct gttcgtcgag atcggcccgc acaccgtgtt ggcggcgtcg atcaaccagg 22440
ccctggccga caagggaacc cagggactgg tgtgcggcgc cttgcacaag cagggcgacg 22500
ccgccctgga gctggccagt attgttgccc gcctgtacga gtggggcgca ggtcccgact 22560
ggcaagcctt ccaacccagg gaggcggcgc tggagctgcc ggcctatccc tggcagcagg 22620
agcgtttctg gtttgccccg gcgccgcggc cgcagccggc agggctcgtg tcccagctgc 22680
gggcgcaggt actggtgtat gacgcccagg gcaatctctg cgcccaggcc aacgatgtgg 22740
cgctgagcgt gccgcagctg gcacaagtcg ctgtgccggc accggccaag gtgtccgcag 22800
cggcgcagcc ggtgggggat gtgcgggcgc agattggtgc actgctgacg cagatcatcg 22860
gcgtggcctg tgccgacccg gacccggatc gaggcttctt cgaactgggc ctgagctcga 22920
tttccctggt tgaattcaag cgcatgctgg agcgccagtt cgccctcaag ctgtcggcga 22980
ccgtgggctt cgactatccc accatcaacc ggctgggcca gtacctggaa gggctgctgt 23040
cccgggagcc ggccagcacc ccggtaacgg tcgatgccgg ggcgaccgac gccgcgggga 23100
gcgtcgccgt ggtggccatg gcgtgccggt ttccccaggc cgacagcccc gaggcactct 23160
ggaagctgat gctggaacag acggacaccg tggggccggt accgccgtcc cggctcgccg 23220
gcgctaagcc ggaggaaacc ttcccgcggt ttgccagcct tatccagcgc cccgaagggt 23280
tcgacgaagc gttcttccgc atttccccca aggaagcccg gagcatggac cccccagcaac 23340 ggctgttgct gatggtggcc tgggaggctc tggaacgggc cggtatccct caggagaagc 23400
tgctggaaca gagggtcggg gtgtttgtcg ggccaactc ccacgactac gaaacccggg 23460
tcctgggtag cgcgcaaggc gtggatgccc actacggcac tggcagttcg ttttcggcga 23520
tctgcgggcg cctctcgcat ttctcggcg tgcgtgggcc gagcctgacg gtggacaccg 23580

```
catgctcgtc atcgctcacg gccatccatc tggcgtgcaa cagcttgcgt gccgcggagt  23640
gcgacatcgc gattgtgggt ggggtgaatg tcatcgcctc ggcgtcgatc tttcaatcca  23700
tggggcaggc cggcgcattg gccccggacg gcatcagcaa ggccttcgac gacagtgccg  23760
acggttacgg tcgaggggag ggctgcggcg tggtcattct caagcgccag gcccaggccg  23820
agcgggagcg tgacccgatt gtcgcgacga ttctcggttc ggcggtcaat cacgacggtg  23880
cctgtgccgg gctgacagtg cccaatggtc cggcgcaaga ggcgctgatc agcgaagcac  23940
tggccaacgc cggcgtgcat ccggggcaag tcagctacgt ggaggcccat ggcaccggca  24000
cggtgctggg tgaccccatc gagctcaacg ccctgcacaa cgcctatcgc caggccagcc  24060
ccgacagtcc gccgctgacg gtggcctcgg tcaaggccaa tatcgggcac ctcgaggcgg  24120
cagcgggcat cgcttcgctg atcaaggcct gcctggtggt ggagcacggc cggattgccc  24180
cgcaagccca tctgcagcgg gccaacaccc gtgtcgactg ggcggccatg aacctcaagc  24240
tggcgcatca ggccatggac tggccgggcc ggccggagtc gcgggtggcc ggggtcagtg  24300
cctttggttt caccgggacc aacgtgcatg tgctgctcaa gggctatacg gcgcccgcga  24360
cagcgccttt gccacccgcc acagcaccag tggccttgtg cctgtccgcg gccaccccgg  24420
cggcattggc ggagctggcc cagcgctatg tgtccttcct gggcgctacc gagcactgcc  24480
cacagaccat ctgctacaac gcgctgatgc ggcgcacggc gttcaaggaa cgcctggtcg  24540
tccacggcca ggattgccgc gagctggctc aggcactaca ggcctggctg gccggtagcc  24600
ccatcgccaa tgaccgcaaa cccgcggccg gcgaaccctg ggcaaccctg gccgaggcct  24660
ttggccgcgg cgcccagtcg ccgggccccg agcgcttgcc ggacggctgt caggccatcg  24720
ggttgcccac ctatccctgg cagctcaacg actactggat cgatgctggc cagccggcta  24780
cggcggtgca gcccgcccgg gcagcctcgg gccatccttg cctgcagggg ctggtacggc  24840
cggccgggca gctctggtac tggtcggggg ctctcgctcc ccaggccggg cattacgacc  24900
cgctgggcga gcaggggtac agggtcaaga ctcacctgtt gctggatgcc gtgctccagg  24960
cggtgcggga aacaccacgg ggcgtgcagc agatccgcga cttgcagatt gcccagctgc  25020
gcctgcgcgg cgaacagcac ctcacttcgc acctgagcat ccacctcacc caggcgcctg  25080
acgcctgctt cgaactggcc ttgcaagggg ccggcgacga gcgccgccag gtctgcatga  25140
gcggaaccct ggttgactgt gcagcgcagt tgcaggagga aaccctgtgc ggggtgtcga  25200
tgctcgatga gccttcaccg ccggcgccgg acgttggcct gtgcccatgg tccgggtgtg  25260
cggccacggg cgggcagcgg gccttgtacc gttttgccca ctccctgacg gcggccgagc  25320
gccagaccca gttgctggcc agtgtggtcg agctgtttga aggcgcccac gccgccgcgc  25380
tggtcgggtt ctccgggctc caggtatggg cagacctgcc ggcgcaggta tggattgtgc  25440
tggccggcca tgacgccgac aaacccgaca gcctgcaggt agtggatgcc cggggttgcc  25500
agctggcgct gttcgaaggt ccgcagtttg gccatcctgg ttcgtggtac ttgcccgacc  25560
tccagaccgc accccctcgac ctgccgatga tcgctcgcca atggcaggac tatccgatgc  25620
cgggcgaggg cgctcggcaa cgcgagggct actggatggt gctggcctgg agcactgccg  25680
aggtccagcc actggctgcg gcgtttgcgg ctgaacagcg tccggttgaa gtcatcgagc  25740
tgcacgccgg gcaacaacct ctggcccgca aactgtcctc ggcgttgcgc ggggcagtgg  25800
ccgatccgtc ctgcctgggg gtgatcgttg ccggcgttga ggctcaggag gccgacggcc  25860
tcggtatatc cctggtggcc tctgcggcgc tggtacaggc cttcgccggt gcgattgcca  25920
gcgtcggaac accggcaaag ccggtctggt tcgcccttca tgccagtgat gctgcgtcgc  25980
```

```
cggccatggc cgctgtccag gccacctggc agggcgccgc gcatatcttc gccctggagc  26040
atcctgcctg gtggggcggt ctggtgactt tgcagggcag cgacagaaga agctacgcca  26100
gcctctgccg gctgttgcac ggccaacctg gccatgatca ctttgcgatc agcggcgccc  26160
gggtcgaggt gcaatacctg gtggaggatc aagccgaccc gctacagcgt ctggagccgc  26220
cggcgctgaa cggaaccgtt gtgctgcatg ccgtcccggg atctgacctg gagactgtgc  26280
tgacggcgct cgggcagcgg ggtgtgcagc gtgtgctgct gctctgcgag gcccccgggc  26340
aactgcacat gcctgagcgg atgcccgaag cgatggcgat cagcagcctc tcggacctga  26400
gccgggaaaa cctggctgac accttcgcga cgctgcgagc gcaagaccgc atcgccggct  26460
ttatccacct cgatcttgac tggcgcacgg ttgcgctcaa ggagccagag tttgtcgtgc  26520
gaatgcagga aggcgttcgg ccgcttgagg tcttgcagca ggttcaccag ctgatcgatg  26580
accctgaagc gttcttcctg atcctgggca gcgtgtcttc cctgcttggc ggggccggct  26640
tcgcccgctc ggcgattgcc gatgcatatg ccttgtgggt gcatgcacag cgccggcgcc  26700
aggggttgaa ctgccagctg ctgcacctga cgcagagcga acaggagctt gagcaggacg  26760
ccgcagcccg cacggccatg caaggcagcg gcctgcagcc tttgcagcgc tcgcagatag  26820
tgcaggccat agcccgcgtg ctgggtggcc agggccagtg cgggctgctc aatgtcgact  26880
ggcaacaact caaagggctg tacctgagcg tgctgccctg gcccttgctc gaacacctgg  26940
gtgcagcgga tagcgcagcg gatcagcgtc tggccgagct gattggcctg ccaccgctgc  27000
agcagcgccg ggccatgcag gcgctggtct gcgaggtagt ggggcaggtg ttcggcgttg  27060
ccgatggcct ggagctcgat gtcaggaagg gcttcttcga catgggcatg tcctcggtca  27120
tgtcgctgga cctgcgctca cggctgggcc gggcgttgag catcgacctg ccttcgacct  27180
tcggcttcga atacacctcc atcgaacagg tcacggacta cctcatgggc cagctcctgg  27240
cgcctgaaac ccgggagccg gtggcggcgc ccgaacctgt gtcgccagcg tcgcggcatc  27300
aggacctgca tgaactgtca cgggccgagc tgattggtgc tctcgaagac gagctgcgcg  27360
atatcgccaa ttactagccc tggggctgga tgacaactgc cagagaatca ctgatcgagg  27420
cctttatgga taacgatgtc cgcgatgtaa gcaaggaaca gctgcaagag agtcttgctc  27480
aggcaatcac taccatccgt gcgctcaagg aaaaggtggc cggcaagagc tcggcgcctg  27540
tcgaaccgat cgccgtagtg ggcctggggt gccggctacc gggcagtgcc gacacaccga  27600
agcggctgtg gagcctgctg aaacatgcca ccgatgcggt gggcgacatg cccagcgacc  27660
gtctgtacgg caccgactat taccatcctg atccccaggc acccggcaag gcctacgtca  27720
tgcgcggtgg cttcatcgag gggggtggatc agttcgaccc gggcttcttc ggcatttcgc  27780
ccaaggaagc cgaaggcatg gacccccagc agcgcctggc cctggaggtt gcctgggagg  27840
ccctggagaa cgccgcgatc gcccccgaca gcctgcatgg caagaagctc ggcgtgttca  27900
tgggggtcag taccaatgat tacgtgcgcc tgcgccagca gttgggcgcg gtcgaggacg  27960
tcaacgccta ccagttctat ggcgaaacca gcttcgtggc cgggcgcatt gcctacaccc  28020
tgggctccag gggcccggcg gtggtgctcg acacctcctg ctcctcatcc ctggtggccc  28080
tgcaccaggc ctgcaacagc ctgcgcagcc gcgagagcga gctggcgctg gccggtgggg  28140
tcaacctgat cctgtcgccc tacggtttca tcctggtcag caagctgcgg gccgtggccc  28200
ccgatggccg ctgcaagacc ttcgacgcgg cggccgatgg ctacgggcgc gccgaaggct  28260
gcgtgatcct tgcgctcaag cggctgagcg atgcggtacg cgaccaggac ccggtgctgg  28320
```

-continued

```
ccgtgatcga gggtagtgcg gtcaacaacg acggcgccag cagcggcatc accgtgccca  28380
acatccacgc ccaggaagag gtgatcaggc tggcgctcgg ccaggccggg ctccagggca  28440
gcgaggtcga ctatgtcgag gcccatggca ccggcaccgc gctgggcgac ccgatcgaac  28500
tgcacgccct gcatgcggta ctgggcaagc agcggcccgt cgatgcaccg ctgctggtgg  28560
gctcgatcaa ggccaacatg gggcatctcg aaccggtcgc cggggtgacc gggctggcca  28620
aggtcctgct gtgcctgcaa caagaggccc tggtgcccca ggtgcacttc aacacgccca  28680
acccgcggat cgaatgggat cgcctggccc tgaaggtggt caccgaatcc acgccctggc  28740
cacgccaggg caaggcgcgg cacgccggtg tcagttcgtt tggtgtcacc ggcaccaacg  28800
cccatgtgct agtgggcgac gcgccgctgc gcgaacgtgc ccaggggcgc gacaacccct  28860
ggcagctgat cactctgtcg gccaagggcg agacgccccg gcgccagatt gccggacgct  28920
atgaacgttt tatcgccgac aacagccagc tcgaactcaa ggacctgtgc tacacggcga  28980
acgtcgggcg ggcgcacttt ggccatcgtt tcgcggccgt ggccgatagc cgtgaggggc  29040
tgcgcgagca actggcagcc tatgcgtcac gcaaggtcgt ggggcatgta ttcgaagggc  29100
gctgccaggg agcggcggcg ccgctggtga tgctctttcc ggggcagggc tgccagtacc  29160
gggcaatggc ccaggcactg tatgacagcg aaccattctt caaggcgcag atcgatgaat  29220
gccgcgccct gttgcagccg ctgatggacg tggacctgct gaccctggtg ctggacgcgg  29280
gtgcggccag tgacagctac ctgcaacaga cccgctatgc ccagccggcg atattcgcgg  29340
tcgaatatgc cctggcgcgg ttgtggatgc attggggggt cgctgccgat gcgctgttcg  29400
gacacagttt cggcgagatc agtgcaatct gtgtagccgg ggcggtatcc ctggctgacg  29460
cgctgcgtat ggtggaggcg cgtgggcgcc tggcccagca actgatgacg gccggcggcg  29520
cgatgtacgc actgggcatg agcgaggcgc aactgctgga gctgctcaag gaccggcccg  29580
gcagcgcgat cgaactggcg gcggtcaaca gcccgcagga cgtggtggtg gccgggccgc  29640
aagccgaggt ccaggcgctg gccgaagcgg cgctcgccag cggttgcaag gtcaagaagc  29700
ttgcggtttc ccatgccttc cataccgcag ccaccgagcc gatgcttgaa gcgttccgcc  29760
agacggtggc gcagatcacc ttcagcgagc cgcgcttgcc ggtcatcagc agtgtcactg  29820
gccgggtgca tacgctctcc agcctgagct cgcccgatta ctggtgtacg cacacccgcc  29880
aggccgtgag gttctgcgaa ggggtcaaca ccctgatcgc agagctgggg gtgaaaacct  29940
tccttgaagt ggcctccgat gctgtgttga cgccgctgat cggccgtcac cccctggcgg  30000
acggcagcct ggtcctggcc agcctgcgcc gggccggcga tccgtccagg gacctgcgcc  30060
tggccgccgc gcagctctac gtgggcggcc ataacctcga ctgggcccgg ctgcacgagc  30120
atgacggggc cttgcgccag gccttgcccg ggtatgcgtt tcagcgccag cgctactggt  30180
tcgacaacgc cagcggctcg cccctgcaac aggtcgctgc gggagcggtc ggccggctgc  30240
tggggcattc ggtcaatgca cccactccgg cattcgagtc gacgctcgat agcgcgctcc  30300
tgcaggttgt gggcggcgag atccgcgatg acctggcgct gctgcgtcct gaccggttgc  30360
tggcagccct gagcgatgag ctggccggcc acttgcagct ggacacctat ggggtgagcc  30420
tcgccagcat caccccggcc ctggcgttcc atgtcgatga ccagttgcat ctgttcaccg  30480
aactcaagcc gctgtccggg gcggcctggg aggtcaactg ttcggccctg agcgcagcgg  30540
ccaaggttgc cggtgccgat tggcagccgg tcctgtcgct gaccctggaa ggcctgccgg  30600
cggctgtccg gggcggcctg ccggacccgg gccatgccgc cacccaggac gcaggctttg  30660
tctaccacat gcagttgccg gcagaacccg atccgcacgg caatcacctt gggcaggtcc  30720
```

```
tcgagtacct ggggcaggcg gtgccgggcg atgcgccggg ctcgataagc ggcatccgcc  30780
gctgggtcgc cagccggtcc gcttcgcccc gggcacaaag cctggtgatt gccacgagcc  30840
aggcacatcc gcagcagttc gactgcgcct tgtacgatgc gcacggccag tgtgtaggca  30900
gcctggaagg gctgaccctg gctgccgccc cgagtgagga ggcgctgcgt ggcatgcttt  30960
accagcccga cgtgctctac agcctggatt ggctcgaacg ccctcgccag cgcgccgaag  31020
tgccgcagca ggaccgcttg ttcaccctgg tcagccgctc gccggagacc gccgctcccc  31080
tggtcgaaca cctgcagcgt ggcgggcatc gtgcccgggt cctgtgcccg cagcagttgc  31140
tcgatagcgc gcggagggtg ctggcccagg acccgagcca ggcattgacc gatgaaggcg  31200
aggccttggc cgccgatatc atcgtgctcg atggcaaaga catcgaggat gccggctcga  31260
ccacgctgca gagcctgtcg agcctgcagg cgacactgtt ccacccgttg ctggagatgg  31320
tccaggcgct catcgaactg ggcccgcgcg gtggccggtt gtggctggtg acccaagggg  31380
caaaccctgt tggcctggat cgcgaccagc ccctgcaagt ggcgaccggg ccgttgtggg  31440
ggctgggcaa gacgctcgcc ctggagcacc ccgaacactg gcgcgggctg atcgacctgg  31500
cccccgacga tcctcactgg gcaagggcgc tggccgaaga agtcagcgac tccgatggcg  31560
acgacaagat ctgcctgcgc ccgggcaagc gttatgtcca gcgcctgaac catttcagcg  31620
ctgcgcagtt gccagcacag gcctatgcac cttgcccgca gggcagttac ctgattaccg  31680
gcggcatggg tggaattggc ctggccatgg cccagtggct tctggataaa ggcgcgggcg  31740
ctgtgctgat caccggccgg cggccactgg aggatgtcgc cacgggcctg gagcgcttcg  31800
gcgctgcggc atcgcgggtg agttacgtcc aggccgacat cacctcgccc caggacatgc  31860
agcggctgtt ctgcggtctg gaggcgtcgg gcgcgagcct gaagggcatc tttcatgccg  31920
ccgggatttc aattccgcag gatctcaagg acgtcgaccg tgacagtttc gaccaggtga  31980
tgcggcccaa ggtcgagggc acctggttgt tgcacgaact gtccctgggg ctggacctgg  32040
acttctttgt cctgtgttcg agcatcgcca gtgtctgggg ttcgcagcat gtcgccagct  32100
acgcagccgc caatcagttc ctcgacagcc tggcgtggca gcgtcgggcc atgggcctga  32160
gtgccctggt gatcgactgg gggctgtggg ccggcggcag tcacctgttc gacgagcagg  32220
tgctgaattt cctcaccagc gttggcttga aacagatcgc cccggtacag aacgtcggcc  32280
tgctgtcgcg gattctggcc agcgagctgc cccagatggt ggtgtcaggg gtggactgga  32340
atcgcttcaa gccactgctc gaatcccgcg gcccgcaacc gctgctgcag tacatccgca  32400
gccaggctcc gaccgccagg gccggcgaca gcagcaacgt ggagatcctg cagcaactgg  32460
cgggcgccga tgaagccgct gccctggcat tgctggatga ctacgtgtgg gagcagtacg  32520
cgcagttgct cggggtcaag accgaacagg tgcgggccaa gctcgaggat ggcggcagcc  32580
tgatggacta cggcctggac tcgctgctgg tgatggacat ggtcgcccgc tgccggcgcg  32640
atctgaagct ggagatcaag gcccgcgagt ttcttgagtg tccgggcctg atgtggccgg  32700
acttcctggc ccgttcgata aaggaacagg gctgcgtggc cgaggcctga cgggccgcgg  32760
gcagtgcaac ccagacccat gatctgtgat tgaggtggtt atgaacgatg tgcagtctgg  32820
caaggcgcca gagcattacg acattctctt ggcgggcaac agcatcagcg tgatcatgct  32880
cgccgcctgc ctggcccgga acaaggtccg ggtcggtttg ttgcgcaacc ggcagatgcc  32940
ccccgacctt accggtgagg cgacgattcc ctatacctcg atgattttcg agctgattgc  33000
cgaccgctat ggcgtgccgg aaataaagaa tatcgcccgc acccgggata tccagcagaa  33060
```

```
ggtgatgccg tcttccgggg tcaagaagaa cctcgggttc atctatcacc agcgcagccg  33120
ggcggtggac ctgggccagg cgctgcaatt caacgtgccc tccgagcatg gcgagaacca  33180
tctgttcagg cccgatatcg atgcctatct gctggcggcg gccatcggtt atggcgcgca  33240
gctggtggag atcgataaca gcccagaggt gctggtcgag gacagcgggg tcaaggtagc  33300
tacggcactg gggcgctggg tcactgccga tttcatggtt gatggcagcc agggcggcca  33360
ggtgctggcg cggcaggctg gcctggtcag ccaggcttcg acgcagaaga cccggaccct  33420
ggaattctcc actcatatgc tcggggtggt gccgttcgat gagtgcgtgc agggcgattt  33480
tcccggccag tggcatggcg gcactctgca tcacgtgttc gatgggggct gggtgggggt  33540
catcccgttc aacaaccatc agcactcgcg caaccctttg gtcagcgtgc tggtttcact  33600
gcgtgaggac ctctgcccga gcatggacgg cgaccaggtc ctggccggcc tgatcgagct  33660
gtaccccggc ctggggcggc acctgtccgg cgcccggcgg gtgcgcgagt gggtgctgcg  33720
ccagccgccc cggcaggtct atcgcacggc gctcgaacgc cgctgcctga tgttcgacga  33780
gggcgccgcg agcaacgatc tgttgttctc gcgcaagctg tccaatgctg cggaactggt  33840
tctggccctg gcgcaccggc tgatcaaggc ggcgcacagc ggtgactacc gcagcccggc  33900
cctgaatgat tttgtcctga cccaggacag catcatcagc ttgagtgacc ggatcgcctt  33960
agcggcttat gtgtcgtttc gcgaccccga gttgtggaat gccttcgccc gtgtctggct  34020
gctgcagtcg attgccgcca ccatcaccgc gcgcaagatc aacgatgcct ttgccaagga  34080
cctggacccg cgagtgttcg atgaaatcga ccagctcgca gaggacggtt tctggatgcc  34140
tctgtatcgg gggtacaagg atattctcaa cactacgctg ggcctttgtg atgacgtcaa  34200
aagcgccaag gtctctgctg cgcacgcggc gagcagcatc tttgcggagc ttgccaacgc  34260
cagttttgtt ccgcctattt ttgattttgc taatcctcac gctcgtgtct atcaactgac  34320
caccttgaga aagctcaagg cgctctggtg gggcctgatg caagtgccct cagaggtcgg  34380
acggctgatt ttctatcgat ccttcagaaa accttccctg cgcaaggaga gttgaaatgg  34440
acttcaacta cgacgatacc cagaaaaaac atgcggccat gatcgcccag gtgtgtgccg  34500
agcaattggc ggcctgtggc aatgaacact cgcggtattt cactgcccgg caatgggcga  34560
tctgcggcga ggccggattg ctggggctgt cgattccccg ggaatacggt ggccagggcc  34620
tgggtgcact gtcgacggcc attgccatgc acgcctttgg cctgggttgc acagacatgg  34680
gcctggtgtt cgcggcggcg gcccaccagt ttgcctgtgc gatgccgatc gtcgagttcg  34740
caacagcgga aaccaaacgc gatgtgttgc ccaaactcgc cagcggtgaa ttcatcggct  34800
ccaacgcgat caccgaaccc gaggccggct ccgactccag caatttgaag agccgtgcct  34860
ggccccaggc cgatggcagt tatcgccttg acggccacaa gagctttgcc ggcaatgcgc  34920
cgattgccga catcttcgtg acctatgcca ccacccagcc cgagtacggt gccctggggg  34980
tcagcggttt tatcgtccac cgcagcagtg cggggctcag ggtcagtgag cccctggaca  35040
aggtatgcct gagaagctgc cccgcgggtg aagtgttctt tgacgattgc agggttcctg  35100
aggtcaaccg cctgggtgag gaggggcagg gccggcaggt gttccagagc tccatgggct  35160
gggagcgtgc ctgcctgttc gcagcgttcc tggggatgat ggagcggcaa ctggaacaga  35220
ccatcgagca tgcgcgcacc cggcgccagt ttggcaagcc gattggcgac aaccaggcgg  35280
tttcgcaccg tatcgcgcaa atgaagctgc gcctggagtc ggcgcggttg ctgctgttcc  35340
gggcgtgctg gggcatggac cagggcgatc cggggcagct caacattgcc ctgtcgaaac  35400
tggccatcag tgaaggggcg ctggcatcta gcatcgatgc ggtgaggatt ttcggcggcc  35460
```

```
ggggctgcct ggagtctttc gggatcgagg cgatgctgcg cgactccatc ggcactacga  35520
tcttttccgg caccagcgac atgcagcacg agatcattgc ccgggagctg aagctatgaa  35580
gctgctccat gaacggatga tgcacagcct tgcccgctac ccgcggcaga cggcggtggt  35640
ggatgagcag gatgccttga gctacgaggc gctggagctc aggatccggg aattcgtggc  35700
aatgctctgt gccctggggg tcggccaggg gcagcggatc ctgctctggg cgcacaagtc  35760
ggtggacctg gtggcggtca tgcaggcggc cctgcggctg gggtggtgt atgtgccggt  35820
ggaccctctg agcccggtgt cgcgcctgga aaagatcgcc ggggattccc aggccgtgct  35880
ggtcctctgc accgcggcac gcctggaaga actcgccggc tccgcgcttg cccaggtgcg  35940
cagcgtggtc ctggacgacc cggccagcgc cggctactgg cgcaacatcg ataccggctc  36000
cagcgtagtg ccgacgctgg ccatccagcc ggacgatctg gcctacatcc tctacacctc  36060
cgggtccacc ggcgtgccca aaggggttgc gctcagccac ggcaatgccc tggccttcgt  36120
cgactgggcg tgcgagcgct attgcttcca gcctggcgag cgtttcgcca accatgcccc  36180
cctgcatttc gacctgtcgg tcctggacat ctactgcgcg ctcaatgtgg gcgcgacggt  36240
gtgcctggtt cccgagtcga tcgcgttctc gccgcggctg ctgaccgact tcatccgcca  36300
gcacgaaatc agcatctggt actcggtgcc ctcggtactc atgatgatga tgcaagacgg  36360
cgacttgctc agcgatatcc aggacaccct gcgggtactg ttgttcgccg gcgagccttt  36420
tccggtcaag cacctgcgtg acctgcgcgc ggcctatgcc gatgtgcgtc tggccaatct  36480
cttcggcccc acggaaacca atgtgtgcac cgcattcgag gtcggcgcca tcgatcccga  36540
gcgcgtgctc ccggtgccca tcggcacggc cgcctccggc aaccaggtgt gggcgcaaaa  36600
gcctgatggc agccgctgcg cagtgggtga agaaggtgag ctggtggtgc aggggcctac  36660
ggtcatgctg ggctatttcg ccaagccggc tcaggagggg ccctacaaga ccggcgatat  36720
ggtcaggcag cggcctgacg gcaactacga atacctgggg cgtcgtgacg acatgctcaa  36780
ggtgcgtggc aaccggatcg agcgcgggga agtcgaagcc gcgctgctgg cccatcccca  36840
ggtcagcgag gccgccgtgc tggtggtcgg ggaggggatg aacgcgcagt tgtggggcgt  36900
gctggtcgct cacacccggg acgctctttc gctgatcgac ctcaagcgcc actgcgccca  36960
gcgcctgcct cgctacatga tcatcgacaa ggtgctgtgc ctggacgcac tgccacgcaa  37020
cgccaatggc aaggtcgatc gcttcgccct ggccaggcag gtggagggct gacccatggg  37080
aactccatca cgcgtggcca aggacgcctg gtttccctat gccagccggc ctcggggcaa  37140
gatgcgcctg ttcacctttc cctatgccgg gagtggggcc tcggtctttc atcgctggtt  37200
cctgcccctg tacgaccagg tcgacctgta tgccttgcag ttgccgggcc gcgagggtcg  37260
cagccaggag gcctgctaca gcgacatgca ggcggcggcc aatgacgtgg ccgactgcct  37320
ggagcagttt ggcgatgaca tcccctgctg tttcttcggc cacagcatgg gcgccttgct  37380
ggcctttgcg gtcgccggtg tgctgcagga gcggcggttg ccgatgccgc agcaactgat  37440
gctctcgggc atggttgcgc cccatgtgcg gcaacgggta gcaccgctgc accagctgcc  37500
ggcagagcag gccatcgccg cgctgcaggc catggggggc gtgccggcgg tggtgctggc  37560
cgaggaggac ctgatgcaga tgtacctgcc catcattcag gccgacatac agatggtcta  37620
ctcctacgcc ggtgcccagc cgcagccgct ggacacccgc atgatctgcc tgagcggcgc  37680
ccaggacctg attgcgccgc ctgcgcagat gcagcagtgg cggcgctaca ccctgggcgg  37740
cttcgagcag ttcgtgtttg ccggtggcca tttctttctc gacgcccagg tcatgtcgcg  37800
```

```
ggtcaaaaca gtgctgggca gcgccctgca caatcagcct ggcagtctgg cggtgtgagc  37860
cgactattgg gcaatggccg cgaggccgga cctggcgaac agcttgaagt gggctttcag  37920
ggcgttggcg tcgtgttgca ggacggcttg cagcgggctg ggctgctggc gatctatcac  37980
cgccagcatc aggcagggcg cgatgatgct gatggtgcaa cgcgccagcg ccgggtcacc  38040
gatcggaaag ccggtgatct cgctgatgag cgcttccagc agacggaatt tgggcatcac  38100
ttcttcttgc acaaggctgg tgaaatggac agtgggcgcc agtatttccc gtgcacagac  38160
tttgctttgc cagctctgct catcgagcac ccgggtgacg atggcatcga tgaagctatc  38220
gagcttgatc agcgccggct cttcgctttg cgccagctgc gacagggctt cgaagctcac  38280
cagctgcttg tgtccctcga tcagcaccgc cttgtacagg gcttcccggc taccgaagtg  38340
gtagttgatg gcggcgaggt cggcgccggc ttcttcacag atgagcttgc tcgcggtgtt  38400
ggcatagcca tgctgggcaa acaggcgggc agccacttcg agaatgcgga ttttagtgtg  38460
ttcgccgtcg cttctgctgg ttctgcgtcg cgtgttcatg atgttcctcg tggtctgagc  38520
ggggggttgc ttcatggcca gtatctgtta ttttctaatt taaattcaaa ttgaatttta  38580
attaggcctt ggcaaacaaa ggactcatgg atgaagaagc agttgattgt aggggttgcc  38640
gtactgctgg tggccacagc gggtgtttcc tggtttctcc ttcgccccga gaagcagaac  38700
gaccacctca agctccatgg caacgtcgac attcgccagg tgtcactggc gttcgacggc  38760
agtgagcgaa tcgccgcgct gtatgccgaa gagggcgacc tggtgcagcc aggccaggtc  38820
ctggcggaac tcgacacacg cacactgcgc ctggaaataa atcgctccaa ggccaggatc  38880
ggcgcccagg aacaggcgct gctgcgcttg aaaaatggca cacggcctca agaggtcgag  38940
cagtccaagg cacgttttga tgccgcccag gcgcaaatgc agctggctca actgcacatg  39000
cagcgcctgc gcaggatcgc cgacgacacc cagggcaagg gcgtcagcca gcaacgcctg  39060
gaccaggcag ccgcccgctt gcaagtggcc aaggcccagt cgcaggagca gcgcgaatcc  39120
tggaccctgg ccaagatcgg cccacgcaat gaagacatcg cccaggccac ggccgacctg  39180
caagcctcca gggccgacct ggacctgctg gaacattacc tggcgcgcgc tcagctcaag  39240
gcgccgaccc aggcccggat ccgcacgcgc ctgctggagc cgggggatat ggcctcgccc  39300
cagcgcccgg tgtttgccct ggccctgacc gaccccaagt gggtacgggc ctatgtcaac  39360
gaacgccagt tgggccacat acgtgcggac cagatggcgc gggtctacac cgacagcttt  39420
cctgaccagg ccatcgacgg caaagtcggc tacatctcct cggttgccga attcaccccc  39480
aagtcggtgg aaacggaaga cctgcgcacc agcctggtct acgagatccg ggtgctggtc  39540
aaggaccctg acgatcgcct gcggctcggt atgccggcga ccgtctacct tgaccaggca  39600
ccggtggccg gggccacgcc atgagtgcgc cagcggtaac ggttcaggct gttgaactgg  39660
tcaagcgctt tcgcagtgga acgcgagaac agttggctct ggagcaggtt tctctggagg  39720
tgcccagtgg caagttgagt gccctggtgg ggccggacgg ggccggaaaa accaccctgt  39780
tgcggatgat tgccggcttg ctcaaggccg acgaagggct gttgaaggtg ctggggctgg  39840
acgtcgccgc agatccgcag caggtgcagg acctcatcag ctacatgccc cagaagttcg  39900
gcctgtacga agacctgacg atccaggaaa acctcgaact ctacgccgac ctgcatggcg  39960
tgcgcgccca gcagcgcgag gagcgctttt cccggttgct gcagatgatg gacctgacgc  40020
gttttcgcga ccggctggcc ggacagcttt ccggcggcat gaaacagaaa ctggggctgg  40080
cctgtaccct ggtccgttca ccgcaactgt tgctgctgga cgagcccacc gtgggggtgg  40140
atccgctgtc gcggcgggaa ctgtggagca tcatcgaaca actgatcgag caggaaaacc  40200
```

```
tcacggtgct gatcagcact gcctacatgg acgaggccca gcgttgcgcc caggtctttg  40260
tgctatacca ggggcggctg atcgcccagg ggccaccggc gcagttgtgc catctggcgc  40320
agggcctgtg ctatggcgtc ggccccgagg ccggcacccc ggccaggctg ttgcaggcgc  40380
gcttgcttga cgacaatgaa cacatcatcg atgccgtgcc cgaaggcggc atggttcgct  40440
ttatccgtag cgcccaggtg cctctgcagg ccattccatc cctggctggc caggcctctc  40500
cccaggcgct ggaggcccgc ctcgaagatg gcttcatggt gttgctccgg caacaggttg  40560
gcagcgttgc aagcctggac gagccggcgc aggcgcccgc cagctacggc cagggcgacg  40620
ctgcctctgg gcgtgcggtg gtcatcgagg tccgcgacct ggtgcgcaag ttcggggact  40680
tcaccgcggt tgccagcacc tcgttcgagg tgttgaaggg cgagatattc ggcttgctgg  40740
gccccaacgg agccggcaag accaccacgt ttcgcatgct ctgcggtttg cttcccgcct  40800
ccagcgggta ccttgaggtg gctggcgtca acctgcgcac cgcacgggcg gcggcgcggc  40860
gcaagatcgg ctacgtctcg cagaagttcg ccctgtacgc gaacctgtcg gccctggaga  40920
acctgcgctt cttcggcggc gcctatggcc tgcacggcgc gaagctgaaa gcgcgggtgg  40980
cgttgatgct cgaacagttc gacctcgacg aacacaagca cctgcgcagc ggcgagctgc  41040
ccggtggcta caagcagcgc ctggccatgg cggtcgcgct gctgcacgag ccacagatcc  41100
tgtttctcga cgaacccacc agcggtatcg accccttggc ccgccgggcg ttctggcgcc  41160
gtatcaccgc cctggcgcaa agcggcacga cgatcgtgat caccacccac ttcatggaag  41220
aggccgagta ctgcgaccgt atcgtcatcc aggatgccgg acggctgctg gccctgggca  41280
ctccggaaca ggtacgccac cagggcagcg agtcgcttgc cgacatgaac agcgccttca  41340
ttgccgtggt cgagcgtgct cgggcccagg ccagcgcccc ggtgcagtga ggaatgacca  41400
tgactgactc caatcgatcc gcctcagggt tcaggcgcag gctcattgcg ctcacccgaa  41460
aggagttgcg ccaattgatg cgtgacaaga gcaacctggc gataggcatt gtcctgccca  41520
tcgtactgat cctgatattt ggctacggcc tgtccctgga cattcgcaac acgccgctgg  41580
ccgtggtcct ggaagacagc tcccccagcg cccgcagcgt ggtggcgaag cttgcgagtt  41640
cggactactt ctcggtggtc caggtgacca gcatggccga ggcccgagcg ctgatggaca  41700
agcgtcgggt cgacggcatc gtgcgcgtgc cggcggattt ttccaggcgc ctcgaacagc  41760
aggatgcgcg cttgcaattg ctcctgcatg gcgccgatgc caacagcgcg gcgacccttg  41820
gacgctatgt caggggcgcg ctgaatgtct ggcaacagca gcagttcgac cgctcccggc  41880
agccccagtc ggccggtcgg gtgctggtcg tcgaacgcat gtggttcaac gccgccaaca  41940
gcagtacctg gtacctggtg cccgggctca tcgccctgat catgaccctg gtgggtgcct  42000
tcctgacctc tctggtactg gcccgggagt gggagcgggg cacgctcgaa tcactgttcg  42060
tcaccccggt caggtcgatc gaaatactcc tggccaagat cattccctat ttcctggtgg  42120
gcctgctggg cctggtgatg tgcctggttt cggcgcggtt gctgttcgag gtaccgatcc  42180
agggttcgct ggtgctcctg ctgttgagct ccatgctcta cctgctggtc accctgggca  42240
ttggcctgct gatttcggcg aagacacgca accagttcct ggccagccag atcgcgatca  42300
tcttcagctt cctgccggcg ctgatgctct cggggttcct cttcgatctg cgcaatgtgc  42360
cgacgttcat ccgcgtggtg ggctcgatcc tgccggcgac ttacttcatg gaactggtca  42420
agaccctgtt cctggctggc aacaactggc cattgatcgc caagaacctc gcaatcctcg  42480
cggcctacgc cgtgttcctg ttgaacgctg cacgcctgtg cacccgcaag aagctggatt  42540
```

```
gaagccatgg acaagctgat gaatttccta cgcgagttgc tgttcctgtt tcagaaggag  42600
ttcctggcca tcgtcaagga cccggccaac cgggtgatcc tgattgcccc ggcgatcgtc  42660
cagtcattgc tgttcggcta cggcgccacc tacgacctga actacgtgcc ctatgccgtg  42720
ctggatcaga gccaggggcg cgcttcgaca gagcttttgg cacgcttcga tgcctccggg  42780
gtatttgccc gagtgtcgac cctgaccagc gtcgatgaga tcgccccggt gatcgaccgg  42840
ggcagtgcct tgctggtgct gcatatcgcc gcagacttcg acgagcgcct gagccggcat  42900
gaaaacgccg gcttgcagtt gatcctggat gggcgtaact cgacgaccgc gggaatggcg  42960
gccgggcata tcgccaacct ggtggctgac ttcaaccagc agttcctggc ggtggacaac  43020
gcgccggtac gcctggagac ccgtgcctgg ttcaacccca acctgcaaac ccgctggaac  43080
atagtgccgg gcctgatcgc cgcgctgagc atgatccaga ccctgatgct ggcggcgttg  43140
tcggtagcca gggagcgcga gcagggcacc ttcgaccaac tgctggtgac tccgctgacg  43200
cctttcgtga tcctgctggg caaggccctg ccgtcggtac tgatcggtct cttgcagtcc  43260
agcctgatcc tcctcatcgg cctgttctgg ttcaagatcc ccatgatcgg ctccgtgctg  43320
gacctgtacc tggggctgtt cgtcttcacc agcgcctgcg tgggcatcgg gctgtcgatc  43380
tcggcgctgt cggccaacat gcagcaggcc atggtgtaca ccttcgtgct gatgatgccg  43440
ctgatcctgc tctccggcct gatcaccccg gtgcacagca tgcccgaggc cctgcaactg  43500
ctgacctatc tcgatccgct gcgctttgcc atcgacctgg tcaggaggat ctacctggag  43560
ggggcaacgc tggcggatgt gtcctggaac ctggtgccca tgcttgccgt tgcgctggtg  43620
accctgccgc tggctgcgtg gctgtttcgc aatcgattgg tgtgataagg aacgtcatga  43680
aaactactca ctctggatac ctgcgtaatg ggctgacgct ggccatgctg ctggccatca  43740
ccgcctgcac cgtcgggccc gatttcaagg cgccggcagt taccagcccg gaacgctgga  43800
cggattggca cagtggcccg ccagcgtctt cggtgccggg caaagccccg gcgaccacct  43860
cgcaaaccgc agacggcaac tggtggcagg tgtttggcga cccggtgctg gaccagctgc  43920
aggcccaggt gcgcgaaggc agcccggacc tgcacacggc cttgctgcgg tttgcccagg  43980
tgcggttgca acgccagata gtcgcttccc tggaaacgcc cgaagtgtcc ttttccgcgg  44040
cggcttcgcg aaaccggcaa agccggtatg cgccgaacaa tcgaatgctt gaagccttgg  44100
gcagcgacag tgatgccctg gaaaaggtgc ttaccgaccc ttatagcctg taccaggccg  44160
ggttcgacgt ttcatgggag ctggatctct gggggcgggt gtcacgcctg ggtgaagccg  44220
cccaggccga ggtcgatggt gcggccgcga ccctggacga cgtgttgctc agtgtctcca  44280
gcgagctggc gcgaaactac ttcgaagtgc gtaccgcaca gcgccagacc cgtcttctgg  44340
agcaggaggc acagatcctg gccgcgcacc tgcaagtggt tgccgtccag gcccgggagg  44400
gcgaggaaga cgggttcgcg gtggaacgcc aagaggcacg gctggcctcg ctgcatgcac  44460
agataccggg ttggaaggcg ctgcacaccc aggcgggcaa ccgtattgcg ctgttgctgg  44520
gggagcatcc cggagccctg gaaaccttgc tcgcggagcg gcctgataat gccttgagcc  44580
gcccgctgcc caacctgcag ttgggcctgc ctggcgacct ggcccgggag cgtccggaca  44640
tccgcgcggc ccaggcccgc ttgcatcggg cgacggcggg catcggagtg gccgaggccg  44700
aactgtaccc gagcgtgatg ctgggggccg acttcggctt cgaatcctac aagagcggcc  44760
agtttgccga ctggagcagc cgcacctggt cggtagggcc gcgcctggac ctgccgctgt  44820
tcgaccgtgg gcggcgcagc aagaccgtgg tcctgcgcac actcgaacag caagaggcgg  44880
ccgtggcatt tcaccggacc gtactggcag cctggcagga agtggacgat gcgatgagcc  44940
```

```
gctaccacaa cgaataccag cgtgccgcgc acctcaagga cagctatgac agcaaggccc  45000
gcacctatga gtggacccgc gtccggtacg cggccgggga ggccagctac ctggaggaac  45060
tggaagcgca gcgcaccgtg ctggaggcgc agcgcgacct ggtcaatagc gacagtcaac  45120
tgcgtactca cctgatcagc atttacaaat ccatgggtgg gcattccacc tgagcccctg  45180
aaacgctgcc tctggcagca ctccccccag acccactttc ctaacggaat aggaagccat  45240
gcaaatggat gacctctaca agatcgcgct tttttcgtcc ctgatactgg tagtgccggg  45300
gccctcaaac accttgctgc tggcctcggg cttcaagttc ggcgtgttgc gctcgctgcc  45360
actggtgttg atcgaaatgc tcggctacac cgtttcgatc tgcacctggg gctgggggct  45420
tgtgctgctg tcccacgact acccgtggct gatccacctg atcaagctgc tgtgcgcctt  45480
gtacatcgcg gcgctggcct tgaagacctg gaagacctcc accaccggag cccagcacac  45540
cgagcgcttt gagagctggc cacggcacct gttgattgcg accttgctca accccaaggg  45600
gctgatcttc gccagtgtga tcttcccggc cagctcattc gccagcctgg gggatttcct  45660
gccgtcattg agcgctttct tcctggcact ggcgccaata gccttgctct gggtctcgct  45720
gggggcgggc attcgagccc aatacctggg gcgggtttct ggaccgctgt tttcccgggg  45780
caccgccgtc gttctggcgc tgttttccgc caccctcact tacaccgtgg ttcgtgcggt  45840
gtaggtgttt ttgccgcggc tttcagcgcc caagtgaggc tggggcaatg gcgctgctga  45900
gagaggccct tgtacccccc gtgttccagc accactctgt tgtcgccaac acccgggggg  45960
gctcattcca cgtagcgcaa ccacaaatgg gtgcgaccgc gaacagcctc gacaaccgtt  46020
gaaaccacgg cttgccggtt ttcctcggag gccttgatcc gatgaacagg gcgtttggcg  46080
gatgttaatc tgcgcctccc ggacaaacgg tgggccagtg gatgcagagg atgttgagtg  46140
aagccgagct tcacaaggtg ctggaatcga tcgaaagcga ctcctgccat gacctgaatc  46200
ttctgtatga cgggatgcag atagaccggt gtgctctttt caatcaagtc gccatggcgg  46260
tggcccggct ctttatcgag gggcagcgcg acttccatta cggcgatgcg gtcatgtggg  46320
tcgcggccag nntgggtcgc ggccagaacc gccggcgaac tcacgcggtt tcgctacggc  46380
tccagcatca agcggcgcca aagaatcggc ggcgcgacag cagcggccgg cgcttgcggc  46440
tccggcttct ccggcgcctg ggctgacgtt gcctcgcggg gctcaggcgc tcttgtcgac  46500
tcggtcgggt catcggtcgg cgatggggtc atttgatcct gaccaccacc ttgcccttgg  46560
ttcgtccctg ctcgacgtac tgcaaggcct ctgccgtcga ttcgaaactg aagctgcggt  46620
caaccacagg cttgatgatt ccggcctcga tcagcgcggt gatctgttgc agctgggcgc  46680
catcggcccg catgaacaca aaggcgtagc ggacgtcccg ctggcgcgcc ttgcgccgga  46740
taccgaagct caagaggcgc atgacctgct gcaacggcca ggccagccct tgctcctggg  46800
cgaattgcac cgtgggtggc ccggagatgg aaatcagctg tccgccgggc ttgaggacct  46860
tgagggactt ttccagtacg tcgctgccca ggctgttcaa caccaggtcg tagccatgca  46920
agaggctttc gaagttctgc tgcttgtagt cgatcacctg atcggcgccc agggctttga  46980
cccattcgac attcgccgtg ctggtggtgg tcgcgacgaa agcgccgagg tgtttggcca  47040
gctggatggc aagggtgccg acaccgcctg cgcctgcgtg gatcagcact ttctggccct  47100
ttttcagttg ggcggtttcc accagcactt gccaggcggt gagtgcgacc aaggggatcg  47160
acgcggcctc ggtcatggtg gtgttggcag gtttcagggc gattgcgttt tcgttcacgg  47220
cgatccactg ggcgaacgtc ccgatccgtg tttcaggcgg gcgcgcgtag acttcgtctc  47280
```

```
ccggcttgaa gcgttgcact tgggggccaa cctcaaccac gacgcccgcc aggtcgttgc  47340
ccagtaccag cggcaatgca tagggcagga tcagcttgaa ttcgccgttg cggatcttcg  47400
agtccagcac gttgacgctg ctggcgtgga cctcgatcaa cacgtcgtgg gcacccagcg  47460
tgggcgtggg cgcttcgccc atgcgcccac tgttcttgcc atagcgatca attagaaagg  47520
ctttcatcgt ggtgcggctc ttgtcggttg gaataggtgt gggcggtgct tgggtggggt  47580
tgctgtcatg gggctctgtc gtcaaggaac gcccggacct tggccacgaa gtccgcgtgg  47640
tactggaaaa tgccgccgtg cccggcgtcc tcatacatca ctagctgtgc gttggggaca  47700
cgcttggcca gggcatggga gttggcgctg ggcaccatga tgtcgttgtc gccattgacg  47760
atcagcgtcg gcgcccgcaa gcgcccgaga tcctgcggcg cctgtttgcc ccacgcggtg  47820
atggcttgca gctggcgcag gaaagcgccg ggcgttgggc ccttgtcgcg atgcttgctg  47880
cgggctttca ggcgttgcag atattccgag gcggctcgac gaccatgggg cgtcgaggta  47940
aagaacaggt agtacttggg atcgcgcaag gtcagcaagc ctttgagcat caagggccag  48000
gtcaccgagc cgaccttgtc gataccgatg ccgccggccg gtccggtgcc ggtgagaatc  48060
aagcggtgca ccaattgggg ggcttgcagg gcgatgtcct gagcgacgaa gccgccgagt  48120
gagaagccca ggatatcgac gctcttgaac cccagggcct gtatcagctc aatggcgtct  48180
tgcgccatgt cgccgaccgt caggggggcg gttccacccg agccgccgat gccgcgatag  48240
tcggtggtga tgactcgccg ggtctgtgcc agcccatcga tgattgccgg gtcgaagttg  48300
tccagcaccg cgccccagtg gttaaacagc accaggggca cgccgcccgc gggaccggta  48360
tcgcgatagg cgaagggaat gcccctgacc atgatcgact ggttcgccgc gttgatgaac  48420
gacgtctgca aagccggggg gaaggttgtc tgcgttggat tcattgctac tccgaacagc  48480
ggaccggatt cgtcgcagtg cctgccgcga atccgccgcg aatgctcgct acctgaagat  48540
cactcttggg tctggtaacg ctgggcaacc tcggattgac ggatgtgccc cagcaggccc  48600
tgacgtgcgc tctgcaggtc atcccagggt tcagcctgtt gcagtggcgg gatggtcacc  48660
ggttcgcgcc gatcgaaacc gaccagtgcg gcatccacca gatcgcccac ttccatgatt  48720
tcgtccaggg tattgatgtc gacgccggag cggtcccaga tttccgtgcg ggtggcggcc  48780
ggcagcacgg cctgcacgta cacgccccgg ggcgacagtt ccaggctcag gccctgagac  48840
aggaacagca cgaaagcctt ggttgcacca tagaccgtca tgccgaactc cggcgccagg  48900
cccaccaccg aaccgatgtt gatgatcgcg ccgtcaccgg ctttggccag gcgcggggca  48960
atggcactgg ccagccgcac cagtgccgtg gtgttgaggg caaccagttg cgctacgctg  49020
tcggtgcttt gctcgatgaa gttgccggac agcgcggcgc cggcgttatt gatgaggatg  49080
ccgatacggg cgtcgtcgcg caggcggctt tcaacggttg tcagatcgct gagttgggtc  49140
aaatccgctt tcatcacctc gacggcgacc ccgtgttcgc cgcgcagtcg ggctgcaagt  49200
gcgtccaggc gtgcccggtc gcgggcaacc aggaccagat catggccacg ttgcgcgaag  49260
cgctcggcgt agatggctcc gatgccagtg gaggcgccag tgatgagaac ggtagggcga  49320
gtgttcatgg ggtcatctct ctttcaaaat gggtgaaaac ggacagctcg gtttctgctt  49380
gctcagcttg cgctggcgct cgaatcaacc agcgtcgggt agtcgatgta gcctgccgcg  49440
ccgccgccgt agagggtggc gggattgaat gcggacaagg cggcgccggt cttgagacgc  49500
tccaccagat ccgggttgcc gatgaacggg cgaccgaacg cgatcagatc ggcctggtct  49560
tcggcgagcc gtgaggttgc cagctccagg tcatagccgt tgttggcgat gtaggtgttt  49620
ttgaaacgct ggcgcagggc ggtgaaatcc aatggcgcca cgtcacgtgg gccaccggtc  49680
```

```
gcgccttcga ccatgtgcag gtaaacgacg tcgagggcgt cgagttgatc gacgacgtaa  49740
ttgaattgcg cctgcggatt gctgctggag acaccgttgg ccggcgacac cggcgacaag  49800
cgcaccccgg tgcgatccgc gccgatttca ttgaccacgg cagcggtgac ttcgagcaac  49860
agacgcgcac gattttcaat cgagccgccg taagcatcgg tgcgtacgtt ggcgctgtcc  49920
ttgaggaact gatccagcaa atagccgttc gcgccgtgaa tttccacgcc atcgaacccg  49980
gcagcgatag cgtttgccgc ggcctggcgg aaatcggcga cgatccccgg cagctcgctg  50040
atgtccagtg cgcggggctc gctggcgtct tcaaagcggt tgttgacgaa caccttggtg  50100
gccgcacgca gcgcggaagg ggccacgggg gcggcgccgt tttcttgcag atcaacgtgg  50160
gacacgcggc cgacatgcca cagttgcaca aagatctttg cgccctgggc gtggaccgcg  50220
tcggtcaccg tgcgccagcc atcaatctgc gcctgggtgt agatcccggg ggtgtcctga  50280
tagccctggc cctgttggga aatctgcgtg gcttcgctga tcagcaagcc tgcgctagcg  50340
cgttggctgt aataggtggc ggcgaattcg ctgggaacaa agcctgcgcc cgcgcggttg  50400
cgggtcagtg gcgcgaggac gatgcggttc gccagcgcga gggcgccaag ggtgtaaggg  50460
gtgaacagat tctgatcggt catctggtgt ctcttccgtg cccgtgggtg gaggtcggtg  50520
gtgtgtgcaa ttaggatgat gatcgaaatc taaactgtca acggttttga ttatgatcga  50580
catctatgta tgattgggcc catgatttcc caatgaacat gaggtattgc acgtgagagt  50640
gagcaaggcc caggcgcagg ccaatcgaga gcacatcgtt gaaacggcct cagagttgtt  50700
ccgtgagcgc ggcttcgacg gtgtgggtgt gtcggatctc atggcggcgg ccggtttcac  50760
ccacggcggc ttttacaagc atttcggctc gaaggccgac ctcatggccg aggcctcggc  50820
ctgcagcctt gccaagtcgc tggcaggcgt gcaggcgctg gatgtgcctg gcttcatcga  50880
cgtctatgtg accagggaac atcgcgacgg acgtggcagc ggttgcacca tggccgcgtt  50940
gtgtggcgat gcggcgcgcc aatcggatga tgtgaaagcg acgtttgccg aaggggtcga  51000
gcacaccctg caaaccctgg gggacaaata cccgacccgg ccggatgccg ctccggagga  51060
gggcagacgg aaaatgatcg acctgctgtc ccgcgcggtg ggtgcgatca tgttgtcgcg  51120
tgcctgcccg gatgattccg ccctggcgaa tgagattctt gaggtgtgcc gcgctgagat  51180
gtttgcttcg ttgccggttg ataaaggcga gtcggcgtag aggggcccca tgccagggcc  51240
ctgcgcttgc gaggtgcctg cttnnnnnnn nnnnnnnnnn nnnnnnnnnn nnnnnnnnnn  51300
nnnnnnnnnn nnnnnnnnnn nnnnnnnnnn nnnnnnnnnn nnnnnnnnnn nnnnnnnnnn  51360
nnnnnnnnnn nnnnnnnnnn nnnnnnnnnn nnnnnnnnnn nnnnnnnnnn nnnnnnnnnn  51420
nnnnnnnnnn nnnnnnnnnn nnnnnnnnnn nnnnnnnnnn nnnnnnnnnn nnnnnnnnnn  51480
nnnnnnnnnn nnnnnnnnnn naccacaaat gggtgcgacc gcgaacagcc tcgacaaccg  51540
ttgaaatcac tgcttgccgg ttctcatcag aggtgttgta gagcgcacaa aaatccttcg  51600
ccacggcgtt ggcgacgtgc aggtcagcag gcgctgcacg caggaaaccg aggtaagacg  51660
cgcccacccc gatcaactca tagccatggg cctgggcgaa atggcgggcc actgcaaagt  51720
tctgcgcggg gcccaggtcg caactgaagt agccgttggg aaaagcggcg agcgcctgac  51780
aggactgctc gacgggcacc aggagtgccg agaggggctg gtcgagcagt gatacagggt  51840
tttgctgata gtccacccat tcgtgcaggg ctggcgcatc aagggtcagg ccgtgggcgc  51900
aagcgtcttc gaacgagctg cctgccacca ggtcagtgaa gttgcgcaag cagatcgcga  51960
actcggcctt ggtggtgggg tagcccaggt attcaccctg ttcgaagcat tctgcaggta  52020
```

```
gcagggcgat ctcctgctcc gaggcatcgt ccagccccag gttgttgcgg gcgtgcccgg  52080

aggtgtagcg ggcctggggc agatcatcca gcgagagaag gggctggaaa cccgggtggt  52140

cgccagcgat cttgcggtag gcgtcgatca gctcatccag gctggaaatg gcgctcaggc  52200

tgtattcatc gcaggtgcca gcggcggggt tgccaggcat tgcgttaccg cgaaattgga  52260

tatccatcga atggctaccg gctccatgtg ggtgttcagg cgaatgagca acgctcggtc  52320

gaacgtacgt gagcctgctg gtgctctcgc tgttcgtgcc aggcctgtga gttcattcca  52380

ggcccggggc ctagcttaaa gagagcacat cctgcctggg catgaagaag cgtgcaaaga  52440

gttcggactg tgacttgatg ttcaacttgg cgtagatgtt gcggcggtgc actttgatcg  52500

tctctgtgga gagggagagc tttcctgcga tttccttgtt ggaaaagcca ctgagcagca  52560

gcctgagcac atcactttcc cgcgtggtta tctgggtacc aaactgggtg atcgtctccg  52620

gccattgcgg cggttcgctg aggctttttt ccacatcgac ttcgaagcac atgcgttgat  52680

gcatgagtgc cgtgacccac ggcttgatga tgtccagcat ggtgatgtgt tcctggctga  52740

aatgggcgtt                                                          52750
```

```
<210> SEQ ID NO 3
<211> LENGTH: 41086
<212> TYPE: DNA
<213> ORGANISM: Pseudomonas protegens PBL3
<220> FEATURE:
<221> NAME/KEY: misc_feature
<222> LOCATION: (1)..(41086)
<223> OTHER INFORMATION: Pyrrolnitrin biosynthesis gene cluster
<220> FEATURE:
<221> NAME/KEY: misc_feature
<222> LOCATION: (26090)..(26091)
<223> OTHER INFORMATION: N is an A, T, C, or G

<400> SEQUENCE: 3

acctgctggc ggtgggttat gccggcgccg cgcactacca ggatgtgccc catgcggtag     60

cggaccagcg cgtgatcacc gccccgggca gcgctccagt gagtttcatg gcacagattc    120

tcggcgccct gggcatcagc gacgacaacc tgaccttcta cctgggcctg cacgccgccg    180

agcaccgcca gcaaacctga ccctcccctg taggagccgg cttgccggcg aaggcgatct    240

cccggccgcc ttggctggca agccagcgcc tacgcaaggt agtgggtggg cggcagtgcg    300

ggcgtgtgcc gtggattatt tcaccagccg aaaatcccgg tggcccaacc aggccgcaaa    360

gtccgcagcg ctgaaaatgc tctcgccctc atgctcgatg atcgccagcc ccgccagaaa    420

ttcgctgtcc cgggtgtagg catggatgct ggcgccgaag gccagtacgc catccaggtg    480

acgggccaag gtcagcgccg cctgccctag gcgctggtga tccgcctggt ctttatccat    540

ggccgccagg ctcagaatgt cttcagggag ccatcccagt tgcccggcca gcccggcata    600

ttccgccagc tcccctggat attcggcccc catcccgaac agcatggggc tgccgtcaat    660

gaagaacgag ctcgtaccgg cccagggttg atccgcaatt gcggccagac aggcccgcac    720

ccggttttcg agcaagccat cgatctggcg cggtaaaagc accctgacag tcggcccggc    780

cattgagtca tctcctccag cgcaccgcat ccgcaactgg gataacgggc gagcccttgt    840

tcgctgcatc agcaggcatc aatgctcaag cccgctgccg gtcagtgcat tcaccggacc    900

gggagcataa aagcccgtgg tgcaatagcc aagctcagcg cctggaacca ttgaccccca    960

acacctcttc caaccgcttc gcctcgccct ccgtcaacaa gggcgcaggc ggttggacaa   1020

ggcgctggct ggacagggcg ggcaccgggg ccgttggttg ggccgtcttc gcagtacggg   1080

tgcggctcgc gctgctttgc gggtacagcg cttcatccag gcatttgtcg cgcatgccct   1140
```

```
ggctggacag gccgtggcaa ccggtgccgt tggacagggc acgggcaccg caggtggcct   1200
tgctgtcggg gtccttgagg tcgatgcagc ccagggaacc aaagccatgg cccagtaccg   1260
aggcgggatc ttcggcgcaa gctgcgccgg cacacaggaa cagggaggtc agcacaagtg   1320
catttcgcat aggggcgcgt ccatggctag cgtaggtccc ccggcgcctt tccggccgcc   1380
gggcaggtct gtcgagggaa aaagccgttg tagcagatga acatgaccgt ttcccttccc   1440
cataaccacc gctgttgcgt gactagcgga aacgccccgc caggaagggt tgcaggttca   1500
cgctcggggt cagcccgctg gcctgttccg ccaccagttg cccactgatg gcggccaagg   1560
tcaggccaac gtgaccgtgg ccgaagttgt agtgcacctg gggcagcagc cgcgactggc   1620
cgagcaccgg tttgctgtcc ggcagcgagg gacgaaagcc catccaccgg gaaaccggtt   1680
cgtggtgcag ggtcaggaag cgtcgcgccg cccgggccag gtagtgatag cggcgcgggt   1740
ccggcgcggc gtcgaggccg ccgaactcca ccgtgcccgc cacccgcagc ccttgggcca   1800
tgggcgtcag gtagaaaccg ccggcgcccc agcacaccgg gcggctgagc aagccgccgg   1860
cctgatcgaa cagcacgtga taaccgcgct cggtgtccag gggaatctcg tcccccaggc   1920
tctgtgccag gcggcgggac caggcgccgc tgcacaacac caggcgttcg gcggacagtt   1980
gctcgccact gccgaggcgg gcaagcaccc gctcgccgtc ctgggcgctg cgctcgaccc   2040
cctgcaactc atcgcggcga aacactccgc cgcgctcgat gaagcaccgc agcaagcgct   2100
ggctcaatgc gaagggatcg agggtgcggc tgacctgggg cagttccagc gccagggccg   2160
cacgggcgtt gagggccggc tccatggccc gtagctccgg cccttgcacc aggcgcatgg   2220
gcacctcgaa cccctggtga taggccagca tgtcgatagc gctctgccgc tcgtgggcct   2280
cgaagatgta cagcgagccg tcatggcgca ccaggtcgtt ggccccggca tcgtcgaaca   2340
acgcctgcca ggcgcccatg cagggcttga gcaggctgtg caggtcatga ctgatggcct   2400
tgacccgcgg ctcgctggag ctttgcaaaa agcgccatag ccagggggcg atccgtggca   2460
ggtaacccgg gcggatcgcc agcgggctgt cgcgccgcaa cagcatgccc ggggcctggc   2520
gccagatgcc gggggttgcc actggctcca cggcataggt ggcgaaggta caggcattgc   2580
cgaaggaagt gccgctgccc ggcggctggc ggtccagcag ggtcacccgc cagcccaggc   2640
gctgcagcca caaggcgctg gccaggccca ccaccccggc ccccaccacc acggcgtggc   2700
cgcgttgttg ctgacttgca atcatgccgt gctcctcatg tgccgctgac gacccgggtc   2760
cacaggcgag tgctcaggcg catgccggcc ggggtcatgg tcttgatcgg gaacagcgta   2820
tcgagcaccg actgcggcgg gtaggccgcc gggttgctgc gcaactgcgg ttcgatgtag   2880
ggcaaggacg ccgcattgcc gttggcgtac tgcacgaagt tgctgatgtt ggcgatcacc   2940
ttggggtcca gcaggtagtt caggtaggcg taggcgttgt ccaggtgcgg ggcgttcctg   3000
ggaatcacca ccatgtccat ggccacggtg gagccttccc tgggaatgct gtagccgagg   3060
ttcacgccgt ttttcgcctg ctgcgcggtg gccatggctt gcagcacgtc gccgctgaaa   3120
cccacggcca cgcagatgtt gccgttggcc aggtcgctga cgtacttggc ctggtggaag   3180
tagaggatcg aggggcgaat cgcctgcagc gccgcttcgg cctttttcag gtccgccggc   3240
tgttcactgt ggggggccag gcccagggca ttgagggtga tgggcaccat ctgtgtcggg   3300
ttgtcgagaa aggccacgcc gcactgcttg agcttctgga tgttctccgg cttgaacagc   3360
agctgccagg actgggtgac atcggtgtcg ccgaagatcg ccttgatctt gtcgacgttg   3420
tagccgatgc ccacggtcac ccacatatag ggaatgccgt acctattgcc cgggtcgctg   3480
```

```
gtttccagca gcttcatcag cttgggatcg aggttgttcc agttgggcag cttgctgcga   3540
tccaggggct ggatcgcccc ggcctggatc agccgcggca gaaagtggtt ggacgggctg   3600
gccaggtcat agccgctgcc gccggtcatc agcttggcct cggtggtctc gttgctgtcg   3660
atcacgtcgt aggtggtctg gattccggtg cgctgggtga actgggccag ggtgtccgga   3720
gcgatatagc cgctccagtt ggcgatgctc acggtctcgg ccgcctggac gcttgcggcg   3780
cacaaggcca gggataacag tgccgtagtg gtgcgattga tcatgttgcc gccctctgtg   3840
ctcttattat tgcggcgttt cattcgccgc gacggttaac gttcgtgtcg cgcgcgctgc   3900
acttcccagc ccatgcgcaa gcttgctcca atgtcgaaaa acggtcgggg tggcaggtag   3960
ccgggccggg cctgggacag cacgtcacgc agcagcgagg agtcgcaacc ggcggccatt   4020
tccaccagca gccggcccca cagggtgccc cgcgccaccc ccgagccgtt gcagccggcc   4080
accgcgtgca ggccttcggc gacccggctg aagtacggct cgccggaacg ggtgccgctc   4140
aggtgcccgg tccaggtgta ttgcaggtcg gtatcggtaa tgccgggaaa gcgcttttgc   4200
aggccccgca ggtgttcctg gcggcgcacc gccaactgcg ccgggccgag atcgcgctgg   4260
cgatactcga cggtgttgcg catcagcagg cggcgcccgg gcaacaggcg caccgtggcc   4320
gccccgggca aggtggagag cacgccccag ccctgctcat ccagcagccg ctgccagtga   4380
tcttcctgca ggggccgggt gatgctggcg ctcagttcca gggggaaggt gcgactgtgc   4440
cggacaccga gccggggcag gaaggcaccg acacaggcca gcacctgggg cgcctggatc   4500
tcgccctccc cggtcaccgc ccgccagccc cggcccggca gaggctgcag gtcctgcacc   4560
gggctgttct cgaacacctc cacccgctcc ggcaggcgct ccagcaggcc cttgacgtat   4620
ttggccggct gcagcagcgc gttgccaccg gcgcagtgga tggcccgctg gtagaagccg   4680
ctgcccaggc gctgctgcaa ggccgcgcct tccaggtacc gggcctgggc gcccgcggca   4740
ttcagggtag cgactcgggc gccgctgtcc tgcaagtgct gcccctggtg cacggcgaag   4800
tgatagccac cagcgtcgaa ctcgcactcg atgcccaact cgtcaatgcg ccggcgcacc   4860
tcttcaccgg cagcgatgcc gatgccgcag gcaagctgat aggccgagtg gccgggcgg    4920
cccagcaact catcggcgcc gggcaattca tggctgacca caaaccccga gttgcgcgcc   4980
gaagccccct gggccgcccg ctggcgatcc agcaggacga tgcgttgctg gggcaacatc   5040
cgcgccaggg catgggccgc cgagaggccg gtgatgccac cgccaatgat cagccagtcg   5100
gctttctgta ggcccttgag ggttggccgc tgggaagcct gccctgccag ggcgatccag   5160
ccacatacat tgttcaaagc ctgtcactcc tgcacaatcc atgcgcccgg agcattcaac   5220
agaacactca acccggcgcc acatgcctac aatctatgga tatgacggct ttatttcgaa   5280
cgttattaat tcatccatct attcggaaaa cgcatggata accctcttcg actaccctcg   5340
ttgcaggccc tgcagaccct ggtcagcgtg gcccagaccc acagcttcac cgagtccgcg   5400
gcgcgcctgc acctgaccca gagcgcggtg agccggcaga tccagcaact ggaggagcac   5460
tatggggtca gcctgttcga gcgcagcagc cgaagggtct cgctgaccga acaggggcgc   5520
gatgtctgca cggtggccac tcaagtcctg aggtccctcg gctccctgca ggaacgcctg   5580
gccccggcgc ccctggaccg gccgtttcgc atccgcatct ttgtctccct ggcggtgcgc   5640
tggttgctgc cgcggctcag cggtttctac gccgccaacc ccgggctgtg cctgtcgatc   5700
gagaccgtgg gcggggccac ggtagacccc ggcggcgatt gcgacgccta tgtgctgtac   5760
ctgccggaag gcctggacga gcggccgctg accccgctgt tcgacgaata cctggtaccg   5820
gtgtgtgccc caacgctcag tgacgggcaa ttgccgccgc gctccctgga ggaactggcc   5880
```

```
gggcacgcgc tgatccacgg ttctaccagc cgccaggaat ggaccgcctg gctgcaggcc   5940
caggacgacc agacgcccca cagttacaag cacctgctgt tcaacctcga cgacctggcc   6000
ctggacgccg cggcccgggg gctgggggtg gccatgacgg acctgatcct ggcccaggac   6060
tcgattgccc ggggcagcct gctgatcccc tttggccagg cgctcaagac cggcggggtc   6120
tatgccctgt ggctacgcga cagcggcgcc gcgcatccgg cctgcgaaac tgtattgaac   6180
tggttccagg ctcaggcagc cgaacgggat ctgcccgcgg cacaaggcct ggctgggacg   6240
attgcagcag ccctgggcac gcctggacgg cagtcgatcc caggctgaat gactggacca   6300
ggccctgctg ctcatgggcc tgggcaaaca acattgaagg gccgatgaac actgcccggg   6360
aaagctcgag cgccgccggc gctcagctgt agagcgtcac cattgcccag gcaaaacacg   6420
ccagcaccag ggccatcccc actacataca ccgctaaagc acgacccaca gcatcactcc   6480
acgaaccagg cagacatcaa cacactcact ctcggggtga gtcatggcgc gcattctagc   6540
agcgcgcgac gtcattttga cacgagactc taagcctgat taaaagcctc ccgacaaatg   6600
gtattggcgt caatttaatg gcttaagtca gcctgattct tcttaccggg tagccgaact   6660
gcgaaacatc atcttgcatt gcgcccagtg ttttcttccc gccaagaaac ctgctgcctc   6720
caggatcaat gcaagccccc ttttcccgct aaaccgcgaa cctgagcgct atcagcgcct   6780
gcactcctgg ttggacaaga gtgatcctga ctgctttgat ctcaacgcca ggtccggttt   6840
tcacaatccc agggaggggt ccatgtcgtt caaggtcatg atggttttcg gtacacgccc   6900
tgaggcgatc aagatggcac cactggctcg ggttctaagg cactggccag gtatcgagct   6960
gcacatctgt tccaccggcc agcatcggga aatgctcaaa caggtactcg acgcctttga   7020
gctcgaggtc gatgtggacc tgcaagtgat gacccagggc cagaccctca acggcttgtc   7080
gcagcaactg ctgatccatc tggacaccag ctacgagcgt ctgcaaccgg acatcgtgct   7140
ggtccatggc gacaccacca ccagttttat cgccgccctc gccgccttca accggcagtt   7200
gcccatcggc cacgtcgagg ccggcctgcg cactggcaac ctccaggcac cctggcccga   7260
agaagccaac cggcgcctga ccggggtcat cgccgacctg cacttcaccc cgaccgccag   7320
gtccgcaacc aacctgctgc gggaaaacgt gcccgctgaa aacatcgaag tcaccggcaa   7380
cacggtgatc gacgcgctac tgtggatgcg caaccggcag aagcacaccc actggcgccc   7440
cgcggccaac tcgcccctgg cggtgctcga cgacagccgg cgcatggtgc tgatcaccgg   7500
ccaccgccgg gagaacttcg gtgacggttt ccgcgatatc tgcgaagccc tggcaaccct   7560
ggccgagcgc tacccggacg tgcagttcgt gtacccggta cacctcaacc cccaggtaca   7620
gaacgcggtg tacggcctgc tctcgaacaa gccgaacatc tacctggtag caccccagga   7680
ctatcagcat tttgtctggc tgatgggacg ttcgcacttc atcctcagcg actccggcgg   7740
tgtccaggaa gaggccccgg ccatcggcaa gcccttgctg gtgctgcgcg aggtcaccga   7800
acggccgtcg gtgctggaag gcggcaccgt gctgctggtg ggcaccgatc gcgagcgcat   7860
cgtgcaccac gccagcgaac tgctggacga tgcacagctg catgcccgca tgagccgcgt   7920
gcacagcccc tacggtgacg gccgcgccag cgaacacatc gcccgccgcc tgtgctcctg   7980
gctggaggcc caagcccccc gtactccggc atgagcccgg gcagcccccc gcagcccgca   8040
gtcgcaaaac gtccagttgg ccatatggct ccacactctg tgcgagaact ggaagctacc   8100
ggtcactggc aggtacctgc caattgaact ggacgactta cactttcaag cagcggatcg   8160
tcgcgccccc tccaacccca gcgcggtgtt ctccctgcgc tatcgcccct ggggcaagcc   8220
```

-continued

```
gctgcaggat catcagctca catccaaggc ccgcgatgtt cagaaccctt gaagaacaag   8280
tgttcaaaca ggccgctccg gcggccctga agcttgaatt cgcgcaacat gatttcgaac   8340
gcctgcgcag tttctgcgtc ctgatctaca ccgccagcat cctgatctgg ctgatcttcg   8400
acctgatcgt cagctttccc gggcagcagg gcttcaccgc ctattcgatg gtctttctga   8460
gcattctgtc cttcaccacc atcatcctcg gcttcacccg ccagggccgg cacttccagt   8520
gggtcaacct gctgttcgtg ctgaccatca ccatcggcgt acgcctggtg atcgaggggc   8580
tgcccatcga ccagcgcccg gtctggctga ttctcggcgc gtcgagcatg ctctacggcg   8640
cctcggtgat gcctctgcga cgctggtcgt tcgtcagcgc gatcttcatc acttggctgg   8700
tgctcaatcc gttctggcgc accagcacca ccctgcagga actcaagggg ctgctggtgc   8760
tggtgtacgc gctgtttctc agcgcattga ccctctacag cttcatcacc ctgcgccggg   8820
cccggctgca caactacatc atgtccaagt tgctgctgga ccaggcctac ctcgacaccc   8880
tcaccgagat ccccaaccgc cgctcgttca tggcccgtgc cggccagcgc ctgcaggctc   8940
tgccccggga gcacgaccat tacctggcga tggtcgacat cgacaacttc aagaaggtca   9000
acgatgtgta cgggcatgac atcggcgacg aagtgctcaa gcgcatcgcc gccgatatca   9060
agggagtgat gagggatttc gactatgccc gcctgggcgg cgaggagttc gccatctacc   9120
tggccgacgt gccccgcgcg gatgtggagg cgctggccac gcgactgtgc caggtggtgc   9180
gcgaccagcc gacccggcac ccggtgacca tcagcatggg cctggcccgg gtcgagcctg   9240
gcgaaaccct gaaccaggcc ctgatcaagg ccgaccaggc gctgtacgaa tccaagcacg   9300
gcggcaagga tcgctatacc ttccatccag ccgccaggcc cgcaccaccc acgtaggagc   9360
tggcttgcca gcgaagaggc cccagtgtca gtccacgctc ctgcgcgaca gcagcacctg   9420
ggttacccgg cgctcctcca ctgccctgac ctgcaggctc cagcccgccc actccacccg   9480
atcgcccttg accggcaggc ggtccagcag gctcatcacc agaccggcca gggtctggta   9540
gtcctcggtg ggttcagcgc cgaagccggt ccgctggcgt acctgaggca ggttcagcgc   9600
accattgacc aggaacccgc cctcttcttc gatcacatcc gggccttcga tctcgctggc   9660
atccggcagc tcgccggcaa tggattcgag aatgtcggtc atggtcagga tgcccatgaa   9720
gtcaccgaat tcgttgatca caaaggcaat gtgagtggac gcctggcgca tctgttccag   9780
ggcgttgagg atcgaaaagc tgtccagcag gttgatggtc ttgcgcgcca gatgctcaag   9840
gttcggctca ctgcccgcca ggtactcctt gagcagttcc ttcttgtgca cgaagcccaa   9900
aggctcatcc accgcaccat cgcgaatcag cggcaggcgc gagtacgaag aatgcatcag   9960
cttggtacga atactctccg ggctgtccgt aaggtcgatg cagtcgacct cggcacgcac  10020
cgtcatcagg ctgcggatcg gccgctccgc cagttgcagc acaccactga tcatcacccg  10080
ctcacggcgg tcgaacagct cgctgctggg ggcctcatca gtttccagca agtcggcaat  10140
ttcctcgccc acttcttccg ccgccagcct gcgcccaccc agcaggcgca tcaccgcata  10200
ggccgtgcgc tcgcgcatcg gccgcaggcc ctgcatggat ttcttgcgcc gggcccgggc  10260
gatctggttg aacacctcga tcaggatcga gaagccgatg gccgcataca ggtaaccctt  10320
gggaatatgg aaacccaagc cttcggcggt caggctgaag ccgatcatca tcaagaagcc  10380
caggcacagc atgatcaccg tcgggtgcgc gttgacaaag cgggtcagcg gcttgctggc  10440
gacgatcatc acgccgatgg acaccaccac cgcgatcatc atcaccgaca ggtgctcgac  10500
catgcccacc gcggtgatca ccgcgtccag ggagaacacc gcatcgagca ccacgatctg  10560
cgccacgatc ggccagaaca aggcgtaagt ggtactgccg gcgcgctggc tgacatggcc  10620
```

```
ctccaggcgt tcatgcaact ccatggtggc cttgaacagc aggaacacac caccgaacag  10680
catgatcagg tcacgccccg agaagctgtg ctcgaagacc tcgaacagcg gctgggtcag  10740
ggtcaccatc cacgagatgc tggccagtag gcccaggcgc atcaacaacg ccagggacag  10800
gccgatgatc cgcgcacggt cgcgctgctc gggcggcagc ttgtccgcga ggatggcgat  10860
aaacaccagg ttgtcgatgc ccagcaccag ctccaggacg atcagggtca aaaggccaag  10920
ccaggccgtg gggtctgcga tccattccat aacgacgact caagtgctcc ggaaaattca  10980
aacggccagg cgcgacgcag cgccaaggtg caggggctgc aaaacctcgg gtacgggcgg  11040
ataaaggcag gaagtggcaa gtgccaggca agtgcaaccg ggagaatggc tgcctgagcg  11100
tctggggctc agggccgccg gatggcgcga gaagtcatgg ggcaaagcga ggaaagagcg  11160
ccgactgggg ggctccgaga gcgtgttcat gcaagtcctg aaggaaaaaa cggacttgga  11220
gattacaggg agggcaaggc gattccccag cgggaaatca ttacaagatt ttatccggcc  11280
cgcgtctctg acgcaggccg gcaccgctac aactgctcgg aaatctcgat caggttcagg  11340
tccgggtccc gcaggtacac cgaacggatc gggccggtgg cgccggtgcg cggcaccggc  11400
ccttcgatga tcggccagtt ggcctgttgc agatgggcaa tcacctgttc caggggcacg  11460
ctggcgatga agcacaaatc cagcgccccc ggcaccggca ggtgggcctt gggttcgaac  11520
tcctggccgc gcacatgcag gttgatcttc tggttgccgt acttgaaggc cttgcgcccg  11580
ccggcaaagg tttccagttg catgcccagc acgcggacgt agaaatcctc ggcggcaatc  11640
gggtcgatgg tggtcagtac caggtggtca aggtggtcga tcatcgaaga cgcggctcct  11700
gaagcgaaag gaatggcccg gggattatgc gacccgggcc gtcgcttgaa catgccccat  11760
caggctttgc cgcggtactc gcgccgtacc tgctcgatgt agcgcaccac cgccggtgcc  11820
tgctcgaaac gccggtggat cagcgacagc caggacgtcg ccgagctgcc gccaatcggc  11880
cggtacagca catggggcag gctgatgtgg cccaccaccg actccggcac caccgccacg  11940
ccctgcccca gggacaccag ggccagtacc gccaccaggc cgccgggctg ggccccagc  12000
ttgggggcgt aggcaccctg ggccgccacc tgcaaggtgc cgctgatctg ctccggaaga  12060
atgaaggttt cattgagcag gtgttcggag gcgatctgcg gcaggcggca cagccaggat  12120
tcgtcggaca gcgccaggac aaagccctcg gcgtccaggc gaatggcctc gaccccttcc  12180
ggcaatgtca tgggcgagcg aatgtagccc acgtccaggc gaccatcggc aatccgcgcc  12240
ggcagcgtcg ccatcgggca ctcccgcacg ttgaggctga cgtccgggca gtcgcggcca  12300
aagccctgca cctgtttctg caacagcccg caatacaccg ccgaggccac atagcccagt  12360
tcgatatggc cgatctcgcc gcgcccggca cgctgggcat tgcgctgggc aaactcgaac  12420
tggcgcaccg tggcctcggc ttccagcagc agggtggcgc cggcctcggt caggctgacc  12480
tcgcgttgct ggcgcaggaa cagccgggtg ccaagggtgt tctccatgtc ctggatctgc  12540
cggctcaggg tgggcggggc aatccccaat tgctcggcgg cgcgggtgaa attgcgctgc  12600
cgggccaccg ccaggaagta gcgaaagtga cgaatttcca tgatgggcat tagctcaaag  12660
gtaatgaact ggtcgccagc agctaacaaa gaccgcgaaa ggccgggata agctgagcga  12720
accttcacag tagagagcct ctgccatgcg cgtcaaaccc ctgtttctgg caatgatcac  12780
ctgctgcgtg ctgcagaccg cggccgccga ggacagccaa cccgtcattg cccacaaggc  12840
aatccttacc ctggacaacg cccagcgcct gctcagggcc gcccagcaaa ccgcccaggc  12900
caagggctgg ccctgcgccg tggcaatcgt cgacgacggc ggctggccga tactgggcgc  12960
```

```
gcgcatggac ggcgccccag tggtggccgg agtcgagctg gcccagggca aggcacgcac  13020
ctcggcattg ttcaagcggc cctccgggga tctggaaaac gccgtcaatg gcggccgccc  13080
cgccgccctc agcgccggcc tggtgatgat gaaaggcgcc cagccgatca tcgtcgacgg  13140
ccaggtgatc ggcgccatcg gggtcagtgc cgacaccccg gcccacgacg atgaaatcgc  13200
cctggccgcc ctcgccaccc tcagtcggca ggccacgcaa tgaaccgctc cgtcaacccg  13260
cgcctgaccc tgctcaccgc atccggggtc tgttcgctga tcgttctgga caccaacatc  13320
gtcgccgtgg cgctgccgag catcgcccgt gacctggggg ccaacttcgc cgatatcgag  13380
tgggtggtca gcgcctacat gctggccttc gccgccctgc tgctgcccgc cggcagcctg  13440
gccgaccgct tcggccgcaa gcgcaccctg ctctgcggcc tgggcctgtt catcctcgcc  13500
tccctgggct gcggcgcggc gcccaacgcc ctgctgctgg acatcgcccg ggcgctcaag  13560
ggggtgggcg cggcgctgct gctgacctcg gccctggcct ccatcggcca taccttccac  13620
gacgaagtgg aacgggccaa ggcctgggcc ttctggggcg cctgcatggg catggccatg  13680
actgccgcgc ccacggtcgg cgggctgatc accgagtact tcggctggcg ctggatcttc  13740
tacttcaacc tgccggtggg tgcgttgctg ctgtggagtg tgctacgcaa cgtgccggaa  13800
tcccgggata cccaggcggc gcgcctcgac ccctggggca gcctggcctt cagcgccagc  13860
ctgctgtgcc tgatctgggg cctgatcgag gccaaccgca tcggctggag ccacccggcg  13920
accaccaccc gcctgctggc aggcgtggcg ctgctggggc tgttcgtgct gatcgagcgg  13980
ctgcaaagcc ggcccatggt ggacctgcaa ctgttccgcc acccgcgctt catcggcgcc  14040
ctgctgggca tgttcgccta cgccggctgt gcccaggtga tgatgacgct gctgcccttc  14100
tacctgcaga acggcctggg cttctcggcc atcgcctcgg gcctgggcat gctgcccttc  14160
gccctgacca tgctcatctg cccgcggatc ggcgcacgcc tggccgggcg ctatgcgccg  14220
gccacgctga tggccgcagg gctgaccctg gtgggctgcg gcaacctgct cagcgcctgg  14280
gcggtacacg ccgggggcta cctgaacttc gccctggcaa tcgccgtgac cggcgccggg  14340
gccggattgc tcaatggcga cacgcagaaa aacatcatgg cctgcgtgcc gcgggaacgc  14400
accggcatgg cctcgggcat gagcaccacc atgcgcttta gcgccatcat gctggccatc  14460
ggggtgttcg gtgcgctgct ggccagccat acccagcagc tcttgcaggg cagcctgcac  14520
gccgtgcccg ggcactggct ggagcaggca ccggagattg cctcacgggt ggtggccggg  14580
gatatgcagg gcgcgatggc cggcttgccg cccgatgccc gggccctggt cgagcccctg  14640
gcccggcagg cctttgtcgg tggtttcggc ctggtgctga cggtggccgg gatgctcgcc  14700
ctgctcggcg ccctggtggt gggccggctg atgcgcaatc cactgcccca ggcgtcgggg  14760
ctgacgctga agctgcaata gcccaggcac tgcacaaacc gctgccgcgc ctgcggcagc  14820
ggtcctggcc cgcccgcttg caatttcaca acactcgttc aattgctggg gcaatccgcc  14880
acggttaagg tgcgcccttc gcaacgcccc attgaatgga taacgaggtg agcgtgaagc  14940
cttcaagcgt gatcgtggtg ggcgccggga ttgtcggcgc cgccattgcc taccacctgg  15000
cccggcaggg cgcgcaggtg accgtgctgg aacaggacag cccgggctcg ggcgtcaccc  15060
gccactcctt tgcctggatc aacccccacg gcgagttccc ggcagccgcc cgcgccctgc  15120
gggcccaggc gctggcagac taccgccgcc tgcagcacga actgccggcc ttgcagatcc  15180
gctggtccgg cgcgctgacc tacggcgcgg ccgaccagca agcgccagat accgacgagc  15240
caaccgccga ggcctcgacc cggtggctgg accgggccgg cgttgcccaa ctggaacccc  15300
acctgcaagt gctgccggag cgtgcccgct atgcacccgg cgaaggcagc ctggacccgg  15360
```

```
tggccgccac ccgcaccctg ctcgatgcgg cctgcaccca cggcgcccgg gtgttcgacc  15420
agacccgggt acttagcttg cgggtcgaag gccagcgggt actcggggta aacaccgccg  15480
ccgggctcca ccgtgccgac caggtgctgc tcgccagcgg ctgcgccacc ccggccctgc  15540
tcgcgcccct gggtattcag ttgccggtgc aggcctcgcc gtcgatcctg atccgcgtca  15600
atgcgccacc gggcctggtc aagaccctgg tctccaacag ccagctggaa atccgcgaag  15660
cggcggacgg cagcctgctg ctggccgagg actatatcga tgcccagggt ccactggggc  15720
ccgaggccat cgcgcaacag gccctggcca gcatccgcca gctgttccgt ggcgcccagg  15780
ccatcacctt gcgcagcgtg gaagttggcc tgcggccgat gcccggggac caactgccga  15840
tcatcggccc cagcacccgc taccagggcc tgtacctggc ggtgatgcac gccggagtga  15900
ccctggcccc cacggtggcg cgcctgatca gccaggaact gctgcacggg caaacctgcg  15960
ccgaactggc cgcctgccga ccggcacgct tcgcctgaac accagcccct gtcgccacac  16020
cgcggcaggg cctgcaagat ttcacggaat catccgccct cgcctgttgt cctcttttga  16080
ttgcacgact tcttaagcgg accgcaggag ctcttcatgg cgaacatcac catcgcccag  16140
caactggcaa ccacccttga acaggccggg gtcaagcgta tctgggggct gaccggcgac  16200
agcctcaacg gcctcaccga cgctctgcac agcatgcaga ccatcgagtg gatgcatgtg  16260
cgccacgaag aggtggccgc ctttgccgcc ggcgccgaag ccgccaccac cgggcaactg  16320
gcggtgtgcg ccggcagctg cgggccgggc aacctgcacc tgatcaatgg cctgttcgac  16380
tgtcaccgca accatgtgcc ggtactggcc atcgccgcac agatcccctc ctcggagatc  16440
ggcctcgact attttcagga aacccaccct caggagctgt tcaaggagtg cagccacttc  16500
gtcgaactgg tgagcaaccc ggcgcagatg cccgaggtgc tgcaccgggc catgcgcagc  16560
gcgatcctca accgcggcgt ggcggtggtg gtgatccccg gcgacgtggc cctgcagcag  16620
gtacccgccg ccagcaagcc atggccggcc ctgcacgcac cgcgcaccct gcccgccccc  16680
cacgacctgg acaaactggt ggagttgctg agccagagca aggccgtgac cctgctctgc  16740
ggcagcggct gcgctggcgc ccacgatcag gtggtggccc tggccgacgc cctcggcgca  16800
ccggtggtgc atgccttgcg cggcaaagag catgtggaat gggacaaccc cttcgacgtc  16860
ggcatgaccg gcctgatcgg cttcagctcc ggctaccacg ccatgctcaa ctgcgacacc  16920
ctggtgatgc tcggcaccga ctttccctat cgccagttct accccagcga cgcctgcgtc  16980
atacagatcg accgcaaccc ccaggccctg ggccggcgag tgccgctgga cctggggatc  17040
gccgccgacg tcggcgaaac cctcgccgca ctgctgccgc gcctgcccta taagggcgac  17100
cgccgctttc tcgaagaatc cctcaagcac tacgccaagg cgcgccaggg cctggacgac  17160
ctggcccagc cctcgcccgc tggccggccg atccacccgc agtacctgac ccggctgctc  17220
agcgaactgg cagacgaaga cgccatcttc actgccgacg tcggcacccc cacggtgtgg  17280
gccgcgcgct acctgaaaat gaacggccag cggcgcctgc tgggctcttt caaccacggc  17340
tccatggcca acgccatgcc ccaggccatg ggcgcccagg ccgccttccc ccagcgccag  17400
gtgatctcgc tgtccggcga tggcggcttc agcatgctga tgggcgactt catctccctg  17460
gcccagctca agctgccggt gaagatcgtg gtctacgaca acgcctccct gggcttcgtg  17520
gccatggaaa tgaagtccgc cggctacctg gacaccggca ccgacctgca caacccggac  17580
tttgccgcca tggccaacgc catgggcatt ctcggcctgc gggtggaaaa ctccgaagaa  17640
ctggaaggcg ccctgcgcac cgccctggcc catgacggcc cggtgctggt ggacgtggtc  17700
```

```
accgccaccc aggaactggc catgccgccg gccatcaagc tggaacaggc caagggcttc  17760
agcctgtaca tgctcaaggc ggtgatgagc gggcgtggcg acgaggtgat cgaactggcc  17820
aggaccaatt ggctcaagga cagttggttc aagatcacct agaaaggctc tacccccggg  17880
catgccatcg cagcctctaa tgcacccaca ttagaggcct gtgtccatga aaagggtggc  17940
agtagcatcc atcgagggtg gcgttgggaa aaccaccacc tccgcaggcc tcgcctctta  18000
tccattaaga caagacgttt cgactgcacg ccaacggatt ggccgtaagc acaagcggga  18060
caaggaagcc gtcaggctct gtcagtgatc cgatcatttt tgagcggctc gcctctttca  18120
agatcggcag cggatgaagg catgcccaaa cgtcagcccc cccctcagcg gccgactgat  18180
caggcgcaaa aaacctacgc aatattttcc tttagaccaa atgcctttgc ttttttgaat  18240
gctaattcgg aaacggaagg tgcatcgctt ttccggcagg ctagagtcta aatccgacaa  18300
gcacattgat gtgcctcttg cacggatgca cagagactgg cggccttccc ctcctcacag  18360
acagcccgcc tcgaaacagg gagtgttatg aacaagccaa tcaagaatat cgtcatcgtg  18420
ggcggcggca ccgcgggctg gatggccgct tcgtacctcg tccgggcgct ccaacagcag  18480
gtaaacatca cgctcatcga gtctgcggcg atcccccgga tcggcgtggg cgaggcgacc  18540
atcccgagtt tgcagaaggt gttcttcgac ttcctcggga taccggagcg ggagtggatg  18600
ccccaagtga acggcgcctt caaggccgcg atcaagttcg tgaactggag aaaatctccc  18660
gacccatcgc gcgaagatta cttctaccat ttgttcggca gcgtgccgaa ctgcgacggc  18720
gtgccgctta cccactactg gctgcgcaag cgcgaacagg gcttccagca gccgatggcg  18780
tacgcgtgct atccgcagcc cggggccctc gacggcaagc tggcaccctg cctggccgac  18840
ggcacccgcc agatgtccca cgcgtggcac ttcgacgcgc acctggtggc cgacttcttg  18900
aagcgctggg ccgtcgagcg cggggtgaat cgcgtggtcg acgaggtcgt ggaggttcaa  18960
ctgaacgacc gcggctacat ctccaccctg ttaaccaagg aagggcggac gctggaggcg  19020
gacctgttca tcgactgctc cggcatgcga gggctcctga tcaatcaggc cctgaaggaa  19080
cccttcatcg acatgtccga ctacctgctg tgcgacagcg cggtcgccag cgccgtgccc  19140
aacgacgacg cgcgcgaggg ggtcgagcct tacacctccg cgattgccat gaactcggga  19200
tggacctgga agattccgat gctgggccgg ttcggcagcg gctacgtctt ctcgagcaag  19260
ttcacctcgc gcgaccaggc caccgccgac ttcctcaaac tctggggcct ctcggacaat  19320
cagcagctca accagatcaa gttccgggtc gggcgcaaca agcgggcgtg ggtcaacaac  19380
tgcgtctcga tcgggctgtc gtcgtgcttt ctggagcccc tggaatcgac gggaatctac  19440
ttcatctacg cggcgcttta ccaactcgtg aagcacttcc ccgacacctc gttcgacccg  19500
cggttgcgcg acgcattcaa cgccgagatc gtctacatgt tcgacgactg ccgagacttc  19560
gtccaggcgc actatttcac tacgtcgcgc gaagacacgc cgttctggct cgcgaaccgg  19620
cacgaactgc ggctctcgga cgccatccag gagaaggttg agcgctacaa ggccgggctg  19680
ccactgacca ccacctcgtt cgacgattcc acgtactacg agaccttcga ctacgaattc  19740
aagaacttct ggttgaacgg caactactac tgcatctttg ccggcctggg catgctgccc  19800
gaccggtcgc tgccgctcct gcagcaccga ccggagtcga tccagaaggc cgaagcgatg  19860
ttcgccagca tccggcgcga agccgagcgc ctgcgcacga gcctgccgac gaactacgac  19920
tacctgcggt cactgcgtga cggcgcgcag ctgtcgcgca accagcacgg gccgacgctc  19980
gcggctcagg aacgccagta gtggaacgca ccttgaaccg ggtatccgca ttcgcggcca  20040
cacacgctgc cgtggcggcc tgcgatccgc tacaggcacg cgcgctggtt ctgcagctgc  20100
```

```
cggccctgaa ccgtgacaag gacgtgcccg gcatcgtcgg cctgctgcgc gatttcctcc  20160
cggtgagcgg cgtgccctcc agctggggct tcgtcgaagc cgccgccgcg atgcgggaca  20220
tcggtttctt cctggggtcg ctcaagcggc acggacatga gcccgtggac ctggtgcccg  20280
ggcttgaacg ggtgctgctc gacctggcac gggtgaccga cttgccgccg cgcgagacac  20340
tcctgcatgt gacggtctgg aacccggcgg cggccgatgc gcagcggagc tacaccgggc  20400
tgcccgacga agcgcacctg ctcgagagcg tgcgcatctc gatggcggcc ctcgaggcgg  20460
ccatcgcgtt gaccgtcgag ctgtccgatg tatccctgcg ctcgcccgcg ttcgcgcaag  20520
ggtgcgatga gctggaagcc tacctgcaga aaatggtcga atcgatcgtc tacgcgtacc  20580
gcttcatctc gccccaggtc ttctacgatg agctgcgccc cttctacgaa ccgattcgag  20640
tcgggggcca gagctacctc ggccccggcg ccgtagaaat gcccctcttc gtgctggagc  20700
acgtcctgtg gggctcgcaa tcggacgacc cagcttatcg agaattcaaa gagacatacc  20760
tgccctacgt gcttcccgcg tacagggcgg tctacgctcg gttcgccaca aagccggcgc  20820
tcatcgaccg tgcgctcgac gaggcgcgag cggtgggtac gcagggcgag cacgtccggg  20880
ctgggctgac ggccctcgag cgggtcttca aggtcctgct gcgcttccgg gcgcctcacc  20940
tcaaattggc ggagcgggca tacgaagccg ggcgcagcgg ccccacaacc ggcagcgggg  21000
gctacgcgcc cagcatgctc ggcgatctac tcacgctcac ctgtgccgcg cggtcccgca  21060
tccgtgccgc gctcgatgaa tcctgatgcg cgcgacccag tgttatctca caaggagagt  21120
ttgcccccat gactcagaag agccccgcga acggacacga tagcaaccac ttcgacgtaa  21180
tcatcctcgg ttcgggcatg tccggtaccc agatgggggc catcctggcc aaacaacagt  21240
ttcgcgtgct gatcatcgag cagtcgtcgc acccgcggtt cacgatcggc gaatcgtcga  21300
tccccgaaac gtctctcatg aaccgcatca tcgctgatcg ctacgacatt ccggagctcg  21360
gccacatcac ctcgttctac tcgacgcagc gttacgtttc gtcgagcacg ggcatcaagc  21420
gcaacttcgg cttcgtgttc cacaaacctg gccaggagca cgacccgaag gagttcaccc  21480
agtgcgtcat tcccgagctg ccgtgggggc cggagagcca ttattaccgg caggacgtcg  21540
acgcctatct gttgcaagcg gccatcaaat atggctgcac ggtccgccag aagacgagcg  21600
tgaccgaata tcacgcggac aaggacggcg tcgcggtgac caccgccgag ggcgagcggt  21660
tcaccggccg gtacatgatc gactgcggag gacccggcgc gccgctggcg accaagttcg  21720
ggctccgcga agagccgtgt cgcttcaaga cgcactcgcg cagcctctac acgcacatgc  21780
tcggggtcaa gccgttcgac gacatcttca aggtcaaggg gcagcgctgg cgctggcacg  21840
aaggaaccct gcaccacatg ttcaccggcg gctggctctg ggtgattccg ttcaacaacc  21900
acccgcgctc gaccaataac ctggtgagcg tcggcctgca gctcgacccg cgtgtctacc  21960
cgaaaaccga cattcccgcg cagcaggaat tcgacgagtt cctcgcgcgg ttcccgagca  22020
tcggcgctca gttccgggac gccgtgccag tgcgcgactg ggtcaagacc gaccgcctgc  22080
agttctcgtc gaacgcctgc gtcggcgacc gctactgcct gatgctgcac gcgaacgggt  22140
tcatcgaccc gctcttctcc cgggggctcg agaacaccgc ggtgaccatc cacgcgctcg  22200
cggcgcgcct catcaaggcg ctacgcgacg acgacttctc ccccgagcgc ttcgagtaca  22260
tcgagcgcct gcagcaaaag cttttggacc acaacgacga cttcgtcagc tgctgctaca  22320
cggcgttctc ggacttccgc ctatgggacg cgttccaccg gctgtgggcg gtcggcacta  22380
tcctcgggca gttccggctg gtgcaagccc acgcgaggtt tcgcgcgtcg cgcgacgagg  22440
```

```
gcgacctcga tcacctcgac aacgacccgc cgtacctcgg gtacctgtgc gcggacatgg  22500
agcagtacta ccagttgttc aacgacgcca aagccgaggt cgaggctgtg agcgccgggc  22560
acaagtcggc cgaggaggcc gcgttgcgga ttcacgccct catcgacgaa cgagacttcg  22620
ccaagccgat gttcggcttc gggtactgca tcaccgggga caagccgcag ctcaacaact  22680
cgaagtacag cctgataccg gcgatgaagc tgatgtactg gacgcaaacc cgcgcgccgg  22740
cagaggtgaa gaagtacttc gactacaacc cgatgttcgc gctgctcaag gcgtacatca  22800
ccacccgcat cggcttggct ctgaagaagt agtcggccaa ggacggcaca cacgcgatga  22860
acaacattca attggatcaa gcgaacgtca agaagcatcc cccgggggcg tacgacgcga  22920
ccacacgcgt ggccgcgagc tggtacgtcg cgatgcgctc gaacggcctc agggacaagc  22980
cgaaggagtt gacgctcttt ggccgtccgt acgtggcgtg gcgcgcagcg acggggcagg  23040
ccgtggtgat ggaccgccac tgctcgcacc tgggcgcgaa cctggctgac gggcggatca  23100
aggacgggtg catccagtgc ccgtttcacc actggcgcta cgacgagcaa ggcaagtgcg  23160
ttcacatccc cggccacagc gaggtggtgc gccagctgga gccggtgcca cgcgcggcgc  23220
gccagccgac gttggtcacc accgagcgat acggctacgt gtgggtctgg tacggctccc  23280
cgcagccgct gcacccgctg cccgaaatca ccgcagccga cgtcgacaac ggcgacttca  23340
tgcacctgca cttcgcgttc gagacgacga cggcggtctt gcggatcgtc gagaacttct  23400
acgacgcaca gcacgcaacc cccgtgcacg cgctcccgat ctcggccttc gaactcaagc  23460
tcttcgacga ctggagccgg tggccggagg ttgagtcgct ggcccgggcg ggcgcgtggt  23520
tcggtgccgg gatcgacttc cacgtgaacc gctacttcgg cccccctcggc atgctgtcgc  23580
gcgcgctcgg cctgaacatg tcgcagatga acctgcactt cgatggctac cccggcgggt  23640
gcgtcatgac cgttgccctg gacgcagacg tcaaatacaa actgctccag tgtgtgacac  23700
cggtgagcga cggcaagaac atcatgcaca tgctcatctc gatcaagaag gtgggcggcg  23760
tcctgcgccg tgcgaccgac ttcgtgctgt tcgggctgca gaccagacag gcagcggggt  23820
acgacgtcaa aatctggaac gggatgaagc ccgacggcgg cggcgcttac agcaagtacg  23880
acaagctcgt gctcaagtac cgtgcgttct accgcggctg ggtcgaccgt gtcgcgagtg  23940
agcagtaatg cgtgaggccg agccggtagc ggtcgcgtcg cgctgcccgg cgcttgcgaa  24000
cctttcgagc tgcgtcacgg agatcacggc gtacggcgcg gcgggcccgc ttgggctcgc  24060
ggccacccgc ttggtgtcgg tgtcgctctt tgcgaggtat tgatgaccat ctggctgttg  24120
caactcgtgc tggtgatcgc gctctgcaac ctctgcggcc gccttgccga acggctcggc  24180
cagtgcgcgg tggtcggcga gatcgcggcc ggcctgctgt tggggccttc gctgttcggc  24240
gtgatcgcac cgagtttcta cgacctgttg ttcggcccac gtacgctgtc agccatggcg  24300
caagtcggcg aagtcggcct gatactgctg atgtttcaga tcggtctgca tatggagttg  24360
agcgagacgc tgcgcggcaa gcgctggcgc atacctgtcg cgatcgcggc gggcgggctc  24420
atagcgccgg ccgcgatcgg catgatcgtc gccatcgtct cgaaagatac gctcgccagc  24480
gacgtgccgg cgctgcccta catactcttt tgcggtgtcg cacttgcggt atcagcggtg  24540
ccggtgatgg cgcgcatcat cgacgacctg gcgctcggcg ccatggtcgg cgcacggcac  24600
gcaatgtctg ccgcgatgct gacggatgcg ctcggctgga tgctgctggc aacgattgcc  24660
tcgctatcga gcgggcctgg ctgggcattt gcgcacatgc tcgtcagcct gctcgtgtac  24720
ctggtgctat gcgcgctcct ggtgcgcttc gtggtgcgac cggtgcttgc gcggctcgcc  24780
tcgactgcgc atgcgacgcg cgaccgcttg gccgtgttgc tctgctttgt aatagcctcg  24840
```

```
gcactcgcga cgtcgctgat cggattccat agtgcatttg gcgcacttgc ggcggcgctg  24900
ttcgtgcggc gcgtgcccgg cgtcgcgaag gagtggcgcg ataacgtcga aggtttcgtc  24960
aagcttgtac tgatgccggt gttcttcgcg tgtgcggggc tgcatgcgtc ggtcggcacg  25020
atagacgacg cggcatcatg gatgtggtgc ggggtattcc tcgtgggcgg attcatcggc  25080
aagttcggcg gcagctatct gggcgcgcgt ggcactgggc tggcgccaca cgatgcgatg  25140
ctggcgagct cgttgatgaa tacgcgcggg ttgatggagc taatcgtcct gtcaatcggc  25200
ctgcagatgc agattcttcc gccaaaggtc tacacgatcc tcgtggtgtt cgcgctggtg  25260
acgacggcgc tgaccgcacc gctggttcga ttcacgctgc gcatgcaaac acgcgcaatg  25320
agccaacagg ccgcctgagc cagcttgagg ggagagctca ccatgaatgc tgccaccgaa  25380
accaaagttc acgatttgct cgatgccgag ggccgcgatg tccgcgatgc ccgtgaactg  25440
cgcaacgtgc tggggcagtt tgctaccggt gtgaccgtaa tcaccacccg caccgcagac  25500
ggccgcaacg tcggtgtgac ggccaactcg ttctcctcac tgtcgctgtc accggcgctg  25560
gtgctctgga gcctggcacg cacggcaccg agcctgaagg tcttttgctc ggcgagccac  25620
ttcgccatca acgtactggg cgcgcaccag ctccacctgt cggagcagtt cgcacgggca  25680
gcagccgaca agttcgccgg tgtagctcat tcctatggca aggcgggagc cccggtgctg  25740
gacgatgtgg tggcagtgct ggtgtgccgc aacgtcaccc agtacgaggg cggtgaccac  25800
ctgatcttca ttggcgagat cgaacaatac cgctacagcg gtgcagaacc gctggtcttc  25860
catgcaggcc agtaccgggg gctagggagc aatagagcag aaagcgtcct caagcacgaa  25920
tagcccggct catgtgatct tttgccggga aggatcactg atccaggtgc cccttgatgt  25980
ggcagcagct caacctcagt ggctcgctgc gcagcgcccc agcgaacaac cagcccgacc  26040
agccaagcgc ccgcgacagc tatttgtagt ttccctcctc ctcctcctcn ncctcctcct  26100
cctcctcctc ctcctcctcc tcctcctcct ctgaagtcga tccgacaccc acgccaggaa  26160
atgaataatc actattgggt ttgtgcccaa tgagaaagcc cttgtagtac gtttttttcg  26220
aatgccttag gcccttgaag cctggccatc ccagcgcgag gcttgcccag gcgctgctga  26280
ttgaggctca caaaatgcat ttgataatca tttgcaatca aggatagaat cccgcccccct  26340
cgtctgatcc cgccttgaat gatcgccgcc gtgtcttatc tcagcgataa actcgagctc  26400
tacctttccc accgtaccgc gctggtcgac tattcggcgc ccattgtcgg ttgtcgggct  26460
caagccgaag aagtggtcca ggaggcctgg ctgcgcttct gcggccaggc cgatagcgcc  26520
gcccagccga gcaacccggt gggctacctg taccgcatcg tgcgcaacct gtcctttgac  26580
ctgctgcggc gctcgaccct ggaaaatcgt catcccgatg gcgccgatct gctgaacgag  26640
ctgccctcga gtacgccatc accggagcat caggcgctgc acagcgacca gttgcgcctg  26700
ctgcaagatg cgctggcact gctgccggag cgcacgcgcc gggccttcca catgcaccgc  26760
ctgcaacacc tgaccttcca ggaaattgcc gctgagctga agatctcctc cagcttggcg  26820
caccagctgg tgcgtgacgc actgacccac tgtgcggagc acctggccga tgactgatac  26880
ccccttgcct caacctgtat ccggttcact gaaggacgac cccgtgtggc aggcggcgat  26940
ggattggctg ctgcaatgcc actcggcgcc ggatgacgcc ttgctgcaac aggcccatgc  27000
gcgctggctg gccgctgacg agcgccatgc tgtcgcctgg cgcaaggccg agaaagtctg  27060
gttgctcagt ggcggcctgg cgccgctgga accacccgtg ccccagcctt tgcccacccc  27120
gctccgggct cggcgcaaca ggccgcggcg ggcactgaag gcgcttgcac tggcagcctg  27180
```

-continued

```
cctgctgttg ctggccgggc cgacaccacc gaccgcccat accagcccag ccggcgagca  27240
ccgacaagtg ctcttgagtg acggcagccg tattgaactg ggcagcgaca gcgctattcg  27300
agtggacttc gaacccggta cgcgggcggt caccctgctc agggggcagg cgttcttcga  27360
ggtcagccac gatgcctcgc gcccgttcac ggtgcaggct gcggacgtca aggtcagggt  27420
catagggacc gcgttcgacg tggacctcag ccgcaccgcc gtggtggtag ccgtacagag  27480
cggcgctgtc caggttcgcg atgggcgcgg cgaactcgcg gtgccggccc tgggcccggg  27540
cgatagcctt cgccttggcc tggaccaggg cccgccgcag cgcggtcggc tattgcctgg  27600
ccaggttgcc ccctggcgcc agtggcagtt gctggtcaat gaccggccac tctccgaggt  27660
ggttgaagcg ctgcaggact attaccccgg tgtactgcta ttgacggacc ctgctctggg  27720
cgagcggcgc atcaccgctt cgctgaacct gcgctcgcca gtcagcgcac tgcaactggc  27780
gatcgctccg ttgggtgggc atctgcggca atggggcccc tacctcacgc tgatccgcaa  27840
agagccgcaa gtgccggcaa aacaataaat ttcaaaattt tctggaagtt ctcgatcgcc  27900
gttcgtttat tgccccgctg agttaatcat aattattctc attagcatgt gcgtattgtt  27960
cgcactgaac ggggagttca ccagagcatg tccattttcc cccaacaggg acttcagggt  28020
tgccgacgca gtgcgcggct gttgtggctg tcagtggggc tggcggtgtc cctgccggcc  28080
ttggccagtg accatcggac acggcatagc atcgacatcg cacgccagcc gttaagcacg  28140
gcgctgatgg cgctggcaca gcagaccggc ctgcagatca gcgtcgagag ccaactgctg  28200
ctcaacctga acgctccggc ggtgcagggc gaactgagcg ccgagcaggc gctggcgaag  28260
ctgctcaaag gcagccagct ggagtggatc tacatcggtg acgacgcgct gatggtgcaa  28320
cgggcgactc gcccgcgtac cgacccggtc cgcctgggca ataccaaggt gcctggcgag  28380
ttgtcgctgc cccagggtga aacccgagtg gaccgcgcga cgatcgaagc aatgccggcg  28440
ggcaatggcg acatcaccag cctgttgcgc agccatccca acgtgcagtt cgacgacgct  28500
cagctgagca gcaagacccc tggcgaaatc ggcccggcca acatcagcat caacggggcg  28560
cagttctacc agaatgcctt cctggtcgat ggcatcaaca tgaacaatga catcgatccg  28620
gccgaatacc gggtgcaatt gctggacgcg gtaccggggc gcagccaggg cctggcactg  28680
gacaccgacc tgctggagaa catcacggtc ctggacagca acgtgccagc ggcctatggc  28740
ggcttcaacg gtggcgtcat cgatgcacag acccgtgcac cgacccaggc gctgcacggc  28800
aaattctcgg tgcagaccac ccgctccgcc tggacccaat atcacgtcga cgaaagcgaa  28860
gaacaacgca tggaaaactc gggctctccc gacgagcagc ccaagttcga caaggtcacc  28920
gttcgtggca cgctgcaggg ccacctgacc gacaatttcg gcctgcttgg cagcttcagc  28980
cagaagcgct cgaccatccc cctgggtttc tactcctaca acaatgtcga ggagatgggc  29040
tttcacgagg agaagcagca acggcgcatc gacaactact tcctcaagtc ggtatggaaa  29100
gccagcgatc aactcactgt tgagaccagc gtgacccatg cccccgagga gagtcactac  29160
ttccgtgcca acgtggccaa ctcgggttat gacaacaagg ccggcggcac ccaagtgaac  29220
ctgcgcaccg tctgggatgg cgacctggcg cgcgtcgaac agaacctggc gtggagcggc  29280
caggaacaga gccgccaatc ggactccgcc gattactgga cctggcgcaa gtcggccacc  29340
aaggactggg gcatcggcaa caaggccacc tccaataccc ttgaaggcgg ttggggtgat  29400
atcgagcagc agcagcgtac ctggcagtac aagctcaatg ccgactggcg cagcgtcgac  29460
tggctgggca tgactcaccg cccgcagacc ggcctggagt tctcccgcca gtacgtgcgc  29520
tacgagcgcc tgaccgacag cagcacctat gtcacccccg cggccaccac cacctgcacc  29580
```

```
aacggcgccg gggttaccga cagcgtcgcc tgcaacatcg gccagaccct gaacggctgg  29640
gcgggccagt acatgaaaag ccgtacccgc tatgccactg gcgaattcga cttcaccacc  29700
acctcctggg gcagctggct gcaggacgag atcaccctcg gccaactgac cttgcgcccc  29760
ggcgtgcgcg tggacagcga cgactacatg gacaagacca cctgggcgcc gcgcttctcc  29820
ctggaatatg acctgttcgg tgaccgcacc accttgctca atgccggcgt caaccgttac  29880
tacgggcgca gcgtcagcag ctggcagctg caggacgggc gcaaccgcct gcgcttcaac  29940
gaaacccgcg acagcctgga caaaccctgg gtggtcaaat ccaacgcggc caaccaggtg  30000
cgcttcaatc agctggacat cccctacgac gacgagctga tgctgggcgt ggtgcagcaa  30060
tgggccgggg tcgaatatgc cctcaagtat gtcaatcgca aggggcgcga ccaggtggtt  30120
caggtgtccg gcaagacctt gggcgagccc tccacggacc cgacgctggc gagcaactac  30180
accacctaca ccaacgacgg caagagcgag accgacacct acaccctgac ggtgacaccg  30240
ttgcagcgct ggacactgct gggcacccag accggcgggc aactggcgct caactggacc  30300
gacagcaagg cctccgcacc gacctacgtc gcggccgaga acctgtacta ccagaacagc  30360
gtcatccagt accagggcag cttcatcaat tatgacgacc gcccggccag caacttcaac  30420
cggccctgga cggcccgcct gacgaccatc accgagatcc cccaggccaa tctgcagtgg  30480
agcaacttct ggcgctaccg cgccggctac aagcgcattg gcgacacggg gcgcaatgtg  30540
gactacatgg gcacctcggt ggatgtctgg gaggaacaga aattccaggc ggcgctgacc  30600
tgggacacgc gcctgggctg gcgtattccc accgccaggg accagaacgt gttcatcaat  30660
gtcgacgtgt tcaacgtgct cgacaagaag tcggtcaatg ccaaccagac ggtcaacagc  30720
aactcggtct cgacctatga ggtgggccgc cagtactggc tcgaagtcgg atacgcgttc  30780
tgaaatgcgc cggtccctga agagcctgca ggtcatgctc ggcatggtgc tggtgattgg  30840
cccgcagcac gtgctggcct gcgccacgag cgaaccgtct tgcctgcgcg agttgtacag  30900
ccgccccccc gcgcagtggc cggcgccgca ggtggatgcc ggcgtggcct ggcaagagct  30960
gggccccttg cccgagcggg cgccgtcccc ggcgtacaac ccctacacgc agcagaaggc  31020
cgatctgggc cgccggctgt tcttcgaccc gcgcctgtcg cgttcggggc agattgcctg  31080
cgcctcctgc catgaaccgg acctggggtt cgccgacggg cgtcgggttt cgttcgggca  31140
tgaccgtgcc gcgggccggc gcaatgcacc gagcctggtg gccagcggcc tggccaagaa  31200
gctgttctgg gacgggcgcg ccgacagcct ggagatgcag gccctgatgc cggtcgtcga  31260
ccccaaggag atggccttca ctgtcgcgca actggtggcc cggctgcgtg acaccacgga  31320
ctacccggca cagttcgccc aggtatttcc cggacaggcg ctgggtgccg agcaggtggc  31380
ggcggcattg gcgacttatc agcgtggcct gctgcgggtt gcccaacgca ccccccttcga  31440
gcgttttcta cgggggcagg cgaaggcgct cagcgaccag caattgcagg ggctgcacct  31500
gtttcgcacc aaggcacgct gcatgaactg ccacttcggc ccggggatgc aggacgaccg  31560
cttccacaat gcaggcctga ccttctatgg gcgcctgcgc gaagacctcg ggcgctatga  31620
agtcaccggg ctggcgcagg atgtcgggcg catgcgcaca ccttcactgc ggctggtgag  31680
ccataccggc ccctggtttc acaacgggct ggccagcagc ctcgatcagg tgctgttgtt  31740
ctacaacgca ggcatgccca ggcccgtacc caaggagggg cagctgcaag acccgctgtt  31800
tcccgtgacg tcggcacaat tgaaggtatt ggagctggac cggaccgaac tgaaggcact  31860
gaaggctttc ctggaggccc tatgagaggt tggccgcggc ggctgcacat cggtgtgccc  31920
```

```
acacagggcc agcgccaggg acttgatcac ctcctgcccg ctgcggatac cgctgtcgag  31980
ccagacttcg aggcgctggg caacaggcgc ctggcggcag cgggccggcg gctggcgatc  32040
taaagagttc gtaaagtctg cccgcccgcc cctcccggca cctggcaaat gcgcttcaat  32100
agcctgcaag ccaagcctga agctcccgga gaagcccatg agcaaagtcg cccgctatct  32160
gcaggtcgaa gacatcctcc tggcggtcaa tgtcacgaac aagcagcgcc tgttcgagca  32220
ggtcggccag cacctgcaag agacccggca actgccggcg gattgggtgg ccgccagcct  32280
gtggcgccgg gagctggccg ccagtaccgc catcggtgaa ggggtggcgg tgccccacgc  32340
gcgactcgcc gagctcgatc gcattcatgc gctgtacctg cggccgcaga ccgccatggc  32400
ctttgccgcc ccggaccagc agccggtcag cgatatcctg gtgctgctgg tgcccgctcc  32460
cgccgatcag cagcacctgg acctgctggc cgacaccgcc cggctgttta ccaacccgcg  32520
gtttcgccag gccctgctgc gctgtactgc accgatgcag gtcaaacagc tgttcgatca  32580
ctggtagctt gacccagaca cctgctccag cacgcaatac ccatttgccg ctccccgcgg  32640
caaatgggat agcccaagcc ccaccgatca ccttccggca caagatttca tctattggcg  32700
gttagccgac tcatccatta acgttcacta cacctcacgc agcccagcgc ttgagggggg  32760
cgcctgccct gccgtcgcgc cgctctccat attcctgttg aactcactca ctgattgctc  32820
aattagagag aatatgaaca agccacagct gctgcctgta gccactggcg gccggcgtcc  32880
tcacagggac gaaggtaccg gtcgaaaatc ctctgggcac ctgtctcttc tgttgcttgc  32940
ccgctcgtcc ctgaacctga tctgcatcgt agccctcgcc agctgcgccg tggggccgga  33000
tttcagccgc ccggaactga gccgggacgc cggctacagc gccacgcccc tgccgccccg  33060
caccgtcacg gcgggggtcg ccgccggtgg cgcggcgcag cgactggtga acggcatgga  33120
cattcccggg cagtggtgga cgctgttccg ctcgccgcaa ctcgatgccc tggtgcagga  33180
agcgctgcag gccaacccgg atatcgacgc cgcccaggcc gcgctgcgcc aggccaatga  33240
actggtgtac gccgaacagg cgtcgctgtt tccctccctc agcgcctcgg cctcgaaaac  33300
ccgcgagaag gtgtccgccg ccagcgccct gggctccagc ggcggtgcgg cagcggccgg  33360
gggctctgcg gcgcagatct tcacggtcaa ctcggcgtcc ctgagtgtgt cctacgcccc  33420
cgacgtgttt ggcggcaccc gccggcagat cgaggccagc ggtgcccagg ccgactacca  33480
gcgctaccag ctggaggcga cctacctgac cctcaccgcc aacctggtga acaccgccat  33540
cagcctggcc tcgatccgtg accaaatcgc cgccaccgaa accgtgattc gcctgcagag  33600
cgaccagctc gacctgctgc aggcccagcg tcgactgggt gccatcggcg acagcgatct  33660
gctgacccag caagcgaccc tggcccagac ccgcgccacc ctgccgccct tgcagaaaca  33720
gctggcccag acccgcaacc agttgcaggc ctacctgggt cgcttcccca gccaggaccg  33780
tggcgaacac ttccagctgg cctccctgca cctgcccgag gaactgcccc tgagcctgcc  33840
ttcggccatc gtcgagcagc ggcccgacgt gcgttccgcc gaggcccagt tgcatcaggc  33900
cagcgccgat atcggcgtgg ccatcgccaa ccagttgccg cagttcagca ttaccggttc  33960
cctggggtcc acggcgctgg cgggcaccaa actgttttcc tccggcaccg gggtctggag  34020
cctggccggc tccatcgccc agccgctgtt cgacgccggc gccctggagc atcgcaagcg  34080
cgccgcggtg gccgcctatg agcaggccgc agcgcgctat cgcggcacgg tgatcaccgc  34140
cttccaggac gtagccaatg ccctgcgtgc cctgcaggcc gacgccgagg ccctgcaaca  34200
gcaagtgctg gccgagaccg ccgcgcgcca gagcctggac ctggcccagg cccagtaccg  34260
cctgggcgcg gtgggctacc tgaacctgct gaccgcgcag cagacctacc agaacgcgat  34320
```

```
tgtcagccgg gtgcgggccc aggccgcccg ctacagcgac accacggcgc tgttccaggc  34380
cctgggggc ggctggtggc agcgccagga tgtcgacccc gacagcctcg gcagccccga  34440
tcgtttcggc tggccgtcgc tcaaggagat gtacccgccg cccgcggccc agcaccgcga  34500
acaggctcaa gccggccagc cgggccggct ccaggggccg gcagcagccg cgccgtccac  34560
tcgacctgca cccttgcctt aagtgagatc cgccatggcc gatgtccact ccagcccctc  34620
ccctgcgccc cccggcgcgg ccccccaggc gccgcgcaag cgccggctgc tgcggccgat  34680
gctgatcatg ctcggcgtgg tgctgctgat cgtcgcggtg atcggcgggg tcaagttcgc  34740
gcagatctcc aagctgatcg cccaggccaa ggtgcccctg ccgcccgcgg tggttaccgc  34800
catcaaggcc cagtacgaag agtggcagcc cagcgtctcc gcagtgggct cgatgaagac  34860
tgtgcgcggg gtggacgtga ccaccgaggt cggcggcatc gtgcgcagca tcggcttcaa  34920
gcccggccag gaagtggccg ccggcgacct gctggtgcag ttgaatgccg actccgacat  34980
cgcccagttg cattccctgg aagccaccgc ggccctggcc ggcacggtgc tcaagcgcga  35040
ccgggcgcaa ctgaaggtga gcgcggtgtc ccaggccctg gtcgaggccg acgaagccga  35100
cctcaaggcc aaactggccg ctgccgaaca gcagcgcgcg ctggtggcga agaagagcat  35160
ccgcgcgccc tttgccgggc gcatcggcat caccgcggtc aaccccgggc aatacctcaa  35220
cccgggggac aagatcgcca acctgcagac cttcgacccg atctacatcg acttcaacgt  35280
gccccaggcc caggtgcagc aggtggccct gggccagagc gtcacggtca gcgccgacgg  35340
cctgcccaaa cagacgttca ccggccgggt cagctccatc gacacccagt tcgaccccaa  35400
cacccgcaac gtcacggtgg aagccaccat cgacaacccc aagcgcagcc tggtgcccgg  35460
catgttcgcc cgggccgtgg tggcctccgg cggcacccag cgttacctga ccctgcccca  35520
gaccgcggtc acctataacc cctacggcac cacggtgttc atcgccagcc agaagaacaa  35580
cgaccagggc gacgcagtgc tcaccgcgca gcagaccttc atcgaaaccg gccccaaccg  35640
tggcgaccag gtggcggtgc tgtcaggggt caaggaaggc gacctggtga tcaccagcgg  35700
ccagatgaaa ctcaagaacg gctcgccggt gaaagtcgac aacagccacg cgccgcgcaa  35760
cgatccttcg ccgacgccgc aagagcacta gggcccgcca tgaacttcac cgataccttt  35820
atcaagcgcc cggtctgggc cgtggtggtc tcgctgttca tcctgatcct gggcctgcgc  35880
tcgatcttcg agctgccggt gaaccagtgg ccgcgcacgg aaaacaccgt ggtcacaatc  35940
agcacctatt actacggggc cgacgccgcc accgtggccg gtttcattac ccagcccctg  36000
gaggccgcca tcgcccaggc ccagggcatc gactatctgt cgtccaccag catcaccggg  36060
ctctccacca ttaccgcgac cctgcgcctg aactacgact ccagcaaggc gctgaccgag  36120
atcaacaccc aggtcaactc ggtgaagaac cagttgccgg cccagtccca ggaaccggtg  36180
ctgacggtag cggtgggcca gaccaccgac gccatgtacc tggggttcta cagcgacacc  36240
ctggccacca acaacatcac cgactacctg gtgcgggtgg tcaagcccaa gctcgattcc  36300
ctggaaggcg tgcagaccgc agagatcctc ggcggccgcc agttcgccct gcgggcctgg  36360
ctcgacccgg acaagctggc ggcccacaac gtcaccgccc aggatgtggc cacggccctg  36420
ggcaacaaca actacctgtc cgccgtgggc tccaccaagg ggcagatgat caccgtggac  36480
ctcaccgccg gcaccgacct gcacacggtg gacgaattca agcgcctggt ggtcaagcac  36540
aacggcgacg ccctggtgta cctggaggac ctgggcaacg tcaccctggg ggcggaaaac  36600
tacgacagca gcgtggcttt ctccggcaag cgctcggtgt tcatcggcat caaggcagcg  36660
```

-continued

```
cccaccgcca acatcctcaa cgtcgccgac aacgtgcgca aagccttccc cgaactgcaa  36720
tcgcaactgc cggccggggt gcgcggcgag atcgtctacg actccacggc cttcatcaac  36780
acctcgatct tcgaggtggt gaagaccctg gtggaagcca tgatcatcgt ctcggtggtg  36840
atctacctgt tcctcggctc gttccgtgcg gtgatcgtgc cgctggtggc gatcccgctg  36900
tcgctggtgg gcaccttctt cgtcatgtac ctgctgggtt actccatcaa cctgctgacc  36960
ctgctggccc tggtgctggc catcggtctt gtggtggacg acgccatcat cgtggtggaa  37020
aacgtcgacc ggcatatcaa ggagcaaggc cgcggcgtac tggaggcggc gctgctggcg  37080
gcccgcgagc tgggcggccc gatcatcgcc atgaccgtgg tgctgatcgc cgcctacgtg  37140
cccatcggcc tgcgcagcgg cctgaccggg gcgctgttca aggagttctg tttttccctg  37200
gccggcgcag tgacggtgtc ggcggtgatc gccctgaccc tgtcgccaat gatgacctcg  37260
cggctgttca agagcggcca ggaggaaggc cggttcgcca agcgcctgga ccgctacttc  37320
gactggctgc gggggcgcta ccaccgggtg ctggcggccg ggctggatag ctggccggtg  37380
ctggtgacct tcggcttcct gctgttcgtg ctggtggccg ccagtggcct gaccgccaag  37440
agcgagctgt cgcccaccga ggaccagggc ctggtgttca tgcagatcaa gggcgcgccc  37500
accgcctcgc cgcagcagat ggagtggatt gccgaccagg cgttccagat cgccaacaag  37560
gagcccgagt acctgcagat gttccagctc accggcctgc cctcgctgaa ccagggcctg  37620
ggcggggtgc tgctcaagtc ctgggaggat cgtgaccgct cccaggcgca gttgatcctc  37680
gacctgcaac agaagtggaa ccaggtgccc ggcgccacca tcgccgcctt ccccctgccc  37740
tcgctgcccg gcgcccaggg cctgccggtg cagttcgtga tcagcaccac cgagtcggtg  37800
gccaacctca acgaggtggc ccaggcggta ctggccgagg ccaccaagca gcagctgttc  37860
tggttttccg acctggacct caagctcgac aagccccagg ccaagctggt ggtggaccgg  37920
gaaaagatcg ccgccctggg catgacccag gccgacgtcg gcgccgcgct ctcggcggcc  37980
ctgggggca actacgtgaa ctacttctcc accgccgggc gctcctacaa ggtgatcccc  38040
caggtgctgc aggtggaccg gctgaacccc gaacagatcc tcgactacta catccgtacc  38100
ccgtcggggg cgatgattgc agcgcgcacc gtggcccata tcgaaacctc caccgagcct  38160
gagtcggtca accacttcca gcagctcaac tcggcgaccc tgtccggggt cagcggcgtg  38220
tcccagggcg agttgctggc ccggctcaag ggcattctgg aacaggtggc gccatccggt  38280
tactccagcg actacgccgg cgaatcacgg cagttcatcc aggaatcggg ggggttcgtc  38340
ggcctgctgc tgttctcgat cctgatcgtc tacctggccc tggcgttcca gttcgagagc  38400
taccgcgacc cggtggtgat cctgttctcg gtgccgccgg cgctgttcgg cgccctggcc  38460
ttcatcacca tggggttcgc ctcgatcaac gtctacaccc aggtcgggct ggtgacgctg  38520
ctggggctga tcaccaagca cgggatcctc atcgtgcagt ttgccaacca attgcagcgc  38580
gccggccaca ataagcgcga agccatcgaa gaagccgccg cagtgcgcct gcggccgatc  38640
ctgatgacca ccgcggccat ggtcctgggg gtggtgccgc tggtctgggc ttccggcgcc  38700
ggcgcggcgg gccgccacga catgggcctg gtgatctttg ccgggctgtc catcggcacc  38760
ctgctgaccc tgttcatggt gccggccatg tacctgttca ttggcagtac gcactctgcc  38820
gcaagcatcg agaacccggg ggcgcaggcg gatgccggag cttccgacag cgcctgaacc  38880
cctgctcgat cgaaaccgcc gggtatcagg ccggcacgcc caggatgatg tgggacgcct  38940
tgatcaccgc cgtggcgctg acgcccgggg ccaggcccag ttcggtcacc gcatcgcggg  39000
tgacgatgga atacacctgg ctgccgccgc tgagctccag caccacttcg gcgttgaccg  39060
```

```
caccatcggt gacgctgatc accttgcccc gcaggcagtt gcgagcggac aggcggatgc  39120

cctcggcatc ggtcatgagc atcacccagg gtgccttgac cagggccagg gcctcggtgc  39180

ccggggcgat gcccaggcta cgcaggcttt gcagggtcac caccgccaca agttgctcgc  39240

cgccctccag ggacagcacc acctcggcgt tgaccgaacc ctcttccacc tggctgaccc  39300

ggcctttgaa cacgttgcgt gcactgactt tcatgttgca ttccttttat tgactgcggg  39360

gttaggatcg cccggcatga tccgggcgca cgttgtggag aaacaaccat agcgcccgcc  39420

acccaaggcc ggatatttct cgcaggcccc gggtcaatcc tgctcttgca ggtgttcgat  39480

aaaggtcgtg ccgctatagc gctcgcgaaa cagccccgcc tccaccagca tcggtatcac  39540

ctgttccagg aaaatgtgca tcgaacggat cgagcccccc ggcgcggcga taaagccgtc  39600

catggcgccg gcctcggccc attcgacgat ctgtgcaaat gcatcttcgg cggtgcctat  39660

cacttgccag tgggccgcgg aaatcacttc cgggcgcagc agcagttcgt ccaggcgcag  39720

ggtttcgcgc tcgatcaacc gccgcagcag gttggtgtgg gtgcggctgc cggggttgtg  39780

caccggggcc ggcaggtcgg cggcgctcac cgggcggtcc aggggccagt cgcttaaatc  39840

gaggccgatc atctgctgga tcgaggcgaa cttgcgcgcg ttgtccgggc gcccgtgggt  39900

ttgcatgaac agctcgcggg cctgttcccg ggtcggcgcc aggtacaggc tcaggcccgg  39960

cagcaggcgg atgtcctcgg ggcggcggcc gtggcgccgg gcccgttgcg agaggtcgcg  40020

acgcagttcc agggccgcat ccttgtccgg ggtcggggcg aacaccaggt cggccaccga  40080

ggcggcaaag tcgcgaccgg tgtccgaggc gccggcctgg accaggggaa tccgtgcctt  40140

gccgaacgcc ggcaggttga gcgggccgcg cacccggaag tattcgccgg catggtccac  40200

cgggtgcacc tggctgcggt cggcgtaacg gccgttctcc cggtccagta gcagcgcctg  40260

gttggggtag ctggcccaca ggtcgtgcac caggcgggtg aactctgccg cccgggcata  40320

gcgctcatcc gcgccgggca tggcctccag gccgaagttc tcgtggccct gcaaggcggt  40380

gacgatgttc cagccggcgc ggccgttgct cacccaatgc agcgactgca actggcgcgc  40440

caccacatag ggcgggaaga aggtggtgga aacggtggac accaggccga tgcgggacgt  40500

ctcccgggcg atgcacgcca gcagcaccgt gggatcgagg ctggcgaaac ccgagccgct  40560

ttccaggccg tccatgttca ggcaactgac gtcggggcgg aacacgaaat ccaggtgcgc  40620

ggcctcggaa cgcttggcga tgtccacggc gaagtcggcg ctgtagatgc cttcgatatt  40680

gctgtcgggc tggcgccagg catcgccact gagccaggtg gggggccaggg acatgccgat  40740

atgcaggcgt ttgcggttac tcatctgttg ccaatctcct gtgtacgagt gaacgccggc  40800

agcgcctcgg ggggcggccg gcgacgggtt cccgggggcc tcagaacgcc cctttgacgc  40860

cgatgcccag ggtccgtggc tgggtcatgc tggcctcgat gccgccgatg ccgcggttct  40920

gctgcatgta ggtgggcgag cggtcgtcga agacgttctt gacgtagcca tagagctgca  40980

cctggtcgtt gaagcggtag ctcatgcgcg catcggtcag ggtgtagggc ttgatcgaat  41040

aggccgaggt gttggcggta tccgagtagt agccgtccag gtagcg                41086
```

<210> SEQ ID NO 4
<211> LENGTH: 20
<212> TYPE: DNA
<213> ORGANISM: Artificial Sequence
<220> FEATURE:
<223> OTHER INFORMATION: Synthetic - primer for 16S rRNA amplification

<400> SEQUENCE: 4

-continued

```
agagtttgat cctggctcag                                              20


<210> SEQ ID NO 5
<211> LENGTH: 19
<212> TYPE: DNA
<213> ORGANISM: Artificial Sequence
<220> FEATURE:
<223> OTHER INFORMATION: Synthetic - primer for 16S rRNA amplification

<400> SEQUENCE: 5

ggttaccttg ttacgactt                                               19
```

PSEUDOMONAS PROTEGENS AND PRODUCTS THEREOF TO CONTROL BACTERIAL PANICLE BLIGHT OF RICE

CROSS-REFERENCE TO RELATED APPLICATIONS

This application claims priority to U.S. Provisional Application No. 63/036,202 filed on Jun. 8, 2020, the contents of which are incorporated by reference in their entireties.

STATEMENT REGARDING FEDERALLY SPONSORED RESEARCH

NR

SEQUENCE LISTING

A Sequence Listing accompanies this application and is submitted as an ASCII text file of the sequence listing named "2021-08-17_169946_00623_ST25.txt" which is 246,251 bytes in size and was created on Aug. 17, 2021. The sequence listing is electronically submitted via EFS-Web with the application and is incorporated herein by reference in its entirety.

BACKGROUND

Bacterial panicle blight (BPB) of rice, which is caused by the bacterium *Burkholderia glumae*, is emerging as a serious threat to rice production, especially as global temperatures increase (Ham et al., 2011, Shew et al., 2019). Since its identification in 1967 in Japan, this disease has spread throughout the rice growing areas of the world causing major yield losses (Nandakumar et al., 2007, Nandakumar et al., 2009, Zhou, 2014, Mondal et al., 2015, Shew et al., 2019). *Burkholderia glumae* causes rotting of the seeds during germination as well as stunting and chlorosis in seedlings (Iiyama et al., 1995). In older plants, symptoms can appear in leaves and stems, and are characterized by gray lesions surrounded by brown margins (Nandakumar et al., 2009). During the reproductive stages, the bacterium infects reproductive tissues affecting grain development and causing the main symptoms of the disease in the panicle, which include discolored spikelets with stained, rotten, or unfilled kernels (Nandakumar et al., 2009, Wamishe et al., 2015). The effects of the disease on grain development are reflected in a reduction in grain weight of up to 75% and seed abortion with concomitant yield losses (Fory et al., 2014). The disease symptoms are mostly associated with the production of the toxin toxoflavin, which is considered the main virulence factor (Iiyama et al., 1995, Karki et al., 2012). While other virulence factors have been identified by homology with virulence factors from other phytopathogenic bacteria (Devescovi et al., 2007, Degrassi et al., 2008, Kang et al., 2008, Lim et al., 2009, Fory et al., 2014, Knapp et al., 2015), their contribution to pathogenesis and virulence is not clear.

*Burkholderia glumae* is transmitted through contaminated seeds. Thus, the use of pathogen-free seeds as well as cultural practices such as early planting, reduction in nitrogen fertilizer, and reduction in planting density can mitigate the effects of this disease (Wamishe et al., 2015). Chemical control using the quinolone antibiotic oxolinic acid has been restricted to Asia (Hikichi, 1993, Lee et al., 2015), but it is not very effective due to the development of resistance by the pathogen (Maeda et al., 2004). To date, there are no commercially available rice cultivars that show complete resistance to *B. glumae*, but it would be possible to develop them given that quantitative trait loci (QTLs) associated with resistance to the disease have been identified (Mizobuchi et al., 2013, Mizobuchi et al., 2016). In addition, high levels of resistance against *B. glumae* have been achieved by overexpression of BSR1 (Broad-Spectrum Resistance 1), a gene encoding a receptor-like kinase (Dubouzet et al., 2011, Maeda et al., 2016). Even with these promising findings, the development of completely resistant cultivars will take several years. Thus, there remains a need in the art for alternative methods to control bacterial panicle blight of rice.

SUMMARY

In a first aspect, the present invention provides biosynthetic products produced by a *Pseudomonas protegens* strain designated as PBL3 and deposited as NRRL Accession No. B-68083. The biosynthetic products are selected from orfamide A/C, pyoluteorin, and pyrrolnitrin.

In a second aspect, the present invention provides vectors encoding gene products required for the synthesis of the biosynthetic products described herein. The vectors comprise a heterologous promoter operably linked to at least one open reading frame (ORF) found within SEQ ID NO:1, SEQ ID NO:2, or SEQ ID NO:3, which are the sequences of the gene clusters responsible for the synthesis of orfamide A/C, pyoluteorin, and pyrrolnitrin, respectively.

In a third aspect, the present invention provides organisms comprising the vectors described herein.

In a fourth aspect, the present invention provides methods of inhibiting the growth of a microorganism. In one embodiment, the methods comprise contacting the microorganism with an effective amount of a biosynthetic product described herein. In a second embodiments, the methods comprise contacting the microorganism with an organism comprising a vector described herein or a biosynthetic product produced by the organism.

*protegens* PBL3 or *E. coli*, each diluted to $OD_{600}$=0.125. Disease symptoms were evaluated after eight days (A). Bars represent average lesion lengths (B). Each error bar indicates the standard deviation from replications of three independent experiments. Treatments were compared using ANOVA and means were compared using Tukey's HSD with P-value=0.001.

Figure 3:
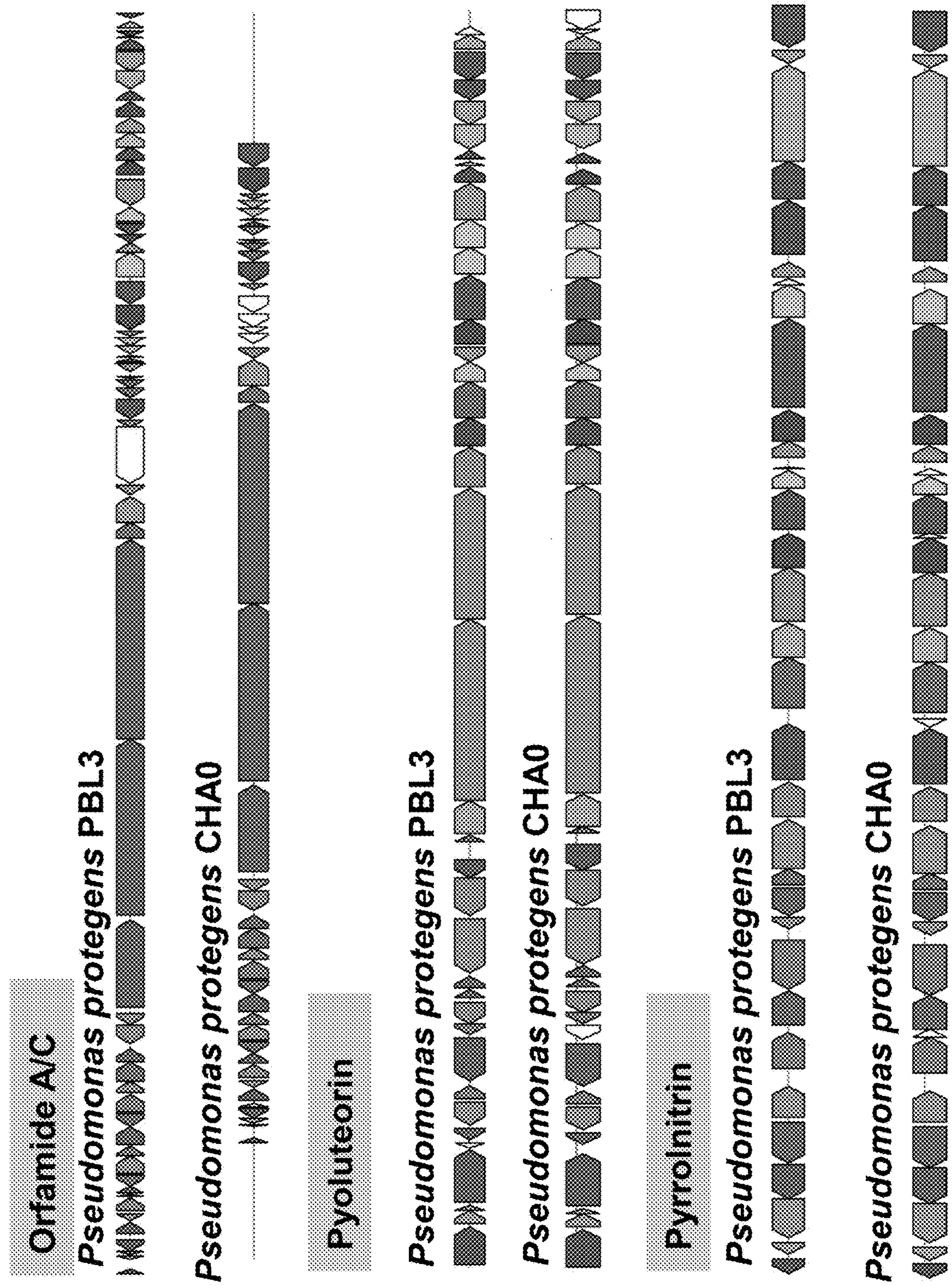

FIG. 3 demonstrates that *Pseudomonas protegens* PBL3 encodes biosynthetic operons for orfamide A/C, pyoluteorin, and pyrrolnitrin. The *Pseudomonas protegens* PBL3 genome was sequenced by Illumina. Illumina reads were assembled using Shovill (github.com/tseemann/shovill) and compared with the genome of the reference strain *P. protegens* CHA0 (NCBI CP003190) using anti-SMASH. Colored arrows represent individual open reading frames (ORFs) within gene clusters associated with the biosynthesis of orfamide A/C, pyoluteorin, and pyrrolnitrin. The sequences for the genes associated with each of these operons are attached and submitted herewith as SEQ ID NOs:1-3.

Figure 4:
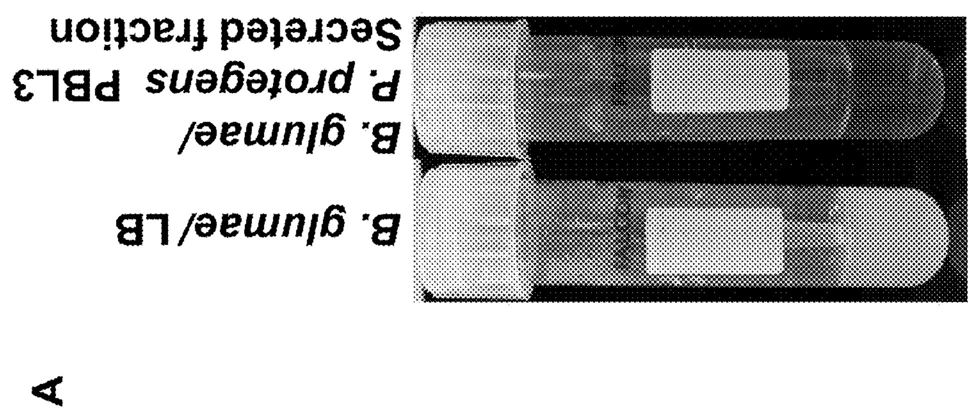
Figure 4:
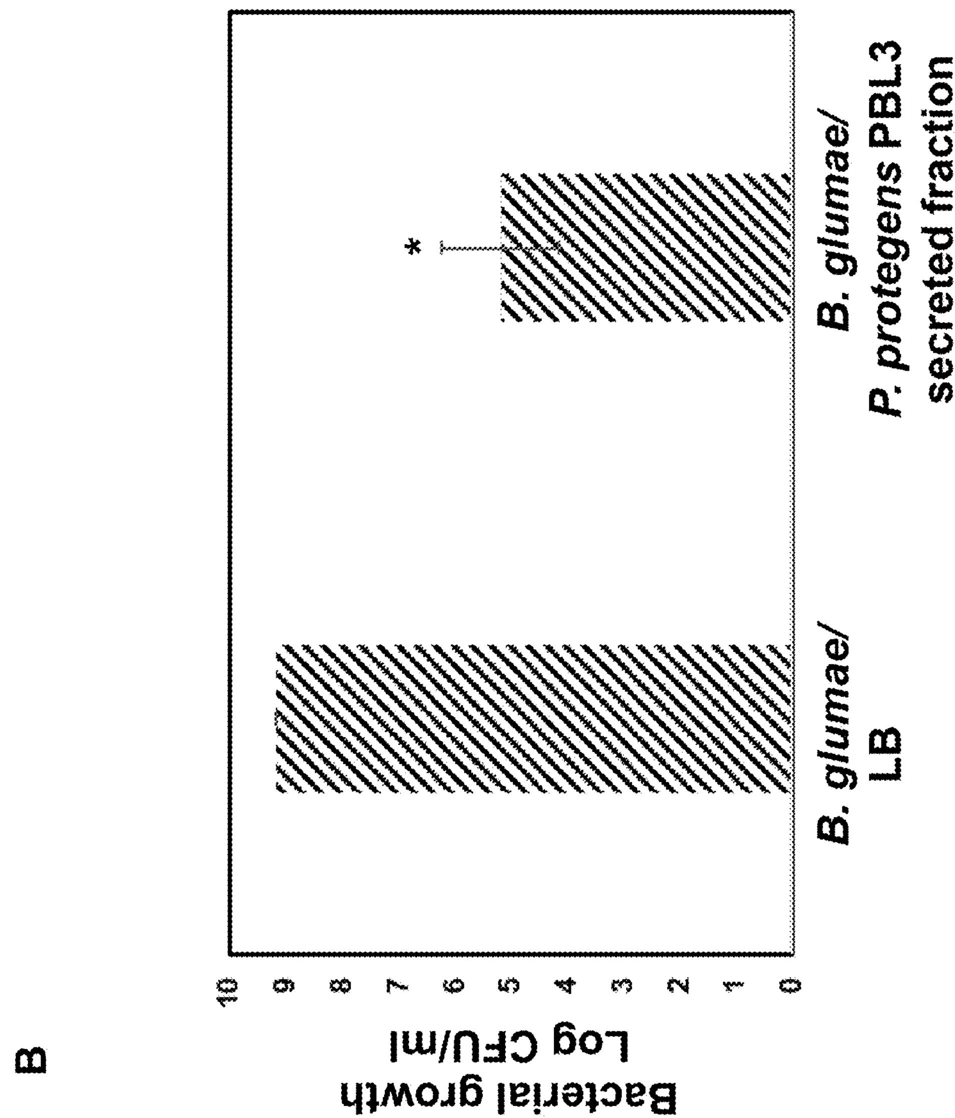

FIG. 4 demonstrates that the secreted fraction from *P. protegens* PBL3 interferes with the growth of *B. glumae*. LB broth and the secreted fraction from *P. protegens* PBL3 were lyophilized, resuspended in sterile water to a final concentration of 0.1 g/ml, and filter-sterilized. Resuspended LB or resuspended secreted fraction from *P. protegens* PBL3 were mixed in a 1:1 ratio (V/V) with KB broth. A single *B. glumae* colony was added to these tubes and grown for 24 h at 28° C. with agitation. After 24 h of incubation, growth of *B. glumae* was visually evaluated (A), and aliquots were taken, serially diluted, and plated to count the number of bacteria on KB plates (B). Bars represent the average growth of *B. glumae* (in CFU/ml) in both conditions. Each error bar indicates the standard deviation from replicates from three independent experiments. Asterisk denotes statistically significant difference using T-test with a P-value=0.05.

Figure 5:
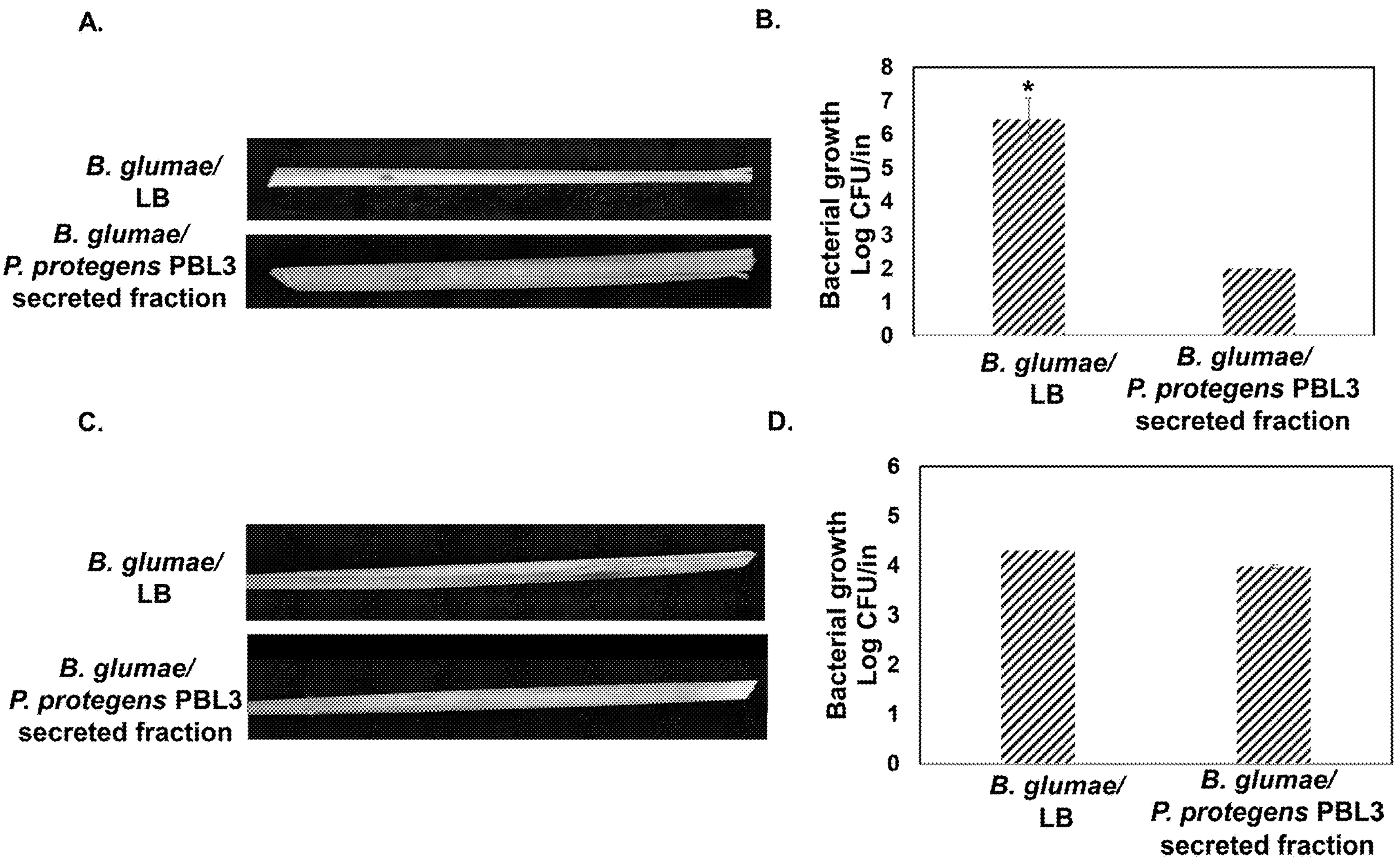

FIG. 5 demonstrates that the secreted fraction from *P. protegens* PBL3 reduces disease symptoms caused by *B. glumae*. Lyophilized LB and secreted fraction from *P. protegens* PBL3 were resuspended in sterile water at a final concentration of 0.5 g/ml, filter sterilized, and mixed in equal volume with *B. glumae* at $OD_{600}$=0.125 ($1\times10^7$ CFU/ml). Twenty microliters of the respective inocula were injected onto the sheaths of ten-week old Nipponbare rice plants (A-D). Inoculated sheaths were used to evaluate disease symptoms and to quantify bacterial growth at 2 dpi (A and B) and 7 dpi (C and D). Bars in B and D represent average bacterial numbers (Log CFU/in). Each error bar indicates the standard deviation from replicates of three independent experiments. Asterisk in B denotes statistically significant difference using T-test with a P-value=0.05.

Figure 6:
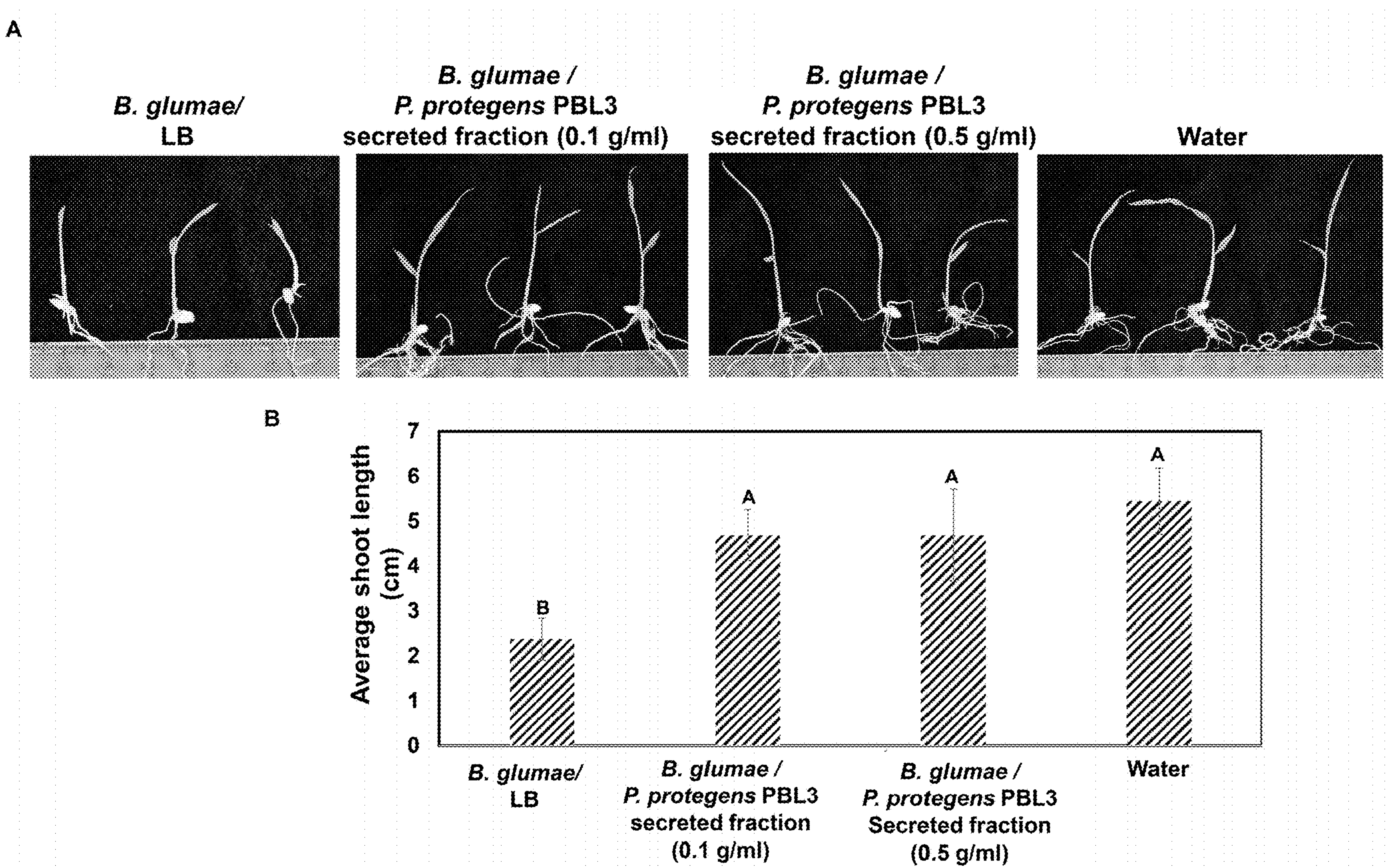

FIG. 6 demonstrates that the secreted fractions from *P. protegens* PBL3 reduces disease in seedlings. *B. glumae* at $OD_{600}$=0.001 ($1\times10^5$ CFU/ml), was mixed with lyophilized and resuspended LB at 0.5 g/ml, or lyophilized and resuspended secreted fraction of *P. protegens* PBL3 at 0.1 g/ml or 0.5 g/ml. Sterile water was used for the control. Twenty sterile seeds of cultivar Nipponbare were incubated with either *B. glumae* mixed with resuspended LB or with *B. glumae* mixed with the resuspended secreted fraction of *P. protegens* PBL3 for 30 min. Inoculated seeds were plated on MS plates and incubated for 2 days at 28° C. and then transferred to a growth chamber 25° C. under long day conditions (16 h light/8 h dark) for five days. Shoot length of rice seedlings was measured 7 dpi (A and B). Bars represent average shoot length. Each error bar indicates the standard deviation from replicates from three independent experiments. Letters above bars represent statistical significance using ANOVA and comparing means with Tukey's HSD tests with a P-value of =0.05.

Figure 7:
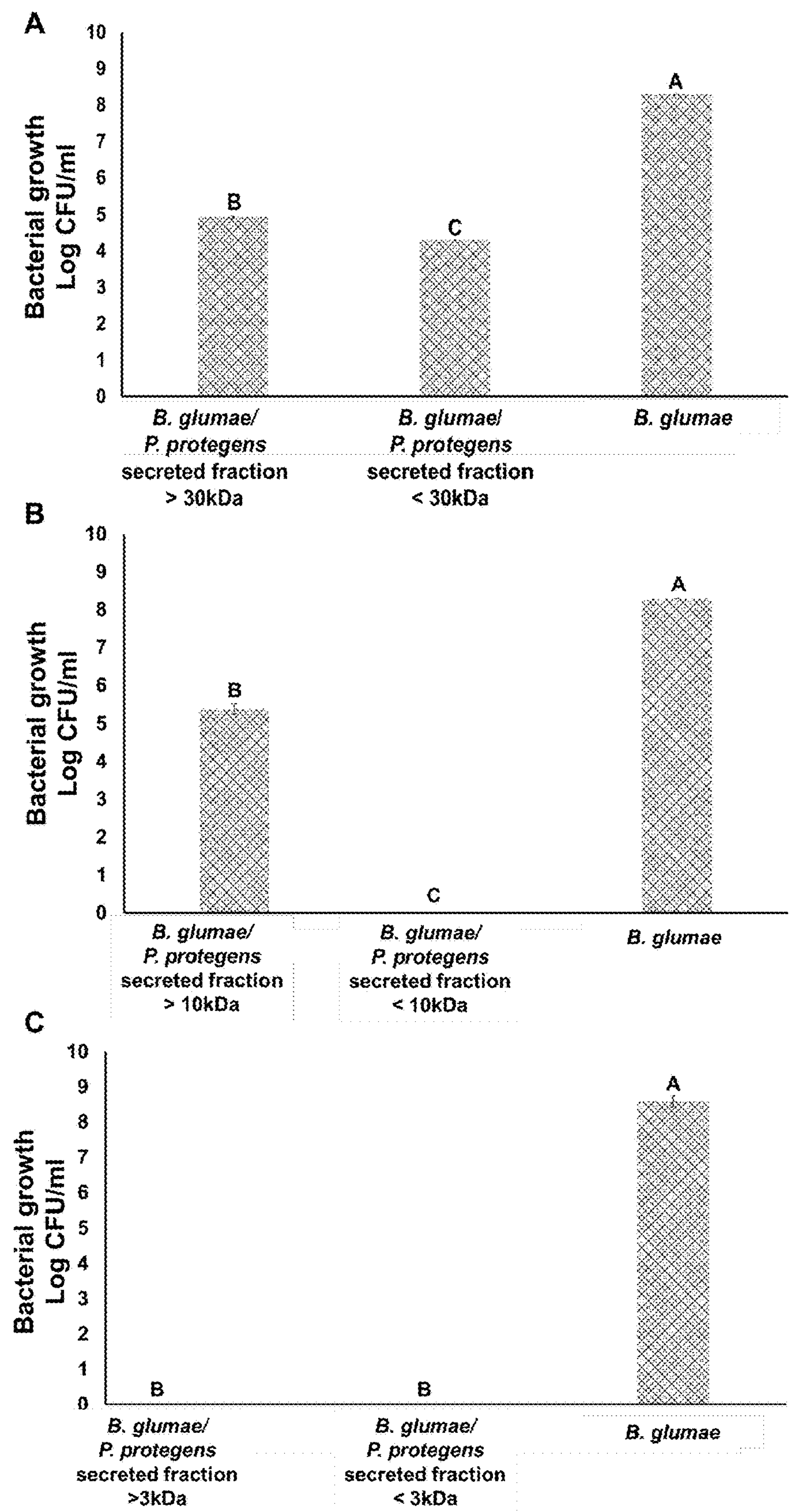

FIG. 7 demonstrates that *Pseudomonas protegens* PBL3 antimicrobial activities against *B. glumae* are related to molecules of different molecular weights. The lyophilized secreted fraction of *P. protegens* was reconstituted in sterile water and concentrated with ultrafiltration centrifugal concentrators of different molecular weight cut-offs: 30 kDa (A), 10 kDa (B) and 3 kDa (C). Sub-fractions higher and lower than the nominal molecular weight cut-off were filter sterilized and mixed (V/V) with KB broth. Water was also mixed with KB broth and used as control. KB amended with the different sub-fractions preparations was used to grow a single colony of *B. glumae* at 28° C. with constant agitation for 18 h. Cultures were serially diluted and plated on KB agar to enumerate bacterial populations (in Log CFU/ml). Bars represent average and standard deviation of bacterial growth for three replications. Different letters above the bars indicate statistically significant difference among treatments based on ANOVA and Tukey's HSD test with a P-value of 0.05.

Figure 8:
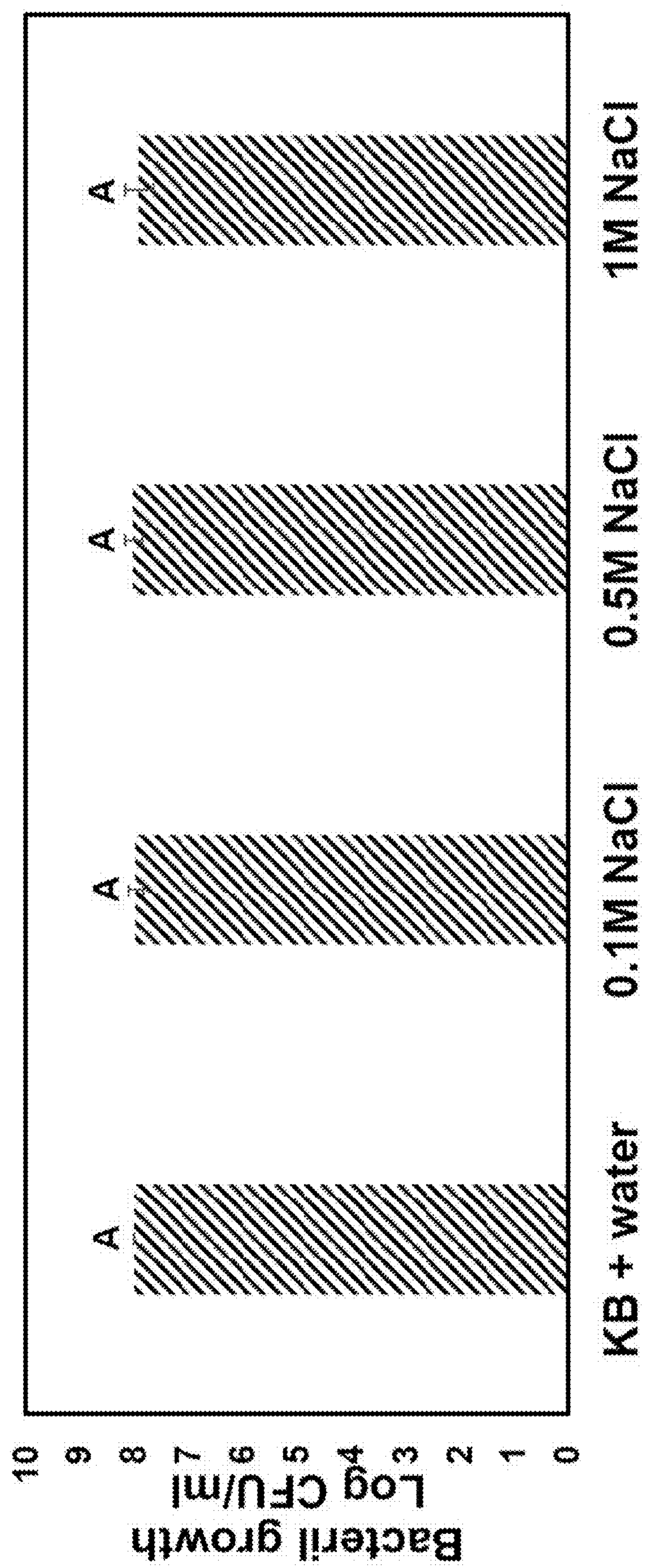

FIG. 8 shows the effect of NaCl on the growth of *B. glumae*. Different concentrations of NaCl (0.1M, 0.5 M and 1M) were added to KB broth in a 1:1 v/v ratio and used to grow a single colony of *B. glumae* at 28° C. for 22 h with constant agitation. After 22 h, a bacterial aliquot of each treatment was serially diluted and plated on KB agar to enumerate bacterial populations. Bars represent average and standard deviation of three replications. Letters above bars represent statistical significance using ANOVA and Tukey's HSD tests with a P-value of =0.05.

Figure 9:
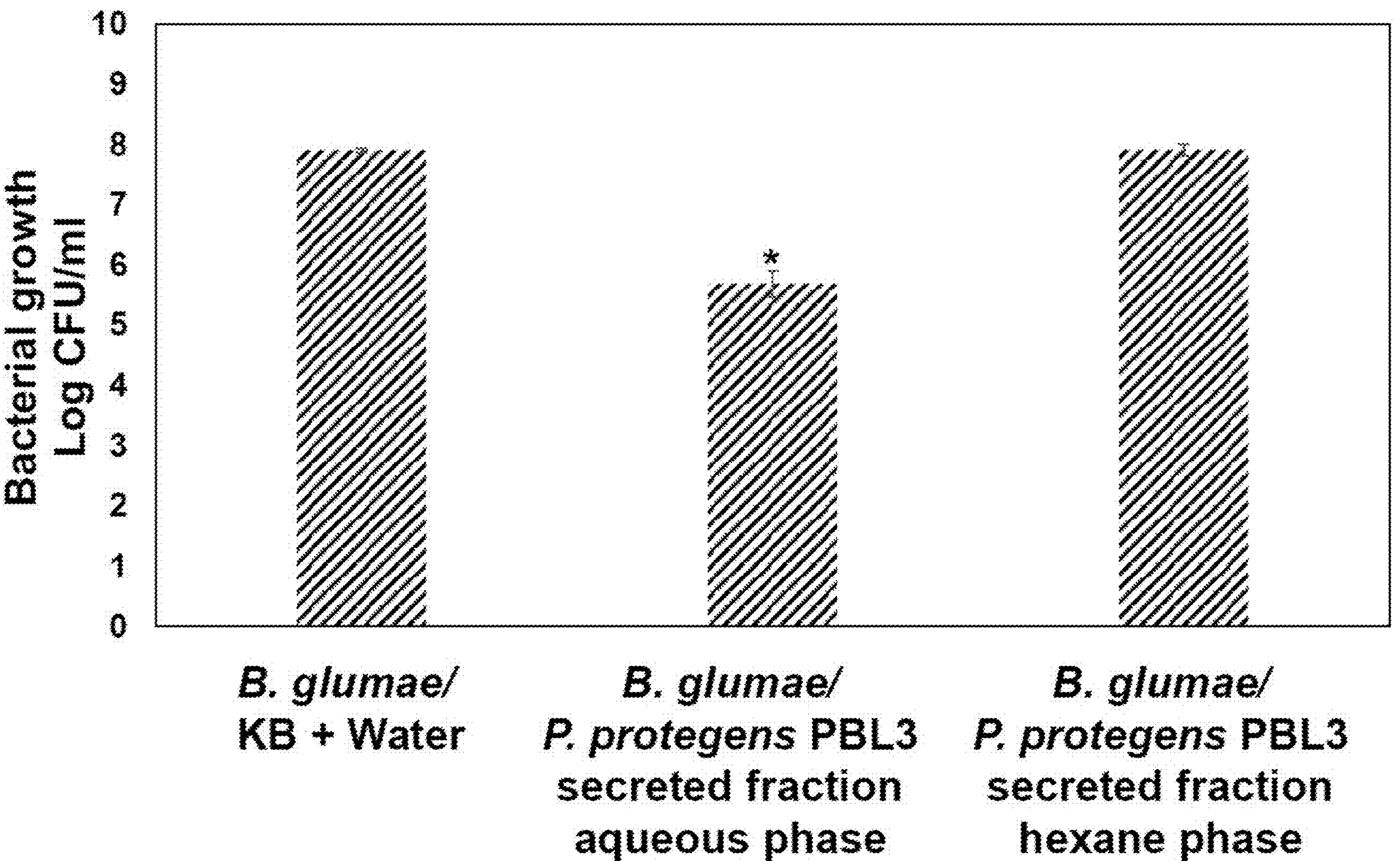

FIG. 9 demonstrates that the organic phase of the *P. protegens* PBL3 secreted fraction does not contain antimicrobial activity. The secreted fraction of *P. protegens* PBL3 was lyophilized and resuspended in water at a final concentration of 0.1 g/m. Fifteen milliliters of the resuspended fraction were mixed with 15 ml of hexane, transferred to a separatory funnel, and mixed by inversion five times. After phase separation, the aqueous phase was collected in one beaker, and the organic phase was collected in another beaker. The organic phase was set aside, and the aqueous phase was once again added to the separatory funnel and other 15 ml of hexane were added to the separatory funnel and again separated into aqueous and organic phases. This process was repeated one more time for a total of three times. The hexane layer was then blown down to dryness with nitrogen gas and resuspended in 3 ml of water. An aliquot of each of the phases were mixed with KB broth in a 1:1 v/v and used to culture a single colony of *B. glumae* by incubation at 28° C. in a shaker incubator for 22 h. Fractions were then serially diluted and plated on KB agar to count the number of bacteria (in CFU/ml). Bars represent average bacterial growth for three replications. Asterisk denotes statistically significant difference among treatments using ANOVA and Tukey's HSD tests with a P-value of = 0.05.

Figure 10:
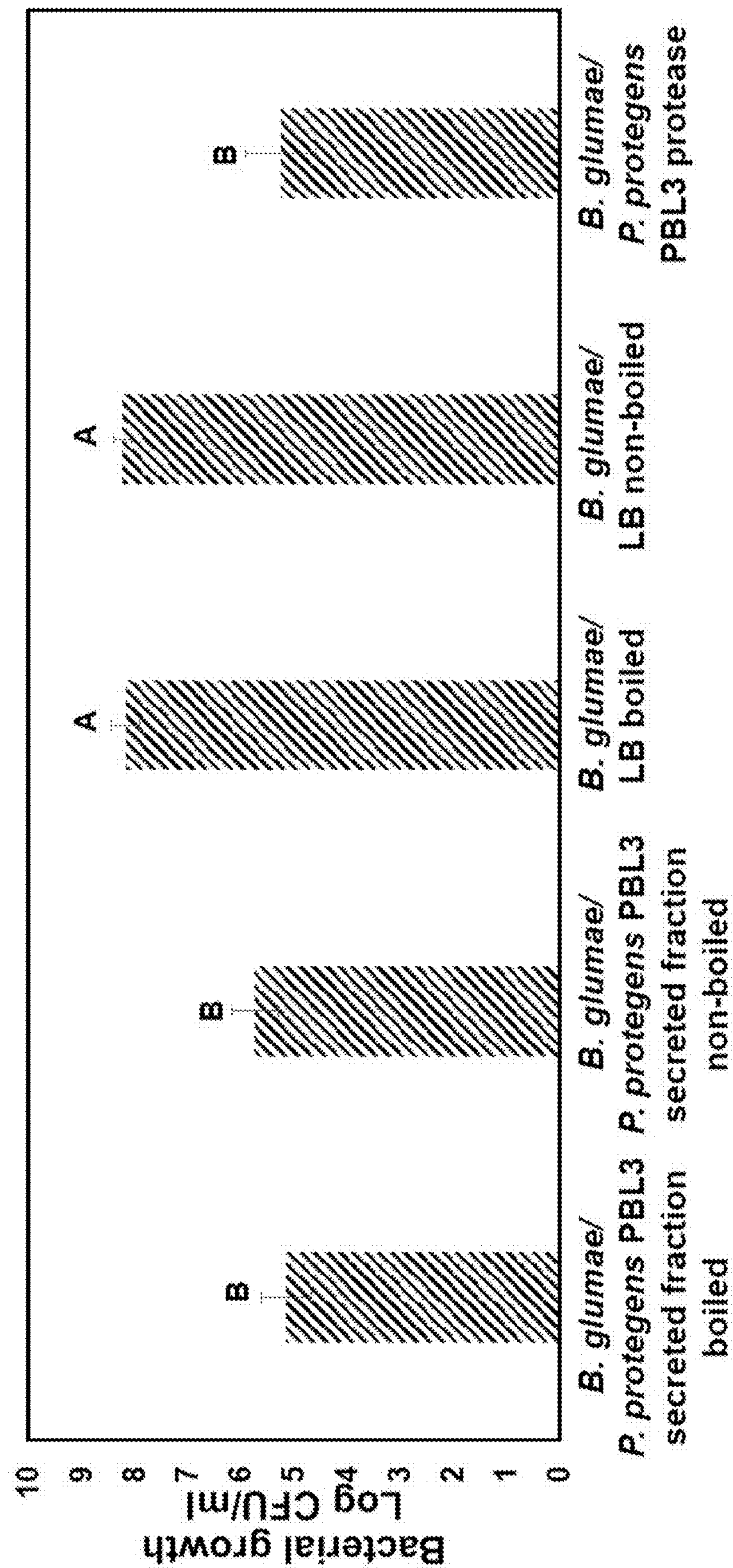

FIG. 10 demonstrates that the antimicrobial activity of the secreted fraction of *P. protegens* PBL3 is retained after boiling and protease treatment. LB and the secreted fraction of *P. protegens* PBL3 were lyophilized and resuspended in water to a final concentration of 0.1 g/ml. Two hundred microliters of resuspended LB and 200 μl of the resuspended secreted fraction from *P. protegens* PBL3 were boiled in water for 5 min. After removal from heat, samples were mixed with 200 μL of KB broth. As controls, 200 μl of non-boiled LB and 200 μl of non-boiled secreted fraction from *P. protegens* PBL3 were also added to 200 μl of KB.

All these amended KB broths were used to grow a single colony of *B. glumae* at 28° C. for 22 h with constant agitation. After 22 h, bacteria were serially diluted and plated on KB agar to enumerate bacterial populations. In addition, 200 μL of the non-boiled secreted fraction from *P. protegens* PBL3 was mixed with 10 μL of Proteinase K and incubated at 37° C. for 30 min. Protease was deactivated by heating it at 65° C. for 10 min. The protease-treated secreted fraction of *P. protegens* PBL3 were added to KB broth in a 1:1 v/v ratio and used to grow a single colony of *B. glumae* at 28° C. for 22 h, as previously described. After 22 h, bacteria were serially diluted and plated on KB agar to enumerate bacterial populations. Bars represent average and standard deviation of bacterial growth (in Log CFU/ml) for three replications. Different letters above bars represent statistically significant difference among treatments using ANOVA and Tukey's HSD tests with a P-value of =0.05.

DETAILED DESCRIPTION

Biological control using microorganisms that compete or have antagonistic activities against *B. glumae* is one promising approach to control bacterial panicle blight of rice. Previously, several strains of *Bacillus* methylotrophicus, *Bacillus amyloliquefaciens, Bacillus subtilis*, and *Streptomyces* sp. with antagonistic activity against *B. glumae* were identified in vitro (Shrestha et al., 2016, Suarez-Moreno et al., 2019). Five of the *B. amyloliquefaciens* strains also caused a reduction of disease symptoms when plants were pre-treated with these antagonistic bacteria before inoculation with *B. glumae*, but follow-up experiments in the field were inconsistent (Shrestha et al., 2016).

The present application is based on the inventors' discovery of a strain of *Pseudomonas protegens* that inhibits the growth of *B. glumae*. As is described in the Examples, the inventors evaluated the potential of several bacteria to control bacterial panicle blight. They tested seven bacterial strains that were previously investigated for their biological control activities against the oomycete pathogen *Pythium* sp. (Milus & Rothrock, 1997). The inventors identified one strain of *Pseudomonas protegens*, designated as PBL3 and deposited as NRRL Accession No. B-68083, which inhibited the growth of *B. glumae* in vitro and reduced disease symptoms in rice when co-inoculated with *B. glumae*. Further, they demonstrated that these activities were associated with the cell-free secreted fraction of PBL3. These findings suggest that the bioactive compounds produced by this bacterium can be used to control bacterial panicle blight of rice.

Accordingly, the present invention provides biosynthetic products (i.e., orfamide A/C, pyoluteorin, and pyrrolnitrin) that may be useful for controlling bacterial panicle blight of rice. Also provided are vectors encoding proteins involved in the synthesis of these biosynthetic products, organisms comprising these vectors, and methods of using the organisms and biosynthetic products to inhibit the growth of a microorganism.

Biosynthetic Products:

In a first aspect, the present invention provides biosynthetic products produced by a *Pseudomonas protegens* strain designated as PBL3 and deposited as NRRL Accession No. B-68083. The biosynthetic products are selected from orfamide A/C, pyoluteorin, and pyrrolnitrin.

As used herein, the term "biosynthetic product" refers to a product produced by a living organism. The biosynthetic products of the present invention are secondary metabolites that are responsible for antifungal activities in the closely related reference strain *P. protegens* CHA0. Thus, one or more of these products may be responsible for the anti-*B. glumae* activity that is present in the secreted fraction of *P. protegens* PBL3. The biosynthetic product may be combined with other products in an agricultural composition. The other products included in an agricultural composition may include a fungicide, an herbicide, an insecticide, a biosanitizer product, or a fertilizer.

Orfamides are lipopeptide biosurfactants that are produced by *Pseudomonas* and are involved in lysis of oomycete zoospores, biocontrol of *Rhizoctonia* and *Magnaporthe oryzae*, and insecticidal activity against aphids. Pyoluteorin is an antibiotic that inhibits Oomycetes, including the plant pathogen *Pythium ultimum*, and suppresses plant diseases caused by this oomycete. Pyoluteorin is synthesized from a hybrid nonribosomal peptide synthetase or from the polyketide synthase pathway, depending on the producer strain. Pyrrolnitrin is a pyrrole antifungal agent that has been isolated from several *Pseudomonas, Serratia*, and *Burkholderia* species. Pyrrolnitrin has a broad-spectrum of activity and can be used for biological control of soil and seed-borne plant diseases.

Orfamide A/C, pyoluteorin, and pyrrolnitrin are produced by four biosynthetic gene clusters that were identified within the genome of PBL3. The DNA sequences of these gene clusters are provided herein as SEQ ID NO:1, which encodes gene products necessary for the synthesis of orfamide A/C; SEQ ID NO:2, which encodes gene products necessary for the synthesis of pyoluteorin; and SEQ ID NO:3, which encodes gene products necessary for the synthesis of pyrrolnitrin.

Vectors:

In a second aspect, the present invention provides vectors encoding gene products required for the synthesis of the biosynthetic products described herein. The vectors comprise a heterologous promoter operably linked to at least one open reading frame (ORF) found within SEQ ID NO:1, SEQ ID NO:2, or SEQ ID NO:3, which are the sequences of the gene clusters responsible for the synthesis of orfamide A/C, pyoluteorin, and pyrrolnitrin, respectively.

In some embodiments, the at least one ORF included in the vector encodes a gene product that is involved in the synthesis of orfamide A/C, pyoluteorin, or pyrrolnitrin. As used herein, the term "gene product" refers to a protein or functional RNA that is encoded by a gene. Thus, the vectors of the present invention can be used to produce gene products that are necessary to synthesize the biosynthetic products disclosed herein.

In some embodiments, the vectors comprise a plurality of ORFs found within SEQ ID NO:1, SEQ ID NO:2, or SEQ ID NO:3. In some embodiments, the vectors comprise a full-length gene cluster selected from SEQ ID NO:1, SEQ ID NO:2, or SEQ ID NO:3.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors". Vectors suitable for use with the present invention comprise one or more ORF described herein and heterogeneous sequence (i.e., sequence from a difference species than the polypeptide) necessary for proper propagation of the vector and expression of the encoded gene product.

As used herein, the term "promoter" refers to a DNA sequence capable of controlling the expression of a sequence to which the promoter is operably linked. In contrast to native promoters that are derived in their entirety from the corresponding native gene, "heterologous promoters" are derived from a gene that is completely separate from gene to which they are operably linked. Heterologous promoters may be composed of multiple promoters elements derived from different promoters found in nature, or may even comprise synthetic DNA segments. It is understood by those skilled in the art that different promoters may direct the expression of a gene in different tissues or cell types, or at different stages of development, or in response to different environmental conditions.

An "open reading frame (ORF)" is a part of a gene that can be translated. ORFs comprise continuous stretches of DNA that typically begin with a start codon (usually ATG) and end at a stop codon (usually TAA, TAG or TGA).

Organisms:

In a third aspect, the present invention provides organisms comprising the vectors described herein. The organisms can be used to produce gene products encoded by the vectors, i.e., by expressing the gene product(s) encoded by the at least one ORF included in the vector. Thus, for clarity, these organisms are also referred to herein as "producer organisms". Any organism that is suitable for heterologous protein expression may be used with the present invention. Exemplary organisms include, for example, *Escherichia coli, Corynebacterium, Pseudomonas fluorescens*, yeasts (e.g., *S. cerevisiae* or *Pichia pastoris*), filamentous fungi (e.g., *Aspergillus* or *Trichoderma*,) and plants (e.g., *Nicotiana* sp.). In some embodiments, the organism is *E. coli.*

Methods of Inhibiting Microorganism Growth:

In a fourth aspect, the present invention provides methods of inhibiting the growth of a microorganism. In one embodiment, the methods comprise contacting the microorganism with an effective amount of a biosynthetic product described herein. In a second embodiments, the methods comprise contacting the microorganism with an organism comprising a vector described herein (i.e., a producer organism) or a biosynthetic product produced by the organism. Thus, the methods of the present invention inhibit the growth of a microorganism by contacting it with a composition comprising (1) a biosynthetic product produced by *P. protegens* PBL3, as described in the section titled "Biosynthetic products"; (2) a producer organism, as described in the section titled "Organisms"; or (3) a biosynthetic product produced by a producer organism.

The growth of any microorganism may be inhibited by the methods of the present invention. Suitably, the microorganism is a bacterium or fungus. In the Examples, the bacterial strain *P. protegens* PBL3 and cell-free secreted fractions thereof were only tested against the rice pathogen *Burkholderia glumae*. However, in previous work, the inventors have shown that this strain inhibits the growth of several additional plant pathogens, including bacterial pathogens from the genera *Burkholderia, Xanthomonas*, and *Erwinia*, as well as fungal pathogens from the genera *Rhizoctonia, Pythium, Magnaporthe*, and *Fusarium*. See US Patent Application No. 2020/0068900 (note: PBL3 is referred to as *Pseudomonas fluorescens* PBL13 in this application, but was later reclassified based on 16S rRNA sequencing, as is described in the Examples). Thus, in some embodiments, the microorganism is a bacterium of the genera *Burkholderia, Xanthomonas*, or *Erwinia*, or a fungus of the genera *Rhizoctonia, Pythium, Magnaporthe*, or *Fusarium*. In preferred embodiments, the microorganism is *Burkholderia glumae*.

Inhibition of growth of a microorganism may be assessed using any method known in the art. Suitable methods include, for example, plate inhibition assays. In embodiments in which the microorganism is a plant pathogen, the biosynthetic product or producer organism can applied to the plant (e.g., injected into the plant or applied to the seeds of the plant), and the growth of the microorganism on the plant or the microbial damage to the plant can be measured.

"Effective amount" is intended to mean an amount of a biosynthetic product or producer organism described herein that is sufficient to inhibit the growth of a microorganism by, for example, 10%, 20%, 50%, 75%, 80%, 90%, 95%, or 1-fold, 3-fold, 5-fold, 10-fold, 20-fold, or more compared to a negative control that does not comprise the biosynthetic product or producer organism.

In some embodiments, the methods are used to inhibit the growth of a microorganism that is on a plant. As used herein, a "plant" includes any portion of the plant including, without limitation, a whole plant or a portion of a plant such as a part of a root, leaf, stem, seed, pod, flower, cell, tissue plant germplasm, asexual propagate, or any progeny thereof. For example, a rice plant refers to the whole rice plant or portions thereof including, without limitation, the leaves, roots, seeds or otherwise. Suitable "plants" may include, without limitation, rice, tomato, onion, cotton, soybean, wheat, ryegrass, crucifers, *prunus*, beans, kiwi fruit, mango, apple, pear, sunflower, maple, European horse chestnut, Indian horse chestnut, beet, hazelnut, barley, cucumber, cabbage, mulberry, cherry, millet, pea, olive, tobacco, *camellia*, sorghum, or corn. In some embodiments, the plant is a rice plant.

Several methods of "contacting" may be used to apply a biosynthetic product or producer organism described herein to a plant. Suitable application methods include, without limitation, spraying or dusting. Contacting may also be carried out indirectly via application, for example, to the soil surrounding a plant or to plant media or substrates. Alternatively, the biosynthetic product or producer organism may be injected into the plant. The contacting step of the present methods may be carried out before or after the microorganism grows on the plant. In some embodiments, the leaves or seeds of the plant are contacted with the biosynthetic product or producer organism. In some embodiments, the contacting is carried out before flowering or during panicle formation.

In some embodiments, the plant may be contacted at least 2, 3, 4, 5, or more times with a biosynthetic product or producer organism described herein. For example, the seeds of the plant could be treated with the biosynthetic product or producer organism prior to planting and then the biosynthetic product or producer organism could be sprayed onto the growing plants at one or more stage of development. The methods may be used as a preventative measure or may be used only on plants or in fields that microbial damage is suspected or noted.

In methods in which the microorganism is on a plant, the biosynthetic product or producer organism may be applied as part of an agricultural composition. An "agricultural composition" is a composition formulated for application to a plant or plant part. Agricultural compositions are commonly formulated as a liquid (i.e., liquid suspension) for application by spraying or soaking, but may also be formulated in a solid, granular, or powder form for rehydration or application by dusting or dry coating. The agricultural composition may be concentrated (e.g., by lyophilization) for dilution in water or another solvent. The agricultural compositions may be prepared for administration to plants or may be prepared for administration to seeds. The agricultural compositions may include a biosynthetic product or producer organism described herein and a carrier. As used herein, a "carrier" may be solid or liquid and may include substances ordinarily employed in formulations applied to plants. Suitable carriers include buffers, water, oils, nonionic surfactants, ionic surfactants, or agricultural by-products. In some embodiments, the agricultural compositions also include an additional active ingredient.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

The following examples are meant only to be illustrative and are not meant as limitations on the scope of the invention or of the appended claims.

EXAMPLES

Bacterial panicle blight of rice is a seed-borne disease caused by the bacterium *Burkholderia glumae*. This disease has affected rice production worldwide and its effects are likely to become more devastating with the continuous increase in global temperatures, especially during the growing season. The bacterium can cause disease symptoms in different tissues and at different developmental stages. In reproductive stages, the bacterium interferes with grain development in the panicles and, as a result directly affects rice yield. Currently, there are no methods to control the disease as chemical control is not effective and completely resistant cultivars are not available. Thus, a promising approach is the use of antagonistic microorganisms. In the following Example, the inventors identified one strain of *Pseudomonas protegens* and one strain of *Burkholderia cepacia* with antimicrobial activity against *B. glumae* in vitro and in planta. They characterized the antimicrobial activity of *P. protegens* and found that this activity is associated with bacterial secretions. Cell-free secretions from *P. protegens* inhibited the growth of *B. glumae* in vitro and prevented *B. glumae* from causing disease in rice. Although, the specific molecule(s) associated with these activities have not been identified, these findings suggest that the secreted fractions from *P. protegens* could be harnessed as biopesticides to control bacterial panicle blight of rice.

Materials and Methods:

Bacterial Strains

*Burkholderia glumae* was isolated from infected rice panicles in fields of Arkansas (Mulaw et al., 2018), and grown on a modified CCNT media (Kawaradani et al., 2000) (2 g/L yeast extract, 1 g/L proteose peptone, 4 g/L Myo-inositol, 10 mg/L Cetrimide, 18 g/L agar, pH 4.8) or King's B (KB) media (King et al., 1954), depending on the experiment. Other bacterial strains used in this study are listed in Table 1. These strains were grown on Luria Bertani (LB) (Bertani, 1951) or KB media, depending on the experiment.

TABLE 1

Bacterial strains used in this study

| Strain | Source |
|---|---|
| *Burkholderia glumae* | Y. Wamishe |
| *P. fluorescens* PFS JA 4092/*P. protegens* PBL3 | (Milus & Rothrock, 1997)/This study |
| *P. fluorescens* 5-40 | (Milus & Rothrock, 1997) |
| *P. fluorescens* 1-30 10-99 | (Milus & Rothrock, 1997) |
| *B. cepacia* | C. Rothrock, unpublished |
| *Pseudomonas* sp. | C. Rothrock, unpublished |
| *P. fluorescens* 2-79 | D. M. Weller |
| *Burkholderia* sp. | C. Rothrock, unpublished |
| *Escherichia coli* DH5α | (Hanahan, 1983) |

Bacterial identification was confirmed by the Polymerase chain reaction (PCR) of the 16S rRNA region using primer 27F (5'-AGAGTTTGATCCTGGCTCAG-3'; SEQ ID NO:4) and 1492R (5'-GGTTACCTTGTTACGACTT-3'; SEQ ID NO:5) (Lane, 1991). The reaction mix consisted of 2 μL of template DNA, 2 mM MgCl2, 0.2 mM dNTPs, 0.2 mg/ml Bovine Serum Albumin, 0.2 μM of forward and reverse primers, 1× buffer and 1 U of GoTaq polymerase (Promega, WI, USA). The amplification conditions included an initial denaturation at 94° C. for 5 min, followed by 30 cycles consisting 1 min at 94° C., 1 min at 45° C., and 2 min at 72° C., and a final extension for 10 min at 72° C. The PCR product was visualized in a 1% agarose gel stained using Gel Red® Nucleic Acid Gel Stain (Biotium, CA, USA) and then purified with the GeneJet PCR purification kit (Thermo Fisher Scientific, Waltham, MA). Purified PCR product was sequenced at Macrogen, Inc. (Rockville, MD). Forward and reverse sequences were assembled using SeqMan (DNAStar, Madison, WI), and compared with 16S rRNA bacterial sequences available in The Ribosomal Database Project (RDP) (Cole et al., 2014).

Rice Seed Sterilization, Germination, and Fertilization

Rice cultivars used in this study include the long grain cultivar Wells and the short-grain cultivar Nipponbare, both of which are moderately susceptible to bacterial panicle blight (Temesgen et al., 2018, Mizobuchi et al., 2018). Rice seeds were de-husked and surface sterilized with 70% ethanol for 30 seconds, followed by shaking for 15 min in a solution containing 30% bleach and 20% sodium dodecyl sulfate (SDS). The bleach/SDS treatment was repeated one more time. After decanting the bleach/SDS solution, seeds were rinsed with sterile water five times. Surface-sterilized rice seeds were placed on sterile filter paper in petri plates with enough water to saturate the filter paper. Sterilized seeds were pre-germinated at 28° C. in the dark for 4-5 days. Seedlings were transferred onto Pro Mix potting soil and transplanted when they were 2-3 inches tall. All Purpose Plant Food Miracle-Gro (Scotts Miracle-Gro, Marysville, OH) was added to fertilize plants after transplanting and every week afterwards. During vegetative growth, plants were also supplemented with iron (Sulfate Sprint 330 10% iron chelate, BASF, Germany) at 0.473 lbs/gal, twice a week.

Screening for Antagonistic Activity Against *B. glumae*

Overnight liquid cultures of *P. fluorescens* PFS JA 4092 (herein renamed as *P. protegens* PBL3), *P. fluorescens* 5-40, *P. fluorescens* 1-30, *B. cepacia, Pseudomonas* sp, *P. fluorescens* 2-79, *Burkholderia* sp., and *B. glumae* grown in KB were collected by centrifugation at 6,000 rpm for 10 min and bacterial pellets were washed with sterile water three times. The concentrations of bacterial strains to be tested as biocontrol agents were adjusted to an optical density at 600 nm ($OD_{600}$) of 1 ($1\times10^8$ CFU/ml). *B. glumae* was directly added to molten KB agar to a final concentration of $OD_{600}$=0.001 ($1\times10^5$ CFU/ml), and poured into sterile Petri plates. After plates solidified, five 6 mm diameter sterile filter paper disks were placed on plates. Five microliters of testing bacteria were added to four of the filter disks, and five microliters of sterile water were added to the fifth disk as a negative control. Plates were incubated at 28° C. and pictures were taken after 48 h. Pictures were uploaded into ImageJ (Rasband, 1997) to calculate the diameter of the zone of inhibition, which is visualized as a clearing around the disks containing potentially inhibitory bacteria. The area of the filter disk was subtracted from the area of the zone of inhibition. Each of the disks were used as replicates for a given experiment, and each combination of pathogen-antagonist was tested in two plates. The experiment was repeated three times. Differences in growth inhibition were determined by one-way analysis of variance (ANOVA) followed by Tukey's honestly significant difference (HSD) tests.

Genome Sequencing and Genome Analysis of *P. protegens* PBL3

*P. protegens* PBL3 genomic DNA was extracted from a 3 ml culture grown overnight using the GeneJET Genomic DNA Purification kit (ThermoFisher Scientific, Waltham, MA). DNA quality was visualized in a 1% agarose gel and stained using Gel Red® Nucleic Acid Gel Stain (Biotium, CA, USA). Total DNA was quantified using a Qubit 4 fluorometer (Thermo Fisher Scientific, Waltham, MA) and was sequenced using an Illumina tagmentation library approach on a NextSeq 550 instrument with 150-bp paired-end reads (Baym et al., 2015). A total of 6,768,192 pair-end reads and 926,660,108 bp (~47× coverage) were obtained, and the genome was assembled using shovill 1.0.9 (github.com/tseemann/shovill) using parameter "--minlen 500 --trim" and defaults for remaining analyses. Initial processing consisted of trimming with Trimmomatic v0.39 (Bolger et al., 2014), followed by error correction with Lighter v1.1.2 (Song et al., 2014) and merging overlapping reads using Flash v1.2.11 (Magoč & Salzberg, 2011). This resulted in 1.4 million reads merged and 1.1 million reads unmerged. These files were used to assemble the genome using spades v3.14.0 (Bankevich et al., 2012) and the resulting assembly was polished with Pilon v1.23 (Walker et al., 2014) resulting in 24 contigs. A second scaffolding approach was done using SSPACE v3.0 (Boetzer et al., 2011), resulting in a 7.04 Mbp assembly containing 14 scaffolds. To finalize the assembly, *Pseudomonas protegens* CHA0 (NC_021237.1) was used to complete the chromosome using AlignGraph (Bao et al., 2014). The assembly was annotated using prokka v1.14.5 (Seemann, 2014). Raw data was submitted to Sequence Read Archive (SRA) (Bioproject PRJNA626017 and Biosample number SAMN14614890). The genome assembly was also submitted to NCBI (Accession CP051673). In order to identify putative biosynthetic gene clusters involved in the production of secondary metabolites that could be responsible for the antagonistic activity, the genome sequence was mined using antiSMASH (Blin et al., 2019).

The sequence information obtained may be found at the following webpages: "Pprot annotation.txt" at: documentcloud.adobe.com/link/track?uri=urn:aaid:scds:US:2c49034f-c7b5-4ddb-b570-4a1d0c927f76 [documentcloud.adobe.com] "Pprot coordinates.txt" at: documentcloud.adobe.com/link/track?uri=urn:aaid:scds:US:dd2eb2a5-bead-433f-93b0-1a1d089f7089 [documentcloud.adobe.com] "Pprot.txt" at: documentcloud.adobe.com/link/track?uri=urn:aaid:scds:US:1d0948d9-9bf6-4253-9dff-2b707269866a [documentcloud.adobe.com].

Preparation and Evaluation of the Secreted Fraction from *P. protegens* PBL3

*P. protegens* PBL3 cultures were grown overnight in 250 ml of LB broth and incubated at 28° C. by shaking. Cultures were centrifuged for 10 min at 6,000 rpm and the supernatant was collected and lyophilized in a Labonco Freezone® 12 freeze dry system (Labconco, MO, USA) for 3 days until a dried powder was obtained. Sterile LB was also lyophilized using the same conditions and used as a negative control. For the experiments, 0.1 or 0.5 g of lyophilized LB or lyophilized secreted fraction from *P. protegens* PBL3 were resuspended in 1 ml of sterile water to obtain concentrations of 0.1 g/ml or 0.5 g/ml, respectively, depending on the experiment. Reconstituted LB or reconstituted secreted fraction from *P. protegens* PBL3 were filter-sterilized using a 0.22 μM filter to remove residual bacteria or possible contamination during lyophilization.

Reconstituted LB or reconstituted cell-free secreted fraction from *P. protegens* PBL3 were independently added to KB broth at 1:1 ratio in a final volume of 3 ml and used to grow a single colony of *B. glumae*. Cultures of *B. glumae* were grown in a shaker at 30° C. for 24 h. After 24 h, cultures were serially diluted and plated on KB to enumerate bacterial populations. This experiment was repeated three times with equivalent results.

To generate sub-fractions of the *P. fluorescens* PBL3 secreted fraction, the reconstituted secreted fraction at a final concentration of 0.1 g/ml was separated by molecular mass ranges using ultrafiltration centrifugal devices equipped with polyethersulfone (PES) membranes of defined molecular mass cutoffs: 30 kDa, 10 kDa, and 3 kDa (ThermoFisher Scientific, Waltham, MA). Sub-fractions higher and lower than each of the molecular mass cut-offs were filter-sterilized and added to KB. KB alone or supplemented with the subfractions was used to grow *B. glumae* to evaluate bacterial populations. Each of these experiments was repeated three times.

Pathogenicity Assays

To evaluate the effect of *P. protegens* PBL3 on disease development caused by *B. glumae*, overnight cultures of *P. protegens* PBL3 and *B. glumae* were prepared in KB media and diluted to an $OD_{600}$=0.125 ($1\times10^7$ CFU/ml). *E. coli* DH5a prepared in the same way was used as a negative control. Twenty microliters of *B. glumae* inoculum alone, or in combination with *P. protegens* PBL3 or *E. coli* DH5a at 1:1 ratios were injected into the sheath of eight-week-old plants from moderately susceptible cultivar Wells grown in soil. Plants were also injected with water and used as mock controls. Plants were transferred to growth chambers with day/night temperatures of 35° C./28° C., photoperiod of 16 h light/8 h dark and 60-65% relative humidity for eight days. Plants were monitored each day and lesions were measured at 8 days post-inoculation (dpi). The experiment was repeated three times with similar results.

To evaluate the effect of cell-free secreted fraction from *P. protegens* PBL3 on the pathogenicity of *B. glumae*, cell-free reconstituted secreted fraction from *P. protegens* PBL3 at 0.5 g/L was also added to a prepared inoculum of *B. glumae* at $OD_{600}$=0.125. Reconstituted LB at 0.5 g/L was also added to a prepared inoculum of *B. glumae* at $OD_{600}$=0.125, and used as control. Twenty microliters of *B. glumae* mixed with the cell-free reconstituted secreted fraction from *P. protegens* PBL3, or mixed with reconstituted LB were injected into the sheaths of 10-week-old Nipponbare rice plants in triplicates. At 2 and 7-days dpi, three inches of sheath (1.5 inches above and below injection site) were ground in 2 ml of sterile water and 0.5 g of sand. Samples were serially diluted and plated on modified CCNT media to enumerate *B. glumae* populations. Plates were incubated at 28° C. and colonies were counted after two days.

We also evaluated the effect of cell-free reconstituted secreted fraction from *P. protegens* PBL3 on *B. glumae* infection on seeds. For that purpose, seeds from cultivar Nipponbare were sterilized as described above. Twenty sterile seeds were inoculated with 2 ml of *B. glumae* at $OD_{600}$=0.001 ($1\times10^5$ CFU/ml) either containing 0.5 g/ml of lyophilized and resuspended LB, or cell-free lyophilized fractions of *P. protegens* (0.1 g/ml or 0.5 g/ml). Seeds were incubated with inocula by shaking at 100-150 rpm for 30 min. Bacterial inoculum was decanted and the seeds were plated on Murashige and Skoog (MS) axenic media containing 0.01% Myo-inositol and 0.02% pimaricin (0.2 ml/L). Plates were wrapped with surgical tape, and incubated in a 28° C. in the dark for two days. Plates were then transferred to a growth chamber set up at 25° C. and photoperiod of 16 h light/8 h dark for 5 days. Shoot length of rice seedlings was measured at 7 dpi using ImageJ (Rasband, 1997). All these experiments were repeated three times.

Statistical Analysis

Means and standard deviations were calculated for all treatments within each experiment. Differences between treatments were determined by analysis of variance (ANOVA) using one-way ANOVA or T-test depending on the number of treatments using JMP Pro 14 software (SAS, NC, USA). Analyses were performed at P=0.05 or P=0.001 level and when differences were significant with ANOVA, means were compared using Tukey's honestly significant difference (HSD).

Results:

Identifying Bacterial Strains with Antagonistic Activity Against *B. glumae*

Figure 1:
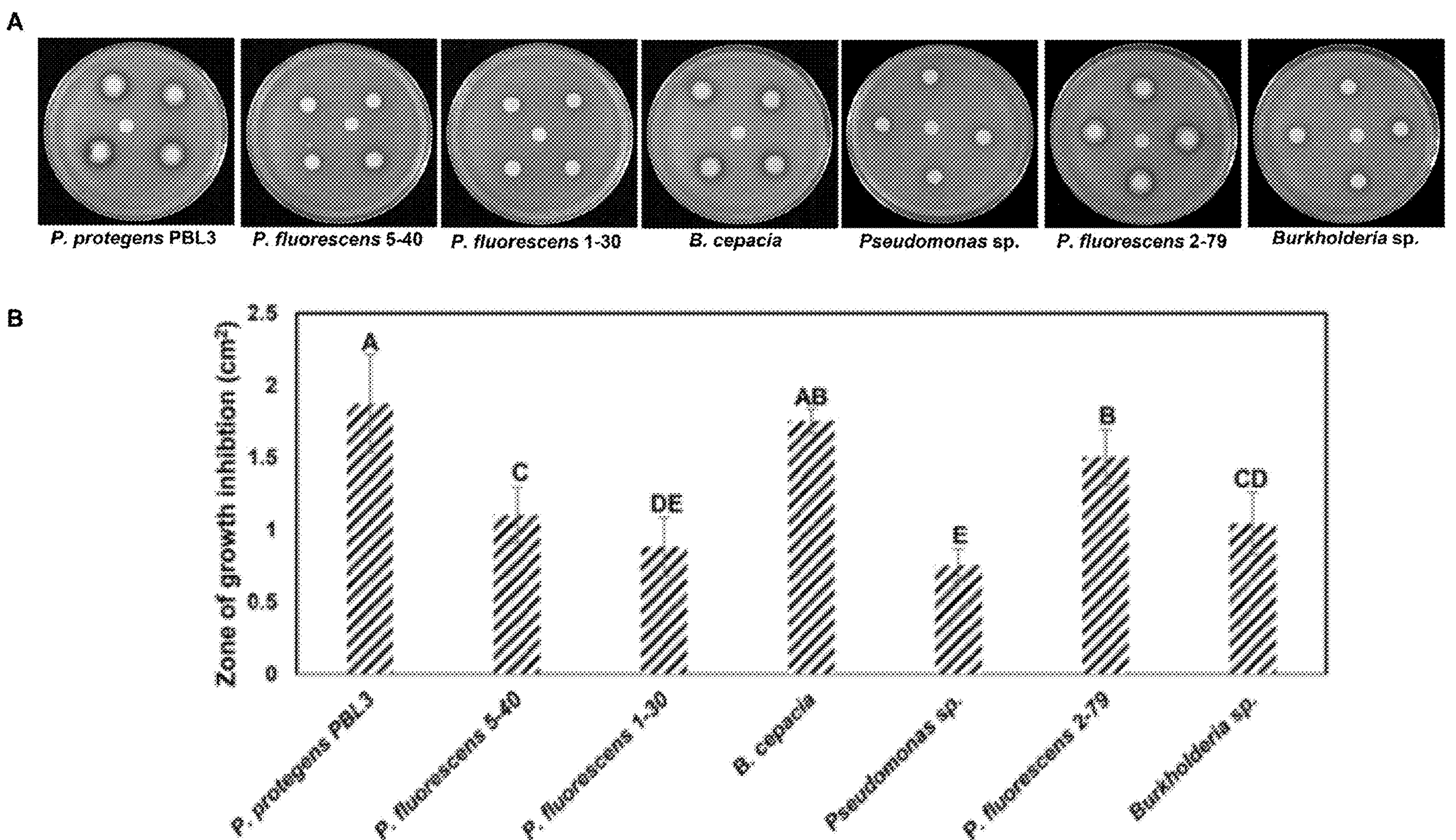
FIG. 1 shows the identification of bacteria with antagonistic activities against *Burkholderia glumae. Burkholderia glumae* was mixed with molten KB agar to a final $OD_{600}$=0.001 and poured into plates. After agar solidified, five sterile filter paper disks were placed on the agar surface. Overnight cultures of seven bacterial strains: *P. protegens* PBL3, *P. fluorescens* 5-40, *P. fluorescens* 1-30, *B. cepacia, P. fluorescens* sp. *P. fluorescens* 2-79 and *Burkholderia* sp. were diluted to $OD_{600}$=1 ($1\times10^8$ CFU/ml), and 5 μl of bacteria were pipetted onto four of the filter paper disks. Water was added to the fifth center disk and used as negative control. Plates were incubated at 28° C. for 48 h. The clear zones of growth inhibition (A) were measured and plotted (B). Bars represent the average area of *B. glumae* growth inhibition by different bacteria from replicates of three independent experiments. Each error bar indicates the standard error from replications. Treatments were compared using ANOVA and means were compared using Tukey honestly significant difference (HSD) test with P-value=0.05.

Seven bacterial strains, including *P. protegens* PBL3, *P. fluorescens* 5-40, *P. fluorescens* 1-30, *B. cepacia, P. fluorescens* sp., *P. fluorescens* 2-79 and *Burkholderia* sp., were previously investigated for their potential as biological control agents against soil-borne pathogens (Milus & Rothrock, 1997). Because these strains were already available in our lab, we decided to investigate if they could be used to control bacterial panicle blight of rice. We used a plate inhibition assay wherein *B. glumae* was grown in the presence of the tested bacteria (FIG. 1). We found that two of the strains: *P. protegens* PBL3 and *B. cepacia* significantly inhibited the growth of *B. glumae*, as shown by a clear area around the disks containing these bacteria (FIG. 1A). Both *P. protegens* PBL3 and *B. cepacia* caused the same growth inhibition with an area of 1.75 $cm^2$ (FIG. 1B). The other bacteria tested (*P. fluorescens* 5-40, *P. fluorescens* 1-30, *Pseudomonas* sp, *P. fluorescens* 2-79, and *Burkholderia* sp) had a reduced effect on growth inhibition that ranged from 0.75 $cm^2$ to 1.5 $cm^2$ (FIG. 1B). Since other strains of *P. protegens* have been widely recognized as wide-spectrum biological control organisms, we decided to investigate this bacterium in more detail.

Bacterial Identification and Genome Sequencing

*P. protegens* PBL3 was previously named *P. fluorescens* PFS JA4092. Our initial analysis of the 16S rRNA sequence of *P. protegens* PBL3 revealed that it had 99% similarity to the 16s rRNA sequence of *P. protegens* CHA0 (Genbank NR_114749.1), based on the sequences available from the Ribosomal Database Project (RDP) (Cole et al., 2014). To resolve the discrepancy in the original naming, we sequenced the bacterial genome. The assembled scaffolds were submitted to the Ribosomal Multilocus Sequence Typing tool (rMLST; pubmlst.org/rmlst/) (Jolley et al., 2012), and this analysis extracted 54 different regions that supported the ID of the strain as *P. protegens* (Table 2).

TABLE 2

Regions supporting the identification of *P. protegens* PBL3

| Locus | Allele | Length | Contig | Start position | End position | Linked data values |
|---|---|---|---|---|---|---|
| BACT000001 (rpsA) | 207 | 1695 | P_protegens_PBL3 | 4678588 | 4680282 | species: *Pseudomonas protegens* [n = 7] |
| BACT000002 (rpsB) | 177 | 738 | P_protegens_PBL3 | 1332708 | 1333445 | species: *Pseudomonas protegens* [n = 7] |
| BACT000003 (rpsC) | 144 | 687 | P_protegens_PBL3 | 5853892 | 5854578 | species: *Pseudomonas protegens* [n = 15]; *Pseudomonas* sp. [n = 14] |
| BACT000004 (rpsD) | 142 | 621 | P_protegens_PBL3 | 5845765 | 5846385 | species: *Pseudomonas protegens* [n = 9]; *Pseudomonas* sp. [n = 7] |
| BACT000005 (rpsE) | 125 | 501 | P_protegens_PBL3 | 5849398 | 5849898 | species: *Pseudomonas protegens* [n = 7] |
| BACT000006 (rpsF) | 118 | 426 | P_protegens_PBL3 | 667679 | 668104 | species: *Pseudomonas protegens* [n = 37]; *Pseudomonas* sp. [n = 18] |
| BACT000007 (rpsG) | 122 | 471 | P_protegens_PBL3 | 5861554 | 5862024 | species: *Pseudomonas protegens* [n = 29]; *Pseudomonas* sp. [n = 14] |
| BACT000008 (rpsH) | 106 | 393 | P_protegens_PBL3 | 5850809 | 5851201 | species: *Pseudomonas protegens* [n = 27]; *Pseudomonas* sp. [n = 14] |
| BACT000009 (rpsI) | 119 | 393 | P_protegens_PBL3 | 5380880 | 5381272 | species: *Pseudomonas protegens* [n = 7]; *Pseudomonas* sp. [n = 7] |
| BACT000010 (rpsJ) | 111 | 312 | P_protegens_PBL3 | 5857696 | 5858007 | species: *Pseudomonas protegens* [n = 35]; *Pseudomonas* sp. [n = 14] |
| BACT000011 (rpsK) | 95 | 390 | P_protegens_PBL3 | 5846404 | 5846793 | species: *Pseudomonas protegens* [n = 29]; *Pseudomonas* sp. [n = 14] |
| BACT000012 (rpsL) | 119 | 372 | P_protegens_PBL3 | 5862136 | 5862507 | species: *Pseudomonas protegens* [n = 16] |
| BACT000013 (rpsM) | 105 | 357 | P_protegens_PBL3 | 5846824 | 5847180 | species: *Pseudomonas protegens* [n = 7] |
| BACT000014 (rpsN) | 94 | 306 | P_protegens_PBL3 | 5851409 | 5851714 | species: *Pseudomonas protegens* [n = 25]; *Pseudomonas* sp. [n = 7] |
| BACT000015 (rpsO) | 114 | 270 | P_protegens_PBL3 | 963677 | 963946 | species: *Pseudomonas protegens* [n = 29]; *Pseudomonas* sp. [n = 18]; *Pseudomonas saponiphila* [n = 1] |
| BACT000016 (rpsP) | 117 | 252 | P_protegens_PBL3 | 1234557 | 1234808 | species: *Pseudomonas protegens* [n = 27] |
| BACT000017 (rpsQ) | 105 | 267 | P_protegens_PBL3 | 5853006 | 5853272 | species: *Pseudomonas protegens* [n = 25]; *Pseudomonas* sp. [n = 9] |
| BACT000018 (rpsR) | 102 | 231 | P_protegens_PBL3 | 668133 | 668363 | species: *Pseudomonas* sp. [n = 120] *Pseudomonas protegens* [n = 39] *Pseudomonas corrugata* [n = 7] *Pseudomonas koreensis* [n = 5] *Pseudomonas fluorescens* [n = 4] *Pseudomonas mandelii* [n = 4] *Pseudomonas moraviensis* [n = 4] *Pseudomonas palleroniana* [n = 3] *Pseudomonas reinekei* [n = 3] *Pseudomonas vancouverensis* [n = 3] *Pseudomonas jessenii* [n = 2] [*Flavobacterium*] sp. 29 [n = 1] *Pseudomonas helmanticensis* [n = 1] |
| BACT000019 (rpsS) | 91 | 276 | P_protegens_PBL3 | 5854938 | 5855213 | species: *Pseudomonas chlororaphis* [n = 56]; *Pseudomonas* sp. [n = 30]; *Pseudomonas protegens* [n = 11] |
| BACT000020 (rpsT) | 114 | 279 | P_protegens_PBL3 | 5614781 | 5615059 | species: *Pseudomonas protegens* [n = 25]; *Pseudomonas* sp. [n = 14] |
| BACT000021 (rpsU) | 71 | 216 | P_protegens_PBL3 | 5942690 | 5942905 | species: *Pseudomonas protegens* [n = 30]; *Pseudomonas* sp. [n = 9] |
| BACT000030 (rplA) | 163 | 696 | P_protegens_PBL3 | 5872413 | 5873108 | species: *Pseudomonas protegens* [n = 8] |
| BACT000031 (rplB) | 146 | 825 | P_protegens_PBL3 | 5855230 | 5856054 | species: *Pseudomonas protegens* [n = 7] |
| BACT000032 (rplC) | 148 | 636 | P_protegens_PBL3 | 5856980 | 5857615 | species: *Pseudomonas protegens* [n = 7] |
| BACT000033 (rplD) | 130 | 603 | P_protegens_PBL3 | 5856365 | 5856967 | species: *Pseudomonas protegens* [n = 7] |
| BACT000034 (rplE) | 131 | 540 | P_protegens_PBL3 | 5851728 | 5852267 | species: *Pseudomonas protegens* [n = 18]; *Pseudomonas* sp. [n = 14] |
| BACT000035 (rplF) | 148 | 534 | P_protegens_PBL3 | 5850263 | 5850796 | species: *Pseudomonas protegens* [n = 12]; *Pseudomonas* sp. [n = 9] |
| BACT000036 (rplL) | 140 | 366 | P_protegens_PBL3 | 5871268 | 5871633 | species: *Pseudomonas protegens* [n = 29]; *Pseudomonas* sp [n = 9] |
| BACT000038 (rplI) | 176 | 447 | P_protegens_PBL3 | 669321 | 669767 | species: *Pseudomonas protegens* [n = 28]; *Pseudomonas* sp. [n = 16]; *Pseudomonas saponiphila* [n = 1] |
| BACT000039 (rplJ) | 166 | 501 | P_protegens_PBL3 | 5871714 | 5872214 | species: *Pseudomonas protegens* [n = 28]; *Pseudomonas* sp. [n = 14] |

TABLE 2-continued

| Regions supporting the identification of *P. protegens* PBL3 | | | | | | |
|---|---|---|---|---|---|---|
| Locus | Allele | Length | Contig | Start position | End position | Linked data values |
| BACT000040 (rplK) | 150 | 432 | P_protegens_PBL3 | 5873108 | 5873539 | species: *Pseudomonas protegens* [n = 14]; *Pseudomonas* sp [n = 7] |
| BACT000042 (rplM) | 131 | 429 | P_protegens_PBL3 | 5381287 | 5381715 | species: *Pseudomonas protegens* [n = 27]; *Pseudomonas* sp. [n = 7] |
| BACT000043 (rplN) | 115 | 369 | P_protegens_PBL3 | 5852614 | 5852982 | species: *Pseudomonas protegens* [n = 26]; *Pseudomonas* sp. [n = 14] |
| BACT000044 (rplO) | 120 | 435 | P_protegens_PBL3 | 5848781 | 5849215 | species: *Pseudomonas protegen* [n = 20]; *Pseudomonas* sp [n = 9] |
| BACT000045 (rplP) | 96 | 414 | P_protegens_PBL3 | 5853466 | 5853879 | species: *Pseudomonas protegens* [n = 7] |
| BACT000046 (rplQ) | 111 | 387 | P_protegens_PBL3 | 5844312 | 5844698 | species: *Pseudomonas protegens* [n = 17]; *Pseudomonas* sp. [n = 7] |
| BACT000047 (rplR) | 124 | 351 | P_protegens_PBL3 | 5849902 | 5850252 | species: *Pseudomonas protegens* [n = 28]; *Pseudomonas* sp. [n = 15] |
| BACT000048 (rplS) | 130 | 351 | P_protegens_PBL3 | 1236151 | 1236501 | species: *Pseudomonas protegens* [n = 27]; *Pseudomonas* sp. [n = 14] |
| BACT000049 (rplT) | 125 | 357 | P_protegens_PBL3 | 2264001 | 2264357 | species: *Pseudomonas protegens* [n = 29]; *Pseudomonas* sp. [n = 14] |
| BACT000050 (rplU) | 112 | 312 | P_protegens_PBL3 | 5618674 | 5618985 | species: *Pseudomonas protegens* [n = 28]; *Pseudomonas* sp. [n = 17] |
| BACT000051 (rplV) | 212 | 333 | P_protegens_PBL3 | 5854592 | 5854924 | species: *Pseudomonas chlororaphis* [n = 58]; *Pseudomonas protegens* [n = 38]; *Pseudomonas* sp. [n = 26]; *Pseudomonas lutea* [n = 1]; *Pseudomonas saponiphila* [n = 1] |
| BACT000052 (rplW) | 203 | 300 | P_protegens_PBL3 | 5856069 | 5856368 | species: *Pseudomonas chlororaphis* [n = 17]; *Pseudomonas protegens* [n = 13]; *Pseudomonas* sp. [n = 5] |
| BACT000053 (rplX) | 218 | 315 | P_protegens_PBL3 | 5852288 | 5852602 | species: *Pseudomonas protegens* [n = 28]; *Pseudomonas* sp. [n = 14] |
| BACT000056 (rpmA) | 266 | 258 | P_protegens_PBL3 | 5618381 | 5618638 | species: *Pseudomonas protegens* [n = 10]; *Pseudomonas* sp. [n = 7] |
| BACT000057 (rpmB) | 137 | 237 | P_protegens_PBL3 | 6364793 | 6365029 | species: *Pseudomonas protegens* [n = 31]; *Pseudomonas* sp. [n = 15] |
| BACT000058 (rpmC) | 160 | 192 | P_protegens_PBL3 | 5853275 | 5853466 | species: *Pseudomonas* sp. [n = 52]; *Pseudomonas protegens* [n = 39]; *Pseudomonas jessenii* [n = 2]; *Pseudomonas laurylsulfatiphila* [n = 1]; *Pseudomonas mandelii* [n = 1]; *Pseudomonas umsongensis* [n = 1] |
| BACT000059 (rpmD) | 135 | 177 | P_protegens_PBL3 | 5849219 | 5849395 | species: *Pseudomonas protegens* [n = 7] |
| BACT000060 (rpmE) | 193 | 270 | P_protegens_PBL3 | 5196045 | 5196314 | species: *Pseudomonas protegens* [n = 25] |
| BACT000061 (rpmF) | 156 | 183 | P_protegens_PBL3 | 1977194 | 1977376 | species: *Pseudomonas protegens* [n = 8]; *Pseudomonas* sp. [n = 7] |
| BACT000063 (rpmH) | 234 | 135 | P_protegens_PBL3 | 6566162 | 6566296 | species: *Pseudomonas* sp. [n = 158] *Pseudomonas chlororaphis* [n = 69] *Pseudomonas protegens* [n = 39] *Pseudomonas brassicacearum* [n = 17] *Pseudomonas corrugata* [n = 7] *Pseudomonas mandelii* [n = 6] *Pseudomonas mediterranea* [n = 6] *Pseudomonas kilonensis* [n = 5] *Pseudomonas fluorescens* [n = 4] *Pseudomonas lini* [n = 4] *Pseudomonas thivervalensis* [n = 4] *Pseudomonas reinekei* [n = 3] *Pseudomonas vancouverensis* [n = 3] *Pseudomonas jessenii* [n = 2] *Pseudomonas arsenicoxydans* [n = l] *Pseudomonas saponiphila* [n = l] *Pseudomonas umsongensi* [n = 1] |
| BACT000064 (rpmI) | 150 | 195 | P_protegens_PBL3 | 2263776 | 2263970 | species: *Pseudomonas* sp. [n = 114]; *Pseudomonas chlororaphis* [n = 68]; *Pseudomonas protegens* [n = 39]; *Pseudomonas fluorescens* [n = 6]; *Pseudomonas brassicacearum* [n = 2]; *Pseudomonas kribbensis* [n = 2]; *Pseudomonas asplenii* [n = 1]; *Pseudomonas koreensis* [n = 1]; *Pseudomonas saponiphil* [n = 1] |
| BACT000065 (rpmJ) | 19076 | 150 | P_protegens_PBL3 | 4092111 | 4092260 | species: *Pseudomonas protegens* [n = 26]; *Pseudomonas* sp. [n = 14] |
| BACT000065 | 137 | 117 | P_protegens_PBL3 | 5847311 | 5847427 | species: *Pseudomonas* sp. [n = 451] |

TABLE 2-continued

Regions supporting the identification of *P. protegens* PBL3

| Locus | Allele | Length | Contig | Start position | End position | Linked data values |
|---|---|---|---|---|---|---|
| (rpmJ) | | | | | | *Pseudomonas chlororaphis* [n = 71]<br>*Pseudomonas fluorescens* [n = 63]<br>*Pseudomonas protegens* [n = 38]<br>*Pseudomonas synxantha* [n = 11]<br>*Pseudomonas koreensis* [n = 9]<br>*Pseudomonas lurida* [n = 9]<br>*Pseudomonas veronii* [n = 9]<br>*Pseudomonas lactis* [n = 8]<br>*Pseudomonas corrugata* [n = 7]<br>*Pseudomonas simiae* [n = 7]<br>*Pseudomonas azotoformans* [n = 6]<br>*Pseudomonas mediterranea* [n = 6]<br>*Pseudomonas moraviensis* [n = 6]<br>*Pseudomonas prosekii* [n = 6]<br>*Pseudomonas tolaasii* [n = 6]<br>*Pseudomonas lini* [n = 5]<br>*Pseudomonas marginalis* [n = 5]<br>*Pseudomonas palleroniana* [n = 5]<br>*Pseudomonas rhodesiae* [n = 5]<br>*Pseudomonas extremorientalis* [n = 4]<br>*Pseudomonas gessardii* [n = 4]<br>*Pseudomonas mucidolens* [n = 4]<br>*Pseudomonas poae* [n = 4]<br>*Pseudomonas agarici* [n = 3]<br>*Pseudomonas cedrina* [n = 3]<br>*Pseudomonas libanensis* [n = 3]<br>*Pseudomonas mandelii* [n = 3]<br>*Pseudomonas orientalis* [n = 3]<br>*Pseudomonas proteolytica* [n = 3]<br>*Pseudomonas reinekei* [n = 3]<br>*Pseudomonas salomonii* [n = 3]<br>*Pseudomonas trivialis* [n = 3]<br>*Pseudomonas vancouverensis* [n = 3]<br>*Pseudomonas antarctica* [n = 2]<br>*Pseudomonas arsenicoxydans* [n = 2]<br>*Pseudomonas baetica* [n = 2]<br>*Pseudomonas canadensis* [n = 2]<br>*Pseudomonas costantinii* [n = 2]<br>*Pseudomonas grimontii* [n = 2]<br>*Pseudomonas jessemi* [n = 2]<br>*Pseudomonas kribbensis* [n = 2]<br>*Pseudomonas migulae* [n = 2]<br>*Pseudomonas moorei* [n = 2]<br>*Pseudomonas yamanorum* [n = 2]<br>[*Flavobacterium*] sp. 29 [n = 1]<br>*Pseudomonas brenneri* [n = 1]<br>*Pseudomonas extremaustralis* [n = 1]<br>*Pseudomonas granadensis* [n = 1]<br>*Pseudomonas haemolytica* [n = 1]<br>*Pseudomonas helmanticensis* [n = 1]<br>*Pseudomonas kairouanensis* [n = 1]<br>*Pseudomonas lamylsulfatiphila* [n = 1]<br>*Pseudomonas laurylsulfativorans* [n = 1]<br>*Pseudomonas mohnii* [n = 1]<br>*Pseudomonas nabeulensis* [n = 1]<br>*Pseudomonas panacis* [n = 1]<br>*Pseudomonas paralactis* [n = 1]<br>*Pseudomonas saponiphila* [n = 1]<br>*Pseudomonas silesiensis* [n = 1]<br>*Pseudomonas umsongensis* [n = 1] |

*Pseudomonas protegens* PBL3 Reduces Disease Symptoms Caused by *B. glumae*

Figure 2:
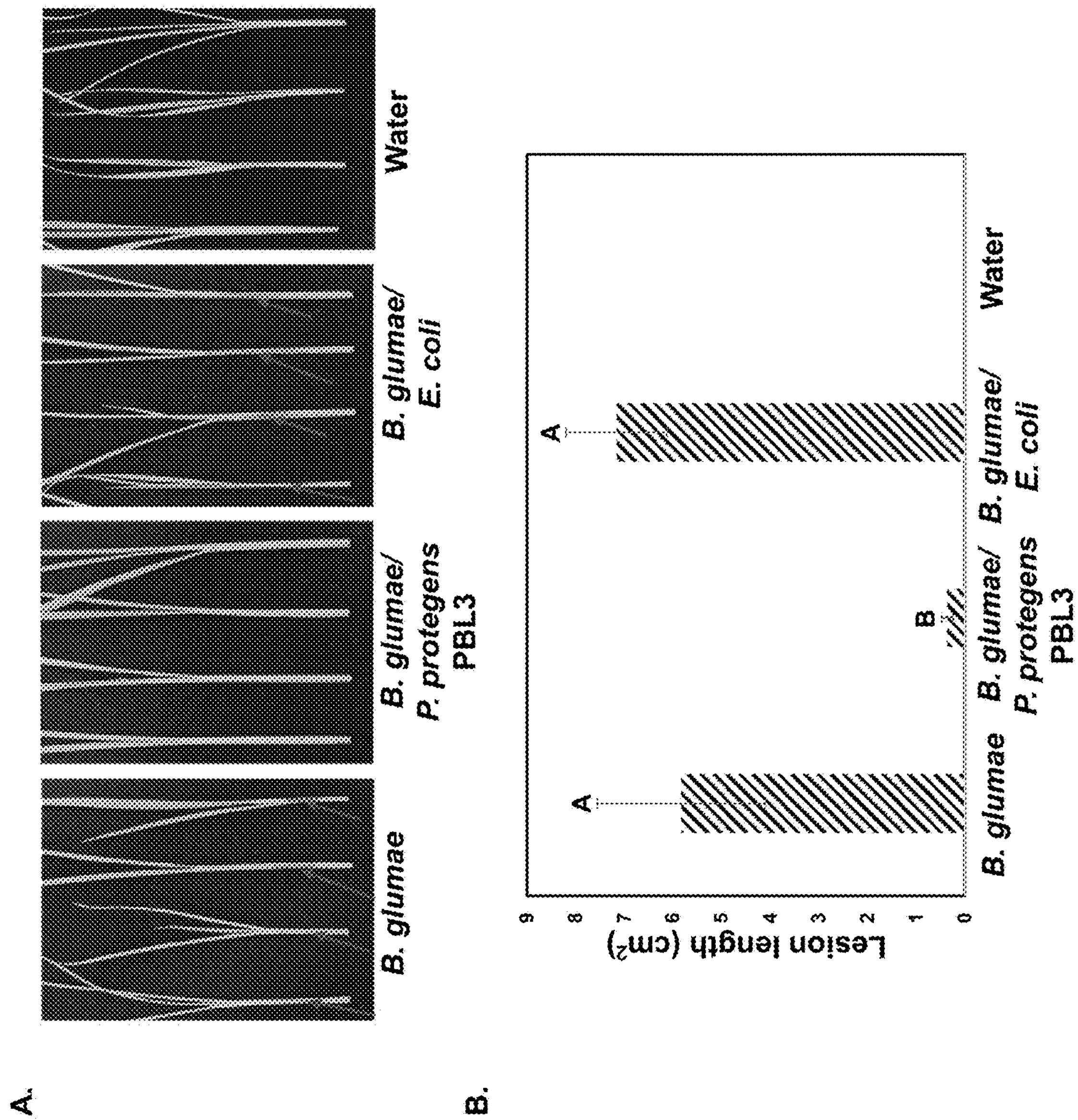
FIG. 2 demonstrates that co-inoculation of *B. glumae* with *P. protegens* PBL3 reduces disease symptoms in rice. Eight-week-old rice plants from cultivar Wells were mock-treated with water or inoculated in the sheath with *B. glumae* diluted to $OD_{600}$=0.125 ($1\times10^7$ CFU/ml), or in combination with *P.*

Our initial observations that *P. protegens* PBL3 inhibited the growth of *B. glumae* prompted us to investigate its effect controlling bacterial panicle blight of rice under controlled conditions. For that purpose, we co-inoculated *B. glumae* with *P. protegens* PBL3 into the susceptible rice cultivar Wells to evaluate symptoms and compare them with those in plants inoculated with *B. glumae* alone. Plants inoculated with *B. glumae* alone showed disease symptoms in the stem characterized by brown lesions surrounding the area of inoculation. However, plants that were co-inoculated with *B. glumae* and *P. protegens* PBL3 had very small lesions (0.36 $cm^2$), almost indistinguishable from plants treated with water (0 $cm^2$). The reduction in symptoms upon co-inoculation with *P. protegens* PBL3 was specific to this bacterium, as no reduction of symptoms was observed when *B. glumae* was co-inoculated with *Escherichia coli* DH5a (FIG. 2A). The lesion sizes for plants inoculated with *B. glumae* alone or co-inoculated with *E. coli* DH5a were 7.16 cm and 5.83 cm, respectively, but did not appear to be different based on statistical analyses. In contrast, co-inoculation of *B. glumae* and *P. protegens* PBL3 resulted in a small lesion sizes with an average lesion size of 0.36 cm that were not statistically different from plants treated with water (FIG. 2B). These results suggest that *P. protegens* PBL3 directly, or indirectly interferes with the pathogenesis of *B. glumae* on rice.

The Genome of *P. protegens* PBL3 Contains Gene Clusters Associated with the Synthesis of Secondary Metabolites To gain mechanistic insight into the antimicrobial activity of *P. protegens* PBL3, we initially investigated the genomic capacity of *P. protegens* PBL3 to synthesize secondary metabolites known to be important in other biological control agents. For that purpose, we searched the genome of *P. protegens* PBL3 looking for biosynthetic gene clusters involved in the production of secondary metabolites. The analysis using the antiSMASH database (Blin et al., 2019) identified 14 putative gene clusters related to biosynthesis of secondary metabolites (Table 3). The identified genes clusters included biosynthetic genes encoding orfamide A and C (Gross et al., 2007), pyoluteorin, and pyrrolnitrin, which are known secondary metabolites responsible for antifungal activities in the closely related reference strain *P. protegens* CHA0 (FIG. 3). The gene clusters necessary for the synthesis of orfamide A and C, pyoluteorin, and pyrrolnitrin in *P. protegens* PBL3 exhibited remarkably similar gene organization and gene content to the respective gene clusters in *P. protegens* CHA0. In the orfamide A and C gene cluster, 88% of the genes are shared between *P. protegens* PBL3 and *P. protegens* CHA0. In the Pyoluteorin gene cluster, there are two additional genes in *P. protegens* PBL3 that are not present in *P. protegens* CHA0, and one gene present in *P. protegens* CHA0 is not present in *P. protegens* PBL3. Other than those differences, the gene organization of both clusters is almost identical and 92% of the genes are conserved between *P. protegens* PBL3 and *P. protegens* CHA0. Regarding the Pyrrolnitrin gene cluster, we found that *P. protegens* PBL3 has an additional gene that is not present in *P. protegens* CHA0, while in turn, *P. protegens* CHA0 has two additional genes that were not found in *P protegens* PBL3. Other than that, 88% of the genes are conserved between both strains.

TABLE 3

Putative biosynthetic gene clusters identified in *P. protegens* PBL3

| PBL3 Genomic region | | Most similar known cluster | Type | Similarity |
|---|---|---|---|---|
| 4,050,249 | 4,091,334 | Pyrrolnitrin | Pyrrole | 100% |
| 3,101,348 | 3,154,097 | Pyoluteorin | Polyketide | 100% |
| 6,522,690 | 6,563,739 | 2,4-diacetylphloroglucinol | Polyketide | 100% |
| 2,371,841 | 2,465,198 | Orfamide A/orfamide C | NRPS[a]: Cyclic depsipeptide | 94% |
| 508,965 | 552,582 | APE Vf | Arylpolyene (APE) (Pigment) | 40% |
| 4,628,974 | 4,698,141 | Pyoverdin | NRPS | 33% |
| 3,914,956 | 3,960,628 | Thiazostatin/watasemycin A/watasemycin B/2-hydroxyphenylthiazoline enantiopyochelin/isopyochelin | NRPS | 26% |
| 4,769,517 | 4,820,431 | Pyoverdin | NRPS | 15% |
| 4,460,042 | 4,483,256 | Fengycin | NRPS: Bectalactone | 13% |
| 5,278,248 | 5,329,277 | Lipopeptide 8D1-1/lipopeptide 8D1-2 | NRPS | 6% |
| 1,471,397 | 1,480,243 | Bacteriocin | Bacteriocin | |
| 6,794,167 | 6,805,012 | Bacteriocin | Bacteriocin | |
| 1,570,952 | 1,591,701 | CDPS | Cyclodipeptides | |
| 4,967,589 | 4,982,421 | NAGGN | N-acetylglutaminylglutamine amide | |

[a]Non-ribosomal peptide synthetase cluster

The Secreted Fraction from *P. protegens* PBL3 Reduces the Growth of *B. glumae*

We hypothesized that the observed inhibitory effect of *P. protegens* PBL3 on the growth of *B. glumae* involves secreted compounds. To test this hypothesis, we obtained and lyophilized the culture supernatant from *P. protegens* PBL3, which contains bacterial secretions. The lyophilized secreted fraction was reconstituted and filter-sterilized to completely remove residual bacteria and ensure that the results obtained were exclusively associated with the secreted fraction and not with residual *P. protegens* PBL3. To test the effect of the lyophilized and resuspended secreted fraction of *P. protegens* PBL3 on the growth of *B. glumae*, we added this lyophilized and resuspended secreted fraction of *P. protegens* PBL3 to the culture media (KB broth), and used this amended KB to grow a single colony of *B. glumae*. Lyophilized and resuspended LB was also used to amend KB and used as control. After overnight incubation, we observed that the growth of *B. glumae* on KB amended with lyophilized and resuspended LB was dense, while its growth in KB amended with the lyophilized and resuspended secreted fraction from *P. protegens* was reduced, as shown by decreased turbidity (FIG. 4A). We further quantified the growth of *B. glumae* by assessing numbers of bacteria and found that the number of *B. glumae* in KB amended with lyophilized and resuspended LB reached $10^9$ CFU/ml, while the number of *B. glumae* in KB amended with the lyophilized secreted fraction from *P. protegens* PBL3 reached $10^5$ CFU/ml (FIG. 4B). Because growth inhibition was only observed in KB amended with the lyophilized and resuspended secreted fraction derived from *P. protegens* PBL3 and not in KB amended with lyophilized and resuspended LB, this growth inhibition was directly related to molecules present in the secreted fraction of *P. protegens* PBL3 and not an indirect effect of the increase in NaCl that resulted from the lyophilization. Independent experiments confirmed that *B. glumae* can grow in KB supplemented with NaCl in concentrations up to 1 M (FIG. 8). We focused on the water-soluble secreted fraction of *P. protegens* PBL3, because hexane-extracted fraction was devoid of antimicrobial activity (FIG. 9).

The Secreted Fraction from *P. protegens* PBL3 Reduces the Disease Symptoms Caused by *B. glumae*

To evaluate the effect of the secreted fraction from *P. protegens* PBL3 on *B. glumae* and its ability to cause disease in rice, lyophilized and resuspended cell-free secreted fractions from *P. protegens* PBL3, or lyophilized and resuspended LB were added to *B. glumae* inoculum and injected into rice plants. Disease development and bacterial populations were investigated at 2 and 7 days post-injection (dpi). At 2 dpi, *B. glumae* mixed with the lyophilized and resuspended LB or with the lyophilized and resuspended secreted fraction of *P. protegens* PBL3 did not produce disease symptoms (FIG. 5A). Interestingly, at 2 dpi, we observed that plants inoculated with *B. glumae* mixed with the lyophilized and resuspended LB showed 5-log higher bacterial populations than plants inoculated with *B. glumae* containing the lyophilized and resuspended cell-free secreted fraction from *P. protegens* PBL3 (FIG. 5B). This result demonstrates that the secreted fraction from *P. protegens* PBL3 contains antagonistic activity against *B. glumae*. At 7 dpi, plants inoculated with *B. glumae* mixed with the lyophilized and resuspended LB showed large lesions (6 cm) that extended beyond the inoculation site throughout the sheath, while plants inoculated with *B. glumae* containing the lyophilized and resuspended cell-free secreted fraction from *P. protegens* PBL3 had a very small lesion (0.48 cm) around the site of inoculation (FIG. 5C). Intriguingly, at 7 dpi, there was no difference in bacterial populations between plants inoculated with *B. glumae* mixed with the lyophilized and resuspended LB or *B. glumae* containing the lyophilized and resuspended cell-free secreted fraction from *P. protegens* PLB3 (FIG. 5D). Altogether, these results showed that the secreted fraction from *P. protegens* PBL3 can inhibit bacterial growth at 2 dpi and reduce the onset of disease symptoms at 7 dpi.

To evaluate other effects of the secreted fraction of *P. protegens* PLB3 on *B. glumae* pathogenesis, Nipponbare seeds were inoculated with *B. glumae* mixed with lyophilized and resuspended LB or with the lyophilized and resuspended cell-free secreted fraction from *P. protegens* PBL3. As shown in FIG. 6, *B. glumae* interferes with either seed germination or shoot growth as seeds inoculated with *B. glumae* mixed with lyophilized and resuspended LB showed reduced shoot length in comparison with water-treated seeds (FIGS. 6A and B). In contrast, seeds inoculated with *B. glumae* containing the lyophilized and resuspended cell-free secreted fraction from *P. protegens* PBL3 at two different concentrations developed normally (FIG. 6A), and their shoot length of approximately 2 cm was not significantly different from water-treated seeds (FIG. 6B).

The Antimicrobial Activities of *P. fluorescens* PBL3 Against *B. glumae* are Related to Molecules of Different Molecular Mass To start dissecting the antimicrobial activity in the *P. protegens* PBL3 secreted fraction, we decided to sub-fractionate it into molecular ranges by using an ultrafiltration centrifugal concentrator of 30 kDa cut-off that separated the *P. protegens* secreted fraction into sub-fractions higher and lower than 30 kDa. We used those fractions to amend KB broth, and that amended KB broth was then used to grow *B. glumae*. *B. glumae* without any secreted fraction grew to $10^9$ CFU/ml. However, sub-fractions higher than 30 kDa and lower than 30 kDa significantly reduced the growth of *B. glumae* to $10^5$ and $10^4$ CFU/ml, respectively (FIG. 7A). This result led us to hypothesize that the activity associated with large molecular weight fractions could be attributed to proteins. However, boiling and protease treatment did not reduce the antimicrobial activity of the *P. protegens* PBL3 secreted fraction (FIG. 10), demonstrating that the *P. protegens* PBL3 antimicrobial activity in the secreted fraction is not associated with proteins.

Similar assays using ultrafiltration centrifugal concentrators with molecular weight cut-off of 10 kDa, showed that the sub-fraction higher than 10 kDa reduced bacterial growth by ~3 logs (FIG. 7B). Interestingly, the sub-fraction lower than 10 kDa completely inhibited the growth of *B. glumae* (FIG. 7B). Using the ultrafiltration centrifugal concentrators of 3 kDa showed that both sub-fractions, higher than 3 kDa and lower than 3 kDa completely inhibited the growth of *B. glumae* (FIG. 7C). The growth inhibition by these smaller molecular size fractions indicates that the activity could be attributed to peptides or secondary metabolites. More work is needed to distinguish between these and other possibilities. Nevertheless, the finding that the antimicrobial activity is found in sub-fractions of different molecular ranges indicates that the overall antimicrobial activity is due to several molecules of different chemical composition.

Discussion:

Bacterial plant diseases are difficult to control and usually require integrated management approaches incorporating cultural practices, plant host resistance, and chemical or biological control (Sundin et al., 2016). Chemical control has mostly relied on copper-containing products or antibiotics that, unfortunately, lose effectiveness over time because bacteria develop resistance, making their use unsustainable (Sundin & Bender, 1993, Manulis et al., 2003, Rodriguez et al., 2006, Barranquero et al., 2013). In the case of bacterial panicle blight of rice, an integrated management approach to control the disease is not feasible because completely resistant cultivars are not available and chemical or biological control methods have proven to be ineffective (Maeda et al., 2004,Shrestha et al., 2016). Considering that rice is a major food staple for the vast majority of people, this disease can have detrimental consequences globally. Thus, identifying sustainable methods to control it is an urgent need.

In this work, we identified one strain of *P. protegens*, strain PBL3, that inhibited the growth of *B. glumae* in vitro, and reduced or eliminated disease symptoms upon co-inoculation with the bacterial pathogen *B. glumae* under controlled conditions. We further showed that the secreted fraction of *P. protegens* PBL3 is biologically active against *B. glumae*. The antagonistic effect of *P. protegens* PBL3, or molecules derived from it, on *B. glumae* has not been reported before. This discovery is important, because although several *Pseudomonas* sp. have been commonly recognized as biological control agents (Haas & Defago, 2005), most studies have focused on their effect on fungal or oomycete pathogens and not in bacterial pathogens.

The biological control strategies that *Pseudomonas* sp. utilizes have been extensively characterized (Haas & Defago, 2005). These strategies mostly rely on competition for nutrients and antibiosis. It is well-known that *Pseudomonas* sp. competes with pathogens for iron through the production of the siderophore pseudobactin that chelates iron and by doing so, prevents pathogens from acquiring this essential element (Haas & Defago, 2005). Studies have demonstrated that this strategy has enabled *Pseudomonas* sp. to control diseases caused by the fungal pathogens *Fusarium oxysporum* and Gaeumannomyces *graminis* var. *tritici* (Kloepper et al., 1980, Lemanceau et al., 1992), and the bacterial pathogen *Xanthomonas oryzae* pv. *oryzae* (Yasmin et al., 2016). Several *Pseudomonas* sp. are also known for producing several antibiotics, defined as "low molecular weight secondary metabolites with antimicrobial activities" (Thomashow et al., 1997), including: phloroglucinols, phenazines, pyoluteorin, pyrrolnitrin, pyocyanine, hydrogen cyanide (HCN), and cyclic lipopeptides such as orfamides (Haas & Defago, 2005, Weller, 2007). Each one of these antibiotics has been associated with the control of specific plant diseases caused by fungal or oomycete pathogens especially soil-borne pathogens (Haas & Defago, 2005). For example, *P. fluorescens* produces 2,4-diacetylphloroglucinol that was demonstrated to be effective for suppressing the fungal pathogens *Thielaviopsis basicola* and Gaeumannomyces *graminis* var. *tritici* (Keel et al., 1992). Phenazines from *P. fluorescens* have activity against Gaeumannomyces *graminis* var. *tritici, Fusarium oxysporum* and *Rhizoctonia solani* (Thomashow and Weller, 1988, Chin et al., 2000, Mazurier et al., 2009, D'Aes et al., 2011). Pyoluteorin had activity against *Pythium ultimum* (Howell & Stipanovic, 1980, Maurhofer et al., 1994), while Pyrrolnitrin was effective against *Rhizoctonia solani* (Howell & Stipanovic, 1979). Moreover, analysis of wild-type and mutant strains of *P. fluorescens* under controlled conditions revealed the importance of HCN and cyclic lipopeptides in controlling *Thielaviopsis basicola* and *Rhizoctonia solani*, respectively (Voisard et al., 1989, D'Aes et al., 2011, Olorunleke et al., 2015).

Our initial experiments showing that co-inoculation of *P. protegens* PBL3 with *B. glumae* reduces disease symptoms suggests that *P. protegens* may be useful for controlling bacterial panicle blight of rice. However, understanding the mechanisms behind this observation is critical to properly design a biological control strategy that would be effective under field conditions. Our co-inoculation experiments did not allow us to distinguish between competition or antibiosis. However, analysis of the *P. protegens* PBL3 genome revealed that it contains a repertoire of gene clusters encoding secondary metabolites, similar to those present in other fluorescent *Pseudomonas* sp. with demonstrated antibiosis against plant pathogens. This information led us to hypothesize that our strain of *P. protegens* PBL3 use antibiosis to control *B. glumae*. Because secondary metabolites are secreted molecules, we tested that hypothesis by preparing a cell-free secreted fraction from *P. protegens* PBL3 and testing its activity in vitro and in planta. Our results showed that the cell-free secreted fraction from *P. protegens* PBL3 and sub-fractions of defined molecular mass significantly reduced the growth of *B. glumae* in vitro. Moreover, the addition of the cell-free secreted fraction to the *B. glumae* inoculum revealed important effects on the pathogenesis of *B. glumae* including: 1) reduction of bacterial numbers in planta at early stages of pathogenesis, 2) reduction of disease symptoms at later stages of pathogenesis and, 3) protection of seed germination. Our current data favors a model in which the secreted fraction of *P. protegens* PBL3 have a bacteriostatic effect inhibiting the growth of *B. glumae* but not killing it. Thus, at early stages of pathogenesis, secretions of *P. protegens* PBL3 interfere with bacterial growth as reflected in the difference in cell numbers between plants inoculated with *B. glumae* containing resuspended LB and plants inoculated with *B. glumae* containing the resuspended secreted fraction of *P. protegens* PBL3. However, those differences in bacterial populations had no effect in the onset of the disease. However, at later stages of pathogenesis, those initial differences in bacterial populations have an effect in the development of symptoms although indirectly, likely associated with the production of toxoflavin. Because the production of toxoflavin by *B. glumae* is regulated by quorum sensing (Kim et al., 2004), the initially larger populations of *B. glumae* in plants that were inoculated with *B. glumae* containing resuspended LB causes these plants to reach the population thresholds required for the production of toxoflavin earlier than plants that were inoculated with *B. glumae* containing the resuspended secreted fraction of *P. protegens* PBL3. It is also possible that molecules produced by *P. protegens* trigger plant defense responses at the expense of the pathogen, another facet of *Pseudomonas* sp, triggering induced systemic resistance (ISR) (Pieterse et al., 2014). More work is needed to distinguish between these two possibilities.

This work does not present direct evidence that *P. protegens* PBL3 actually produces the antibiotics that its genomic sequence predicts, and does not pinpoint a particular molecule or molecules with biological activity against *B. glumae*. Rather, it provides evidence that the secreted fraction of *P. protegens* PBL3, containing a complex mixture of potentially bioactive molecules, has activity against *B. glumae*, likely due to the cumulative effect of several molecules with diverse mode of actions. This finding is important, as it will pave the way towards using the cell-free secreted fraction of *P. protegens* PBL3 to combat bacterial panicle blight of rice instead of using live *P. protegens.*

The use of living organisms to control plant diseases is challenging because the production of bioactive molecules by such organisms depends on multiple conditions (Jamali et al., 2009, Raaijmakers & Mazzola, 2012), that are not necessarily easy to control, especially in the field. As a result, several commercial products containing living organisms, including bacteria such as *P. fluorescens* have not been effective (Nicot et al., 2012, Kohl et al., 2019). It has been argued that products derived from microorganisms (biopesticides) may be more effective that living microorganisms because they are easier to formulate and control (Glare et al., 2012). In our case, the potential use of the secreted fraction of *P. protegens* as a biopesticide would be even more desirable, because it is likely that this preparation contains several bioactive molecules with diverse modes of action. Using a preparation with multiple modes of action can reduce the probability that bacteria develop resistance, which had previously hampered efforts to control bacterial diseases in plants (Sundin & Wang, 2018).

REFERENCES

Bankevich A, Nurk S, Antipov D, et al., 2012. SPAdes: a new genome assembly algorithm and its applications to single-cell sequencing. *J Comput. Biol.* 19, 455-77.

Bao E, Jiang T, Girke T, 2014. AlignGraph: algorithm for secondary de novo genome assembly guided by closely related references. *Bioinformatics* 30, i319-i28.

Baym M, Kryazhimskiy S, Lieberman T D, Chung H, Desai M M, Kishony R, 2015. Inexpensive multiplexed library preparation for megabase-sized genomes. *PLoS One* 10, e0128036.

Bertani G, 1951. Studies on lysogenesis. I. The mode of phage liberation by lysogenic *Escherichia coli. J Bacteriol* 62, 293-300.

Blin, K., Shaw, S., Steinke, K., Villebro, R., Ziemert, N., Lee, S. Y., Medema, M. H., and Weber, T. 2019. antiSMASH 5.0: updates to the secondary metabolite genome mining pipeline. Nucleic acids research 47:W81-W87.

Boetzer M, Henkel C V, Jansen H J, Butler D, Pirovano W, 2011. Scaffolding pre-assembled contigs using SSPACE. *Bioinformatics* 27, 578-9.

Bolger A M, Lohse M, Usadel B, 2014. Trimmomatic: a flexible trimmer for Illumina sequence data. *Bioinformatics* 30, 2114-20.

Chin A W T F, Bloemberg G V, Mulders I H, Dekkers L C, Lugtenberg B J, 2000. Root colonization by phenazine-1-carboxamide-producing bacterium *Pseudomonas chlororaphis* PCL1391 is essential for biocontrol of tomato foot and root rot. *Mol Plant Microbe Interact* 13, 1340-5.

Cole J R, Wang Q, Fish J A, et al., 2014. Ribosomal Database Project: data and tools for high throughput rRNA analysis. *Nucleic Acids Res* 42, D633-42.

D'aes J, Hua G K, De Maeyer K, et al., 2011. Biological control of *Rhizoctonia* root rot on bean by phenazine- and cyclic lipopeptide-producing *Pseudomonas* CMR12a. *Phytopathology* 101, 996-1004.

Degrassi G, Devescovi G, Kim J, Hwang I, Venturi V, 2008. Identification, characterization and regulation of two secreted polygalacturonases of the emerging rice pathogen *Burkholderia glumae. FEMS Microbiol Ecol* 65, 251-62.

Devescovi G, Bigirimana J, Degrassi G, et al., 2007. Involvement of a Quorum-Sensing-Regulated Lipase Secreted by a Clinical Isolate of *Burkholderia glumae* in Severe Disease Symptoms in Rice. *Appl Environ Microbiol* 73, 4950-8.

Dubouzet J G, Maeda S, Sugano S, et al., 2011. Screening for resistance against *Pseudomonas syringae* in rice-FOX *Arabidopsis* lines identified a putative receptor-like cytoplasmic kinase gene that confers resistance to major bacterial and fungal pathogens in *Arabidopsis* and rice. *Plant Biotechnol J* 9, 466-85.

Fory P A, Triplett L, Ballen C, et al., 2014. Comparative analysis of two emerging rice seed bacterial pathogens. *Phytopathology* 104, 436-44.

Glare T, Caradus J, Gelernter W, et al., 2012. Have biopesticides come of age? *Trends Biotechnol* 30, 250-8.

Gross, H., Stockwell, V. O., Henkels, M. D., Nowak-Thompson, B., Loper, J. E., and Gerwick, W. H. 2007. The genomisotopic approach: a systematic method to isolate products of orphan biosynthetic gene clusters. Chem Biol 14:53-63.

Gutierrez-Barranquero J A, De Vicente A, Carrion V J, Sundin G W, Cazorla F M, 2013. Recruitment and rearrangement of three different genetic determinants into a conjugative plasmid increase copper resistance in *Pseudomonas syringae. Appl Environ Microbiol* 79, 1028-33.

Haas D, Defago G, 2005. Biological control of soil-borne pathogens by fluorescent pseudomonads. *Nat Rev Microbiol* 3, 307-19.

Ham J H, Melanson R A, Rush M C, 2011. *Burkholderia glumae*: next major pathogen of rice? *Molecular Plant Pathology* 12, 329-39.

Hanahan D, 1983. Studies on transformation of *Escherichia coli* with plasmids. *Journal of Molecular Biology* 166, 557-80.

Hikichi Y, 1993. Antibacterial activity of oxolinic acid on *Pseudomonas glumae. Japanese Journal Phytopath* 59, 369-74.

Howell C R, Stipanovic R D, 1979. Control of *Rhizoctonia solani* on cotton seedlings with *Pseudomonas fluorescens* and with an antibiotic produced by the bacterium. *Phytopathology* 69, 480-2.

Howell C R, Stipanovic R D, 1980. Suppression of *Pythium ultimum*-induced damping-off of cotton seedlings by *Pseudomonas fluorescens* and its antibiotic, pyoluteorin. *Phytopathology* 70, 712-15.

Iiyama K, Furuya N, Takanami Y, Noraki M, 1995. A role of phytotoxin in virulence of *Pseudomonas glumae* Kurita et Tabeti. *Japanese Journal Phytopath* 61, 470-6.

Jamali F, Sharifi-Tehrani A, Lutz M P, Maurhofer M, 2009. Influence of host plant genotype, presence of a pathogen, and coinoculation with *Pseudomonas fluorescens* strains on the rhizosphere expression of hydrogen cyanide- and 2,4-diacetylphloroglucinol biosynthetic genes in *P. fluorescens* biocontrol strain CHA0. *Microb Ecol* 57, 267-75.

Jolley K A, Bliss C M, Bennett J S, et al., 2012. Ribosomal multilocus sequence typing: universal characterization of bacteria from domain to strain. *Microbiology* (Reading, England) 158, 1005-15.

Kang Y, Kim J, Kim S, et al., 2008. Proteomic analysis of the proteins regulated by HrpB from the plant pathogenic bacterium *Burkholderia glumae. Proteomics* 8, 106-21.

Karki H S, Shrestha B K, Han J W, et al., 2012b. Diversities in virulence, antifungal activity, pigmentation and DNA fingerprint among strains of *Burkholderia glumae. PLoS One* 7, e45376.

Kawaradani M, Okada K, Kusakari S I, 2000. New selective medium for isolation of *Burkholderia glumae* from rice seeds. *J. Gen. Plant Pathol* 66, 234-7.

Keel C, Schnider U, Maurhofer M, et al., 1992. Suppression of root diseases by *Pseudomonas fluorescens* CHAO:

importance of the bacterial secondary metabolite 2,4-diacetylphloroglucinol. *Molecular Plant-Microbe Interactions* 5, 4-13.

Kim J, Kim J G, Kang Y, et al., 2004. Quorum sensing and the LysR-type transcriptional activator ToxR regulate toxoflavin biosynthesis and transport in *Burkholderia glumae. Mol Microbiol* 54, 921-34.

King E O, Ward M K, Raney D E, 1954. Two simple media for the demonstration of pyocyanin and fluorescin. *Journal of Laboratory and Clinical Medicine* 44, 301-7.

Kloepper J W, Leong J, Teintze M, Schroth M N, 1980. *Pseudomonas* siderophores: a mechanism explaining disease-suppressive soils. *Current microbiology* 4, 317-20.

Knapp A, Voget S, Gao R, et al., 2016. Mutations improving production and secretion of extracellular lipase by *Burkholderia glumae* PG1. *Appl Microbiol Biotechnol* 100, 1265-73.

Kohl J, Kolnaar R, Ravensberg W J, 2019. Mode of Action of Microbial Biological Control Agents Against Plant Diseases: Relevance Beyond Efficacy. *Front Plant Sci* 10, 845.

Lee Y H, Ko S J, Cha K H, Park E W, 2015. BGRcast: A Disease Forecast Model to Support Decision-making for Chemical Sprays to Control Bacterial Grain Rot of Rice. *Plant Pathol* J31, 350-62.

Lane, D. J. 1991. 16S/23S rRNA sequencing, p. 115-175. In E. Stackebrandt and M. Goodfellow (ed.), *Nucleic acid techniques in bacterial systematics*. John Wiley and Sons, Chichester, United Kingdom.

Lemanceau P, Bakker P A, De Kogel W J, Alabouvette C, Schippers B, 1992. Effect of pseudobactin 358 production by *Pseudomonas putida* WCS358 on suppression of *fusarium* wilt of carnations by nonpathogenic *Fusarium oxysporum* Fo47. *Appl Environ Microbiol* 58, 2978-82.

Lim J, Lee T H, Nahm B H, Do Choi Y, Kim M, Hwang I, 2009. Complete Genome Sequence of *Burkholderia glumae* BGR1. *Journal of Bacteriology* 191, 3758-9.

Maeda S, Hayashi N, Sasaya T, Mori M, 2016. Overexpression of BSR1 confers broad-spectrum resistance against two bacterial diseases and two major fungal diseases in rice. *Breed Sci* 66, 396-406.

Maeda Y, Kiba A, Ohnishi K, Hikichi Y, 2004. Implications of amino acid substitutions in GyrA at position 83 in terms of oxolinic acid resistance in field isolates of *Burkholderia glumae*, a causal agent of bacterial seedling rot and grain rot of rice. *Appl Environ Microbiol* 70, 5613-20.

Magoč T, Salzberg S L, 2011. FLASH: fast length adjustment of short reads to improve genome assemblies. *Bioinformatics* 27, 2957-63.

Manulis S, Kleitman F, Shtienberg D, et al., 2003. Changes in the Sensitivity of *Erwinia amylovora* Populations to Streptomycin and Oxolinic Acid in Israel. *Plant Dis* 87, 650-4.

Maurhofer M, Keel C, Defago G, 1994. Pyoluteorin production by *Pseudomonas fluorescens* strain CHA0 is involved in the suppression of Phythium damping-off of cress but not of cucumber. *Eur J Plant Pathol* 15, 221-32.

Mazurier S, Corberand T, Lemanceau P, Raaijmakers J M, 2009. Phenazine antibiotics produced by fluorescent pseudomonads contribute to natural soil suppressiveness to *Fusarium* wilt. *ISMS J*3, 977-91.

Milus E A, Rothrock C S, 1997. Efficacy of Bacterial Seed Treatments for Controlling *Pythium Root Rot of Winter Wheat. Plant Dis* 81, 180-4.

Mizobuchi R, Sato H, Fukuoka S, et al., 2013. Mapping a quantitative trait locus for resistance to bacterial grain rot in rice. *Rice* (N Y) 6, 13.

Mizobuchi R, Fukuoka S, Tsushima S, Yano M, Sato H, 2016. QTLs for Resistance to Major Rice Diseases Exacerbated by Global Warming: Brown Spot, Bacterial Seedling Rot, and Bacterial Grain Rot. *Rice* (N Y) 9, 23.

Mizobuchi R, Fukuoka S, Tsuiki C, Tsushima S, Sato H, 2018. Evaluation of major Japanese rice cultivars for resistance to bacterial grain rot caused by *Burkholderia glumae* and identification of standard cultivars for resistance. *Breed Sci* 68, 413-9.

Mondal K K, Mani C, Verma G, 2015. Emergence of Bacterial Panicle Blight caused by *Burkholderia glumae* in North India. *Plant Disease* 99, 1268.

Mulaw T, Wamishe Y, Jia Y, 2018. Characterization and in Plant Detection of Bacteria that Cause Bacterial Panicle Blight of Rice. Research *Journal of Plant Pathology* 1, 1-7.

Nandakumar R, Rush M C, Correa F, 2007. Association of *Burkholderia glumae* and *B. gladioili* with Panicle Blight Symptoms on Rice in Panama. *Plant Dis* 91, 767.

Nandakumar R, Shahjahan A K M, Yuan X L, et al., 2009. *Burkholderia glumae* and *B. gladioli* cause bacterial panicle blight in rice in the Southern United States. *Plant Dis* 93, 896-905.

Nicot P C, Alabouvette C, Bardin M, Blum B, Kohl J, Ruocco M, 2012. Review of factors influencing the success or failure of biocontrol: technical, industrial and socio-economic perspectives. In. *IOBC-WPRS Bulletin.* 78, 95-98.

Olorunleke, F. E., Hua, G. K., Kieu, N. P., Ma, Z., and Hofte, M. 2015. Interplay between orfamides, sessilins and phenazines in the control of *Rhizoctonia* diseases by *Pseudomonas* sp. CMR12a. Environ Microbiol Rep 7:774-781.

Pieterse C M, Zamioudis C, Berendsen R L, Weller D M, Van Wees S C, Bakker P A, 2014. Induced systemic resistance by beneficial microbes. *Annu Rev Phytopathol* 52, 347-75.

Rasband, W. S., ImageJ, U. S. National Institutes of Health, Bethesda, Maryland, USA, https://imagej.nih.gov/ij/, 1997-2018.

Raaijmakers J M, Mazzola M, 2012. Diversity and natural functions of antibiotics produced by beneficial and plant pathogenic bacteria. *Annu Rev Phytopathol* 50, 403-24.

Rodriguez C, Lang L, Wang A, Altendorf K, Garcia F, Lipski A, 2006. Lettuce for human consumption collected in Costa Rica contains complex communities of culturable oxytetracycline- and gentamicin-resistant bacteria. *Appl Environ Microbiol* 72, 5870-6.

Seemann T, 2014. Prokka: rapid prokaryotic genome annotation. *Bioinformatics* 30, 2068-9.

Shew A M, Durand-Morat A, Nalley L L, Zhou X G, Rojas C, Thoma G, 2019. Warming increases Bacterial Panicle Blight (*Burkholderia glumae*) occurrences and impacts on USA rice production. *PLoS One* 14, e0219199.

Shrestha B K, Karki H S, Groth D E, Jungkhun N, Ham J H, 2016. Biological Control Activities of Rice-Associated *Bacillus* sp. Strains against Sheath Blight and Bacterial Panicle Blight of Rice. *PLoS One* 11, e0146764.

Song L, Florea L, Langmead B, 2014. Lighter: fast and memory-efficient sequencing error correction without counting. *Genome Biol.* 15, 509.

Suarez-Moreno Z R, Vinchira-Villarraga D M, Vergara-Morales D I, et al., 2019. Plant-Growth Promotion and Biocontrol Properties of Three *Streptomyces* spp. Isolates to Control Bacterial Rice Pathogens. *Front Microbiol* 10, 290.

Sundin G W, Bender C L, 1993. Ecological and genetic analysis of copper and streptomycin resistance in *Pseudomonas syringae* pv. *syringae*. *Appl Environ Microbiol* 59, 1018-24.

Sundin G W, Castiblanco L F, Yuan X, Zeng Q, Yang C H, 2016. Bacterial disease management: challenges, experience, innovation and future prospects: Challenges in Bacterial Molecular Plant Pathology. *Mol Plant Pathol* 17, 1506-18.

Sundin G W, Wang N, 2018. Antibiotic Resistance in Plant-Pathogenic Bacteria. *Annu Rev Phytopathol* 56, 161-80.

Temesgen M, Wamishe Y, Jia Y, 2018. Characterization and plant detection of bacteria that cause Bacterial Panicle Blight of rice. *American Journal of Plant Sciences* 9, 667-84.

Thomashow L S, Bonsall R E, Weller D M, 1997. Antibiotic production by soil and rhizosphere microbes in situ. In: Hurst C J, Knudsen G R, Mcinerney M J, Stetzenbach L D, Walter M V, eds. *Manual of Environmental Microbiology*, ed. Washington, DC: ASM Press, 493-99.

Thomashow L S, Weller D M, 1988. Role of a phenazine antibiotic from *Pseudomonas fluorescens* in biological control of *Gaeumannomyces graminis* var. *tritici*. *J Bacteriol* 170, 3499-508.

Voisard C, Keel C, Haas D, Defago G, 1989. Cyanide production by *Pseudomonas fluorescens* helps suppress black root rot of tobacco under gnotobiotic conditions. *EMBO J* 8, 351-8.

Walker B J, Abeel T, Shea T, et al., 2014. Pilon: an integrated tool for comprehensive microbial variant detection and genome assembly improvement. *PLoS One* 9, e112963.

Wamishe Y, Kelsey C, Belmar S B, Gerbremariam T, Mccarty D, 2015. Bacterial Panicle Blight of Rice in Arkansas. *University of Arkansas Division of Agriculture Research and Extension: Agriculture and Natural Resources.*

Weller D M, 2007. *Pseudomonas* biocontrol agents of soilborne pathogens: looking back over 30 years. Phytopathology 97, 250-6.

Yasmin S, Zaka A, Imran A, et al., 2016. Plant Growth Promotion and Suppression of Bacterial Leaf Blight in Rice by Inoculated Bacteria. *PLoS One* 11, e0160688.

Zhou X G, 2014. First Report of Bacterial Panicle Blight of Rice Caused by *Burkholderia glumae* in South Africa. *Plant Dis* 98, 566.

DEPOSIT INFORMATION

A deposit of the Board of Trustees of the University of Arkansas proprietary *Pseudomonas protegens* strain designated as PBL3 disclosed above and recited in the appended claims has been made with the ARS Culture Collection (NRRL), 1815 N. University Street, Peoria, IL 61604, and has been accepted under the terms of the Budapest Treaty. The date of deposit was Nov. 17, 2021. The deposit comprises 5 liquid nitrogen stocks of the strain, which were found viable on Nov. 18, 2021. All restrictions will be irrevocably removed upon granting of a patent, and the deposit is intended to meet all of the requirements of 37 C.F.R. §§ 1.801-1.809. The NRRL Accession Number is B-68083. The deposit will be maintained in the depository for a period of thirty years, or five years after the last request, or for the enforceable life of the patent, whichever is longer, and will be replaced as necessary during that period.

What is claimed:

1. A method of inhibiting the growth of *Burkholderia glumae*, the method comprising: contacting the *Burkholderia glumae* with an effective amount of a biosynthetic product, thereby inhibiting its growth, wherein the biosynthetic product is produced by a *Pseudomonas protegens* strain designated as PBL3 and deposited as NRRL Accession No. B-68083, and wherein the biosynthetic product is selected from orfamide A/C, pyoluteorin, and pyrrolnitrin.

2. The method of claim 1, wherein the growth of the *Burkholderia glumae* is inhibited on a plant.

3. The method of claim 2, wherein the plant is a rice plant.

4. The method of claim 2, wherein the contacting is carried out by spraying or dusting the plant or a portion of the plant with a composition comprising the biosynthetic product.

5. The method of claim 2, wherein the contacting is carried out before flowering or during panicle formation.

* * * * *